United States Patent [19]

Ishihara et al.

[11] Patent Number: 5,491,167
[45] Date of Patent: Feb. 13, 1996

[54] HEXAHYDRONAPHTHALENE ESTER DERIVATIVES, THEIR PREPARATION AND THEIR THERAPEUTIC USES

[75] Inventors: Sadao Ishihara; Hiroshi Kogen; Teiichiro Koga; Eiichi Kitazawa; Nobufusa Serizawa, all of Tokyo, Japan

[73] Assignee: Sankyo Company, Limited, Tokyo, Japan

[21] Appl. No.: 189,040

[22] Filed: Jan. 31, 1994

[30] Foreign Application Priority Data

Jan. 29, 1993 [JP] Japan .................................. 5-13063

[51] Int. Cl.⁶ .......................... A61K 31/75; C07C 69/013
[52] U.S. Cl. ................................ 514/510; 560/56
[58] Field of Search ................... 560/56; 514/510

[56] References Cited

U.S. PATENT DOCUMENTS

| | | | |
|---|---|---|---|
| 4,695,587 | 7/1987 | Terahara et al. | 514/510 |
| 4,876,279 | 10/1989 | Lee et al. | 514/510 |
| 4,885,314 | 12/1989 | Vyas et al. | 560/56 |
| 4,902,709 | 2/1990 | Stokker et al. | 560/56 |
| 4,937,263 | 6/1990 | Hoffman et al. | 514/510 |
| 4,937,264 | 6/1990 | Hoffman et al. | 514/510 |
| 4,946,864 | 8/1990 | Progh et al. | 514/510 |
| 4,997,848 | 3/1991 | Kurabayashi et al. | 514/510 |
| 5,010,105 | 4/1991 | Lee | 514/510 |
| 5,021,453 | 7/1991 | Joshua et al. | 514/510 |
| 5,102,911 | 4/1992 | Lee et al. | 514/510 |
| 5,130,306 | 7/1992 | Duggan et al. | 514/510 |
| 5,180,589 | 1/1993 | Yatindra et al. | 514/510 |

FOREIGN PATENT DOCUMENTS 2077264  12/1989  United Kingdom .

*Primary Examiner*—Johann Richter
*Assistant Examiner*—John Peabody
*Attorney, Agent, or Firm*—Frishauf, Holtz, Goodman, Langer & Chick

[57] ABSTRACT

Compounds of formula (I):

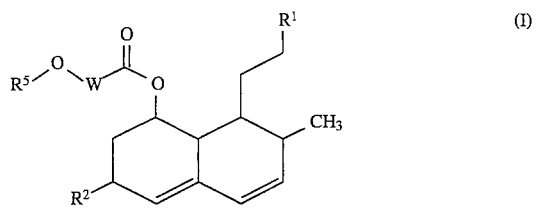

and their salts and esters have the ability to inhibit the synthesis of cholesterol, and can thus be used for the treatment and prophylaxis of hypercholesterolemia and of various cardiac disorders.

87 Claims, No Drawings

HEXAHYDRONAPHTHALENE ESTER DERIVATIVES, THEIR PREPARATION AND THEIR THERAPEUTIC USES

BACKGROUND OF THE INVENTION

The present invention relates to a series of new hexahydronaphthalene derivatives related to the class of compounds known as "ML-236B", which have the ability to inhibit the synthesis of cholesterol, and which can thus be used for the treatment and prophylaxis of hypercholesterolemia and of various cardiac disorders. The invention also provides methods and compositions using these compounds as well as processes for their preparation.

Excessive levels of cholesterol in the body have been implicated in many life-threatening disorders and there is, therefore, a need for drugs which have the effect of reducing blood cholesterol levels. One method by which a drug may achieve this is to inhibit the biosynthesis of cholesterol.

A number of compounds which may be generally described as 7-[substituted 1,2,3,5,6,7,8,8a-octahydro-1-naphthyl]-3,5-dihydroxyheptanoates is known, and such compounds are disclosed, inter alia, in European Patent Publication No. 314 435, which also describes in greater detail than herein the development and forerunners of these types of compound. However, the closest compounds to those of the present invention are believed to be the compounds disclosed in United Kingdom Patent Specification No. 2 077 264 and Japanese Pantent Application Kokai No. Sho. 59-175450, which compounds may be represented by the formulae (A) and (B), respectively:

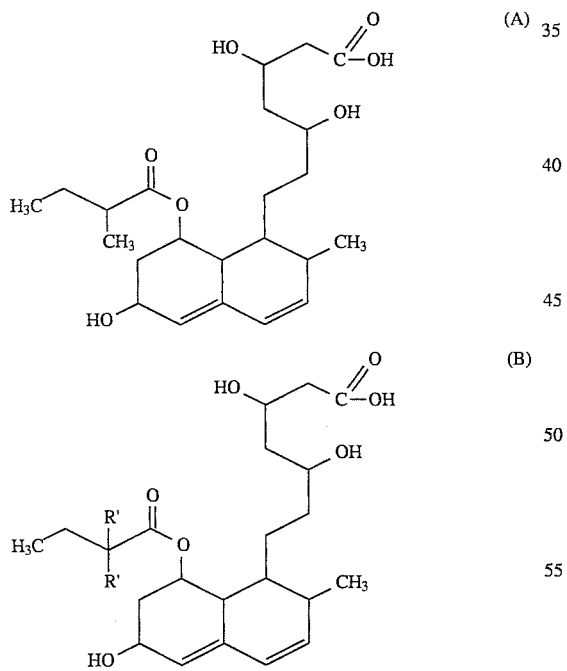

Further hexahydronaphthalene derivatives in this class of prior art compounds are disclosed in a co-pending U.S. patent application, provisionally given the Ser. No. 08/174,661, filed on 28th Dec. 1993.

These prior art compounds, like the compounds of the present invention, have the ability to inhibit the biosynthesis of cholesterol, and can thus be used for the treatment and prophylaxis of the various diseases caused by hypercholesterolemia, such as atherosclerosis and various cardiac disorders.

BRIEF SUMMARY OF THE INVENTION

It is, therefore, an object of the present invention to provide a series of new hexahydronaphthalene derivatives.

It is a further, and more specific, object of the present invention to provide such compounds having the ability to inhibit the biosynthesis of cholesterol.

Other objects and advantages of the present invention will become apparent as the description proceeds.

Thus, the present invention provides compounds of formula (I):

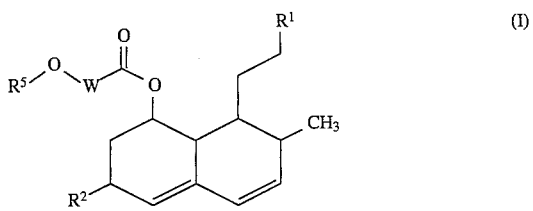

wherein $R^1$ represents a group of formula (II) or (III):

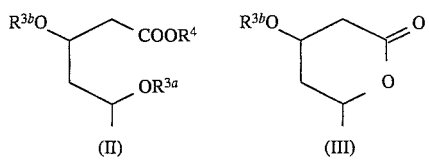

$R^2$ represents a hydrogen atom or a group of formula $-OR^3$;

$R^3$, $R^{3a}$ and $R^{3b}$ are independently selected from the group consisting of hydrogen atoms, hydroxy-protecting groups, alkyl groups having from 1 to 6 carbon atoms, alkanesulfonyl groups having from 1 to 6 carbon atoms, halogenated alkanesulfonyl groups having from 1 to 6 carbon atoms and arylsulfonyl groups, in which the aryl part is an aromatic hydrocarbon ring which has from 6 to 14 ring carbon atoms and is unsubstituted or is substituted by at least one substituent selected from the group consisting of substituents α, defined below;

$R^4$ represents a hydrogen atom or a carboxy-protecting group;

$R^5$ represents an alkyl group having from 1 to 6 carbon atoms; an alkenyl group having from 2 to 6 carbon atoms; an alkynyl group having from 2 to 6 carbon atoms; an aryl group having from 6 to 14 ring carbon atoms; an aryl group having from 6 to 14 ring carbon atoms and substituted by at least one substituent selected from the group consisting of substituents α, defined below; an aralkyl group in which the or each aryl portion has from 6 to 14 ring carbon atoms, and the alkyl portion has from 1 to 6 carbon atoms; an aralkyl group, in which the or each aryl portion has from 6 to 14 ring carbon atoms, and the alkyl portion has from 1 to 6 carbon atoms, substituted on the ring by at least one substituent selected from the group consisting of substituents α, defined below; or a fused polycyclic hydrocarbon having from 8 to 14 ring carbon atoms; and W represents an alkylene group having from 1 to 6 carbon atoms, or an alkylene group having from 1 to 6 carbon atoms and substituted by at least one substituent selected from the group consisting of substituents β, defined below;

said substituents α are selected from the group consisting of alkyl groups having from 1 to 6 carbon atoms, alkenyl groups having from 2 to 6 carbon atoms, alkynyl groups having from 2 to 6 carbon atoms, alkoxy groups having from 1 to 6 carbon atoms, alkylenedioxy groups having from 1 to 6 carbon atoms, alkoxycarbonyl groups having from 1 to 6 carbon atoms, carboxy groups, halogen atoms, amino groups, alkylamino groups in which the alkyl part has from 1 to 6 carbon atoms, dialkylamino groups in which each alkyl part has from 1 to 6 carbon atoms, alkoxyamino groups in which the alkoxy part has from 1 to 6 carbon atoms, alkoxyalkoxyamino groups in which each alkoxy part has from 1 to 6 carbon atoms, hyroxyalkylamino groups in which the alkyl part has from 1 to 6 carbon atoms, haloalkoxyamino groups in which the alkoxy part has from 1 to 6 carbon atoms, aralkyloxyamino groups in which the alkyl part has from 1 to 6 carbon atoms and the or each aryl part has from 6 to 14 ring carbon atoms, hydroxyamino groups, aminoalkylamino groups in which the alkyl part has from 1 to 6 carbon atoms, arylamino groups in which the aryl part has from 6 to 14 carbon atoms, aryl groups having from 6 to 14 ring carbon atoms, cyano groups, nitro groups, halogenated alkyl groups having from 1 to 6 carbon atoms and acyl groups.

said substituents β are selected from the group consisting of alkyl groups having from 1 to 6 carbon atoms, alkenyl groups having from 2 to 6 carbon atoms, alkynyl groups having from 2 to 6 carbon atoms, alkoxy groups having from 1 to 6 carbon atoms, alkoxyalkyl groups in which each of the alkoxy and alkyl parts has from 1 to 6 carbon atoms, aryl groups having from 5 to 14 ring carbon atoms, aryl groups having from 5 to 14 ring carbon atoms and substituted by at least one substituent selected from the group consisting of substituents α, above, fused polycyclic hydrocarbon groups having from 8 to 14 ring carbon atoms; and halogenated alkyl groups having from 1 to 6 carbon atoms;

and pharmaceutically acceptable salts and esters thereof.

The invention also provides a pharmaceutical composition comprising an agent for inhibiting cholesterol biosynthesis in admixture with a pharmaceutically acceptable carrier or diluent, wherein said agent is selected from the group consisting of compounds of formula (I), as defined above, and pharmaceutically acceptable salts and esters thereof.

The invention still further provides a method of treating a mammal suffering from a disorder arising from a blood cholesterol imbalance, which comprises administering to said mammal an effective amount of an agent inhibiting cholesterol biosynthesis, wherein said agent is selected from the group consisting of compounds of formula (I), as defined above, and pharmaceutically acceptable salts and esters thereof.

The invention still further provides processes for the preparation of compounds of formula (I) and pharmaceutically acceptable salts and esters thereof, which are described in more detail hereafter.

DETAILED DESCRIPTION OF INVENTION

Included in the compounds of the present invention are those compounds of formulae (Ia) and (Ib):

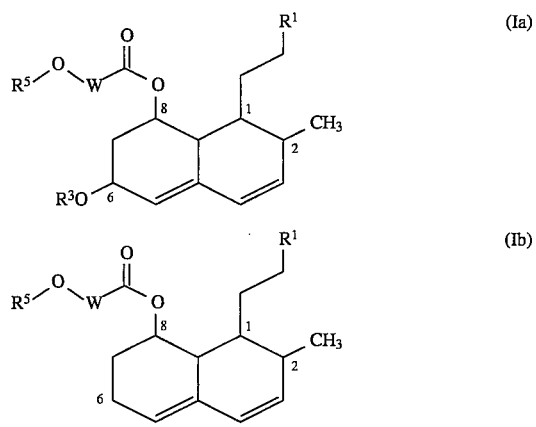

wherein $R^1$, $R^2$, $R^3$, $R^4$, $R^5$ and W are as defined above. For the avoidance of doubt, the above two formulae also show a partial numbering system for the hexahydronaphthalene rings, as employed herein.

In the compounds of the present invention, where $R^5$ represents an alkyl group, this may be a straight or branched chain alkyl group containing from 1 to 6 carbon atoms, preferably from 1 to 4 carbon atoms. Examples of such groups include the methyl, ethyl, propyl, isopropyl, butyl, isobutyl, sec-butyl, t-butyl, pentyl isopentyl, 2-methylbutyl, neopentyl, 1-ethylpropyl, hexyl, 4-methylpentyl, 3-methylpentyl, 2-methylpentyl, 1-methylpentyl, 3,3-dimethylbutyl, 2,2-dimethylbutyl, 1,1-dimethylbutyl, 1,2-dimethylbutyl, 1,3-dimethylbutyl, 2,3-dimethylbutyl and 2-ethylbutyl groups, preferably the methyl or ethyl groups.

Where $R^5$ represents an alkenyl group, this may be a straight or branched chain alkenyl group having from 2 to 6 carbon atoms, preferably from 2 to 4 carbon atoms and more preferably 3 or 4 carbon atoms. Examples of such groups include the vinyl, 1-propenyl, allyl (i.e. 2-propenyl), 1-methylallyl, 2-methyl-1-propenyl, 2-methylallyl, 2-ethylallyl, 1-butenyl, 2-butenyl, 1-methyl-2-butenyl, 2-methyl-2-butenyl, 3-methyl-2-butenyl, 1-ethyl-2-butenyl, 3-butenyl, 1-methyl-3-butenyl, 2-methyl-3-butenyl, 1-ethyl-3-butenyl, 1-pentenyl, 2-pentenyl, 1-methyl-2-pentenyl, 2-methyl-2-pentenyl, 3-pentenyl, 1-methyl-3-pentenyl, 2-methyl-3-pentenyl, 4-pentenyl, 1-methyl-4-pentenyl, 2-methyl-4-pentenyl, 1-hexenyl, 2-hexenyl, 3-hexenyl, 4-hexenyl and 5-hexenyl groups, of which we prefer the vinyl, 1-propenyl and allyl groups.

When $R^5$ represents an alkynyl group, this may be a straight or branched chain alkynyl group having from 2 to 6 carbon atoms, preferably from 2 to 4 carbon atoms and more preferably 3 or 4 carbon atoms. Examples of such groups include the ethynyl, 2-propynyl, 1-methyl-2-propynyl, 2-methyl-2-propynyl, 2-ethyl-2-propynyl, 2-butynyl, 1-methyl-2-butynyl, 2-methyl-2-butynyl, 1-ethyl-2-butynyl, 3-butynyl, 1-methyl-3-butynyl, 2-methyl-3-butynyl, 1-ethyl-3-butynyl, 2-pentynyl, 1-methyl-2-pentynyl, 3-pentynyl, 1-methyl-3-pentynyl, 2-methyl-3-pentynyl, 4-pentynyl, 1-methyl-4-pentynyl, 2-methyl-4-pentynyl, 2-hexynyl, 3-hexynyl, 4-hexynyl and 5-hexynyl groups, of which we prefer the 2-propynyl group.

When $R^5$ represents an aryl group, this may be an aromatic hydrocarbon group having from 6 to 14 ring carbon atoms, preferably from 6 to 10 carbon atoms and more preferably 6 or 10 carbon atoms. Examples of such groups include the phenyl, indenyl, 1-naphthyl, 2-naphthyl, phenanthrenyl and anthracenyl groups, of which we prefer the phenyl group and the naphthyl groups.

When $R^5$ represents a fused polycyclic hydrocarbon group, this may have from 8 to 14 ring carbon atoms and includes an aryl group, as defined above, fused to a cycloalkyl group having from 3 to 10 ring carbon atoms. Examples of such groups include the 1-indanyl, 2-indanyl and tetrahydronaphthalene groups, of which we prefer the 2-indanyl group.

When $R^5$ represents an aryl group substituted by at least one substituent selected from the group consisting of substituents α, defined above and exemplified below, this may be an aryl group containing from 6 to 14 ring carbon atoms substituted on the ring by from 1 to 4 substituents, which may be the same or different, selected from the group consisting of substituents α, defined above and exemplified below. Examples of such groups include the 2-methylphenyl, 3-methylphenyl, 4-methylphenyl, 2-ethylphenyl, 3-propylphenyl, 4-ethylphenyl, 2-butylphenyl, 3-pentylphenyl, 4-pentylphenyl, 3,5-dimethylphenyl, 2,5-dimethylphenyl, 2,6-dimethylphenyl, 2,4-dimethylphenyl, 3,5-dibutylphenyl, 2,5-dipentylphenyl, 2,6-dipropylmethylphenyl, 2,4-dipropylphenyl, 2,3,6-trimethylphenyl, 2,3,4-trimethylphenyl, 3,4,5-trimethylphenyl, 2,4,6-trimethylphenyl, 2,3,6-tributylphenyl, 2,3,4-tripentylphenyl, 3,4,5-tributylphenyl, 2,3,6-tripropylphenyl, 2,4,6-tripropylphenyl, 1-methyl-2-naphthyl, 2-methyl-1-naphthyl, 3-methyl-1-naphthyl, 1-ethyl-2-naphthyl, 2-propyl-1-naphthyl, 3-butyl-1-naphthyl, 3,8-dimethyl-1-naphthyl, 2,3-dimethyl-1-naphthyl, 4,8-dimethyl-1-naphthyl, 5,6-dimethyl-1-naphthyl, 3,8-diethyl-1-naphthyl, 2,3-dipropyl-1-naphthyl, 4,8-dipentyl-1-naphthyl, 5,6-dibutyl-1-naphthyl, 2,3,6-trimethyl-1-naphthyl, 2,3,4-trimethyl-1-naphthyl, 3,4,5-trimethyl-1-naphthyl, 4,5,6-trimethyl-1-naphthyl, 2,4,8-trimethyl-1-naphthyl, 2-vinylphenyl, 3-vinylphenyl, 4-vinylphenyl, 2-butenylphenyl, 3-pentenylphenyl, 4-pentenylphenyl, 3,5-divinylphenyl, 2,5-divinylphenyl, 2,6-dipropenylmethylphenyl, 2,4-dipropenylphenyl, 2,3,6-trivinylphenyl, 2,3,4-tripentenylphenyl, 3,4,5-tributenylphenyl, 2,3,6-tripropenylphenyl, 2,4,6-tripropenylphenyl, 1-vinyl-2-naphthyl, allyl-1-naphthyl, 3-vinyl-1-naphthyl, 3,8-divinyl-1-naphthyl, 2,3-dipropenyl-1-naphthyl, 4,8-dipentenyl-1-naphthyl, 5,6-dibutenyl-1naphthyl, 2-ethynylphenyl, 3-propynylphenyl, 4-ethynylphenyl, 2-butynylphenyl, 3-pentynylphenyl, 4-pentynylphenyl, 3,5-dibutynylphenyl, 2,5-dipentynylphenyl, 2,6-dipropynylmethylphenyl, 2,4-dipropynylphenyl, 2-methoxyphenyl, 3-methoxyphenyl, 4-methoxyphenyl, 2-ethoxyphenyl, 3-propoxyphenyl, 4-ethoxyphenyl, 2-butoxyphenyl, 3-pentoxyphenyl, 4-pentoxyphenyl, 3,5-dimethoxyphenyl, 2,5-dimethoxyphenyl, 2,6-dimethoxyphenyl, 2,4-dimethoxyphenyl, 3,5-dibutoxyphenyl, 2,5-dipentoxyphenyl, 2,6-dipropoxymethoxyphenyl, 2,4-dipropoxyphenyl, 2,3,6-trimethoxyphenyl, 2,3,4-trimethoxyphenyl, 3,4,5-trimethoxyphenyl, 2,4,6-trimethoxyphenyl, 2,3,6-tributoxyphenyl, 2,3,4-tripentoxyphenyl, 3,4,5-tributoxyphenyl, 2,5,6-tripropoxyphenyl, 2,4,6-tripropoxyphenyl, 1-methoxy-2-naphthyl, 2-methoxy-1-naphthyl, 3-methoxy-1-naphthyl, 1-ethoxy-2-naphthyl, 2-propoxy-1-naphthyl, 3-butoxy-1-naphthyl, 3,8-dimethoxy-1-naphthyl, 2,3-dimethoxy-1-naphthyl, 4,8-dimethoxy-1-naphthyl, 5,6-dimethoxy-1-naphthyl, 3,8-diethoxy-1-naphthyl, 2,3-dipropoxy-1-naphthyl, 4,8-dipentoxy-1-naphthyl, 5,6-dibutoxy-1-naphthyl, 2,3,6-trimethoxy-1-naphthyl, 2,3,4-trimethoxy-1-naphthyl, 3,4,5-trimethoxy-1-naphthyl, 4,5,6-trimethoxy-1-naphthyl, 2,4,8-trimethoxy-1-naphthyl, 2-fluorophenyl, 3-fluorophenyl, 4-fluorophenyl, 2-chlorophenyl, 3-chlorophenyl, 4-chlorophenyl, 2-bromophenyl, 3-bromophenyl, 4-bromophenyl, 3,5-difluorophenyl, 2,5-difluorophenyl, 2,6-difluorophenyl, 2,4-difluorophenyl, 3,5-dibromophenyl, 2,5-dibromophenyl, 2,6-dichlorophenyl, 2,4-dichlorophenyl, 2,3,6-trifluorophenyl, 2,3,4-trifluorophenyl, 3,4,5-trifluorophenyl, 2,4,6-trifluorophenyl, 2,3,6-tribromophenyl, 2,3,4-tribromophenyl, 3,4,5-tribromophenyl, 2,3,6-trichlorophenyl, 2,4,6-trichlorophenyl, 1-fluoro-2-naphthyl, 2-fluoro-1-naphthyl, 3-fluoro-1-naphthyl, 1-chloro-2-naphthyl, 2-chloro-1-naphthyl, 3-bromo-1-naphthyl, 3,8-difluoro-1-naphthyl, 2,3-difluoro-1-naphthyl, 4,8-difluoro-1-naphthyl, 5,6-difluoro-1-naphthyl, 3,8-dichloro-1-naphthyl, 2,3-dichloro-1-naphthyl, 4,8-dibromo-1-naphthyl, 5,6-dibromo-1-naphthyl, 2,3,6-trifluoro-1-naphthyl, 2,3,4-trifluoro-1-naphthyl, 3,4,5-trifluoro-1-naphthyl, 4,5,6-trifluoro-1-naphthyl, 2,4,8-trifluoro-1-naphthyl, 2-aminophenyl, 3-aminophenyl, 4-aminophenyl, 3,5-diaminophenyl, 2,5-diaminophenyl, 2,6-diaminophenyl, 2,4-diaminophenyl, 2,3,6-triaminophenyl, 2,3,4-triaminophenyl, 3,4,5-triaminophenyl, 2,4,6-triaminophenyl, 1-amino-2-naphthyl, 2-amino-1-naphthyl, 3-amino-1-naphthyl, 3,8-diamino-1-naphthyl, 2,3-diamino-1-naphthyl, 4,8-diamino-1-naphthyl, 5,6-diamino-1-naphthyl, 2,3,6-triamino-1-naphthyl, 2,3,4-triamino-1-naphthyl, 3,4,5-triamino-1-naphthyl, 4,5,6-triamino-1-naphthyl, 2,4,8-triamino-1-naphthyl, 2-methylaminophenyl, 3-methylaminophenyl, 4-methylaminophenyl, 2-ethylaminophenyl, 3-ethylaminophenyl, 4-ethylaminophenyl, 2-propylaminophenyl, 3-propylaminophenyl, 4-propylaminophenyl, 2-dimethylaminophenyl, 3-dimethylaminophenyl, 4-dimethylaminophenyl, 2-diethylaminophenyl, 3-diethylaminophenyl, 4-diethylaminophenyl, 3,5-bis(methylamino)phenyl, 2,5-bis(methylamino)phenyl, 2,6-bis(methylamino)phenyl, 2,4-bis(methylamino)phenyl, 3,5-bis(dimethylamino)phenyl, 2,5-bis(dimethylamino)phenyl, 2,6-bis(methylamino)phenyl, 2,4-bis(dimethylamino)phenyl, 1-methylamino-2-naphthyl, 2-methylamino-1-naphthyl, 3-methylamino-1-naphthyl, 1-dimethylamino-2-naphthyl, 2-dimethylamino-1-naphthyl, 3-dimethylamino-1-naphthyl, 2-cyanophenyl, 3-cyanophenyl, 4-cyanophenyl, 3,5-dicyanophenyl, 2,5-dicyanophenyl, 2,6-dicyanophenyl, 2,4-dicyanophenyl, 2,3,6-tricyanophenyl, 2,3,4-tricyanophenyl, 3,4,5-tricyanophenyl, 2,4,6-tricyanophenyl, 1-cyano-2-naphthyl, 2-cyano-1-naphthyl, 3-cyano-1-naphthyl, 3,8-dicyano-1-naphthyl, 2,3-dicyano-1-naphthyl, 4,8-dicyano-1-naphthyl, 5,6-dicyano-1-naphthyl, 2,3,6-tricyano-1-naphthyl, 2,3,4-tricyano-1-naphthyl, 3,4,5-tricyano-1-naphthyl, 4,5,6-tricyano-1-naphthyl, 2,4,8-tricyano-1-naphthyl, 2-nitrophenyl, 3-nitrophenyl, 4-nitrophenyl, 3,5-dinitrophenyl, 2,5-dinitrophenyl, 2,6-dinitrophenyl, 2,4-dinitrophenyl, 2,3,6-trinitrophenyl, 2,3,4-trinitrophenyl, 3,4,5-trinitrophenyl, 2,4,6-trinitrophenyl, 1-nitro-2-naphthyl, 2-nitro-1-naphthyl, 3-nitro-1-naphthyl, 3,8-dinitro-1-naphthyl, 2,3-dinitro-1-naphthyl, 4,8-dinitro-1-naphthyl, 5,6-dinitro-1-naphthyl, 2,3,6-trinitro-1-naphthyl, 2,3,4-trinitro-1-naphthyl, 3,4,5-trinitro-1-naphthyl, 4,5,6-trinitro-1-naphthyl, 2,4,8-trinitro-1-naphthyl, 2-trifluoromethylphenyl, 3-trifluoromethylphenyl, 4-trifluoromethylphenyl, 2-trichloromethylphenyl, 3-dichloromethylphenyl, 4-trichloromethylphenyl, 2-tribromomethylphenyl, 3-dibromomethylphenyl, 4-dibromomethylphenyl, 3,5-bis(trifluoromethyl)phenyl, 2,5-bis(trifluoromethyl)phenyl, 2,6-bis(trifluoromethyl)phenyl, 2,4-bis(trifluoromethyl)phenyl, 3,5-bis(tribromomethyl)phenyl, 2,5-bis(dibromomethyl)phenyl, 2,6-bis(dichloromethyl)phenyl, 2,4-bis(dichloromethyl)phenyl, 2,3,6-tris(trifluoromethyl)phenyl, 2,3,4-tris(trifluoromethyl)phenyl, 3,4,5-tris(trifluoromethyl)phenyl, 2,4,6-tris(trifluoromethyl)phenyl, 2,3,6-tris(tribromomethyl)phenyl, 2,3,4-tris(dibromomethyl)phenyl, 3,4,5-tris(tribromomethyl)phenyl, 2,3,6- tris(dichloromethyl)phenyl, 2,4,6-tris(dichloromethyl)phenyl, 1-trifluoromethyl-2-naphthyl, 2-trifluoromethyl-1-naphthyl, 3-trifluoromethyl-1-naphthyl, 1-trichloromethyl-2-naphthyl, 2-dichloromethyl-1-naphthyl, 3-tribromomethyl-1-naphthyl, 3,8-bis(trifluoromethyl)-1-naphthyl, 2,3-bis(trifluoromethyl)-1-naphthyl, 4,8-bis(trifluoromethyl)-1-naphthyl, 5,6-bis(trifluoromethyl)-1-naphthyl, 3,8-bis(trichloromethyl)-1-naphthyl, 2,3-bis(dichloromethyl)-1-naphthyl, 4,8-bis(dibromomethyl)-1-naphthyl, 5,6-bis(tribromomethyl)-1-naphthyl, 2,3,6-tris(trifluoromethyl)-1-naphthyl, 2,3,4-tris(trifluoromethyl)-1-naphthyl, 3,4,5-tris(trifluoromethyl)-1-naphthyl, 4,5,6-tris(trifluoromethyl)-1-naphthyl, 2,4,8-tris-(trifluoromethyl)-1-naphthyl, 2-acetylphenyl, 3-acetylphenyl, 4-acetylphenyl, 3,5-diacetylphenyl, 2,5-diacetylphenyl, 2,6-diacetylphenyl, 2,4-diacetylphenyl, 2,3,6-tripropionylphenyl, 2,3,4-tripropionylphenyl, 3,4,5-tripropionylphenyl, 2,3,6-tributyrylphenyl, 2,4,6-tributyrylphenyl, 1-acetyl-2-naphthyl, 2-acetyl-1-naphthyl, 3-acetyl-1-naphthyl, 3,8-diacetyl-1-naphthyl, 2,3-dipropionyl-1-naphthyl, 4,8-dibutyryl-1-naphthyl, 5,6-dibutyryl-1-naphthyl, 2,3,6-triacetyl-1-naphthyl, 2,3,4-triacetyl-1-naphthyl, 3,4,5-tripropionyl-1-naphthyl, 4,5,6-tributyryl-1-naphthyl and 2,4,8-tributyryl-1-naphthyl groups. Of these, we prefer groups containing at least one substituent selected from the group consisting of alkyl groups having from 1 to 6 carbon atoms, halogen atoms, haloalkyl groups having from 1 to 6 carbon atoms, more preferably aryl groups substituted by at least one alkyl group having from 1 to 6 carbon atoms, for example the 2-ethylpheny, 3-ethylphenyl, 4-ethylphenyl, 2-t-butylphenyl, 3-t-butylphenyl, 4-t-butylphenyl, 2,6-diisopropylphenyl, 2-allylphenyl, 2-methoxyphenyl, 2-cyanophenyl, 3-trifluoromethylphenyl, 2-chlorophenyl, 3-chlorophenyl, 4-chlorophenyl, 2-fluorophenyl, 3-fluorophenyl, 4-fluorophenyl, 2-iodophenyl, 3-iodophenyl, 4-iodophenyl, 2,3-dichlorophenyl, 2,4-dichlorophenyl, 2,5-dichlorophenyl, 2,6-dichlorophenyl, 3,4-dichlorophenyl, 3,5-dichlorophenyl, 2,3-difluorophenyl, 2,4-difluorophenhl, 2,5-difluorophenyl, 2,6-difluorophenyl, 3,4-difluorophenyl, 3,5-difluorophenyl, 2,3-dibromophenyl, 2,4-dibromophenyl, 2,5-dibromophenyl, 2,6-dibromophenyl, 3,4-dibromophenyl, 3,5-dibromophenyl, 2,6-diiodophenyl, 4-nitrophenyl, 2-methylphenyl, 3-methylphenyl, 4-methylphenyl, 2,3-dimethylphenyl, 2,4-dimethylphenyl, 2,5-dimethylphenyl, 2,6-dimethylphenyl, 3,4-dimethylphenyl, 3,5-dimethylphenyl, 2,4,6-trimethylphenyl, 2-isopropylphenyl, 3-isopropylphenyl, 4-isopropylphenyl, 3-diaminomethylphenyl and 2-methyl-1-naphthyl groups.

When $R^5$ represents an aralkyl group, in which the alkyl part has from 1 to 6, preferably 1 to 4 carbon atoms and most preferably 1 or 2 carbon atoms, and the or each aryl part is a carbocylic aromatic group having from 6 to 14 carbon atoms, which may be substituted or unsubstituted and, if substituted, has at least one of substituents α as defined above and exemplified below; there may be 1, 2 or 3 such aryl substituents on the alkyl group; such aralkyl groups include the benzyl, naphthylmethyl, indenylmethyl, phenanthrenylmethyl, anthracenylmethyl, diphenylmethyl (i.e. benzhydryl), triphenylmethyl (i.e. trityl), 1-phenethyl, 2-phenethyl, 1-naphthylethyl, 2-naphthylethyl, 1-phenylpropyl, 2-phenylpropyl, 3-phenylpropyl, 1-naphthylpropyl, 2-naphthylpropyl, 3-naphthylpropyl, 1-phenylbutyl, 2-phenylbutyl, 3-phenylbutyl, 4-phenylbutyl, 1-naphthylbutyl, 2-naphthylbutyl, 3-naphthylbutyl, 4-naphthylbutyl,1-phenylpentyl, 2-phenylpentyl, 3-phenylpentyl, 4-phenylpentyl, 5-phenylpentyl, 1-naphthylpentyl, 2-naphthylpentyl, 3-naphthylpentyl, 4-naphthylpentyl, 5-naphthylpentyl, 1-phenylhexyl, 2-phenylhexyl, 3-phenylhexyl, 4-phenylhexyl, 5-phenylhexyl, 6-phenylhexyl, 1-naphthylhexyl, 2-naphthylhexyl, 3-naphthylhexyl, 4-naphthylhexyl, 5-naphthylhexyl, 6-naphthylhexyl, 4-methylbenzyl, 2,4,6-trimethylbenzyl, 2-trifluoromethylbenzyl, 3-dichloromethylbenzyl, 3,4,5-trimethylbenzyl, 4-methoxybenzyl, 4-methoxyphenyldiphenylmethyl, 2-nitrobenzyl, 4-nitrobenzyl, 3-nitrobenzyl, 4-chlorobenzyl, 4-bromobenzyl, 4-cyanobenzyl, 4-cyanophenyldiphenylmethyl and bis(o-nitrophenyl)methyl groups. Benzyl is the most preferred unsubstituted aralkyl group. The most preferred substituents on the aralkyl group are the alkyl groups having from 1 to 6 carbon atoms, halogen atoms and haloalkyl groups having from 1 to 6 carbon atoms, most preferably halogen atoms and haloalkyl groups having from 1 to 6 carbon atoms, for example the 4-fluorobenzyl and 4-trifluoromethylbenzyl groups.

When W represents an alkylene group having from 1 to 6 carbon atoms, this is preferably a methylene group or a linear alkylene group having from 2 to 6 carbon atoms, preferably a methylene group or a linear alkylene group having from 2 to 4 carbon atoms and most preferably such an alkylene group having 1 or 2 carbon atoms, this includes the methylene, ethylene, trimethylene, tetramethylene, pentamethylene and hexamethylene groups. We most prefer that W is a methylene group.

When W represents an alkylene group having from 1 to 6 carbon atoms, this is preferably a linear alkylene group, preferably having from 1 to 4 carbon atoms substituted by at least one substituent selected from the group consisting of subsituents β, defined above and exemplified below, this includes: linear alkylene groups substituted by alkyl groups having from 1 to 6 carbon atoms, such as the methylmethylene, ethylmethylene, propylmethylene, isopropylmethylene, butylmethylene, isobutylmethylene, t-butylmethylene, dimethylmethylene, diethylmethylene, dipropylmethylene, diisopropylmethylene, dibutylmethylene, diisobutylmethylene, di-t-butylmethylene, 1-methyl-1-ethylmethylene, 1-methyl-1-propylmethylene, 1-methyl-1-butylmethylene, propylene, 1-ethylethylene, 1-propylethylene, 1-isopropylethylene, 1-butylethylene, 1-isobutylethylene, 1-t-butylethylene, 1,1-dimethylethylene, 1,1-diethylethylene, 1,1-dipropylethylene, 1,1-diisopropylethylene, 1,2-dibutylethylene, 1,1-diisobutylethylene, 1,2-di-t-butylethylene, 1-ethyl-1-methylethylene, 1-methyl-1-propylethylene, 1-butyl-1-methylethylene, 1-methyl-2-ethylethylene, 1-methyl-2-propylethylene, 1-methyl-2-butylethylene, 1-methyltrimethylene, 1-ethyltrimethylene, 1-propyltrimethylene, 1-isopropyltrimethylene, 1-butyltrimethylene, 1-isobutyltrimethylene, 1-t-butyltrimethylene, 1-methyltetramethylene, 1-ethyltetramethylene, 1-propyltetramethylene, 1-isopropyltetramethylene, 1-butyltetramethylene, 1-isobutyltetramethylene, and 1-t-butyltetramethylene groups; linear alkylene groups substituted by alkenyl groups having from 2 to 6 carbon atoms, such as the vinylmethylene, 1-propenylmethylene, divinylmethylene, di-(1-propenyl)methylene, 1-vinylethylene, 1-(1-propenyl)ethylene, 1-vinyltrimethylene, 1-(1-propenyl)trimethylene, 1-vinyltetramethylene and 1-(1-propenyl)tetramethylene groups; linear alkylene groups substituted by alkynyl gropus having from 2 to 6 carbon atoms, such as the ethynylmethylene, 1-propynylmethylene, diethynylmethylene, di(1-propynyl)methylene, 1-ethynylethylene, 1-(1-propynyl)ethylene, 1-ethynyltrimethylene, 1-(1-propynyl)trimethylene, 1-ethynyltetramethylene and 1-(1-propynyl)tetramethylene groups; linear alkylene groups substituted by alkoxy groups having from 1 to 6 carbon atoms, such as the methoxymethylene, ethoxymethylene, propoxymethylene, isopropoxymethylene, butoxymethylene, isobutoxymethylene t-butoxymethylene, dimethoxymethylene, diethoxymethylene, dipropoxymethylene, diisopropoxymethylene, dibutoxymethylene, diisobutoxymethylene, di-t-butoxymethylene, 1-methoxy-1-ethoxymethylene, 1-methoxy-1-propoxymethylene, 1-methoxy-1-butoxymethylene, 1-methoxyethylene, 1-ethoxyethylene, 1-propoxyethylene, 1-isopropoxyethylene, 1-butoxyethylene, 1-isobutoxyethylene 1-t-butoxyethylene, 1,1-dimethoxyethylene, 1,1-diethoxyethylene, 1,1-dipropoxyethylene, 1,1-diisopropoxyethylene, 1,2-dibutoxyethylene, 1,1-diisobutoxyethylene, 1,2-di-t-butoxyethylene, 1-ethoxy-1-methoxyethylene, 1-methoxy-1-propoxyethylene, 1-butoxy-1-methoxyethylene, 1-methoxy-2-ethoxyethylene, 1-methoxy-2-propoxyethylene, 1-methoxy-2-butoxyethylene, 1-methoxytrimethylene, 1-ethoxytrimethylene, 1-propoxytrimethylene, 1-isopropoxytrimethylene, 1-butoxytrimethylene, 1-isobutoxytrimethylene, 1-t-butoxytrimethylene, 1-methoxytetramethylene, 1-ethoxytetramethylene, 1-propoxytetramethylene, 1-isopropoxytetramethylene, 1-butoxytetramethylene, 1-isobutoxytetramethylene and 1-t-butoxytetramethylene groups; linear alkylene groups substituted by alkyl groups having from 1 to 6 carbon atoms and by alkoxy groups having from 1 to 6 carbon atoms, such as the 1-methoxy-1-ethylmethylene, 1-methoxy-1-methylmethylene and 1-ethoxy-1-ethylmethylene groups; linear alkylene groups substituted by alkoxyalkyl groups, in which each of the alkoxy and alkyl parts has from 1 to 6 carbon atoms, such as the methoxymethylmethylene, ethoxymethylmethylene, propoxymethylmethylene, isopropoxyethylmethylene, butoxymethylmethylene, isobutoxymethylmethylene, t-butoxymethylmethylene, di(methoxymethyl)methylene, di(ethoxymethyl)methylene, di(propoxymethyl)methylene, di(isopropoxymethyl)methylene, di(butoxymethyl)methylene, di(isobutoxymethyl)methylene, di-(t-butoxymethyl)methylene, 1-(methoxymethyl)-1-(ethoxymethyl)methylene, 1-(methoxymethyl)-1-(propoxymethyl)methylene, 1-(methoxyethyl)-1-(butoxymethyl)methylene, 1-(methoxymethyl)ethylene, 1-(ethoxymethyl)ethylene, 1-(propoxymethyl)ethylene, 1-(isopropoxymethyl)ethylene, 1-(butoxymethyl)ethylene, 1-(isobutoxymethyl)ethylene, 1-(t-butoxymethyl)ethylene, 1,1-di(methoxymethyl)ethylene, 1,1-di(ethoxymethyl)ethylene, 1,1-di(propoxymethyl)ethylene, 1,1-di(isopropoxymethyl)ethylene, 1,2-di(butoxymethyl)ethylene, 1,1-di(isobutoxymethyl)ethylene, 1,2-(di-t-butoxymethyl)ethylene, 1-(methoxymethyl)-1-(ethoxymethyl)ethylene, 1-(methoxymethyl)-1-(propoxymethyl)ethylene, 1-(methoxymethyl)-1-(butoxymethyl)ethylene, 1-(methoxyethyl)-2-(ethoxymethyl)ethylene, 1-(methoxypropyl)-2-(propoxymethyl)ethylene, 1-(methoxyethyl)-2-(butoxymethyl)ethylene, 1-(methoxymethyl)trimethylene, 1-(ethoxyethyl)trimethylene, 1-(propoxymethyl)trimethylene, 1-isopropoxymethyltrimethylene, 1-butoxymethyltrimethylene, 1-isobutoxymethyltrimethylene, 1-t-butoxymethyltrimethylene, 1-methoxymethyltetramethylene, 1-ethoxymethyltetramethylene, 1-propoxymethyltetramethylene, 1-isopropoxyethyltetramethylene, 1-butoxymethyltetramethylene, 1-isobutoxymethyltetramethylene and 1-t-butoxymethyltetramethylene groups; linear alkylene groups substituted by aryl groups having from 6 to 14 ring carbon atoms, in which the aryl group is unsubstituted or substituted by at least one substituent, preferably from 1 to 4 substituents, which substituents may be the same or different, selected from the group consisting of substituents α, defined above and exemplified below, such as phenylmethylene, 1-naphthylmethylene, 2-methylphenylmethylene, 3-methylphenylmethylene, 4-methylphenylmethylene, 2-ethylphenylmethylene, 3-propylphenylmethylene, 4-ethylphenylmethylene, 2-butylphenylmethylene, 3-pentylphenylmethylene, 4-pentylphenylmethylene, 3,5-dimethylphenylmethylene, 2,5-dimethylphenylmethylene, 2,6-dimethylphenylmethylene, 2,4-dimethylphenylmethylene, 3,5-dibutylphenylmethylene, 2,5-dipentylphenylmethylene, 2,6-dipropylmethylphenylmethylene, 2,4-dipropylphenylmethylene, 2,3,6-trimethylphenylmethylene, 2,3,4-trimethylphenylmethylene, 3,4,5-trimethylphenylmethylene, 2,4,6-trimethylphenylmethylene, 2,3,6-tributylphenylmethylene, 2,3,4-tripentylphenylmethylene, 3,4,5-tributylphenylmethylene, 2,3,6-tripropylmethylphenylmethylene, 2,4,6-tripropylphenylmethylene, 1-methyl-2-naphthylmethylene, 2-methyl-1-naphthylmethylene, 3-methyl-1-naphthylmethylene, 1-ethyl-2-naphthylmethylene, 2-propyl-1-naphthylmethylene, 3-butyl-1-naphthylmethylene, 2-fluorophenylmethylene, 3-fluorophenylmethylene, 4-fluorophenylmethylene, 2-chlorophenylmethylene, 3-chlorophenylmethylene, 4-chlorophenylmethylene, 2-bromophenylmethylene, 3-bromophenylmethylene, 4-bromophenylmethylene, 3,5-difluorophenylmethylene, 2,5-difluorophenylmethylene, 2,6-difluorophenylmethylene, 2,4-difluorophenylmethylene, 3,5-dibromophenylmethylene, 2,5-dibromophenylmethylene, 2,6-dichlorophenylmethylene, 2,4-dichlorophenylmethylene, 2,3,6-trifluorophenylmethylene, 2,3,4-trifluorophenylmethylene, 3,4,5-trifluorophenylmethylene, 2,4,6-trifluorophenylmethylene, 2,3,6-tribromophenylmethylene, 2,3,4-tribromophenylmethylene, 3,4,5-tribromophenylmethylene, 2,3,6-trichlorophenylmethylene, 2,4,6-trichlorophenylmethylene, 1-fluoro-2-naphthylmethylene, 2-fluoro-1-naphthylmethylene, 3-fluoro-1-naphthylmethylene, 1-chloro-2-naphthylmethylene, 2-chloro-1-naphthylmethylene, 3-bromo-1-naphthylmethylene, 3,8-difluoro-1-naphthylmethylene, 2,3-difluoro-1-naphthylmethylene, 4,8-difluoro-1-naphthylmethylene, 5,6-difluoro-1-naphthylmethylene, 3,8-dichloro-1-naphthylmethylene, 2,3-dichloro-1-naphthylmethylene, 4,8-dibromo-1-naphthylmethylene, 5,6-dibromo-1-naphthylmethylene, 2-trifluoromethylphenylmethylene, 3-trifluoromethylphenylmethylene, 4-trifluoromethylphenylmethylene, 2-trichloromethylphenylmethylene, 3-dichloromethylphenylmethylene, 4-trichloromethylphenylmethylene, 2-tribromomethylphenylmethylene, 3-dibromomethylphenylmethylene, 4-dibromomethylphenylmethylene, 3,5-bis(trifluoromethyl)phenylmethylene, 2,5-bis(trifluoromethyl)phenylmethylene, 2,6-bis(trifluoromethyl)phenylmethylene, 2,4-bis(trifluoromethyl)phenylmethylene, 3,5-bis(tribromomethyl)phenylmethylene, 2,5-bis(dibromomethyl)phenylmethylene, 2,6-bis(dichloromethyl)phenylmethylene, 2,4-bis(dichloromethyl)phenylmethylene, 2,3,6-tris(trifluoromethyl)phenylmethylene, 2,3,4-tris(trifluoromethyl)phenylmethylene, 3,4,5-tris(trifluoromethyl)phenylmethylene, 2,4,6-tris(trifluoromethyl)phenylmethylene, 2,3,6-tris(trifluoromethyl)phenylmethylene, 2,3,4-tris(tribromomethyl)phenylmethylene, 3,4,5-tris(dibromomethyl)phenylmethylene, 2,3,6-tris(tribromomethyl)phenylmethylene, 2,4,6-tris(dichloromethyl)phenylmethylene and tris(dichloromethyl)phenylmethylene groups; and linear alkylene groups substituted by halogenated alkyl groups having from 1 to 6 carbon atoms, such as the trifluoromethylmethylene, trichloromethylmethylene, difluoromethylmethylene, dichloromethylmethylene, tribromomethylmethylene, bis(trifluoromethyl)methylene, bis(trichloromethyl)methylene, bis(difluoromethyl)methylene, bis(dichloromethyl)methylene, bis(tribromomethyl)methylene, 1-trifluoromethyl-1-trichloromethylmethylene, 1-trifluoromethyl-1-dichloromethylmethylene, 1-trifluoromethyldimethylene, 1-trichloromethylethylene, 1-difluoromethylethylene, 1-dichloromethylethylene, 1-tribromomethylethylene, 1,1-bis(trifluoromethyl)ethylene, 1,1-bis(trichloromethyl)ethylene, 1,1-bis(difluoromethyl)ethylene, 1,1-bis(dichloromethyl)ethylene, 1,2-bis(tribromomethyl)ethylene, 1-trifluoromethyl-1-tribromomethylethylene, 1-trifluoromethyl-2-trichloromethylethylene, 1-trifluoromethyltrimethylene, 1-trichloromethyltrimethylene, 1-difluoromethyltrimethylene, 1-dichloromethyltrimethylene, 1-tribromomethyltrimethylene, 1-trifluoromethyltetramethylene, 1-trichloromethyltetramethylene, 1-difluoromethyltetramethylene, 1-dichloromethyltetramethylene and 1-tribromomethyltetramethylene groups. Of these, we prefer the linear alkylene groups substituted by an alkyl group having from 1 to 6 carbon atoms or an alkylene group substituted by an aryl group having from 5 to 14 carbon atoms, more preferably linear alkylene groups substituted by alkyl groups having from 1 to 6 carbon atoms.

The term "carboxy-protecting group", as used in the definition of $R^4$, signifies a protecting group capable of being cleaved by chemical methods (such as hydrogenolysis, hydrolysis, electrolysis or photolysis) to generate a free carboxy group, or a protecting group capable of being cleaved in vivo by biological methods such as hydrolysis.

Examples of carboxy-protecting groups which can be cleaved by chemical means include ester and other groups, such as:

alkyl groups having from 1 to 20 carbon atoms, more preferably from 1 to 6 carbon atoms, such as those exemplified above in relation to $R^5$ etc., and higher alkyl groups such as are well known in the art, for example the heptyl, octyl, nonyl, decyl, dodecyl, tridecyl, pentadecyl, octadecyl, nonadecyl, and icosyl groups, but most preferably the methyl, ethyl and t-butyl groups;

halogenated alkyl groups having from 1 to 6, preferably from 1 to 4, carbon atom, in which the alkyl part is as defined and exemplified in relation to the alkyl groups above, and the halogen atom is chlorine, fluorine, bromine or iodine, such as the 2,2,2-trichloroethyl, 2-haloethyl (e.g. 2-chloroethyl, 2-fluoroethyl, 2-bromoethyl or 2-iodoethyl), 2,2-dibromoethyl and 2,2,2-tribromoethyl groups;

cycloalkyl groups having from 3 to 7 carbon atoms, for example the cyclopropyl, cyclobutyl, cyclopentyl, cyclohexyl and cycloheptyl groups;

aralkyl groups, in which the alkyl part has from 1 to 3 carbon atoms and the or each aryl part is a carbocyclic aromatic group having from 6 to 14 carbon atoms, which may be substituted or unsubstituted and, if substituted, has at least one of substituents α defined above and exemplified below; there may be 1, 2 or 3 such aryl substituents on the alkyl group; examples of such aralkyl groups include the benzyl, phenethyl, 1-phenylethyl, 3-phenyl-propyl, 2-phenylpropyl, α-naphthylmethyl, β-naphthylmethyl, 2-(α-naphthyl)ethyl, 2-(2-naphthyl)ethyl, benzhydryl (i.e. diphenylmethyl), triphenylmethyl (i.e. trityl), α-naphthyldiphenyl-methyl, 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 3-nitrobenzyl, 4-chlorobenzyl, 4-bromobenzyl, 4-cyanobenzyl, 4-cyanophenyldiphenylmethyl, bis(o-nitrophenyl)methyl, 9-anthrylmethyl and piperonyl groups;

alkenyl groups having from 2 to 6 carbon atoms, such as the vinyl, allyl, 2-methylallyl, 1-propenyl, isopropenyl, 1-butenyl, 2-butenyl, 3-butenyl, 1-pentenyl, 2-pentenyl, 3-pentenyl, 4-pentenyl, 1-hexenyl, 2-hexenyl, 3-hexenyl, 4-hexenyl and 5-hexenyl groups, of which the vinyl, allyl, 2-methylallyl, 1-propenyl, isopropenyl and butenyl groups are preferred, the allyl and 2-methylallyl groups being most preferred.

substituted silylalkyl groups, in which the alkyl part is as defined and exemplified above, and the silyl group has up to 3 substituents selected from alkyl groups having from 1 to 6 carbon atoms and phenyl groups which are unsubstituted or have at least one substituent selected from substituents α, defined above and exemplified below, for example a 2-trimethylsilylethyl group;

aryl groups having from 6 to 14 carbon atoms and optionally substituted by one or more of substituents α, defined above and exemplified below, for example the phenyl, α-naphthyl, β-naphthyl, indanyl and anthrenyl groups, preferably the phenyl or indanyl group and more preferably the phenyl group; any of these aryl groups my be unsubstituted or substituted, and, if substituted, preferably have at least one alkyl group having from 1 to 4 carbon atoms or acylamino group; examples of the substituted groups include the tolyl and benzamidophenyl groups;

phenacyl groups, which may be unsubstituted or have at least one of substituents α defined above and exemplified below, for example the phenacyl group itself or the p-bromophenacyl group; and cyclic and acyclic terpenyl groups, for example the geranyl, neryl, linalyl, phytyl, menthyl (especially m- and p-menthyl), thujyl, caryl, pinanyl, bornyl, norcaryl, norpinanyl, norbornyl, menthenyl, camphenyl and norbornenyl groups.

Examples of carboxy-protecting groups which are capable of being cleaved in vivo by biological methods such as hydrolysis include ester and other groups, such as:

alkoxyalkyl groups, in which the alkoxy and alkyl parts each have from 1 to 5, preferably from 1 to 4, carbon atoms, especially alkoxymethyl groups, and such groups which have at least one, preferably from 1 to 5, more preferably from 1 to 3, and most preferably 1, substituents, preferably: lower alkoxymethyl groups and other alkoxyalkyl groups (such as the methoxymethyl, ethoxymethyl, propoxymethyl, isopropoxymethyl, butoxymethyl and t-butoxymethyl groups); lower alkoxy-substituted lower alkoxymethyl groups (such as the 2-methoxyethoxymethyl group); halogenated lower alkoxymethyl groups [such as the 2,2,2-trichloroethoxymethyl and bis(2-chloroethoxy)methyl groups] and lower alkoxy-substituted ethyl and higher alkyl groups (such as the 1-ethoxyethyl, 1-methyl-1-methoxyethyl and 1-isopropoxyethyl groups);

other substituted ethyl groups, preferably: halogenated ethyl groups (such as the 2,2,2-trichloroethyl group); and arylselenyl-substituted ethyl groups, in which the aryl part is as defined above, preferably a phenyl group [such as the 2-(phenylselenyl)ethyl group];

aliphatic acyloxyalkyl groups, in which the acyl group is preferably an alkanoyl group (which my be unsubstituted or may have at least one substituent selected from the group consisting of amino groups, alkylamino groups and dialkylamino groups), and more preferably an alkanoyl group having from 2 to 6 carbon atoms, and the alkyl part has from 1 to 6, and preferably from 1 to 4, carbon atoms such as the acetoxymethyl, dimethylaminoacetoxymethyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl and 1-butyryloxyethyl groups;

alkoxycarbonyloxyalkyl groups, especially 1-(alkoxycarbonyloxy)ethyl groups, in which the alkoxy part has from 1 to 10, preferably from 1 to 6, and more preferably from 1 to 4, carbon atoms, and the alkyl part has from 1 to 6, preferably from 1 to 4, carbon atoms, such as the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl and 1-(1,1-dipropylbutoxycarbonyloxy)ethyl groups, and other alkoxycarbonylalkyl groups, in which both the alkoxy and alkyl groups have from 1 to 6, preferably from 1 to 4, carbon atoms, such as the 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl and ethoxycarbonyloxymethyl groups;

cycloalkylcarbonyloxyalkyl and cycloalkyloxycarbonyloxyalkyl groups, in which the cycloalkyl group has from 3 to 10, preferably from 3 to 7, carbon atoms, is mono- or poly-cyclic and is optionally substituted by at least one (and preferably only one) alkyl group having from 1 to 4 carbon atoms (e.g. selected from those alkyl groups exemplified above) and the alkyl part has from 1 to 6, more preferably from 1 to 4, carbon atoms (e.g. selected from those alkyl groups exemplified above) and is most preferably methyl, ethyl or propyl, for example the cyclohexyloxycarbonyloxymethyl, 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyloxy)propyl, 2-(1-methylcyclohexylcarbonyloxy)propyl, 1-(cyclohexylcarbonyloxy)propyl, 2-(cyclohexylcarbonyloxy)propyl, 2-methyl-1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl, 1-adamantylcarbonyloxyethyl and cyclohexyloxycarbonyloxy(cyclohexyl)methyl groups;

cycloalkyl-substituted aliphatic acyloxyalkyl groups, in which the acyl group is preferably an alkanoyl group and is more preferably an alkanoyl group having from 2 to 6 carbon atoms, the cycloalkyl substituent has from 3 to 7 carbon atoms, and the alkyl part has from 1 to 6, preferably from 1 to 4, carbon atoms, such as the (cyclohexylacetoxy)methyl, 1-(cyclohexylacetoxy)ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl and 2-methyl-1-(cyclopentylacetoxy)propyl, groups;

cycloalkylalkoxycarbonyloxyalkyl groups in which the alkoxy group has a single cycloalkyl substituent, the cycloalkyl substituent having from 3 to 10, preferably from 3 to 7, carbon atoms and mono- or poly-cyclic, for example the cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxyalkyl and terpenyloxycarbonyloxyalkyl groups, in which the terpenyl group is as exemplified above, and is preferably a cyclic terpenyl group, for example the 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl and 3-pinanylcarbonyloxymethyl groups;

5-alkyl or 5-phenyl [which may be substituted by at least one of substituents α, defined above and exemplified below] (2-oxo-1,3-dioxolen-4-yl)alkyl groups in which each alkyl group (which may be the same or different) has from 1 to 6, preferably from 1 to 4, carbon atoms, for example the (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl and 1-(5-methyl-2-oxo-1,3-dioxolen-4-yl)ethyl groups; and the phthalidyl group, which may be unsubstituted or may be substituted by at least one substituent selected from the group consisting of substituents α, defined above and exemplified below, preferably an alkyl or alkoxy group, for example the phthalidyl, dimethylphthalidyl and dimethoxyphthalidyl groups;

any one of the alkyl groups exemplified above;

carboxyalkyl groups having from 2 to 7 carbon atoms, such as the carboxymethyl group; and amide-forming residues of an amino acid, such as phenylalanine.

Examples of substituents α, referred to above, include:

alkyl groups, alkenyl groups and alkynyl groups as exemplified above with respect to $R^5$;

straight or branched chain alkoxy groups having from 1 to 6 carbon atoms, preferably from 1 to 4 carbon atoms, such as the methoxy, ethoxy, propoxy, isopropoxy, butoxy, isobutoxy, sec-butoxy, t-butoxy, penfoxy, isopentoxy, 2-methylbutoxy, neopentoxy, hexyloxy, 4methylpentoxy, 3-methylpentoxy, 2-methylpentoxy, 3,3-dimethylbutoxy, 2,2-dimethylbutoxy, 1,1-dimethylbutoxy, 1,2-dimethylbutoxy, 1,3-dimethylbutoxy and 2,3-dimethylbutoxy groups;

halogen atoms, such as the fluorine, chlorine, bromine or iodine atoms, preferably a fluorine, chlorine or bromine atom;

alkylenedioxy groups having from 1 to 4 carbon atoms, such as the methylenedioxy group;

acylamino groups, including acylamino groups corresponding to the aliphatic and aromatic acyl groups exemplified hereafter in relation to the hydroxy-protecting groups, preferably an acetamido or benzamido group;

alkoxycarbonyl groups having from 2 to 7, preferably from 2 to 5, carbon atoms, such as the methoxycarbonyl, ethoxycarbonyl, propoxycarbonyl, isopropoxycarbonyl, butoxycarbonyl, isobutoxycarbonyl and t-butoxycarbonyl groups; and alkylamino or dialkylamino groups in which the, or each, alkyl part has from 1 to 6 carbon atoms, such as the methylamino, ethylamino, dimethylamino, butylamino, diethylamino and propylamino groups;

alkoxyamino groups in which the alkoxy part has from 1 to 6 carbon atoms, such as the methoxyamino, ethoxyamino, butoxyamino and hexyloxyamino groups;

alkoxyalkoxyamino groups, in which each of the alkoxy parts has from 1 to 6 carbon atoms, such as the 2-methoxyethoxyamino, 3-methoxypropoxyamino and 2-ethoxybutoxyamino groups;

haloalkoxyamino groups, in which the alkoxy part has from 1 to 6 carbon atoms, such as the 2,2,2-trichloroethoxyamino and 3,3-dibromomethoxyamino groups;

aralkyloxyamino groups in which the aralkyl part is substituted or unsubstituted and substantially as defined above with reference to $R^5$, such as the benzyloxyamino, phenethyloxyamino, 3-phenylpropoxyamino, 1-naphthylmethoxyamino, 2-naphthylmethoxyamino, diphenylmethoxyamino, triphenylmethoxyamino, 1-naphthyldiphenylmethoxyamino, 9-anthrylmethoxyamino, 4-methylbenzyloxyamino, 2,4,6-trimethylbenzyloxyamino, 3,4,5-trimethylbenzyloxyamino, 4-methoxybenzyloxyamino, 4-methoxyphenyldiphenylmethoxyamino, 2-nitrobenzyloxyamino, 4-nitrobenzyloxyamino, 4-chlorobenzyloxyamino, 4-bromobenzyloxyamino, 4-cyanobenzyloxyamino, 4-cyanobenzyl-diphenylmethoxyamino, bis(2-nitrophenyl)methoxyamino and piperonyloxyamino groups;

hydroxyamino groups, cyano groups, nitro groups, carboxy groups and amino groups;

hydroxyalkylamino groups, in which the alkyl part has from 1 to 6 carbon atoms, such as the hydroxymethylamino, 2-hydroxyethylamino and 3-hydroxypropylamino groups;

aminoalkylamino groups, in which the alkyl part has from 1 to 6 carbon atoms, such as the 2-aminoethylamino and 3-aminopropylamino groups;

arylamino groups, in which the aryl part has from 6 to 14 carbon atoms and is substantially as defined and exemplified above with respect to $R^5$;

halogenated alkyl groups, in which the alkyl part has from 1 to 6 carbon atoms, such as the trifluoromethyl, trichloromethyl, difluoromethyl, dichloromethyl, dibromomethyl, fluoromethyl, 2,2,2-trichloroethyl, 2,2,2-trifluoroethyl, 2-bromoethyl, 2-chloroethyl, 2-fluoroethyl and 2,2-dibromoethyl groups, preferably a fluorinated alkyl group, more preferably the trifluoromethyl group; and aryl groups, such as those exemplified above, save that any such aryl group which is included in substituents α is not further substituted by an aryl group.

aliphatic acyl groups, preferably: alkanoyl groups having from 1 to 25 carbon atoms, more preferably from 1 to 20 carbon atoms, still more preferably from 1 to 6 carbon atoms, and most preferably from 1 to 4 carbon atoms, (such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups); halogenated alkanoyl groups having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part has from 1 to 6, preferably from 1 to 3, carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups] and;

aromatic acyl groups, preferably arylcarbonyl groups, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, selected from the group consisting of substituents α, defined and exemplified above, for example: unsubstituted groups (such as the benzoyl, α-naphthoyl and β-naphthoyl groups); halogenated arylcarbonyl groups (such as the 2-bromobenzoyl and 4-chlorobenzoyl groups); lower alkyl-substituted arylcarbonyl groups, in which the or each alkyl substituent has from 1 to 6, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 6, more preferably from 1 to 4, carbon atoms (such as the 4-anisoyl group); carboxy-substituted arylcarbonyl groups (such as the 2-carboxybenzoyl, 3-carboxybenzoyl and 4-carboxybenzoyl groups); nitro-substituted arylcarbonyl groups (such as the 4-nitrobenzoyl and 2-nitrobenzoyl groups); lower alkoxycarbonyl-substituted arylcarbonyl groups, in which the or each alkoxycarbonyl substituent preferably has from 2 to 6 carbon atoms [such as the 2-(methoxycarbonyl)benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group);

Where substituent β is an alkyl, alkenyl, alkynyl, alkoxy or halogenated alkyl group, this may be as exemplified above with respect to substituents α.

When substituent β is an alkoxyalkyl group, this may be an alkoxyalkyl group as exemplified above with respect to the carboxy-protecting groups.

When substituent β is an unsubstituted or substituted aryl group or a fused polycyclic hydrocarbon group, this may be an aryl group as exemplified above with respect to $R^5$.

In order to determine whether a protecting group is capable of being cleaved by biological means, a compound containing such a group, or a pharmaceutically acceptable salt thereof is administered by intravenous injection to a test animal, such as a rat or mouse, and the metabolic products subsequently recovered from the body fluids of the animal used are examined to determine whether the group has been cleaved. Of the protecting groups described above, those capable of being cleaved in vivo by biological methods such as hydrolysis are preferred. It will, of course, be appreciated that at least some of these groups which are capable of being cleaved in vivo by biological methods may also be cleaved by chemical means.

The term "hydroxy-protecting group", as used in the definitions of $R^3$, $R^{3a}$ and $R^{3b}$, signifies a protecting group capable of being cleaved by chemical methods (such as hydrogenolysis, hydrolysis, electrolysis or photolysis) to generate a free hydroxy group, or a protecting group capable of being cleaved vivo by biological methods such as hydrolysis.

Examples of hydroxy-protecting groups which may be cleaved by chemical means include:

aliphatic acyl groups, preferably: alkanoyl groups having from 1 to 25 carbon atoms, more preferably from 1 to 20 carbon atoms, still more preferably from 1 to 6 carbon atoms, and most preferably from 1 to 4 carbon atoms, (such as the formyl, acetyl, propionyl, butyryl, isobutyryl, pivaloyl, valeryl, isovaleryl, hexanoyl, heptanoyl, octanoyl, lauroyl, myristoyl, tridecanoyl, palmitoyl and stearoyl groups, of which the acetyl group is most preferred); halogenated alkanoyl groups having from 2 to 6 carbon atoms, especially halogenated acetyl groups (such as the chloroacetyl, dichloroacetyl, trichloroacetyl and trifluoroacetyl groups); lower alkoxyalkanoyl groups in which the alkoxy part has from 1 to 6, preferably from 1 to 3, carbon atoms and the alkanoyl part has from 2 to 6 carbon atoms and is preferably an acetyl group (such as the methoxyacetyl group); and unsaturated analogs of such groups, especially alkenoyl or alkynoyl groups having from 3 to 6 carbon atoms [such as the acryloyl, methacryloyl, propioloyl, crotonoyl, isocrotonoyl and (E)-2-methyl-2-butenoyl groups];

aromatic acyl groups, preferably arylcarbonyl groups, in which the aryl part has from 6 to 14, more preferably from 6 to 10, still more preferably 6 or 10, and most preferably 6, ring carbon atoms and is a carbocyclic group, which is unsubstituted or has from 1 to 5, preferably from 1 to 3 substituents, selected from the group consisting of substituents α, defined and exemplified above, for example: unsubstituted groups (such as the benzoyl, α-naphthoyl and β-naphthoyl groups); halogenated arylcarbonyl groups (such as the 2-bromobenzoyl and 4-chlorobenzoyl groups); lower alkyl-substituted arylcarbonyl groups, in which the or each alkyl substituent has from 1 to 6, preferably from 1 to 4, carbon atoms (such as the 2,4,6-trimethylbenzoyl and 4-toluoyl groups); lower alkoxy-substituted arylcarbonyl groups, in which the or each alkoxy substituent preferably has from 1 to 6, more preferably from 1 to 4, carbon atoms (such as the 4-anisoyl group); carboxy-substituted arylcarbonyl groups (such as the 2-carboxybenzoyl, 3-carboxybenzoyl and 4-carboxybenzoyl groups); nitro-substituted arylcarbonyl groups (such as the 4-nitrobenzoyl and 2-nitrobenzoyl groups); lower alkoxycarbonyl-substituted arylcarbonyl groups, in which the or each alkoxycarbonyl substituent preferably has from 2 to 6 carbon atoms [such as the 2-(methoxycarbonyl)benzoyl group]; and aryl-substituted arylcarbonyl groups, in which the aryl substituent is as defined above, except that, if it is substituted by a further aryl group, that aryl group is not itself substituted by an aryl group (such as the 4-phenylbenzoyl group);

heterocyclic groups having 5 or 6 ring atoms, of which 1 or 2 are hetero-atoms selected from the group consisting of oxygen, sulfur and nitrogen atoms, preferably oxygen or sulfur atoms, which groups may be unsubstituted or may have at least one substituent selected from the group consisting of substituents α and oxygen atoms, preferably halogen atoms and alkoxy groups; examples include: the tetrahydropyranyl groups, which may be substituted or unsubstituted, such as the tetrahydropyran-2-yl, 3-bromotetrahydropyran-2-yl and 4-methoxytetrahydropyran-4-yl groups; tetrahydrothiopyranyl groups, which may be substituted or unsubstituted, such as the tetrahydrothiopyran-2-yl and 4-methoxytetrahydrothiopyran-4-yl groups; tetrahydrofuranyl groups and tetrahydrothienyl groups, which may be substituted or unsubstituted, such as the tetrahydrofuran-2-yl group and tetrahydrothien-2-yl group;

tri-substituted silyl groups, in which all three or two or one of the substituents are alkyl groups having from 1 to 5, preferably from 1 to 4, carbon atoms, and none, one or two of the substituents are aryl groups, as defined above, but preferably phenyl or substituted phenyl groups, preferably: tri(lower alkyl)silyl groups, such as the trimethylsilyl, triethylsilyl, isopropyldimethylsilyl, t-butyldimethylsilyl, methyldiisopropylsilyl, methyldi-t-butylsilyl and triisopropylsilyl groups; and tri(lower alkyl)silyl groups in which one or two of the alkyl groups have been replaced by aryl groups, such as the diphenylmethylsilyl, diphenylbutylsilyl, diphenyl-t-butylsilyl, diphenylisopropylsilyl and phenyldiisopropylsilyl groups;

alkoxyalkyl groups, in which the alkoxy and alkyl parts each have from 1 to 6, preferably from 1 to 4, carbon atoms, especially alkoxymethyl groups, and such groups which have at least one, preferably from 1 to 5, more preferably from 1 to 3, and most preferably 1, substituents, preferably: lower alkoxymethyl groups and other alkoxyalkyl groups (such as the methoxymethyl, ethoxymethyl, propoxymethyl, isopropoxymethyl, butoxymethyl and t-butoxymethyl groups); lower alkoxy-substituted lower alkoxymethyl groups (such as the 2-methoxyethoxymethyl group); halogenated lower alkoxymethyl groups [such as the 2,2,2-trichloroethoxymethyl and bis(2-chloroethoxy)methyl groups] and lower alkoxy-substituted ethyl groups (such as the 1-ethoxyethyl, 1-methyl-1-methoxyethyl and 1-isopropoxyethyl groups);

other substituted ethyl groups, preferably: halogenated ethyl groups (such as the 2,2,2-trichloroethyl group); and arylselenyl-substituted ethyl groups, in which the aryl part is as defined above [such as the 2-(phenylselenyl)ethyl group];

aralkyl groups, preferably alkyl groups having from 1 to 4, more preferably from 1 to 3 and most preferably 1 or 2, carbon atoms which are substituted with from 1 to 3 aryl groups, as defined and exemplified above, which may be unsubstituted (such as the benzyl, phenethyl, 1-phenylethyl, 3-phenylpropyl, α-naphthylmethyl, β-naphthylmethyl, diphenylmethyl, triphenylmethyl, α-naphthyldiphenylmethyl and 9-anthrylmethyl groups) or substituted on the aryl part with a lower alkyl group, a lower alkoxy group, a nitro group, a halogen atom, a cyano group, or an alkylenedioxy group having from 1 to 3 carbon atoms, preferably a methylenedioxy group, such as the 4-methylbenzyl, 2,4,6-trimethylbenzyl, 3,4,5-trimethylbenzyl, 4-methoxybenzyl, 4-methoxyphenyldiphenylmethyl, 2-nitrobenzyl, 4-nitrobenzyl, 4-chlorobenzoyl, 4-bromobenzyl, 4-cyanobenzyl, 4-cyanobenzyldiphenylmethyl, bis(2-nitrophenyl)methyl and piperonyl groups;

alkoxycarbonyl groups, especially such groups having from 2 to 7, more preferably 2 to 5, carbon atoms and which may be unsubstituted (such as the methoxycarbonyl, ethoxycarbonyl, t-butoxycarbonyl and isobutoxycarbonyl groups) or substituted with a halogen atom or a tri-substituted silyl group, e.g. a tri(lower alkylsilyl) group (such as the 2,2,2-trichloroethoxycarbonyl and 2-trimethylsilylethoxycarbonyl groups);

alkenyloxycarbonyl groups in which the alkenyl part has from 2 to 6, preferably from 2 to 4, carbon atoms (such as the vinyloxycarbonyl and allyloxycarbonyl groups);

sulfo groups; and aralkyloxycarbonyl groups, in which the aralkyl part is as defined and exemplified above, and in which the aryl ring, if substituted, is substituted by at least one substituent selected from the group consisting of substituents α, defined and exemplified above, one or two lower alkoxy or nitro substituents, such as the benzyloxycarbonyl, 4-methoxybenzyloxycarbonyl, 3,4-dimethoxybenzyloxycarbonyl, 2-nitrobenzyloxycarbonyl and 4-nitrobenzyloxycarbonyl groups.

Examples of hydroxy-protecting groups which are capable of being cleaved in vivo by biological methods such as hydrolysis include:

acyloxyalkyl groups, in which the alkyl part has from 1 to 6 carbon atoms, such as the acetoxymethyl, dimethylaminoacetoxymethyl, propionyloxymethyl, butyryloxymethyl, pivaloyloxymethyl and 1-acetoxyethyl groups;

1-(alkoxycarbonyloxy)alkyl groups, in which each of the alkoxy and alkyl parts has from 1 to 6 carbon atoms, such as the methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxymethyl, cyclohexyloxycarbonyloxymethyl, cyclohexyloxycarbonyloxycyclohexylmethyl, 1-methoxycarbonyloxyethyl, 1-ethoxycarbonyloxyethyl, 1-propoxycarbonyloxyethyl, 1-isopropoxycarbonyloxyethyl, 1-butoxycarbonyloxyethyl, 1-isobutoxycarbonyloxyethyl, 1-t-butoxycarbonyloxyethyl, 1-cyclohexyloxycarbonyloxyethyl and 1-ethoxycarbonyloxypropyl groups;

carbonyloxyalkyl groups, including oxodioxolenylmethyl groups, such as the 4-methyl-oxodioxolenylmethyl, 4-phenyl-oxodioxolenylmethyl and oxodioxolenylmethyl groups;

dioxolenylalkyl groups, aliphatic acyl groups and aromatic acyl groups, such as those exemplified above in relation to the carboxy-protecting groups;

the residue which forms a salt of a half-ester of a dicarboxylic acid, such as succinic acid;

the residue which forms a salt of a phosphate;

the residue of an ester of an amino acid; and carbonyloxyalkyloxycarbonyl groups, such as the pivaloyloxymethoxycarbonyl group.

Where $R^1$ represents a group of formula (II), the two groups represented by $R^{3a}$ and $R^{3b}$ may together form one of the following bidentate protecting groups:

a lower alkylidene group having from 1 to 4 carbon atoms, such as the methylidene, ethylidene or isopropylidene group;

an aralkylidene group, in which the aryl part may be as defined above and the alkylidene part has from 1 to 4 carbon atoms, such as the benzylidene group;

an alkoxyethylidene group, in which the alkoxy part has from 1 to 6, preferably from 1 to 4 carbon atoms, such as the methoxyethylidene or ethoxyethylidene group;

the oxomethylene group; and the thioxomethylene group.

Whether or not the protecting groups described above are capable of removal by cleaving by biological methods can be determined in the same way as described above in relation to the carboxy-protecting groups.

Of these hydroxy-protecting groups, we prefer the silyl group and protecting groups capable of being cleaved in vivo by biological methods.

Of these hydroxy-protecting groups, we prefer the silyl group and protecting groups capable of being cleaved in viva by biological methods.

Where $R^3$, $R^3$a or $R^{3b}$ represents an alkyl group, this may be any of the alkyl groups exemplified above in relation to $R^5$ etc.

Where $R^3$, $R^{3a}$ or $R^{3b}$ represents an alkanesulfonyloxy group, this may be a straight or branched chain group having from 1 to 6 carbon atoms, for example the methanesulfonyloxy, ethanesulfonyloxy and propanesulfonyloxy groups.

Where $R^3$, $R^{3a}$ or $R^{3b}$ represents a halogenated alkanesulfonyloxy group, this may be any of the unsubstituted alkanesulfonyloxy groups listed above and is preferably a fluorinated alkanesulfonyloxy group, such as the trifluoromethanesulfonyloxy or pentafluoroethanesulfonyloxy group.

Where $R^3$, $R^{3a}$ or $R^{3b}$ represents an arylsulfonyloxy group, the aryl part may be as defined and exemplified above, and examples of such groups include the benzenesulfonyloxy and p-toluenesulfonyloxy groups.

Of these groups, we prefer the alkyl groups.

Those compounds of the present invention which contain a free carboxy group, for example those where $R^1$ represents a group of formula (II) and $R^4$ represents a hydrogen atom, can form salts. Examples of such salts include: salts with an alkali metal, such as sodium, potassium or lithium; salts with an alkaline earth metal, such as barium or calcium; salts with another metal, such as magnesium, aluminum, iron, zinc, copper, nickel or cobalt; ammonium salts; organic base salts, prticularly salts with organic amines, such as a salt with triethylamine, diisopropylamine, cyclohexylamine, t-octylamine, dibenzylamine, morpholine, glucosamine, phenylglycine alkyl esters, ethylenediamine, N-methylglucamine, guanidine, diethylamine, triethylamine, dicyclohexylamine, N,N'-dibenzylethylenediamine, chloroprocaine, procaine, diethanolamine, N-benzylphenethylamine, piperazine, tetramethylammonium or tris(hydroxymethyl)aminomethane; and salts with a basic amino acid, such as histidine, α,γ-diaminobutyric acid, lysine, arginine, ornithine, glutamic acid or aspartic acid.

Also, where the compound of the present invention contains a basic group in its molecule, it can form acid addition salts. Examples of such acid addition salts include: salts with mineral acids, especially hydrohalic acids (such as hydrofluoric acid, hydrobromic acid, hydroiodic acid or hydrochloric acid), nitric acid, carbonic acid, sulfuric acid or phosphoric acid; salts with lower alkylsulfonic acids, such as methanesulfonic acid, trifluoromethanesulfonic acid or ethanesulfonic acid; salts with arylsulfonic acids, such as benzenesulfonic acid or p-toluenesulfonic acid; salts with organic carboxylic acids, such as acetic acid, fumaric acid, tartaric acid, oxalic acid, maleic acid, malic acid, succinic acid, benzoic acid, mandelic acid, ascorbic acid, lactic acid, gluconic acid or citric acid; and salts with amino acids, such as glutamic acid or aspartic acid.

The compounds of the present invention may contain one or more asymmetric carbon atoms in their molecules, and, in such a case, can thus form optical isomers. Although these are all represented herein by a single molecular formula, the present invention includes both the individual, isolated isomers and mixtures, including racemates thereof. Where stereospecific synthesis techniques are employed or optically active compounds are employed as starting materials, individual isomers may be prepared directly; on the other hand, if a mixture of isomers is prepared, the individual isomers may be obtained by conventional resolution techniques.

Preferred classes of compounds of the present invention are those compounds of formulae (I), (Ia) and (Ib) and pharmaceutically acceptable salts and esters thereof in which:

(A) $R^1$ represents a group of the formula (II);

(B) $R^1$ represents a group of the formula (II) and $R^4$ represents a hydrogen atom;

(C) pharmaceutically acceptable salts of the compounds in which $R^1$ represents a group of the formula (II) and $R^4$ represents a hydrogen atom;

(D) $R^3$, $R^{3a}$ and $R^{3b}$ may be the same or different and each represents a hydrogen atom or a hydroxy protecting group;

(E) $R^3$, $R^{3a}$ and $R^{3b}$ may be the same or different and each represents a hydrogen atom or a protecting group capable of being cleaved in vivo by biological methods;

(F) $R^3$, $R^{3a}$ and $R^{3b}$ represent hydrogen atoms;

(G) $R^4$ represents a hydrogen atom or a protecting group capable of being cleaved in vivo by biological methods;

(H) $R^4$ represents a hydrogen atom;

(I) $R^5$ represents a alkyl group having from 1 to 6 carbon atoms, an alkenyl group having from 2 to 6 carbon atoms, an alkynyl group having from 2 to 6 carbon atoms, an aryl group having from 6 to 14 ring carbon atoms, or an aryl group having from 6 to 14 ring carbon atoms and substituted by a substituent selected from the group consisting of substituents α, defined and exemplified above;

(J) $R^5$ represents an aryl group or an aryl group substituted by a substituent selected from the group consisting of substituents α, defined and exemplified above;

(K) $R^5$ represents an aryl group substituted by a substituent selected from the group consisting of substituents α, defined and exemplified above;

(L) $R^5$ represents a phenyl group substituted by a substituent selected from the group consisting of substituents α, defined and exemplified above;

(M) $R^5$ represents an aryl group substituted by a substituent selected from the group consisting of substituents α', below;

(N) $R^5$ represents a phenyl group substituted by a substituent selected from the group consisting of substituents α', below;

(O) W represents a linear alkylene group having from 1 to 4 carbon atoms or a linear alkylene group having from 1 to 4 carbon atoms substituted by a substituent selected from the group consisting of substituents β, defined and exemplified above;

(P) W represents a linear alkylene group having 1 or 2 carbon atoms or a linear alkylene group having 1 or 2 carbon atoms substituted by a substituent selected from the group consisting of substituents β, defined and exemplified above;

(Q) w represents a methylene group or a methylene group substituted by a substituent selected from the group consisting of substituents β, defined and exemplified above; and (R) W represents a methylene group substituted by a lower alkyl group.

substituents α':
alkyl groups having from 1 to 6 carbon atoms, alkenyl gruops having from 2 to 6 carbon atoms, alkynyl groups having from 2 to 6 carbon atoms and halogen atoms.

Specific exmples of individual compounds of the present invention are given by he following formulae (I-1), (I-1a), (I-2) and (I-2a), in which the various symbols used are as defined in the corresponding one of Tables 1 and 2, that is Table 1 relates to formulae (I-1) and (I-1a) and Table 2 relates to formulae (I-2) and (I-2a). In the Tables, the following abbreviations are used for certain groups:

| | |
|---|---|
| Ac | acetyl |
| All | allyl |
| Bu | butyl |
| tBu | t-butyl |
| Bz | benzyl |
| Cum | cumenyl |
| Et | ethyl |
| Hx | hexyl |
| Me | methyl |
| Mes | mesityl |
| Np | naphthyl |
| Ph | phenyl |
| Pn | pentyl |
| Pr | propyl |
| iPr | isopropyl |
| Tol | tolyl |
| Xy | xylyl |

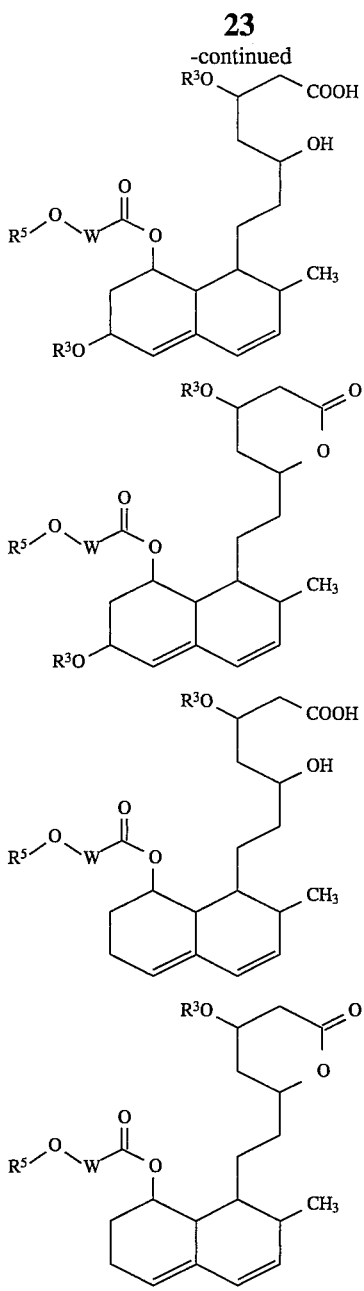

TABLE 1

| Compound No. | R⁵ | W |
|---|---|---|
| 1-1 | Ph | -MeCH- |
| 1-2 | Bz | -MeCH- |
| 1-3 | 1-Np | -MeCH- |
| 1-4 | 2-Np | -MeCH- |
| 1-5 | 2-Tol | -MeCH- |
| 1-6 | 3-Tol | -MeCH- |
| 1-7 | 4-Tol | -MeCH- |
| 1-8 | 2-EtPh | -MeCH- |
| 1-9 | 3-EtPh | -MeCH- |
| 1-10 | 4-EtPh | -MeCH- |
| 1-11 | 2,3-Xy | -MeCH- |
| 1-12 | 2,4-Xy | -MeCH- |
| 1-13 | 2,5-Xy | -MeCH- |
| 1-14 | 2,6-Xy | -MeCH- |
| 1-15 | 3,4-Xy | -MeCH- |
| 1-16 | 3,5-Xy | -MeCH- |
| 1-17 | Mes | -MeCH- |
| 1-18 | 2-Cum | -MeCH- |

TABLE 1-continued

| Compound No. | R⁵ | W |
|---|---|---|
| 1-19 | 3-Cum | -MeCH- |
| 1-20 | 4-Cum | -MeCH- |
| 1-21 | 2-tBuPh | -MeCH- |
| 1-22 | 3-tBuPh | -MeCH- |
| 1-23 | 4-tBuPh | -MeCH- |
| 1-24 | 2,6-diiPrPh | -MeCH- |
| 1-25 | 2-AllPh | -MeCH- |
| 1-26 | 2-MeOPh | -MeCH- |
| 1-27 | 2-CNPh | -MeCH- |
| 1-28 | 3-CF₃Ph | -MeCH- |
| 1-29 | 3-diMeNPh | -MeCH- |
| 1-30 | 2-ClPh | -MeCH- |
| 1-31 | 3-ClPh | -MeCH- |
| 1-32 | 4-ClPh | -MeCH- |
| 1-33 | 2-FPh | -MeCH- |
| 1-34 | 3-FPh | -MeCH- |
| 1-35 | 4-FPh | -MeCH- |
| 1-36 | 2-BrPh | -MeCH- |
| 1-37 | 3-BrPh | -MeCH- |
| 1-38 | 4-BrPh | -MeCH- |
| 1-39 | 2-IPh | -MeCH- |
| 1-40 | 3-IPh | -MeCH- |
| 1-41 | 4-IPh | -MeCH- |
| 1-42 | 2,3-diClPh | -MeCH- |
| 1-43 | 2,4-diClPh | -MeCH- |
| 1-44 | 2,5-diClPh | -MeCH- |
| 1-45 | 2,6-diClPh | -MeCH- |
| 1-46 | 3,4-diClPh | -MeCH- |
| 1-47 | 3,5-diClPh | -MeCH- |
| 1-48 | 2,3-diFPh | -MeCH- |
| 1-49 | 2,4-diFPh | -MeCH- |
| 1-50 | 2,5-diFPh | -MeCH- |
| 1-51 | 2,6-diFPh | -MeCH- |
| 1-52 | 3,4-diFPh | -MeCH- |
| 1-53 | 3,5-diFPh | -MeCH- |
| 1-54 | 2,3-diBrPh | -MeCH- |
| 1-55 | 2,4-diBrPh | -MeCH- |
| 1-56 | 2,5-diBrPh | -MeCH- |
| 1-57 | 2,6-diBrPh | -MeCH- |
| 1-58 | 3,4-diBrPh | -MeCH- |
| 1-59 | 3,5-diBrPh | -MeCH- |
| 1-60 | 2,6-diIPh | -MeCH- |
| 1-61 | 4-NO₂Ph | -MeCH- |
| 1-62 | Me | -MeCH- |
| 1-63 | Et | -MeCH- |
| 1-64 | 4-FBz | -MeCH- |
| 1-65 | Ph | -EtCH- |
| 1-66 | Bz | -EtCH- |
| 1-67 | 1-Np | -EtCH- |
| 1-68 | 2-Np | -EtCH- |
| 1-69 | 2-Tol | -EtCH- |
| 1-70 | 3-Tol | -EtCH- |
| 1-71 | 4-Tol | -EtCH- |
| 1-72 | 2-EtPh | -EtCH- |
| 1-73 | 3-EtPh | -EtCH- |
| 1-74 | 4-EtPh | -EtCH- |
| 1-75 | 2,3-Xy | -EtCH- |
| 1-76 | 2,4-Xy | -EtCH- |
| 1-77 | 2,5-Xy | -EtCH- |
| 1-78 | 2,6-Xy | -EtCH- |
| 1-79 | 3,4-Xy | -EtCH- |
| 1-80 | 3,5-Xy | -EtCH- |
| 1-81 | Mes | -EtCH- |
| 1-82 | 2-Cum | -EtCH- |
| 1-83 | 3-Cum | -EtCH- |
| 1-84 | 4-Cum | -EtCH- |
| 1-85 | 2-tBuPh | -EtCH- |
| 1-86 | 3-tBuPh | -EtCH- |
| 1-87 | 4-tBuPh | -EtCH- |
| 1-88 | 2,6-diiPrPh | -EtCH- |
| 1-89 | 2-AllPh | -EtCH- |
| 1-90 | 2-MeOPh | -EtCH- |
| 1-91 | 2-CNPh | -EtCH- |
| 1-92 | 3-CF₃Ph | -EtCH- |
| 1-93 | 3-diMeNPh | -EtCH- |
| 1-94 | 2-ClPh | -EtCH- |
| 1-95 | 3-ClPh | -EtCH- |

TABLE 1-continued

| Compound No. | R⁵ | W |
|---|---|---|
| 1-96 | 4-ClPh | -EtCH- |
| 1-97 | 2-FPh | -EtCH- |
| 1-98 | 3-FPh | -EtCH- |
| 1-99 | 4-FPh | -EtCH- |
| 1-100 | 2-BrPh | -EtCH- |
| 1-101 | 3-BrPh | -EtCH- |
| 1-102 | 4-BrPh | -EtCH- |
| 1-103 | 2-IPh | -EtCH- |
| 1-104 | 3-IPh | -EtCH- |
| 1-105 | 4-IPh | -EtCH- |
| 1-106 | 2,3-diClPh | -EtCH- |
| 1-107 | 2,4-diClPh | -EtCH- |
| 1-108 | 2,5-diClPh | -EtCH- |
| 1-109 | 2,6-diClPh | -EtCH- |
| 1-110 | 3,4-diClPh | -EtCH- |
| 1-111 | 3,5-diClPh | -EtCH- |
| 1-112 | 2,3-diFPh | -EtCH- |
| 1-113 | 2,4-diFPh | -EtCH- |
| 1-114 | 2,5-diFPh | -EtCH- |
| 1-115 | 2,6-diFPh | -EtCH- |
| 1-116 | 3,4-diFPh | -EtCH- |
| 1-117 | 3,5-diFPh | -EtCH- |
| 1-118 | 2,3-diBrPh | -EtCH- |
| 1-119 | 2,4-diBrPh | -EtCH- |
| 1-120 | 2,5-diBrPh | -EtCH- |
| 1-121 | 2,6-diBrPh | -EtCH- |
| 1-122 | 3,4-diBrPh | -EtCH- |
| 1-123 | 3,5-diBrPh | -EtCH- |
| 1-124 | 2,6-diIPh | -EtCH- |
| 1-125 | 4-NO₂Ph | -EtCH- |
| 1-126 | Me | -EtCH- |
| 1-127 | Et | -EtCH- |
| 1-128 | 4-FBz | -EtCH- |
| 1-129 | Ph | -PrCH- |
| 1-130 | Bz | -PrCH- |
| 1-131 | 1-Np | -PrCH- |
| 1-132 | 2-Np | -PrCH- |
| 1-133 | 2-Tol | -PrCH- |
| 1-134 | 3-Tol | -PrCH- |
| 1-135 | 4-Tol | -PrCH- |
| 1-136 | 2-EtPh | -PrCH- |
| 1-137 | 3-EtPh | -PrCH- |
| 1-138 | 4-EtPh | -PrCH- |
| 1-139 | 2,3-Xy | -PrCH- |
| 1-140 | 2,4-Xy | -PrCH- |
| 1-141 | 2,5-Xy | -PrCH- |
| 1-142 | 2,6-Xy | -PrCH- |
| 1-143 | 3,4-Xy | -PrCH- |
| 1-144 | 3,5-Xy | -PrCH- |
| 1-145 | Mes | -PrCH- |
| 1-146 | 2-Cum | -PrCH- |
| 1-147 | 3-Cum | -PrCH- |
| 1-148 | 4-Cum | -PrCH- |
| 1-149 | 2-tBuPh | -PrCH- |
| 1-150 | 3-tBuPh | -PrCH- |
| 1-151 | 4-tBuPh | -PrCH- |
| 1-152 | 2,6-diiPrPh | -PrCH- |
| 1-153 | 2-AllPh | -PrCH- |
| 1-154 | 2-MeOPh | -PrCH- |
| 1-155 | 2-CNPh | -PrCH- |
| 1-156 | 3-CF₃Ph | -PrCH- |
| 1-157 | 3-diMeNPh | -PrCH- |
| 1-158 | 2-ClPh | -PrCH- |
| 1-159 | 3-ClPh | -PrCH- |
| 1-160 | 4-ClPh | -PrCH- |
| 1-161 | 2-FPh | -PrCH- |
| 1-162 | 3-FPh | -PrCH- |
| 1-163 | 4-FPh | -PrCH- |
| 1-164 | 2-BrPh | -PrCH- |
| 1-165 | 3-BrPh | -PrCH- |
| 1-166 | 4-BrPh | -PrCH- |
| 1-167 | 2-IPh | -PrCH- |
| 1-168 | 3-IPh | -PrCH- |
| 1-169 | 4-IPh | -PrCH- |
| 1-170 | 2,3-diClPh | -PrCH- |
| 1-171 | 2,4-diClPh | -PrCH- |
| 1-172 | 2,5-diClPh | -PrCH- |
| 1-173 | 2,6-diClPh | -PrCH- |
| 1-174 | 3,4-diClPh | -PrCH- |
| 1-175 | 3,5-diClPh | -PrCH- |
| 1-176 | 2,3-diFPh | -PrCH- |
| 1-177 | 2,4-diFPh | -PrCH- |
| 1-178 | 2,5-diFPh | -PrCH- |
| 1-179 | 2,6-diFPh | -PrCH- |
| 1-180 | 3,4-diFPh | -PrCH- |
| 1-181 | 3,5-diFPh | -PrCH- |
| 1-182 | 2,3-diBrPh | -PrCH- |
| 1-183 | 2,4-diBrPh | -PrCH- |
| 1-184 | 2,5-diBrPh | -PrCH- |
| 1-185 | 2,6-diBrPh | -PrCH- |
| 1-186 | 3,4-diBrPh | -PrCH- |
| 1-187 | 3,5-diBrPh | -PrCH- |
| 1-188 | 2,6-diIPh | -PrCH- |
| 1-189 | 4-NO₂Ph | -PrCH- |
| 1-190 | Me | -PrCH- |
| 1-191 | Et | -PrCH- |
| 1-192 | 4-FBz | -PrCH- |
| 1-193 | Ph | -BuCH- |
| 1-194 | Bz | -BuCH- |
| 1-195 | 1-Np | -BuCH- |
| 1-196 | 2-Np | -BuCH- |
| 1-197 | 2-Tol | -BuCH- |
| 1-198 | 3-Tol | -BuCH- |
| 1-199 | 4-Tol | -BuCH- |
| 1-200 | 2-EtPh | -BuCH- |
| 1-201 | 3-EtPh | -BuCH- |
| 1-202 | 4-EtPh | -BuCH- |
| 1-203 | 2,3-Xy | -BuCH- |
| 1-204 | 2,4-Xy | -BuCH- |
| 1-205 | 2,5-Xy | -BuCH- |
| 1-206 | 2,6-Xy | -BuCH- |
| 1-207 | 3,4-Xy | -BuCH- |
| 1-208 | 3,5-Xy | -BuCH- |
| 1-209 | Ph | -diMeC- |
| 1-210 | Bz | -diMeC- |
| 1-211 | 1-Np | -diMeC- |
| 1-212 | 2-Np | -diMeC- |
| 1-213 | 2-Tol | -diMeC- |
| 1-214 | 3-Tol | -diMeC- |
| 1-215 | 4-Tal | -diMeC- |
| 1-216 | 2-EtPh | -diMeC- |
| 1-217 | 3-EtPh | -diMeC- |
| 1-218 | 4-EtPh | -diMeC- |
| 1-219 | 2,3-Xy | -diMeC- |
| 1-220 | 2,4-Xy | -diMeC- |
| 1-221 | 2,5-Xy | -diMeC- |
| 1-222 | 2,6-Xy | -diMeC- |
| 1-223 | 3,4-Xy | -diMeC- |
| 1-224 | 3,5-Xy | -diMeC- |
| 1-225 | Mes | -diMeC- |
| 1-226 | 2-Cum | -diMeC- |
| 1-227 | 3-Cum | -diMeC- |
| 1-228 | 4-Cum | -diMeC- |
| 1-229 | 2-tBuPh | -diMeC- |
| 1-230 | 3-tBuPh | -diMeC- |
| 1-231 | 4-tBuPh | -diMeC- |
| 1-232 | 2,6-diiPrPh | -diMeC- |
| 1-233 | 2-AllPh | -diMeC- |
| 1-234 | 2-MeOPh | -diMeC- |
| 1-235 | 2-CNPh | -diMeC- |
| 1-236 | 3-CF₃Ph | -diMeC- |
| 1-237 | 3-diMeNPh | -diMeC- |
| 1-238 | 2-ClPh | -diMeC- |
| 1-239 | 3-ClPh | -diMeC- |
| 1-240 | 4-ClPh | -diMeC- |
| 1-241 | 2-FPh | -diMeC- |
| 1-242 | 3-FPh | -diMeC- |
| 1-243 | 4-FPh | -diMeC- |
| 1-244 | 2-BrPh | -diMeC- |
| 1-245 | 3-BrPh | -diMeC- |
| 1-246 | 4-BrPh | -diMeC- |
| 1-247 | 2-IPh | -diMeC- |
| 1-248 | 3-IPh | -diMeC- |
| 1-249 | 4-IPh | -diMeC- |

TABLE 1-continued

| Compound No. | R⁵ | W |
|---|---|---|
| 1-250 | 2,3-diClPh | -diMeC— |
| 1-251 | 2,4-diClPh | -diMeC— |
| 1-252 | 2,5-diClPh | -diMeC— |
| 1-253 | 2,6-diClPh | -diMeC— |
| 1-254 | 3,4-diClPh | -diMeC— |
| 1-255 | 3,5-diClPh | -diMeC— |
| 1-256 | 2,3-diFPh | -diMeC— |
| 1-257 | 2,4-diFPh | -diMeC— |
| 1-258 | 2,5-diFPh | -diMeC— |
| 1-259 | 2,6-diFPh | -diMeC— |
| 1-260 | 3,4-diFPh | -diMeC— |
| 1-261 | 3,5-diFPh | -diMeC— |
| 1-262 | 2,3-diBrPh | -diMeC— |
| 1-263 | 2,4-diBrPh | -diMeC— |
| 1-264 | 2,5-diBrPh | -diMeC— |
| 1-265 | 2,6-diBrPh | -diMeC— |
| 1-266 | 3,4-diBrPh | -diMeC— |
| 1-267 | 3,5-diBrPh | -diMeC— |
| 1-268 | 2,6-diIPh | -diMeC— |
| 1-269 | 4-NO₂Ph | -diMeC— |
| 1-270 | Me | -diMeC— |
| 1-271 | Et | -diMeC— |
| 1-272 | 4-FBz | -diMeC— |
| 1-273 | Ph | -Me(Et)C— |
| 1-274 | Bz | -Me(Et)C— |
| 1-275 | 1-Np | -Me(Et)C— |
| 1-276 | 2-Np | -Me(Et)C— |
| 1-277 | 2-Tol | -Me(Et)C— |
| 1-278 | 3-Tol | -Me(Et)C— |
| 1-279 | 4-Tol | -Me(Et)C— |
| 1-280 | 2-EtPh | -Me(Et)C— |
| 1-281 | 3-EtPh | -Me(Et)C— |
| 1-282 | 4-EtPh | -Me(Et)C— |
| 1-283 | 2,3-Xy | -Me(Et)C— |
| 1-284 | 2,4-Xy | -Me(Et)C— |
| 1-285 | 2,5-Xy | -Me(Et)C— |
| 1-286 | 2,6-Xy | -Me(Et)C— |
| 1-287 | 3,4-Xy | -Me(Et)C— |
| 1-288 | 3,5-Xy | -Me(Et)C— |
| 1-289 | Mes | -Me(Et)C— |
| 1-290 | 2-Cum | -Me(Et)C— |
| 1-291 | 3-Cum | -Me(Et)C— |
| 1-292 | 4-Cum | -Me(Et)C— |
| 1-293 | 2-tBuPh | -Me(Et)C— |
| 1-294 | 3-tBuPh | -Me(Et)C— |
| 1-295 | 4-tBuPh | -Me(Et)C— |
| 1-296 | 2,6-diiPrPh | -Me(Et)C— |
| 1-297 | 2-AllPh | -Me(Et)C— |
| 1-298 | 2-MeOPh | -Me(Et)C— |
| 1-299 | 2-CNPh | -Me(Et)C— |
| 1-300 | 3-CF₃Ph | -Me(Et)C— |
| 1-301 | 3-diMeNPh | -Me(Et)C— |
| 1-302 | 2-ClPh | -Me(Et)C— |
| 1-303 | 3-ClPh | -Me(Et)C— |
| 1-304 | 4-ClPh | -Me(Et)C— |
| 1-305 | 2-FPh | -Me(Et)C— |
| 1-306 | 3-FPh | -Me(Et)C— |
| 1-307 | 4-FPh | -Me(Et)C— |
| 1-308 | 2-BrPh | -Me(Et)C— |
| 1-309 | 3-BrPh | -Me(Et)C— |
| 1-310 | 4-BrPh | -Me(Et)C— |
| 1-311 | 2-IPh | -Me(Et)C— |
| 1-312 | 3-IPh | -Me(Et)C— |
| 1-313 | 4-IPh | -Me(Et)C— |
| 1-314 | 2,3-diClPh | -Me(Et)C— |
| 1-315 | 2,4-diClPh | -Me(Et)C— |
| 1-316 | 2,5-diClPh | -Me(Et)C— |
| 1-317 | 2,6-diClPh | -Me(Et)C— |
| 1-318 | 3,4-diClPh | -Me(Et)C— |
| 1-319 | 3,5-diClPh | -Me(Et)C— |
| 1-320 | 2,3-diFPh | -Me(Et)C— |
| 1-321 | 2,4-diFPh | -Me(Et)C— |
| 1-322 | 2,5-diFPh | -Me(Et)C— |
| 1-323 | 2,6-diFPh | -Me(Et)C— |
| 1-324 | 3,4-diFPh | -Me(Et)C— |
| 1-325 | 3,5-diFPh | -Me(Et)C— |
| 1-326 | 2,3-diBrPh | -Me(Et)C— |
| 1-327 | 2,4-diBrPh | -Me(Et)C— |
| 1-328 | 2,5-diBrPh | -Me(Et)C— |
| 1-329 | 2,6-diBrPh | -Me(Et)C— |
| 1-330 | 3,4-diBrPh | -Me(Et)C— |
| 1-331 | 3,5-diBrPh | -Me(Et)C— |
| 1-332 | 2,6-diIPh | -Me(Et)C— |
| 1-333 | 4-NO₂Ph | -Me(Et)C— |
| 1-334 | Me | -Me(Et)C— |
| 1-335 | Et | -Me(Et)C— |
| 1-336 | 4-FBz | -Me(Et)C— |
| 1-337 | Ph | -Me(Pr)C— |
| 1-338 | Bz | -Me(Pr)C— |
| 1-339 | 1-Np | -Me(Pr)C— |
| 1-340 | 2-Np | -Me(Pr)C— |
| 1-341 | 2-Tol | -Me(Pr)C— |
| 1-342 | 3-Tol | -Me(Pr)C— |
| 1-343 | 4-Tol | -Me(Pr)C— |
| 1-344 | Ph | -Me(Bu)C— |
| 1-345 | Bz | -me(Bu)C— |
| 1-346 | 1-Np | -Me(Bu)C— |
| 1-347 | 2-Np | -Me(Bu)C— |
| 1-348 | 2-Tol | -Me(Bu)C— |
| 1-349 | 3-Tol | -Me(Bu)C— |
| 1-350 | 4-Tol | -Me(Bu)C— |
| 1-351 | Ph | -PHCH— |
| 1-352 | Bz | -PHCH— |
| 1-353 | 1-Np | -PHCH— |
| 1-354 | 2-Np | -PHCH— |
| 1-355 | 2-Tol | -PHCH— |
| 1-356 | 3-Tol | -PHCH— |
| 1-357 | 4-Tol | -PHCH— |
| 1-358 | Ph | -Me(Ph)C— |
| 1-359 | Bz | -me(Ph)C— |
| 1-360 | 1-Np | -Me(Ph)C— |
| 1-361 | 2-Np | -Me(Ph)C— |
| 1-362 | 2-Tol | -Me(Ph)C— |
| 1-363 | 3-Tol | -Me(Ph)C— |
| 1-364 | 2-AcPh | -EtCH— |
| 1-365 | 2-AcPh | -Me(Et)C— |
| 1-366 | Me | -diEtC— |
| 1-367 | Et | -diEtC— |
| 1-368 | Me | —CH₂ME(CH₂OMe)C— |
| 1-369 | 2-Me-1-Np | -EtCH— |
| 1-370 | Ph | -iPrCH— |
| 1-371 | 4-CF₃Bz | -diMeC— |
| 1-372 | Me | —CH₂diMeC— |
| 1-373 | 4-NO₂Ph | -diMeC— |
| 1-374 | Ph | -PnCH— |
| 1-375 | Bz | -PnCH— |
| 1-376 | 1-Np | -PnCH— |
| 1-377 | 2-Np | -PnCH— |
| 1-378 | 2-Tol | -PnCH— |
| 1-379 | 3-Tol | -PnCH— |
| 1-380 | 4-Tol | -PnCH— |
| 1-381 | 2-EtPh | -PnCH— |
| 1-382 | 3-EtPh | -PnCH— |
| 1-383 | 4-EtPh | -PnCH— |
| 1-384 | 2,3-Xy | -PnCH— |
| 1-385 | 2,4-Xy | -PnCH— |
| 1-386 | 2,5-Xy | -PnCH— |
| 1-387 | 2,6-Xy | -PnCH— |
| 1-388 | 3,4-Xy | -PnCH— |
| 1-389 | 3,5-Xy | -PnCH— |
| 1-390 | 2-ClPh | -PnCH— |
| 1-391 | 3-ClPh | -PnCH— |
| 1-392 | 4-ClPh | -PnCH— |
| 1-393 | 2-FPh | -PnCH— |
| 1-394 | 3-FPh | -PnCH— |
| 1-395 | 4-FPh | -PnCH— |
| 1-396 | 2,6-diClPh | -PnCH— |
| 1-397 | Ph | -HxCH— |
| 1-398 | Bz | -HxCH— |
| 1-399 | 1-Np | -HxCH— |
| 1-400 | 2-Np | -HxCH— |
| 1-401 | 2-Tol | -HxCH— |
| 1-402 | 3-Tol | -HxCH— |
| 1-403 | 4-Tol | -HxCH— |

TABLE 1-continued

| Compound No. | R⁵ | W |
|---|---|---|
| 1-404 | 2-EtPh | -HxCH- |
| 1-405 | 3-EtPh | -HxCH- |
| 1-406 | 4-EtPh | -HxCH- |
| 1-407 | 2,3-Xy | -HxCH- |
| 1-408 | 2,4-Xy | -HxCH- |
| 1-409 | 2,5-Xy | -HxCH- |
| 1-410 | 2,6-Xy | -HxCH- |
| 1-411 | 3,4-Xy | -HxCH- |
| 1-412 | 3,5-Xy | -HxCH- |
| 1-413 | 2-ClPh | -HxCH- |
| 1-414 | 3-ClPh | -HxCH- |
| 1-415 | 4-ClPh | -HxCH- |
| 1-416 | 2-FPh | -HxCH- |
| 1-417 | 3-FPh | -HxCH- |
| 1-418 | 4-FPh | -HxCH- |
| 1-419 | 2,6-diClPh | -HxCH- |
| 1-420 | Ph | -CH₂EtCH- |
| 1-421 | Bz | -CH₂EtCH- |
| 1-422 | 1-Np | -CH₂EtCH- |
| 1-423 | 2-Np | -CH₂EtCH- |
| 1-424 | 2-Tol | -CH₂EtCH- |
| 1-425 | 3-Tol | -CH₂EtCH- |
| 1-426 | 4-Tol | -CH₂EtCH- |
| 1-427 | 2-EtPh | -CH₂EtCH- |
| 1-428 | 3-EtPh | -CH₂EtCH- |
| 1-429 | 4-EtPh | -CH₂EtCH- |
| 1-430 | 2,3-Xy | -CH₂EtCH- |
| 1-431 | 2,4-Xy | -CH₂EtCH- |
| 1-432 | 2,5-Xy | -CH₂EtCH- |
| 1-433 | 2,6-Xy | -CH₂EtCH- |
| 1-434 | 3,4-Xy | -CH₂EtCH- |
| 1-435 | 3,5-Xy | -CH₂EtCH- |
| 1-436 | 2-ClPh | -CH₂EtCH- |
| 1-437 | 3-ClPh | -CH₂EtCH- |
| 1-438 | 4-ClPh | -CH₂EtCH- |
| 1-439 | 2-FPh | -CH₂EtCH- |
| 1-440 | 3-FPh | -CH₂EtCH- |
| 1-441 | 4-FPh | -CH₂EtCH- |
| 1-442 | 2,6-diClPh | -CH₂EtCH- |
| 1-443 | 2-BrPh | -CH₂EtCH- |
| 1-444 | 3-BrPh | -CH₂EtCH- |
| 1-445 | 4-BrPh | -CH₂EtCH- |

TABLE 2

| Compound No. | R⁵ | W |
|---|---|---|
| 2-1 | Ph | -MeCH- |
| 2-2 | Bz | -MeCH- |
| 2-3 | 1-Np | -MeCH- |
| 2-4 | 2-Np | -MeCH- |
| 2-5 | 2-Tol | -MeCH- |
| 2-6 | 3-Tol | -MeCH- |
| 2-7 | 4-Tol | -MeCH- |
| 2-8 | 2-EtPh | -MeCH- |
| 2-9 | 3-EtPh | -MeCH- |
| 2-10 | 4-EtPh | -MeCH- |
| 2-11 | 2,3-Xy | -MeCH- |
| 2-12 | 2,4-Xy | -MeCH- |
| 2-13 | 2,5-Xy | -MeCH- |
| 2-14 | 2,6-Xy | -MeCH- |
| 2-15 | 3,4-Xy | -MeCH- |
| 2-16 | 3,5-Xy | -MeCH- |
| 2-17 | Mes | -MeCH- |
| 2-18 | 2-Cum | -MeCH- |
| 2-19 | 3-Cum | -MeCH- |
| 2-20 | 4-Cum | -MeCH- |
| 2-21 | 2-ₜtBuPh | -MeCH- |
| 2-22 | 3-ₜtBuPh | -MeCH- |
| 2-23 | 4-ₜtBuPh | -MeCH- |
| 2-24 | 2,6-di_iPrPh | -MeCH- |
| 2-25 | 2-AllPh | -MeCH- |
| 2-26 | 2-MeOPh | -MeCH- |
| 2-27 | 2-CNPh | -MeCH- |
| 2-28 | 3-CF₃Ph | -MeCH- |

TABLE 2-continued

| Compound No. | R⁵ | W |
|---|---|---|
| 2-29 | 3-diMeNPh | -MeCH- |
| 2-30 | 2-ClPh | -MeCH- |
| 2-31 | 3-ClPh | -MeCH- |
| 2-32 | 4-ClPh | -MeCH- |
| 2-33 | 2-FPh | -MeCH- |
| 2-34 | 3-FPh | -MeCH- |
| 2-35 | 4-FPh | -MeCH- |
| 2-36 | 2-BrPh | -MeCH- |
| 2-37 | 3-BrPh | -MeCH- |
| 2-38 | 4-BrPh | -MeCH- |
| 2-39 | 2-IPh | -MeCH- |
| 2-40 | 3-IPh | -MeCH- |
| 2-41 | 4-IPh | -MeCH- |
| 2-42 | 2,3-diClPh | -MeCH- |
| 2-43 | 2,4-diClPh | -MeCH- |
| 2-44 | 2,5-diClPh | -MeCH- |
| 2-45 | 2,6-diClPh | -MeCH- |
| 2-46 | 3,4-diClPh | -MeCH- |
| 2-47 | 3,5-diClPh | -MeCH- |
| 2-48 | 2,3-diFPh | -MeCH- |
| 2-49 | 2,4-diFPh | -MeCH- |
| 2-50 | 2,5-diFPh | -MeCH- |
| 2-51 | 2,6-diFPh | -MeCH- |
| 2-52 | 3,4-diFPh | -MeCH- |
| 2-53 | 3,5-diFPh | -MeCH- |
| 2-54 | 2,3-diBrPh | -MeCH- |
| 2-55 | 2,4-diBrPh | -MeCH- |
| 2-56 | 2,5-diBrPh | -MeCH- |
| 2-57 | 2,6-diBrPh | -MeCH- |
| 2-58 | 3,4-diBrPh | -MeCH- |
| 2-59 | 3,5-diBrPh | -MeCH- |
| 2-60 | 2,6-diIPh | -MeCH- |
| 2-61 | 4-NO₂Ph | -MeCH- |
| 2-62 | Me | -MeCH- |
| 2-63 | Et | -MeCH- |
| 2-64 | 4-FBz | -MeCH- |
| 2-65 | Ph | -EtCH- |
| 2-66 | Bz | -EtCH- |
| 2-67 | 1-Np | -EtCH- |
| 2-68 | 2-Np | -EtCH- |
| 2-69 | 2-Tol | -EtCH- |
| 2-70 | 3-Tol | -EtCH- |
| 2-71 | 4-Tol | -EtCH- |
| 2-72 | 2-EtPh | -EtCH- |
| 2-73 | 3-EtPh | -EtCH- |
| 2-74 | 4-EtPh | -EtCH- |
| 2-75 | 2,3-Xy | -EtCH- |
| 2-76 | 2,4-Xy | -EtCH- |
| 2-77 | 2,5-Xy | -EtCH- |
| 2-78 | 2,6-Xy | -EtCH- |
| 2-79 | 3,4-Xy | -EtCH- |
| 2-80 | 3,5-Xy | -EtCH- |
| 2-81 | Mes | -EtCH- |
| 2-82 | 2-Cum | -EtCH- |
| 2-83 | 3-Cum | -EtCH- |
| 2-84 | 4-Cum | -EtCH- |
| 2-85 | 2-ₜtBuPh | -EtCH- |
| 2-86 | 3-ₜtBuPh | -EtCH- |
| 2-87 | 4-ₜtBuPh | -EtCH- |
| 2-88 | 2,6-di_iPrPh | -EtCH- |
| 2-89 | 2-AllPh | -EtCH- |
| 2-90 | 2-MeOPh | -EtCH- |
| 2-91 | 2-CNPh | -EtCH- |
| 2-92 | 3-CF₃Ph | -EtCH- |
| 2-93 | 3-diMeNPh | -EtCH- |
| 2-94 | 2-ClPh | -EtCH- |
| 2-95 | 3-ClPh | -EtCH- |
| 2-96 | 4-ClPh | -EtCH- |
| 2-97 | 2-FPh | -EtCH- |
| 2-98 | 3-FPh | -EtCH- |
| 2-99 | 4-FPh | -EtCH- |
| 2-100 | 2-BrPh | -EtCH- |
| 2-101 | 3-BrPh | -EtCH- |
| 2-102 | 4-BrPh | -EtCH- |
| 2-103 | 2-IPh | -EtCH- |
| 2-104 | 3-IPh | -EtCH- |
| 2-105 | 4-IPh | -EtCH- |

TABLE 2-continued

| Compound No. | R⁵ | W |
|---|---|---|
| 2-106 | 2,3-diClPh | -EtCH— |
| 2-107 | 2,4-diClPh | -EtCH— |
| 2-108 | 2,5-diClPh | -EtCH— |
| 2-109 | 2,6-diClPh | -EtCH— |
| 2-110 | 3,4-diClPh | -EtCH— |
| 2-111 | 3,5-diClPh | -EtCH— |
| 2-112 | 2,3-diFPh | -EtCH— |
| 2-113 | 2,4-diFPh | -EtCH— |
| 2-114 | 2,5-diFPh | -EtCH— |
| 2-115 | 2,6-diFPh | -EtCH— |
| 2-116 | 3,4-diFPh | -EtCH— |
| 2-117 | 3,5-diFPh | -EtCH— |
| 2-118 | 2,3-diBrPh | -EtCH— |
| 2-119 | 2,4-diBrPh | -EtCH— |
| 2-120 | 2,5-diBrPh | -EtCH— |
| 2-121 | 2,6-diBrPh | -EtCH— |
| 2-122 | 3,4-diBrPh | -EtCH— |
| 2-123 | 3,5-diBrPh | -EtCH— |
| 2-124 | 2,6-diIPh | -EtCH— |
| 2-125 | 4-NO₂Ph | -EtCH— |
| 2-126 | Me | -EtCH— |
| 2-127 | Et | -EtCH— |
| 2-128 | 4-FBz | -EtCH— |
| 2-129 | Ph | -PrCH— |
| 2-130 | Bz | -PrCH— |
| 2-131 | 1-Np | -PrCH— |
| 2-132 | 2-Np | -PrCH— |
| 2-133 | 2-Tol | -PrCH— |
| 2-134 | 3-Tol | -PrCH— |
| 2-135 | 4-Tol | -PrCH— |
| 2-136 | 2-EtPh | -PrCH— |
| 2-137 | 3-EtPh | -PrCH— |
| 2-138 | 4-EtPh | -PrCH— |
| 2-139 | 2,3-Xy | -PrCH— |
| 2-140 | 2,4-Xy | -PrCH— |
| 2-141 | 2,5-Xy | -PrCH— |
| 2-142 | 2,6-Xy | -PrCH— |
| 2-143 | 3,4-Xy | -PrCH— |
| 2-144 | 3,5-Xy | -PrCH— |
| 2-145 | Mes | -PrCH— |
| 2-146 | 2-Cum | -PrCH— |
| 2-147 | 3-Cum | -PrCH— |
| 2-148 | 4-Cum | -PrCH— |
| 2-149 | 2-₀tBuPh | -PrCH— |
| 2-150 | 3-₀tBuPh | -PrCH— |
| 2-151 | 4-₀tBuPh | -PrCH— |
| 2-152 | 2,6-di_iPrPh | -PrCH— |
| 2-153 | 2-AllPh | -PrCH— |
| 2-154 | 2-MeOPh | -PrCH— |
| 2-155 | 2-CNPh | -PrCH— |
| 2-156 | 3-CF₃Ph | -PrCH— |
| 2-157 | 3-diMeNPh | -PrCH— |
| 2-158 | 2-ClPh | -PrCH— |
| 2-159 | 3-Clph | -PrCH— |
| 2-160 | 4-ClPh | -PrCH— |
| 2-161 | 2-FPh | -PrCH— |
| 2-162 | 3-FPh | -PrCH— |
| 2-163 | 4-FPh | -PrCH— |
| 2-164 | 2-BrPh | -PrCH— |
| 2-165 | 3-BrPh | -PrCH— |
| 2-166 | 4-BrPh | -PrCH— |
| 2-167 | 2-IPh | -PrCH— |
| 2-168 | 3-IPh | -PrCH— |
| 2-169 | 4-IPh | -PrCH— |
| 2-170 | 2,3-diClPh | -PrCH— |
| 2-171 | 2,4-diClPh | -PrCH— |
| 2-172 | 2,5-diClPh | -PrCH— |
| 2-173 | 2,6-diClPh | -PrCH— |
| 2-174 | 3,4-diClPh | -PrCH— |
| 2-175 | 3,5-diClPh | -PrCH— |
| 2-176 | 2,3-diFPh | -PrCH— |
| 2-177 | 2,4-diFPh | -PrCH— |
| 2-178 | 2,5-diFPh | -PrCH— |
| 2-179 | 2,6-diFPh | -PrCH— |
| 2-180 | 3,4-diFPh | -PrCH— |
| 2-181 | 3,5-diFPh | -PrCH— |
| 2-182 | 2,3-diBrPh | -PrCH— |
| 2-183 | 2,4-diBrPh | -PrCH— |
| 2-184 | 2,5-diBrPh | -PrCH— |
| 2-185 | 2,6-diBrPh | -PrCH— |
| 2-186 | 3,4-diBrPh | -PrCH— |
| 2-187 | 3,5-diBrPh | -PrCH— |
| 2-188 | 2,6-diIPh | -PrCH— |
| 2-189 | 4-NO₂Ph | -PrCH— |
| 2-190 | Me | -PrCH— |
| 2-191 | Et | -PrCH— |
| 2-192 | 4-FBz | -PrCH— |
| 2-193 | Ph | -BuCH— |
| 2-194 | Bz | -BuCH— |
| 2-195 | 1-Np | -BuCH— |
| 2-196 | 2-Np | -BuCH— |
| 2-197 | 2-Tol | -BuCH— |
| 2-198 | 3-Tol | -BuCH— |
| 2-199 | 4-Tol | -BuCH— |
| 2-200 | 2-EtPh | -BuCH— |
| 2-201 | 3-EtPh | -BuCH— |
| 2-202 | 4-EtPh | -BuCH— |
| 2-203 | 2,3-Xy | -BuCH— |
| 2-204 | 2,4-Xy | -BuCH— |
| 2-205 | 2,5-Xy | -BuCH— |
| 2-206 | 2,6-Xy | -BuCH— |
| 2-207 | 3,4-Xy | -BuCH— |
| 2-208 | 3,5-Xy | -BuCH— |
| 2-209 | Ph | -diMeC— |
| 2-210 | Bz | -diMeC— |
| 2-211 | 1-Np | -diMeC— |
| 2-212 | 2-Np | -diMeC— |
| 2-213 | 2-Tol | -diMeC— |
| 2-214 | 3-Tol | -diMeC— |
| 2-215 | 4-Tol | -diMeC— |
| 2-216 | 2-EtPh | -diMeC— |
| 2-217 | 3-EtPh | -diMeC— |
| 2-218 | 4-EtPh | -diMeC— |
| 2-219 | 2,3-Xy | -diMeC— |
| 2-220 | 2,4-Xy | -diMeC— |
| 2-221 | 2,5-Xy | -diMeC— |
| 2-222 | 2,6-Xy | -diMeC— |
| 2-223 | 3,4-Xy | -diMeC— |
| 2-224 | 3,5-Xy | -diMeC— |
| 2-225 | Mes | -diMeC— |
| 2-226 | 2-Cum | -diMeC— |
| 2-227 | 3-Cum | -diMeC— |
| 2-228 | 4-Cum | -diMeC— |
| 2-229 | 2-₀tBuPh | -diMeC— |
| 2-230 | 3-₀tBuPh | -diMeC— |
| 2-231 | 4-₀tBuPh | -diMeC— |
| 2-232 | 2,6-di_iPrPh | -diMeC— |
| 2-233 | 2-AllPh | -diMeC— |
| 2-234 | 2-MeOPh | -diMeC— |
| 2-235 | 2-CNPh | -diMeC— |
| 2-236 | 3-CF₃Ph | -diMeC— |
| 2-237 | 3-diMeNPh | -diMeC— |
| 2-238 | 2-ClPh | -diMeC— |
| 2-239 | 3-ClPh | -diMeC— |
| 2-240 | 4-ClPh | -diMeC— |
| 2-241 | 2-FPh | -diMeC— |
| 2-242 | 3-FPh | -diMeC— |
| 2-243 | 4-FPh | -diMeC— |
| 2-244 | 2-BrPh | -diMeC— |
| 2-245 | 3-BrPh | -diMeC— |
| 2-246 | 4-BrPh | -diMeC— |
| 2-247 | 2-IPh | -diMeC— |
| 2-248 | 3-IPh | -diMeC— |
| 2-249 | 4-IPh | -diMeC— |
| 2-250 | 2,3-diClPh | -diMeC— |
| 2-251 | 2,4-diClPh | -diMeC— |
| 2-252 | 2,5-diClPh | -diMeC— |
| 2-253 | 2,6-diClPh | -diMeC— |
| 2-254 | 3,4-diClPh | -diMeC— |
| 2-255 | 3,5-diClPh | -diMeC— |
| 2-256 | 2,3-diFPh | -diMeC— |
| 2-257 | 2,4-diFPh | -diMeC— |
| 2-258 | 2,5-diFPh | -diMeC— |
| 2-259 | 2,6-diFPh | -diMeC— |

TABLE 2-continued

| Compound No. | R⁵ | W |
|---|---|---|
| 2-260 | 3,4-diFPh | -diMeC— |
| 2-261 | 3,5-diFPh | -diMeC— |
| 2-262 | 2,3-diBrPh | -diMeC— |
| 2-263 | 2,4-diBrPh | -diMeC— |
| 2-264 | 2,5-diBrPh | -diMeC— |
| 2-265 | 2,6-diBrPh | -diMeC— |
| 2-266 | 3,4-diBrPh | -diMeC— |
| 2-267 | 3,5-diBrPh | -diMeC— |
| 2-268 | 2,6-diIPh | -diMeC— |
| 2-269 | 4-NO₂Ph | -diMeC— |
| 2-270 | Me | -diMeC— |
| 2-271 | Et | -diMeC— |
| 2-272 | 4-FBz | -diMeC— |
| 2-273 | Ph | -Me(Et)C— |
| 2-274 | Bz | -Me(Et)C— |
| 2-275 | 1-Np | -Me(Et)C— |
| 2-276 | 2-Np | -Me(Et)C— |
| 2-277 | 2-Tol | -Me(Et)C— |
| 2-278 | 3-Tol | -Me(Et)C— |
| 2-279 | 4-Tol | -Me(Et)C— |
| 2-280 | 2-EtPh | -Me(Et)C— |
| 2-281 | 3-EtPh | -Me(Et)C— |
| 2-282 | 4-EtPh | -Me(Et)C— |
| 2-283 | 2,3-Xy | -Me(Et)C— |
| 2-284 | 2,4-Xy | -Me(Et)C— |
| 2-285 | 2,5-Xy | -Me(Et)C— |
| 2-286 | 2,6-Xy | -Me(Et)C— |
| 2-287 | 3,4-Xy | -Me(Et)C— |
| 2-288 | 3,5-Xy | -Me(Et)C— |
| 2-289 | Mes | -Me(Et)C— |
| 2-290 | 2-Cum | -Me(Et)C— |
| 2-291 | 3-Cum | -Me(Et)C— |
| 2-292 | 4-Cum | -Me(Et)C— |
| 2-293 | 2-tBuPh | -Me(Et)C— |
| 2-294 | 3-tBuPh | -Me(Et)C— |
| 2-295 | 4-tBuPh | -Me(Et)C— |
| 2-296 | 2,6-di-iPrPh | -Me(Et)C— |
| 2-297 | 2-AllPh | -Me(Et)C— |
| 2-298 | 2-MeOPh | -Me(Et)C— |
| 2-299 | 2-CNPh | -Me(Et)C— |
| 2-300 | 3-CF₃Ph | -Me(Et)C— |
| 2-301 | 3-diMeNPh | -Me(Et)C— |
| 2-302 | 2-ClPh | -Me(Et)C— |
| 2-303 | 3-ClPh | -Me(Et)C— |
| 2-304 | 4-ClPh | -Me(Et)C— |
| 2-305 | 2-FPh | -Me(Et)C— |
| 2-306 | 3-FPh | -Me(Et)C— |
| 2-307 | 4-FPh | -Me(Et)C— |
| 2-308 | 2-BrPh | -Me(Et)C— |
| 2-309 | 3-BrPh | -Me(Et)C— |
| 2-310 | 4-BrPh | -Me(Et)C— |
| 2-311 | 2-IPh | -Me(Et)C— |
| 2-312 | 3-IPh | -Me(Et)C— |
| 2-313 | 4-IPh | -Me(Et)C— |
| 2-314 | 2,3-diClPh | -Me(Et)C— |
| 2-315 | 2,4-diClPh | -Me(Et)C— |
| 2-316 | 2,5-diClPh | -Me(Et)C— |
| 2-317 | 2,6-diClPh | -Me(Et)C |
| 2-318 | 3,4-diClPh | -Me(Et)C— |
| 2-319 | 3,5-diClPh | -Me(Et)C— |
| 2-320 | 2,3-diFPh | -Me(Et)C— |
| 2-321 | 2,4-diFPh | -Me(Et)C— |
| 2-322 | 2,5-diFPh | -Me(Et)C— |
| 2-323 | 2,6-diFPh | -Me(Et)C— |
| 2-324 | 3,4-diFPh | -Me(Et)C— |
| 2-325 | 3,5-diFPh | -Me(Et)C— |
| 2-326 | 2,3-diBrPh | -Me(Et)C— |
| 2-327 | 2,4-diBrPh | -Me(Et)C— |
| 2-328 | 2,5-diBrPh | -Me(Et)C— |
| 2-329 | 2,6-diBrPh | -Me(Et)C— |
| 2-330 | 3,4-diBrPh | -Me(Et)C— |
| 2-331 | 3,5-diBrPh | -Me(Et)C— |
| 2-332 | 2,6-diIPh | -Me(Et)C— |
| 2-333 | 4-NO₂Ph | -Me(Et)C— |
| 2-334 | Me | -Me(Et)C— |
| 2-335 | Et | -Me(Et)C— |
| 2-336 | 4-FBz | -Me(Et)C— |
| 2-337 | Ph | -Me(Pr)C— |
| 2-338 | Bz | -Me(Pr)C— |
| 2-339 | 1-Np | -Me(Pr)C— |
| 2-340 | 2-Np | -Me(Pr)C— |
| 2-341 | 2-Tol | -Me(Pr)C— |
| 2-342 | 3-Tol | -Me(Pr)C— |
| 2-343 | 4-Tol | -Me(Pr)C— |
| 2-344 | Ph | -Me(Bu)C— |
| 2-345 | Bz | -Me(Su)C— |
| 2-346 | 1-Np | -Me(Bu)C— |
| 2-347 | 2-Np | -Me(Bu)C— |
| 2-348 | 2-Tol | -Me(Bu)C— |
| 2-349 | 3-Tol | -Me(Bu)C— |
| 2-350 | 4-Tol | -Me(Bu)C— |
| 2-351 | Ph | -PhCH— |
| 2-352 | Bz | -PhCH— |
| 2-353 | 1-Np | -PhCH— |
| 2-354 | 2-Np | -PhCH— |
| 2-355 | 2-Tol | -PhCH— |
| 2-356 | 3-Tol | -PhCH— |
| 2-357 | 4-Tol | -PhCH— |
| 2-358 | Ph | -Me(Ph)C— |
| 2-359 | Bz | -Me(Ph)C— |
| 2-360 | 1-Np | -Me(Ph)C— |
| 2-361 | 2-Np | -Me(Ph)C— |
| 2-362 | 2-Tol | -Me(Ph)C— |
| 2-363 | 3-Tol | -Me(Ph)C— |
| 2-364 | 2-AcPh | -EtCH— |
| 2-365 | 2-AcPh | -Me(Et)C— |
| 2-366 | Me | -diEtC— |
| 2-367 | Et | -diEtC— |
| 2-368 | Me | —CH₂Me(CH₂OMe)C— |
| 2-369 | 2-Me-1-Np | -EtCH— |
| 2-370 | Ph | —CH(iPr)- |
| 2-371 | 4-CF₃Bz | -diMeC— |
| 2-372 | Me | —CH₂diMeC— |
| 2-373 | 4-NO₂Ph | -diMeC— |
| 2-374 | Ph | -PnCH— |
| 2-375 | Bz | -PnCH— |
| 2-376 | 1-Np | -PnCH— |
| 2-377 | 2-Np | -PnCH— |
| 2-378 | 2-Tol | -PnCH— |
| 2-379 | 3-Tol | -PnCH— |
| 2-380 | 4-Tol | -PnCH— |
| 2-381 | 2-EtPh | -PnCH— |
| 2-382 | 3-EtPh | -PnCH— |
| 2-383 | 4-EtPh | -PnCH— |
| 2-384 | 2,3-Xy | -PnCH— |
| 2-385 | 2,4-Xy | -PnCH— |
| 2-386 | 2,5-Xy | -PnCH— |
| 2-387 | 2,6-Xy | -PnCH— |
| 2-388 | 3,4-Xy | -PnCH— |
| 2-389 | 3,5-Xy | -PnCH— |
| 2-390 | 2-ClPh | -PnCH— |
| 2-391 | 3-ClPh | -PnCH— |
| 2-392 | 4-ClPh | -PnCH— |
| 2-393 | 2-FPh | -PnCH— |
| 2-394 | 3-FPh | -PnCH— |
| 2-395 | 4-FPh | -PnCH— |
| 2-396 | 2,6-diClPh | -PnCH— |
| 2-397 | Ph | -HxCH— |
| 2-398 | Bz | -HxCH— |
| 2-399 | 1-Np | -HxCH— |
| 2-400 | 2-Np | -HxCH— |
| 2-401 | 2-Tol | -HxCH— |
| 2-402 | 3-Tol | -HxCH— |
| 2-403 | 4-Tol | -HxCH— |
| 2-404 | 2-EtPh | -HxCH— |
| 2-405 | 3-EtPh | -HxCH— |
| 2-406 | 4-EtPh | -HxCH— |
| 2-407 | 2,3-Xy | -HxCH— |
| 2-408 | 2,4-Xy | -HxCH— |
| 2-409 | 2,5-Xy | -HxCH— |
| 2-410 | 2,6-Xy | -HxCH— |
| 2-411 | 3,4-Xy | -HxCH— |
| 2-412 | 3,5-Xy | -HxCH— |
| 2-413 | 2-ClPh | -HxCH— |

TABLE 2-continued

| Compound No. | R⁵ | W |
| --- | --- | --- |
| 2-414 | 3-ClPh | -HxCH- |
| 2-415 | 4-ClPh | -HxCH- |
| 2-416 | 2-FPh | -HxCH- |
| 2-417 | 3-FPh | -HxCH- |
| 2-418 | 4-FPh | -HxCH- |
| 2-419 | 2,6-diClPh | -HxCH- |
| 2-420 | Ph | -CH₂EtCH- |
| 2-421 | Bz | -CH₂EtCH- |
| 2-422 | 1-Np | -CH₂EtCH- |
| 2-423 | 2-Np | -CH₂EtCH- |
| 2-424 | 2-Tol | -CH₂EtCH- |
| 2-425 | 3-Tol | -CH₂EtCH- |
| 2-426 | 4-Tol | -CH₂EtCH- |
| 2-427 | 2-EtPh | -CH₂EtCH- |
| 2-428 | 3-EtPh | -CH₂EtCH- |
| 2-429 | 4-EtPh | -CH₂EtCH- |
| 2-430 | 2,3-Xy | -CH₂EtCH- |
| 2-431 | 2,4-Xy | -CH₂EtCH- |
| 2-r432 | 2,5-Xy | -CH₂EtCH- |
| 2-433 | 2,6-Xy | -CH₂EtCH- |
| 2-434 | 3,4-Xy | -CH₂EtCH- |
| 2-435 | 3,5-Xy | -CH₂EtCH- |
| 2-436 | 2-ClPh | -CH₂EtCH- |
| 2-437 | 3-ClPh | -CH₂EtCH- |
| 2-438 | 4-ClPh | -CH₂EtCH- |
| 2-439 | 2-FPh | -CH₂EtCH- |
| 2-440 | 3-FPh | -CH₂EtCH- |
| 2-441 | 4-FPh | -CH₂EtCH- |
| 2-442 | 2,6-diClPh | -CH₂EtCH- |
| 2-443 | 2-BrPh | -CH₂EtCH- |
| 2-444 | 3-BrPh | -CH₂EtCH- |
| 2-445 | 4-BrPh | -CH₂EtCH- |

Of the compounds listed above, preferred compounds are Compounds No. 1-5, 1-14, 1-30, 1-65, 1-67, 1-68, 1-69, 1-70, 1-71, 1-72, 1-74, 1-75, 1-76, 1-77, 1-78, 1-79, 1-81, 1-82, 1-84, 1-88, 1-89, 1-90, 1-91, 1-92, 1-94, 1-96, 1-97, 1-99, 1-100, 1-102, 1-109, 1-113, 1-121, 1-129, 1-209, 1-224, 1-240, 1-243, 1-270, 1-271, 1-272, 1-279, 1-337, 1-341, 1-364, 1-367, 1-368, 1-369, 1-370, 1-372, 2-5, 2-14, 2-30, 2-65, 2-67, 2-68, 2-69, 2-70, 2-71, 2-72, 2-74, 2-75, 2-76, 2-77, 2-78, 2-79, 2-81, 2-82, 2-84, 2-88, 2-89, 2-90, 2-91, 2-92, 2-94, 2-96, 2-97, 2-99, 2-100, 2-102, 2-109, 2-113, 2-121, 2-129, 2-209, 2-224, 2-240, 2-243, 2-270, 2-271, 2-272, 2-279, 2-337, 2-341, 2-364, 2-367, 2-368, 2-369, 2-370 and 2-372.

The more preferred compounds are Compounds No. 1-65, 1-67, 1-69, 1-70, 1-71, 1-72, 1-74, 1-75, 1-76, 1-77, 1-78, 1-79, 1-81, 1-82, 1-89, 1-90, 1-91, 1-94, 1-96, 1-97, 1-99, 1-100, 1-102, 1-109, 1-113, 1-121, 1-129, 1-209, 1-240, 1-243, 1-271, 1-279, 1-337, 1-341, 1-347, 1-369, 1-372, 2-65, 2-67, 2-69, 2-70, 2-71, 2-72, 2-74, 2-75, 2-76, 2-77, 2-78, 2-79, 2-81, 2-82, 2-89, 2-90, 2-91, 2-94, 2-96, 2-97, 2-99, 2-100, 2-102, 2-109, 2-113, 2-121, 2-129, 2-209, 2-240, 2-243, 2-271, 2-279, 2-337, 2-341, 2-367, 2-369 and 2-372.

The most preferred compounds are Compounds No.:

1-65. 3,5-dihydroxy-7-[1,2,6,7,8,8a-hexahydro-6-hydroxy-8-(2-phenoxybutyryloxy)-2-methyl-1-naphthyl]heptanoic acid;

1-67. 3,5-dihydroxy-7-{1,2,6,7,8,8a-hexahydro-6 -hydroxy-8-[2-(1-naphthyloxy)butyryloxy]-2-methyl-1-naphthyl}heptanoic acid;

1-69. 3,5-dihydroxy-7-{1,2,6,7,8,8a-hexahydro-6 -hydroxy-8-[2-(2-methylphenoxy)butyryloxy]-2-methyl-1-naphthyl}heptanoic acid;

1-70. 3,5-dihydroxy-7-{1,2,6,7,8,8a-hexahydro-6 -hydroxy-8-[2-(3-methylphenoxy)butyryloxy]-2-methyl-1-naphthyl}heptanoic acid;

1-71. 3,5-dihydroxy-7-{1,2,6,7,8,8a-hexahydro-6 -hydroxy-8-[2-(4-methylphenoxy)butyryloxy]-2-methyl-1-naphthyl}heptanoic acid;

1-74. 3,5-dihydroxy-7-{1,2,6,7,8,8a-hexahydro-6 -hydroxy-8-[2-(4-ethylphenoxy)butyryloxy]-2-methyl-1-naphthyl}heptanoic acid;

1-75. 3,5-dihydroxy-7-{1,2,6,7,8,8a-hexahydro-6 -hydroxy-8-[2-(2,3-dimethylphenoxy)butyryloxy]-2-methyl-1-naphthyl}heptanoic acid;

1-77. 3,5-dihydroxy-7-{1,2,6,7,8,8a-hexahydro-6 -hydroxy-8-[2-(2,5-dimethylphenoxy)butyryloxy]-2-methyl-1-naphthyl}heptanoic acid;

1-78. 3,5-dihydroxy-7-{1,2,6,7,8,8a-hexahydro-6 -hydroxy-8-[2-(2,6-dimethylphenoxy)butyryloxy]-2-methyl-1-naphthyl}heptanoic acid;

1-79. 3,5-dihydroxy-7-{1,2,6,7,8,8a-hexahydro-6 -hydroxy-8-[2-(3,4-dimethylphenoxy)butyryloxy]-2-methyl-1-naphthyl}heptanoic acid;

1-81. 3,5-dihydroxy-7-{1,2,6,7,8,8a-hexahydro-6 -hydroxy-8-[2-(2,4,6-trimethylphenoxy)butyryloxy]-2-methyl-1-naphthyl}heptanoic acid;

1-82. 3,5-dihydroxy-7-{1,2,6,7,8,8a-hexahydro-6 -hydroxy-8-[2-(2-isopropylphenoxy)butyryloxy]-2-methyl-1-naphthyl}heptanoic acid;

1-89. 3,5-dihydroxy-7-{1,2,6,7,8,8a-hexahydro-6 -hydroxy-8-[2-(2-allylphenoxy)butyryloxy]-2-methyl-1-naphthyl}heptanoic acid;

1-96. 3,5-dihydroxy-7-{1,2,6,7,8,8a-hexahydro-6 -hydroxy-8-[2-(4-chlorophenoxy)butyryloxy]-2-methyl-1-naphthyl}heptanoic acid;

1-97. 3,5-dihydroxy-7-{1,2,6,7,8,8a-hexahydro-6 -hydroxy-8-[2-(2-fluorophenoxy)butyryloxy]-2-methyl-1-naphthyl}heptanoic acid;

1-99. 3,5-dihydroxy-7-{1,2,6,7,8,8a-hexahydro-6 -hydroxy-8-[2-(4-fluorophenoxy)butyryloxy]-2-methyl-1-naphthyl}heptanoic acid;

1-100. 3,5-dihydroxy-7-{1,2,6,7,8,8a-hexahydro-6 -hydroxy-8-[2-(2-bromophenoxy)butyryloxy]-2-methyl-1-naphthyl}heptanoic acid;

1-109. 3,5-dihydroxy-7-{1,2,6,7,8,8a-hexahydro-6 -hydroxy-8-[2-(2,6-dichlorophenoxy)butyryloxy]-2-methyl-1-naphthyl}heptanoic acid;

1-113. 3,5-dihydroxy-7-{1,2,6,7,8,8a-hexahydro-6 -hydroxy-8-[2-(2,4-difluorophenoxy)butyryloxy]-2-methyl-1-naphthyl}heptanoic acid;

1-121. 3,5-dihydroxy-7-{1,2,6,7,8,8a-hexahydro-6 -hydroxy-8-[2-(2,6-dibromophenoxy)butyryloxy]-2-methyl-1-naphthyl}heptanoic acid;

1-129. 3,5-dihydroxy-7-[1,2,6,7,8,8a-hexahydro-6 -hydroxy-8-(2-phenoxyvaleryloxy)-2-methyl-1-naphthyl]heptanoic acid;

1-209. 3,5-dihydroxy-7-[1,2,6,7,8,8a-hexahydro-6 -hydroxy-8-(2-phenoxy-2-methylpropionyloxy)-2-methyl-1-naphthyl]heptanoic acid;

1-243. 3,5-dihydroxy-7-{1,2,6,7,8,8a-hexahydro-6 -hydroxy-8-[2-(4-fluorophenoxy)-2-methylpropionyloxy]-2-methyl-1-naphthyl}heptanoic acid;

1-271. 3,5-dihydroxy-7-[1,2,6,7,8,8a-hexahydro-6 -hydroxy-8-(2-ethoxy-2-methylpropionyloxy)-2-methyl-1-naphthyl]heptanoic acid;

1-279. 3,5-dihydroxy-7-{1,2,6,7,8,8a-hexahydro-6 -hydroxy-8-[2-(4-methylphenoxy)-2-methylbutyryloxy]-2-methyl-1-naphthyl}heptanoic acid;

1-369. 3,5-dihydroxy-7-{1,2,6,7,8,8a-hexahydro-6 -hydroxy-8-[2-(2-methyl-1-naphthyloxy)butyryloxy]-2-methyl-1-naphthyl}heptanoic acid; 2-65. 3,5-dihydroxy-7-[1,2,6,7,8,8a-hexahydro-8-(2 -phenoxybutyryloxy)-2-methyl-1-naphthyl]heptanoic acid;

2-67. 3,5,-dihydroxy-7-{1,2,6,7,8,8a-hexahydro-8-[2 -(1-naphthyloxy)butyryloxy]-2-methyl-1-naphthyl}heptanoic acid;

2-69. 3,5,-dihydroxy-7-{1,2,6,7,8,8a-hexahydro-8-[2 -(2-methylphenoxy)butyryloxy]-2-methyl-1-naphthyl}heptanoic acid;

2-70. 3,5-dihydroxy-7-{1,2,6,7,8,8a-hexahydro-8-[2 -(3-methylphenoxy)butyryloxy]-2-methyl-1-naphphyl}heptanoic acid;

2-71. 3,5-dihydroxy-7-{1,2,6,7,8,8-hexahydro-8-[2 -(4-methylphenoxy)butyryloxy]-2-methyl-1-naphthyl}heptanoic acid;

2-74. 3,5-dihydroxy-7-{1,2,6,7,8,8a-hexahydro-8-[2-(4-ethylphenoxy)butyryloxy]-2-methyl-1-naphthyl}heptanoic acid;

2-75. 3,5-dihydroxy-7-{1,2,6,7,8,8a-hexahydro-8-[2 -(2,3-dimethylphenoxy)butyryloxy]-2-methyl-1-naphthyl}heptanoic acid;

2-77. 3,5-dihydroxy-7-{1,2,6,7,8,8a-hexahydro-8-[2 -(2,5-dimethylphenoxy)butyryloxy]-2-methyl-1-naphthyl}heptanoic acid;

2-78. 3,5-dihydroxy-7-{1,2,6,7,8,8a-hexahydro-8-[2 -(2,6-dimethylphenoxy)butyryloxy]-2-methyl-1-naphthyl}heptanoic acid;

2-79. 3,5-dihydroxy-7-{1,2,6,7,8,8a-hexahydro-8-[2 -(3,4-dimethylphenoxy)butyryloxy]-2-methyl-1-naphthyl}heptanoic acid;

2-81. 3,5-dihydroxy-7-{1,2,6,7,8,8a-hexahydro-8-[2 -(2,4,6-trimethylphenyloxy)butyryloxy]-2-methyl-1-naphthyl}heptanoic acid;

2-82. 3,5-dihydroxy-7-{1,2,6,7,8,8a-hexahydro-8-[2-(2 -isopropylphenoxy)butyryloxy]-2-methyl-1-naphthyl}heptanoic acid;

2-89. 3,5-dihydroxy-7-{1,2,6,7,8,8a-hexahydro-8-[2 -(2-allylphenoxy)butyryloxy]-2-methyl-1-naphthyl}heptanoic acid;

2-96. 3,5-dihydroxy-7-{1,2,6,7,8,8a-hexahydro-8-[2-(4 -chlorophenoxy)butyryloxy]-2-methyl-1-naphthyl}heptanoic acid;

2-97. 3,5-dihydroxy-7-{1,2,6,7,8,8a-hexahydro-8-[2-(2 -fluorophenoxy)butyryloxy]-2-methyl-1-naphthyl}heptanoic acid;

2-99. 3,5-dihydroxy-7-{1,2,6,7,8,8a-hexahydro-8-[2-(4 -fluorophenoxy)butyryloxy]-2-methyl-1-naphthyl}heptanoic acid;

2-100. 3,5-dihydroxy-7-{1,2,6,7,8,8a-hexahydro-8-[2 -(2-bromophenoxy)butyryloxy]-2-methyl-1-naphthyl}heptanoic acid;

2-109. 3,5-dihydroxy-7-{1,2,6,7,8,8a-hexahydro-8-[2 -(2,6-dichlorophenoxy)butyryloxy]-2-methyl-1-naphthyl}heptanoic acid;

2-113. 3,5-dihydroxy-7-{1,2,6,7,8,8a-hexahydro-8-[2 -(2,4-difluorophenoxy)butyryloxy]-2-methyl-1-naphthyl}heptanoic acid;

2-121. 3,5-dihydroxy-7-{1,2,6,7,8,8a-hexahydro-8-[2 -(2,6-dibromophenoxy)butyryloxy]-2-methyl-1-naphthyl}heptanoic acid;

2-129. 3,5-dihydroxy-7-[1,2,6,7,8,8a-hexahydro-8-(2 -phenoxyvaleryloxy)-2-methyl-1-naphthyl]heptanoic acid;

2-209. 3,5-dihydroxy-7-[1,2,6,7,8,8a-hexahydro-8-(2 -phenoxy-2-methylpropionyloxy)-2-methyl-1-naphthyl]heptanoic acid;

2-243. 3,5-dihydroxy-7-{1,2,6,7,8,8a-hexahydro-8-[2 -(4-fluorophenoxy)-2-methylpropionyloxy]-2-methyl-1-naphthyl}heptanoic acid;

2-271. 3,5-dihydroxy-7-[1,2,6,7,8,8a-hexahydro-8-(2 -ethoxy-2-methylpropionyloxy)-2-methyl-1-naphthyl] heptanoic acid;

2-279. 3,5-dihydroxy-7-{1,2,6,7,8,8a-hexahydro-8-[2 -(4-methylphenoxy)-2-methylbutyryloxy]-2-methyl-1-naphthyl}-heptanoic acid;

2-369. 3,5-dihydroxy-7-{1,2,6,7,8,8a-hexahydro-8-[2 -(2-methyl-1-naphthyloxy)butyryloxy]-2-methyl-1-naphthyl}heptanoic acid;

and the ring-closed lactones corresponding to the hydroxy-acids listed above;

and pharmaceutically acceptable salts and esters thereof.

The compounds of the present invention may be prepared by a variety of methods well known for the preparation of compounds of this type. For example, in general terms, they may be prepared by the reaction of a compound of formula (XX):

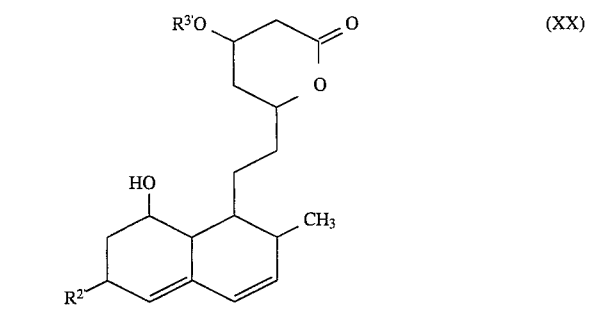

(wherein $R^{2'}$ represents a hydrogen atom or a group of formula $R^{3'}O—$, and the symbols $R^{3'}$ each represents any of the groups represented by $R^3$ but may not represent a hydrogen atom) with a reactive compound containing the group $R^5—O—W—CO—$, preferably with an acylating agent, to give a compound of formula (XXI):

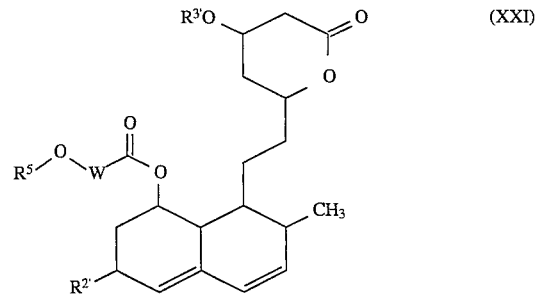

(wherein $R^5$, $R^{3'}$, $R^{2'}$ and W are as defined above) and, if necessary, subjecting the compound of formula (XXI) to ring-opening hydrolysis or solvolysis, and, if desired, where $R^2$ represents a hydrogen atom, introducing a group of formula $R^3O—$.

In more detail, the compounds of the present invention may be prepared as illustrated in the following Reaction Schemes A, B and C.

REACTION SCHEME A

Compounds of formula (Ia) may be prepared as illustrated in the following Reaction Scheme A.

In this method, the starting material, the compound of formula (VI), may be the known compound pravastatin, in which the hydroxy group at the 6-position is in the β-configuration. The stereochemistry of the corresponding groups at the 6-position is retained as the β-configuration throughout the whole of the reaction scheme. Alternatively, an epimeric isomer am the 6-position of pravastatin may be used as the starting material in Step A1, in which case it is possible to prepare the desired compounds of formulae (VIII), (IX) and (X) in which the substituents at the 6-position are in the α-configuration. Although the stereochemistry at the 6- and other positions is not shown in the following formulae, the present invention envisages the use either of individual isolated isomers, e.g. pravastatin or its epimer, or mixtures of these isomers.

Reaction Scheme A

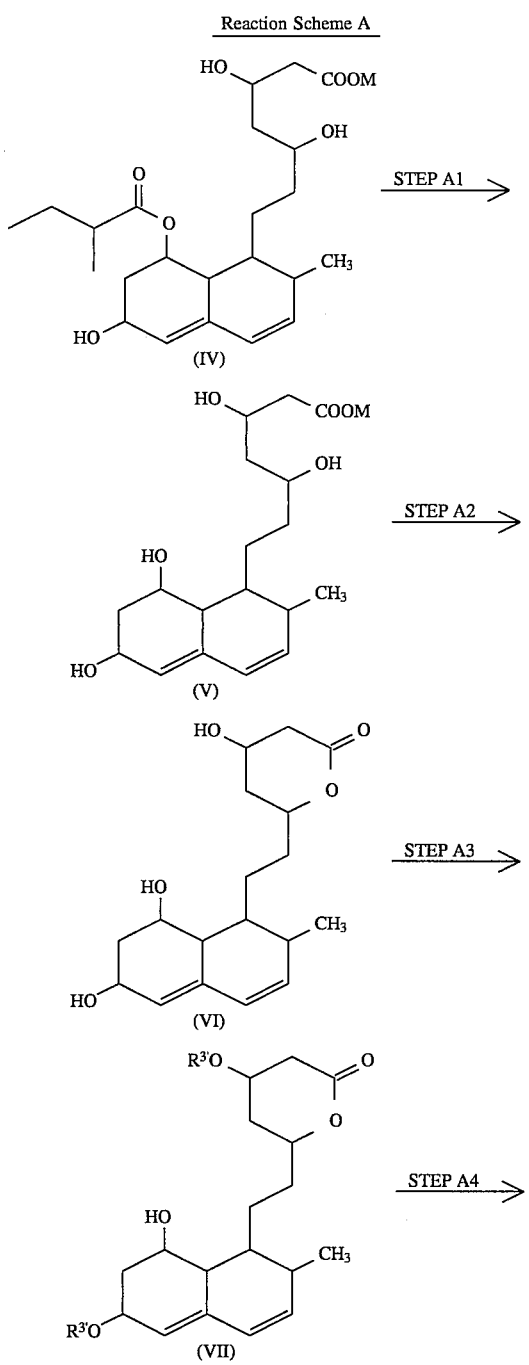

-continued
Reaction Scheme A

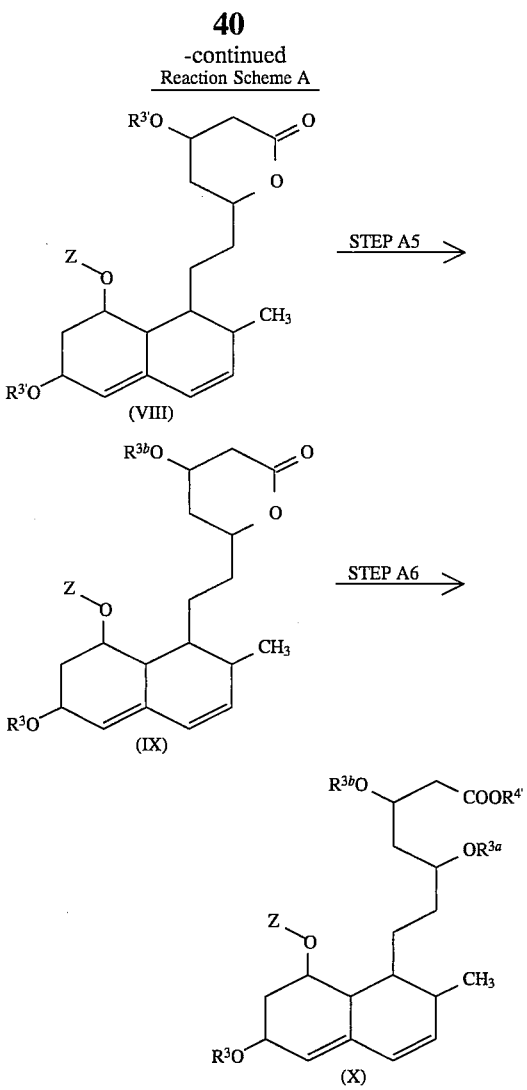

In the above formulae:

R³' represents a hydroxy-protecting group, an alkyl group, an alkanesulfonyl group, a halogenated alkanesulfonyl group or an arylsulfonyl group, all as defined and exemplified above in relation to R³ etc.;

R⁴' represents a hydrogen atom, a carboxy-protecting group, as defined for R⁴, or the cationic portion of a salt;

Z represents a group of formula:

R⁵—O—W—CO—

(wherein R⁵ and W are as defined above); and

M represents a hydrogen atom or the cationic portion of a salt.

Step A1

In Step A1 of this reaction scheme, a compound of formula (V) is prepared by the hydrolysis of a compound of formula (IV) or a pharmaceutically acceptable salt thereof. The hydrolysis may be conducted by conventional means, for example using a base in a solvent to convert the ester side chain at the 8-position to a hydroxy group.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water and organic solvents, such as: ethers, for example tetrahydrofuran, dioxane, dimethoxyethane or diethylene glycol dimethyl ether; alcohols, for example methanol, ethanol, propanol, isopropanol, butanol, isobutanol, t-butanol, isoamyl alcohol, diethylene glycol or methyl cellosolve; and mixtures of water with one or more of these organic solvents.

There is no particular limitation upon the nature of the base used, and any base commonly used as a base in conventional reactions may equally be used here. Examples of preferred bases include: inorganic bases, such as alkali metal carbonates (for example sodium carbonate, potassium carbonate or lithium carbonate), alkali metal hydrogencarbonates (for example sodium hydrogencarbonate, potassium hydrogencarbonate or lithium hydrogencarbonate), alkali metal hydroxides (for example sodium hydroxide, potassium hydroxide, barium hydroxide or lithium hydroxide), and alkali metal alkoxides (for example sodium methoxide, sodium ethoxide, potassium methoxide, potassium ethoxide, potassium t-butoxide or lithium methoxide).

Where an alkali metal carbonate, an alkali metal hydrogencarbonate or an alkali metal hydroxide is used as the base, the reaction is preferably carried out using one or more equivalents of the base per mole of the compound of formula (IV). Where an alkali metal alkoxide is used as the base, the reaction proceeds when more than a catalytic amount of the base is used.

The reaction can take place over a wide range of temperatures, and the precise reaction temperature is not critical to the invention. In general, we find it convenient to carry out the reaction either at a temperature of from −20° C. to 150° C., more preferably from 80° C. to 120° C., or at the temperature of the boiling point of the solvent used. The time required for the reaction may also vary widely, depending on many factors, notably the reaction temperature and the nature of the reagents, base and solvent employed. However, provided that the reaction is effected under the preferred conditions outlined above, a period of from 3 to 100 hours, more preferably from 24 to 60 hours, will usually suffice.

After completion of the reaction, the desired product of formula (V) can be recovered from the reaction mixture by conventional means. For example, in one suitable recovery procedure: the reaction mixture is adequately neutralized; if insoluble materials exist, they are removed by filtration; water and a water-immiscible organic solvent, such as ethyl acetate, are added to the reaction mixture or to the filtrate and the product is extracted into the solvent; the extract is washed with water and dried, for example over anhydrous magnesium sulfate; and then the solvent is distilled off, leaving the desired product as the residue.

The compound of formula (V) thus obtained is a salt of a hydroxy acid and, if necessary, it can be purified by conventional means, for example, by recrystallization, reprecipitation or the various chromatographic techniques. Examples of chromatographic techniques include: partition chromatography through a synthetic absorbent such as Sephadex™ LH-20 (Pharmacia Inc.), Amberlite™ XAD-11 (Rohmand Haas Co.) or Diaion™ HP-20 (Mitsubishi Kasei Corporation); column chromatography through a regular or reverse phase column packed with silica gel or with an alkylated silica gel (preferably high performance liquid chromatography); or a combination of these techniques; followed by eluting with a suitable eluting solvent.

Step A2

In this step, a lactone compound of formula (VI) is prepared by reacting the salt of a hydroxy acid compound of formula (V) with one or more equivalents of an acid to produce a free carboxylic acid and then subjecting the product to a ring closure reaction.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water and organic solvents, such as: ethers (for example tetrahydrofuran, dioxane, dimethoxyethane and diethylene glycol dimethyl ether); alcohols (for example methanol, ethanol, propanol, isopropanol, butanol, isobutanol, t-butanol, diethylene glycol, cyclohexanol and methyl cellosolve); and mixtures of water and one or more of these organic solvents.

There is also no particular limitation upon the nature of the acid used in the first part of this step, and any catalyst conventionally used in this type of reaction may equally be used here. Examples of preferred acids include inorganic acids, such as hydrochloric acid, hydrobromic acid, sulfuric acid, perchloric acid or phosphoric acid.

The reaction can take place over a wide range of temperatures, and the precise reaction temperature is not critical to the invention. In general, we find it convenient to carry out the reaction at a temperature of from −20° C. to 50° C., more preferably at a temperature between 0° C. and about room temperature. The time required for the reaction may also vary widely, depending on many factors, notably the reaction temperature and the nature of the reagents, acid and solvent employed. However, provided that the reaction is effected under the preferred conditions outlined above, it may go to completion immediately after adding the acid; alternatively, a period of up to 2 hours, more preferably a period of up to 30 minutes may be allowed for the reaction.

After completion of the reaction, the desired product of this reaction can be recovered from the reaction mixture by conventional means. For example, in one suitable recovery procedure: the reaction mixture is adequately neutralized; if insoluble materials exist, they are removed by filtration; water and a water-immiscible organic solvent, such as ethyl acetate, are added to the reaction mixture or the filtrate and the product is extracted into the solvent; the extract is washed with water and dried, for example over anhydrous magnesium sulfate; and the solvent is distilled off, leaving the desired product as the residue. Alternatively, after completion of the reaction, the desired compound can be recovered by distilling off the solvent from the reaction mixture; mixing the residue with an organic solvent; filtering off insoluble materials; and distilling off the solvent. Examples of organic solvents which may be used in this recovery procedure include: aliphatic hydrocarbons, such as hexane, heptane, ligroin or petroleum ether; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as methanol, ethanol, propanol, isopropanol, butanol, isobutanol, t-butanol, diethylene glycol, cyclohexanol or methyl cellosolve; and ketones, such as acetone and methyl ethyl ketone.

The desired compound thus obtained can, if necessary, be purified by conventional means, for example, by recrystallization, reprecipitation or chromatographic techniques. Examples of suitable chromatographic techniques include: partition chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); column chromatography through a regular or reverse phase column packed with silica gel or with an alkylated silica gel (preferably high performance liquid chromatography); or a combination of these techniques; followed by eluting with a suitable eluting solvent.

Ring closing lactonization in the second part of the step causes the hydroxy acid to be converted to a lactone ring. The reaction can be conducted by a variety of methods, for example:

Method 1, which involves simply heating the corresponding hydroxy acid in a solvent;

Method 2, which involves treating the corresponding hydroxy acid with an esterifying agent in a solvent.

Method 1

The reaction is effected in the presence of an anhydrous solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; and nitriles, such as acetonitrile or isobutyronitrile.

The reaction can take place over a wide range of temperatures, and the precise reaction temperature is not critical to the invention. In general, we find it convenient to carry out the reaction at a temperature of from 0° C. to the reflux temperature of the solvent used, more preferably from about room temperature to 100° C. The time required for the reaction may also vary widely, depending on many factors, notably the reaction temperature and the nature of the reagents and solvent employed. However, provided that the reaction is effected under the preferred conditions outlined above, a period of from 10 minutes to 6 hours, more preferably from 30 minutes to 3 hours, will usually suffice.

The reaction may be accelerated by the use of an acid as a catalyst. There is no particular limitation upon the nature of the acid used, and any acid which can be used as an acid catalyst in conventional reactions may equally be used here. Examples of such acids include: organic acids, such as acetic acid, formic acid, oxalic acid, methanesulfonic acid, p-toluenesulfonic acid, trifluoroacetic acid or trifluoromethanesulfonic acid; and Lewis acids, such as boron trichloride, boron trifluoride or boron tribromide. Of these, we prefer the organic acids; more preferably the strong organic acids.

Method 2

The reaction of Method 2 is normally and preferably effected in the presence of a solvent. There is no particular restriction on the nature of the solvent to be employed, provided that it has no adverse effect on the reaction or on the reagents involved and that it can dissolve the reagents, at least to some extent. The solvent should, however, be anhydrous. Examples of suitable solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitriles, such as acetonitrile or isobutyronitrile; and amides, such as formamide, dimethylformamide, dimethylacetamide, N-methyl-2-pyrrolidone, N-methylpyrrolidinone or hexamethylphosphoric triamide.

Examples of esterifying agents which may be used in Method 2 include: condensing agents, as exemplified below; alkyl haloformates, such as methyl chloroformate or ethyl chloroformate; and cyanophosphoric acid diesters, such as diethyl cyanophosphonate. Examples of condensing agents include: N-hydroxy derivatives, such as N-hydroxysuccinimide and 1-hydroxybenzotriazole; disulfide compounds, such as 2,2'-dipyridyl disulfide; succinic acid compounds, such as N,N'-disuccinimidyl carbonate; phosphinic chloride compounds, such as N,N'-bis(2-oxo-3-oxazolidinyl)phosphinic chloride; oxalate derivatives, such as N,N'-disuccinimidyl oxalate (DSO), N,N'-diphthalimide oxalate (DPO), N,N'-bis(norbornenylsuccinimidyl)oxalate (BNO), 1,1'-bis-(benzotriazolyl)oxalate (BBTO), 1,1'-bis(6-chlorobenzotriazolyl)oxalate (BCTO) or 1,1'-bis(6-trifluoromethylbenzotriazolyl)oxalate (BTBO); triarylphosphines, such as triphenyl-phosphine; a combination of a di(lower alkyl)azodicarboxylate and a triarylphosphine, such as a combination of diethyl azodicarboxylate and triphenylphosphine; N-(lower alkyl)-5-arylisoxazolium-3'-sulfonates, such as N-ethyl-5-phenylisoxazolium-3'-sulfonate; carbodiimide derivatives including N',N'-dicycloalkylcarbodiimides, such as N',N'-dicyclohexylcarbodiimide (DCC) or 1-ethyl-3-(3-dimethylaminopropyl)carbodiimide (EDAPC); diheteroaryl diselenides, such as di-2-pyridyl diselenide; arylsulfonyl triazolides, such as p-nitrobenzenesulfonyl triazolide; 2-halo-1-(lower alkyl)pyridinium halides, such as 2-chloro-1-methylpyridinium iodide; diarylphosphoryl azides, such as diphenylphosphoryl azide (DPPA); imidazole derivatives, such as 1,1'-oxalyldiimidazole or N,N'-carbonyldiimidazole; benzotriazole derivatives, such as 1-hydroxybenzotriazole (HOBT); and dicarboximide derivatives, such as N-hydroxy-5-norbornene-2,3-dicarboximide (HONB). Of these, we prefer the diarylphosphoryl azides and the cyanophosphoric acid diesters.

The reaction can take place over a wide range of temperatures, and the precise reaction temperature is not critical to the invention. In general, we find it convenient to carry out the reaction at a temperature of from −20° C. to 100° C., more preferably from 0° C. to about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 8 hours, more preferably from 30 minutes to 4 hours, will usually suffice.

After completion of the reaction, the desired compound of formula (VI) can be recovered from the reaction mixture by conventional means. For example, in one suitable recovery procedure: the reaction mixture is neutralized; if insoluble materials exist, they are removed by filtration; water and a water-immiscible organic solvent, such as ethyl acetate, are added to the filtrate or to the neutralized reaction mixture, and the product is extracted into the solvent; the extract is washed with water and dried, for example over anhydrous magnesium sulfate; and then the solvent is distilled off leaving the desired product as the residue.

The desired compound thus obtained can, if necessary, be further purified by conventional means, for example, recrystallization, reprecipitation or the various chromatographic techniques. Examples of suitable chromatographic techniques include: absorption chromatography through a carrier, such as silica gel, alumina or Florisil (containing magnesium-silica gel); partition chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); column chromatography through a regular or reverse phase column packed with silica gel or an alkylated silica gel (preferably high performance liquid chromatography); or an appropriate combination of these techniques; followed by elution with a suitable eluting solvent.

Step A3

In this step, a compound of formula (VII) is prepared by the selective protection of the two hydroxy groups other than the hydroxy group at the 8-position, of a compound of formula (VI), with a group $R^{3'}$.

The protection can be effected by a variety of methods, for example, the following Methods 1 to 3, depending, in part, on the nature of the selected protecting group.

Method 1

This involves reacting a compound of formula (VI) with a suitable amount, for example from 1 to 4 equivalents (more preferably from 2 to 3 equivalents) of a compound of formula: $R^{3'}$—X or a compound of formula: $R^{3'}$—O—$R^{3'}$ (wherein $R^{3'}$ is as defined above, but preferably represents an acyl group, and X represents a leaving group) in a solvent in the presence or absence of a base. In the above formulae, $R^{3'}$ is as defined above, but preferably represents a hydroxy-protecting group, more preferably a silyl group, and most preferably a t-butyldimethylsilyl group.

There is no particular limitation upon the nature of the leaving group, provided that it is a group capable of leaving as a nucleophilic residue, such as are well known in the art. Examples of preferred leaving groups include: halogen atoms, such as the chlorine, bromine and iodine atoms; lower alkoxycarbonyloxy groups, such as the methoxycarbonyloxy and ethoxycarbonyloxy groups; halogenated alkylcarbonyloxy groups, such as the chloroacetoxy, dichloroacetoxy, trichloroacetoxy and trifluoroacetoxy groups; lower alkanesulfonyloxy groups, such as the methanesulfonyloxy and ethanesulfonyloxy groups; lower haloalkanesulfonyloxy groups, such as the trifluoromethanesulfonyloxy and pentafluoroethanesulfonyloxy groups; and arylsulfonyloxy groups, such as the benzenesulfonyloxy, p-toluenesulfonyloxy and p-nitrobenzenesulfonyloxy groups. Of these, we prefer the halogen atoms, lower haloalkanesulfonyloxy groups and arylsulfonyloxy groups.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

There is no particular limitation upon the nature the base used in Method 1, and any base which can be used in conventional reactions of this type may equally be used here. Examples of preferred bases include: organic bases, such as N-methylmorpholine, triethylamine, tributylamine, diisopropylethylamine, dicyclohexylamine, N-methylpiperidine, pyridine, 4-(1-pyrrolidinyl)pyridine, picoline, 4-(N,N-dimethylamino)pyridine, 2,6-di-t-butyl-4-methylpyridine, quinoline, N,N-dimethylaniline and N,N-diethylaniline. If desired, it is possible to use a catalytic amount of 4-(N,N-dimethylamino)pyridine, 4-(1-pyrrolidinyl)pyridine in combination with other bases. In order to promote the reaction effectively, a quaternary ammonium salt (such as benzyltriethylammonium chloride or tetrabutylammonium chloride) or a crown ethers (such as dibenzo-18-crown-6) may be added to the reaction system.

The reaction can take place over a wide range of temperatures, and the precise reaction temperature is not critical to the invention. In general, we find it convenient to carry out the reaction at a temperature of from −20° C. to the reflux temperature of the solvent used, more preferably from 0° C. to the reflux temperature of the solvent used. The time required for the reaction may also vary widely, depending on many factors, notably the reaction temperature and the nature of the reagents, base and solvent employed. However, provided that the reaction is effected under the preferred conditions outlined above, a period of from 10 minutes to 3 days, more preferably from 1 to 6 hours, will usually suffice.

Method 2

This method comprises reacting a compound of formula (VI) with a compound of formula: $R^{3'}$—OH (wherein $R^{3'}$ is as defined above and preferably represents an acyl group) in a solvent in thee presence of an esterifying agent, such as those exemplified above in Method 2 of Step A2, and a catalytic amount of a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

Examples of the bases which may be used in Method 2 are the same as those described for use in foregoing Method 1.

The reaction can take place over a wide range of temperatures, and the precise reaction temperature is not critical to the invention. In general, we find it convenient to carry out the reaction at a temperature of from −20° to 80° C., more preferably from 0° C. to about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to one day, will usually suffice.

Method 3

This method comprises reacting a compound of formula (VI) with a compound of formula: $R^{3'}$—OH (wherein $R^{3'}$ is as defined above and preferably represents an acyl group) in a solvent in the presence of halogenated phosphoric acid dialkyl ester, such as diethyl chlorophosphate, and a base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

Examples of the bases which may be used in Method 3 are the same as those described for use in foregoing Method 1.

The reaction can take place over a wide range of temperatures, and the precise reaction temperature is not critical to the invention. In general, we find it convenient to carry out the reaction at a temperature of from 0° C. to the reflux temperature of the solvent used, more preferably from about room temperature to 50° C. The time required for the reaction may also vary widely, depending on many factors, notably the reaction temperature and the nature of the reagents and solvent employed. However, provided that the reaction is effected under the preferred conditions outlined above, a period of from 10 minutes to 3 days, more preferably from 30 minutes to one day, will usually suffice.

Where $R^{3'}$ represents a lower alkyl group, this may be introduced into the compound of formula (VI) by conventional means, for example, by reacting the compound of formula (VI) with a dialkyl sulfate, such as dimethyl sulfate or diethyl sulfate.

By utilizing protecting reagents having different reactivities, it is possible to prepare a compound having two hydroxy groups which are protected by different groups $R^{3'}$.

After completion of the reaction, the desired compound of formula (VII) can be recovered from the reaction mixture by conventional means. For example, in one suitable recovery procedure: the reaction mixture is neutralized; if insoluble materials exist, they are removed by filtration; water and a water-immiscible solvent, such as ethyl acetate, are added to the reaction mixture or the neutralized reaction mixture, and the product is extracted into the solvent; the extract is washed with water and dried, for example, over anhydrous magnesium sulfate; and then the solvent is distilled off, leaving the desired product.

The compound thus obtained may, if necessary, be purified by conventional means, for example, by recrystallization, reprecipitation or the various chromatographic techniques. Examples of suitable chromatographic techniques include: absorption column chromatography through a carrier, such as silica gel, alumina or Florisil (containing magnesium-silica gel); partition column chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); column chromatography through a regular or reverse phase column packed with silica gel or with an alkylated silica gel (preferably high performance liquid chromatographyl); or a combination of these techniques; followed by elution with a suitable eluting solvent.

Stem A4

In this step, an ester compound of formula (VIII) is prepared by acylating a hydroxy group at the 8-position of a compound of formula (VII) with a group of Z. The reaction is carried out following the procedure described in Step A3, using any one of the methods described below:

Method 1

This comprises reacting a compound of formula (VII) with a suitable amount, for example from 1 to 4 equivalents (more preferably from 2 to 3 equivalents) of a compound of formula: Z—X or Z—O—Z (wherein Z and X are as defined above) in a solvent in the presence or absence of a base.

Method 2

This comprises reacting a compound of formula (VII) with a compound of formula: Z—OH (wherein Z is as defined above) in a solvent in the presence of an esterifying agent, such as those exemplified above in Method 2 of Step A2, and a catalytic amount of a base.

Method 3

This comprises reacting a compound of formula (VII) with a compound of formula: Z—OH (wherein Z is as defined above) in a solvent in the presence of halogenated phosphoric acid diethyl ester, such as diethyl chlorophosphate and a base.

Step A5

In this step, a compound of formula (IX) is prepared by removing the hydroxy-protecting group represented by $R^{3'}$ from the compound of formula (VIII) and, if desired, then protecting some or all of the resulting free hydroxy groups with the same or different protecting groups, preferably ones capable of being cleaved in vivo by biological methods, such as hydrolysis.

The reaction conditions employed to remove the hydroxy-protecting group represented by $R^{3'}$ will vary, depending upon the nature of the protecting group but the reaction is generally carried out by means well-known in the art, for example as follows.

Removal with a Fluoride Anion or an Organic Acid

Where the hydroxy-protecting group is a silyl group, it can usually be eliminated by treating the protected compound with a compound capable of producing a fluoride anion, such as tetrabutylammonium fluoride or hydrofluoric acid, or by treating it with an organic acid, such as methanesulfonic acid, p-toluenesulfonic acid, trifluoroacetic acid or trifluoromethanesulfonic acid. Where a fluoride anion is employed as the deprotecting agent, the reaction can sometimes be accelerated by adding an organic acid, such as formic acid, acetic acid or propionic acid. This removal reaction has the advantage that side reactions are suppressed.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: ethers, such as diethyl ether, diisopropyl ether, tetrahydrofuran, dioxane, dimethyoxyethane and diethylene glycol dimethyl ether; and nitriles, such as acetonitrile and isobutyronitrile.

The reaction can take place over a wide range of temperatures, and the precise reaction temperature is not critical to the invention. In general, we find it convenient to carry out the reaction at a temperature of from 0° C. to 50° C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 2 to 24 hours will usually suffice.

Removal by Reduction or Oxidation

Where the hydroxy-protecting group is an aralkyl or aralkyloxycarbonyl group, it can preferably be removed by contacting the protected compound with a reducing agents (preferably by catalytic reduction employing hydrogen in the presence of a catalyst, for example at about room temperature) in a solvent or by using an oxidizing agent.

The reduction reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: alcohols, such as ethanol and isopropanol; ethers, such as diethyl ether, tetrahydrofuran and dioxane; aromatic hydrocarbons, such as toluene, benzene and xylene; aliphatic hydrocarbons, such as hexane and cyclohexane; esters, such as ethyl acetate and propyl acetate; amides, such as formamide, dimethylformamide, dimethylacetamide, N-methyl-2-pyridone and hexamethylphosphoric triamide; aliphatic acids, such as formic acid and acetic acid; or water. A single one of these solvents or a mixture of two or more of them may be used. Of these, we prefer the alcohols, the aliphatic acids, a mixture of an alcohol and an ether, a mixture of an alcohol and water, or a mixture of an aliphatic acid and water.

There is no particular limitation upon the nature of the catalyst used, and any catalyst commonly used in catalytic reduction may equally be used here. Examples of preferred catalysts include: palladium-on-charcoal, palladium black, Raney nickel, platinum oxide, platinum black, rhodium-on-alumina, a combination of triphenylphosphine and rhodium chloride and palladium-on-barium sulfate.

The hydrogen pressure used in the reaction is critical but the reaction is normally carried out at a pressure between ambient pressure and 10 atmospheres.

The reaction can take place over a wide range of temperatures, and the precise reaction temperature is not critical to the invention, although the preferred temperature may vary depending upon such factors as the nature of the reagents and the catalyst. In general, we find it convenient to carry out the reaction at a temperature of from 0° C. to 100° C., more preferably from 20° C. to 70° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 1 to 24 hours, will usually suffice.

In the case of the oxidation reaction, the reaction is likewise normally and preferably effected in the presence of a solvent. There is also no particular restriction on the nature of the solvent to be employed, provided that it has no adverse effect on the reaction or on the reagents involved and that it can dissolve the reagents, at least to some extent. Examples of suitable solvents include aqueous organic solvents. Examples of such organic solvents include: ketones, such as acetone; halogenated hydrocarbons, such as methylene chloride, chloroform and carbon tetrachloride; nitriles, such as acetonitrile; ethers, such as diethyl ether, tetrahydrofuran and dioxane; amides, such as dimethylformamide, dimethylacetamide and hexamethylphosphoric triamide; and sulfoxides, such as dimethyl sulfoxide.

There is no particular limitation upon the nature of the oxidizing agent used, and any oxidizing agent commonly used in conventional oxidation reactions of this type may equally be used here. Examples of preferred oxidizing agents include: potassium persulfate, sodium persulfate, cerium ammonium nitrate (CAN) and 2,3-dichloro-5,6-dicyano-p-benzoquinone (DDQ).

The reaction can take place over a wide range of temperatures, and the precise reaction temperature is not critical to the invention. In general, we find it convenient to carry out the reaction at a temperature of from 0° C. to 150° C. The time required for the reaction may also vary widely, depending on many factors, notably the reaction temperature and the nature of the reagents and solvent employed. However, provided that the reaction is effected under the preferred conditions outlined above, a period of from 10 minutes to 24 hours will usually suffice.

Removal by Treatment with an Alkali Metal

The protecting group can be eliminated by treatment with an alkali metal, such as lithium metal or sodium metal, in liquid ammonia or in an alcohol, such as methanol or ethanol, at a suitable temperature, for example a temperature of from −78° C. to −20° C.

Removal by Treatment with Aluminum Chloride

It is also possible to remove the protecting group by contacting the protected compound with a mixture of aluminium chloride with sodium iodide or with an alkylsilyl halide, such as trimethylsilyl iodide.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: nitriles, such as acetonitrile; and halogenated hydrocarbons, such as methylene chloride and chloroform. A single one of these solvents or a mixture of two or more of them may be used.

The reaction can take place over a wide range of temperatures, and the precise reaction temperature is not critical to the invention. In general, we find it convenient to carry out the reaction at a temperature of from 0° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 3 days will usually suffice.

Where the reaction substrate contains a sulfur atom, it is preferred to use a mixture of aluminium chloride and sodium iodide.

Removal by Treatment with a Base

Where the hydroxy-protecting group is an aliphatic acyl, aromatic acyl or alkoxycarbonyl group, the protecting group can be removed by treating the protected compound with a base in a solvent.

There is no particular limitation upon the nature of the base used, provided that other parts of the compound are not affected when the protecting group is removed. Examples of preferred bases include: metal alkoxides, such as sodium methoxide; alkali metal carbonates, such as sodium carbonate, potassium carbonate and lithium carbonate; alkali metal hydroxides, such as sodium hydroxide, potassium hydroxide, lithium hydroxide and barium hydroxide; and ammonia, for example in the form of aqueous ammonia or of a mixture of concentrated ammonia and methanol.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; organic solvents, for example, alcohols, such as ethanol and propanol; ethers, such as tetrahydrofuran and dioxane; or a mixture of water and any one or more of these organic solvents.

The reaction can take place over a wide range of temperatures, and the precise reaction temperature is not critical to the invention. In general, we find it convenient to carry out the reaction at a temperature of from 0° C. to 150° C. The time required for the reaction may also vary widely, depending on many factors, notably the reaction temperature and the nature of the reagents and solvent employed. However, provided that the reaction is effected under the preferred conditions outlined above, a period of from 1 to 10 hours will usually suffice.

Where the hydroxy-protecting group is an alkenyloxycarbonyl group, deprotection may also be accomplished by treatment with a base and the reaction conditions are similar to those employed when the hydroxy-protecting group is an aliphatic acyl, aromatic acyl or alkoxycarbonyl group.

Removal by Treatment with an Acid

Where the hydroxy-protecting group is an alkoxymethyl, tetrahydropyranyl, tetrahydrothiopyranyl, tetrahydrofuranyl, tetrahydrothienyl or substituted ethyl group, it can normally be removed by treating the protected compound with an acid.

There is no particular limitation upon the nature of the acid used, and any acid commonly used for this purpose, including Brønsted acids and Lewis acids, may equally be used here. Examples of preferred acids include: inorganic acids, such as hydrogen chloride; hydrochloric acid, sulfuric acid or nitric acid; Brönsted acids, including organic acids, such as acetic acid, trifluoroacetic acid, methanesulfonic acid or p-toluenesulfonic acid; Lewis acids, such as boron trifluoride; and strongly acidic cation resins such as Dowex-50W™.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; esters, such as ethyl formate, ethyl acetate, propyl acetate, butyl acetate and diethyl carbonate; ethers, such as diethyl ether, diisopropyl ether, tetrahydrofuran, dioxane, dimethoxyethane and diethylene glycol dimethyl ether; alcohols, such as ethanol, propanol, isopropanol, butanol, isobutanol, t-butanol, isoamyl alcohol, diethylene glycol, cyclohexanol and methyl cellosolve; ketones, such as acetone, methyl ethyl ketone, methyl isobutyl ketone, isophorone and cyclohexanone; or water. A single one of these solvents or a mixture of two or more of them may be used. Of these, we prefer the halogenated hydrocarbons, esters and ethers.

The reaction can take place over a wide range of temperatures, and the precise reaction temperature is not critical to the invention. In general, we find it convenient to carry out the reaction at a temperature of from −10° C. to 100° C., more preferably −5° C. to 50° C. The time required for the reaction may also vary widely, depending on many factors, notably the reaction temperature and the nature of the reagents and solvent employed. However, provided that the reaction is effected under the preferred conditions outlined above, a period of from 5 minutes to 48 hours, more preferably from 30 minutes to 10 hours, will usually suffice.

Removal with Palladium and Triphenylphosphine or Nickel Tetracarbonyl

Where the hydroxy-protecting group is an aryloxycarbonyl group, it can simply be removed by using a combination of palladium and triphenylphosphine or nickel tetracarbonyl, which has the advantage that side reactions are suppressed.

Introduction of a Hydroxy-Protecting Group

If desired, the resulting free hydroxy group may be subsequently protected with a protecting group, especially with a protecting group capable of being cleaved in vivo by biological methods, such as hydrolysis. This may be carried out using a corresponding reagent containing the desired protecting group following the procedure described in Step A3.

Where there is more than one hydroxy group to be protected, they can be protected with the same protecting group or with different protecting groups, for example:

(1) where two hydroxy groups are protected by different protecting groups each repesented by $R^{3'}$, each of these groups may be eliminated selectively and the resulting free hydroxy group may then be protected one at a time with appropriate protecting reagents to produce a compound having hydroxy groups protected by different groups $R^3$; or (2) two hydroxy groups are protected with different protecting groups represented by $R^3$ by utilizing the difference between the reactivities of the protecting reagents, as is well known in the art.

After completion of the reaction, the desired compound of formula (IX) can be recovered from the reaction mixture by conventional means. For example, in one suitable recovery procedure: the reaction mixture is neutralized; if insoluble materials exist, they are removed by filtration; water and a water-immiscible solvent, such as ethyl acetate, are added to the filtrate or the neutralized reaction mixture, and the product is extracted into the solvent; the extract is washed with water and dried, for example over anhydrous magnesium sulfate; and then the solvent is distilled off from the extract, leaving the desired product as the residue.

The desired compound thus obtained may, if necessary, be purified by conventional means, for example, recrystallization, reprecipitation or the various chromatographic techniques. Examples of suitable chromatographic techniques include: absorption column chromatography through a carrier such as silica gel, alumina or Florisil (containing magnesium and silica gel); partition column chromatography through an absorbent, such as Sephadex™ LH-20 (Pharmacia Inc.), Amberlite™ XAD-11 (Rohm and Haas Co.) or Diaion™ (Mitsubishi Kasei Corporation); liquid chromatography through a regular or reverse phase column packed with silica gel or with an alkylated silica gel (preferably high performance liquid chromatography); or a combination of these techniques; followed by elution with a suitable eluting solvent.

Step A6

In this step, a compound of formula (X), which is a compound of the present invention, is prepared by hydrolysis or solvolysis of the lactone ring of the compound of formula (IX) to produce a salt of a carboxylic acid or a carboxylic acid ester. The reaction can, if desired, be conducted by:

(1) producing a free carboxylic acid;

(2) protecting some or all of the free hydroxy groups with the same or different protecting groups, preferably capable of being cleaved in vivo by biological methods, such as hydrolysis;

(3) protecting the resulting carboxy group with a protecting group, preferably one capable of being cleaved in vivo by biological methods, such as hydrolysis, or producing another salt of the carboxylic acid; and/or (4) if desired, subjecting the carboxylic acid compound to ring-closure again to produce a lactone compound.

The preparation of the salt of a carboxylic acid may be effected by a conventional hydrolysis reaction using a base, preferably from 1 to 2 moles of the base.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include water or a mixture of water with one or more organic solvents, for example: ethers, such as tetrahydrofuran, dioxane or diethylene glycol dimethyl ether; alcohols, such as ethanol, propanol, isopropanol, butanol or isobutanol; ketones, such as acetone or methyl ethyl ketone; nitriles, such as acetonitrile or isobutyronitrile; and amides, such as formamide, dimethylformamide, dimethylacetamide, N-methyl-2-pyrolidone, N-methylpyrrolidinone or hexamethylphosphoric triamide.

There is also no particular limitation upon the nature of the base used, and any base commonly used in conventional reactions may equally be used here. Examples of preferred bases include: alkali metal carbonates, such as sodium carbonate, potassium carbonate or lithium carbonate; alkali metal hydrogencarbonates, such as sodium hydrogencarbonate, potassium hydrogencarbonate or lithium hydrogencarbonate; alkali metal hydroxides, such as sodium hydroxide, potassium hydroxide, calcium hydroxide, barium hydroxide or lithium hydroxide; and alkali metal alkoxides, such as sodium methoxide, sodium ethoxide, potassium methoxide, potassium ethoxide, potassium t-butoxide or lithium methoxide.

The reaction will take place over a wide range of temperatures, and the precise reaction temperature chosen is not critical to the invention. In general, we find it convenient to carry out the reaction at a temperature in the range of from $-10°$ C. to $100°$ C., more preferably from $0°$ C. to about room temperature. The time required for the reaction may likewise vary widely, depending on many factors, notably the reaction temperature, the base used and the nature of the reagents. However, in most cases, a period of from 30 minutes to 10 hours, more preferably from 1 to 5 hours, will normally suffice.

The reaction for preparing the carboxylic acid ester can be effected by solvolysis in the presence of an acid catalyst and a solvent containing an alcohol.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether, diisopropyl ether, tetrahydrofuran, dioxane, dimethoxyethane or diethylene glycol dimethyl ether; ketones, such as acetone, methyl ethyl ketone, methyl isobutyl ketone, isophorone or cyclohexanone; nitriles, such as acetonitrile or isobutyronitrile; and amides, such as formamide, dimethylformamide, dimethylacetamide, N-methyl-2-pyrrolidone, N-methylpyrrolidinone or hexamethylphosphoric triamide. However, we prefer to use as the solvent the alcohol which corresponds to the ester residue which it is desired to introduce, by itself.

There is likewise no particular limitation upon the nature of the acid catalyst used, and any acid commonly used as a catalyst in conventional reactions may equally be used here. Examples of preferred acid catalysts include: inorganic acids, such as hydrochloric acid, hydrobromic acid, sulfuric acid, perchloric acid or phosphoric acid; Brønsted acids, for example, organic acids, including carboxylic acids (such as acetic acid, oxalic acid, formic acid and trifluoroacetic acid) and sulfonic acids (such as methanesulfonic acid, p-toluenesulfonic acid and trifluoromethanesulfonic acid); Lewis acids, such as boron trichloride, boron trifluoride or boron tribromide; and acidic ion-exchange resins. Of these, we prefer the organic acids, and more preferably strong organic acids.

The reaction will take place over a wide range of temperatures, and the precise reaction temperature chosen is not critical to the invention. In general, we find it convenient to carry out the reaction at a temperature in the range of from 0° C. to the boiling point of the solvent used, more preferably from 50° C. to the boiling point of the solvent used. The time required for the reaction may likewise vary widely, depending on many factors, notably the reaction temperature and the nature of the reagents and the solvent used. However, in most cases, a period of from 10 minutes to 6 days, more preferably from 30 minutes to 3 days, will normally suffice.

After completion of the reaction, the desired compound can be recovered from the reaction mixture by conventional means. For example, where the reaction is carried out using acidic ion-exchange resin as the acid catalyst, a suitable recovery procedure comprises: filtering the reaction mixture, and then removing the solvent by distillation from the filtrate, leaving the desired product as the residue. Where the reaction is carried out using another acid as the acid catalyst, a suitable recovery procedure comprises: neutralizing the reaction mixture; if insoluble materials exist, removing them by filtration; adding water and a water-immiscible solvent, such as ethyl acetate, to the neutralized reaction mixture or to the filtrate, and extracting the product into the solvent; washing the extract with water and drying it, for example over anhydrous magnesium sulfate; and then removing the solvent by distillation, leaving the product as the residue.

The desired product thus obtained, if necessary, is purified by conventional means, for example, by recrystallization, reprecipitation or the various chromatographic techniques. Exampes of such chromatographic techniques include: partition column chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); liquid chromatography through a regular or reverse phase column packed with silica gel or with an alkylated silica gel (preferably high performance liquid chromatography); or a suitable combination of these techniques; followed by elution with a suitable eluting solvent.

Preferably, a free carboxylic acid is prepared by adjusting the pH of the filtrate containing a salt of carboxylic acid obtained above to less than pH 5, preferably to a pH of from 3 to 4, by adding a suitable acid.

There is no particular limitation upon the type of the acid used, and any organic acid or mineral acid may be used, provided that it has no adverse effect upon the desired compound. Examples of preferred acids include: inorganic acids, such as hydrochloric acid, hydrobromic acid, sulfuric acid, perchloric acid or phosphoric acid; Brönsted acids including organic acids, such as acetic acid, formic acid, oxalic acid, methanesulfonic acid, p-toluenesulfonic acid, trifluoroacetic acid or trifluoromethanesulfonic acid; and acidic ion-exchange resins.

The free carboxylic acid compound thus obtained may be recovered and purified by conventional means, for example, by extraction, washing, drying or the like and then can be used in the following reactions.

The hydroxy group of the resulting compound (which contains a carboxylic acid salt group, a carboxylic acid ester group or a free carboxylic acid group in its molecule) can be protected, preferably by a protecting group capable of being cleaved in vivo by biological methods, such as hydrolysis. The reaction conditions employed for introducing this protecting group are similar to those employed in Step A5.

Where the product includes a group of formula (II) containing two free hydroxy groups, the hydroxy groups can be protected simultaneously by a diol-protecting group, such as an isopropylidene, benzylidene or ethylidene group, by reacting the compound with a suitable reagent, in the presence of an acid catalyst.

There is no particular limitation upon the nature of the reagent used to introduce the diol protecting group, and any such reagent commonly used in the protection of a diol group my equally be used here. Examples of preferred reagents include: aldehyde derivatives, such as benzaldehyde; ketone derivatives, such as acetone; and dimethoxy compounds, such as 2,2-dimethoxypropane or dimethoxybenzyl.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: halogenated hydrocarbons, such as methylene chloride or chloroform; ethers, such as dioxane or tetrahydrofuran; aliphatic hydrocarbons, such as hexane or pentane; aromatic hydrocarbons, such as benzene or toluene; esters, such as ethyl acetate; and polar solvents, such as dimethylformamide or acetone.

There is no particular limitation upon the nature of the acid catalyst used, and any acid commonly used as a catalyst in conventional reactions of this type may equally be used here. Examples of preferred acid catalysts include: organic acids, such as p-toluenesulfonic acid, camphorsulfonic acid and pyridinium p-toluenesulfonate; and inorganic acids, such as hydrochloric acid.

The reaction will take place over a wide range of temperatures, and the precise reaction temperature chosen is not critical to the invention, although the preferred temperature will vary, depending upon the nature of the acid catalyst and starting compound used. However, in general, we find it convenient to carry out the reaction at a temperature in the range of from 0° C. to 100° C. The time required for the reaction may likewise vary widely, depending on many factors, notably the reaction temperature and the nature of the reagents. However, in most cases, a period of from 0.1 to 24 hours will normally suffice.

Where the protecting group capable of being cleaved in vivo by biological methods used as the carboxy-protecting group is an alkyl or analogous group, the compound containing a carboxylic acid salt group or a free carboxylic acid group can be protected by the following methods:

Method 1

In this method, the compound to be protected is reacted with a compound of formula $R^{4''}—X'$ (wherein $R^{4''}$ represents a protecting group capable of being cleaved in vivo by biological methods, included in the definition of $R^4$, and $X'$ represents a group or atom capable of leaving as a nucleophilic residue). Examples of groups and atoms capable of leaving as a nucleophilic residue include: halogen atoms, such as the chlorine, bromine and iodine atoms; lower alkanesulfonyloxy groups, such as the methanesulfonyloxy and ethanesulfonyloxy groups; haloalkanesulfonyloxy groups, such as the trifluoromethanesulfonyloxy and pentafluoroethanesulfonyloxy groups; and arylsulfonyloxy groups, such as the benzenesulfonyloxy, p-toluenesulfonyloxy and p-nitrobenzenesulfonyloxy groups. Examples of such compounds include: aliphatic acyloxymethyl halides, such as acetoxymethyl chloride, pivaloyloxymethyl bromide and pivaloyloxymethyl chloride; lower alkoxycarbonyloxyalkyl halides, such as ethoxycarbonyloxymethyl chloride, isopropoxycarbonyloxymethyl chloride, 1-(ethoxycarbonyloxy)ethyl chloride and 1-(ethoxycarbonyloxy)ethyl iodide; phthalidyl halides; and (5-methyl-2-oxo-5-methyl-1,3-dioxolen-4-yl)methyl halides.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aliphatic hydrocarbons, such as hexane or heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide.

The reaction is also effected in the presence of a base. There is no particular limitation upon the nature of the base used, and any base commonly used in conventional reactions of this type may equally be used here. Examples of preferred bases include: alkali metal carbonates, such as sodium carbonate, potassium carbonate and lithium carbonate; alkali metal hydrogencarbonates, such as sodium hydrogencarbonate, potassium hydrogencarbonate and lithium hydrogencarbonate; alkali metal hydrides, such as lithium hydride, sodium hydride and potassium hydride; alkali metal hydroxides, such as sodium hydroxide, potassium hydroxide, barium hydroxide and lithium hydroxide; alkali metal fluorides, such as sodium fluoride and potassium fluoride; alkali metal alkoxides, such as sodium methoxide, sodium ethoxide, potassium methoxide, potassium ethoxide, potassium t-butoxide and lithium methoxide; alkali metal alkylthiolates, such as sodium methylthiolate and sodium ethylthiolate; organic bases, such as N-methylmorpholine, triethylamine, tributyl-amine, diisopropylethylamine, dicyclohexylamine, N-methylpiperidine, pyridine, 4-(1-pyrrolidinyl)pyridine, picoline, 4-(N,N-dimethylamino)pyridine, 2,6-di(t-butyl)-4-methylpyridine, quinoline, N,N-dimethylaniline, N,N-diethylaniline, 1,5-diazabicyclo[4.3.0]nona-5-ene, 1,4-diazabicyclo[2.2.2]octane (DABCO) and 1,8-diazabicyclo[5.4.0]undec-7-ene (DBU); and organic metal bases, such as butyllithium, lithium diisopropylamide and lithium bis(trimethylsilyl)amide.

The reaction will take place over a wide range of temperatures, and the precise reaction temperature chosen is not critical to the invention. In general, we find it convenient to carry out the reaction at a temperature in the range of from −20° C. to 120° C., more preferably from 0° C. to 80° C. The time required for the reaction may likewise vary widely, depending on many factors, notably the reaction temperature and the nature of the reagents. However, in most cases, a period of from 0.5 to 10 hours will normally suffice.

Method 2

This method comprises reacting the unprotected compound with a compound of formula $R^4$—OH (wherein $R^{4''}$ is as defined above) in a solvent in the presence of an esterifying agent and a catalytic amount of a base. The reaction is carried out following the procedure described in Method 2 of Step A3.

Method 3

This method comprises reacting the unprotected compound with a compound of formula $R^4$—OH (wherein $R^{4''}$ is as defined above) in a solvent in the presence of a halogenated phosphoric acid diethyl ester, such as diethyl chlorophosphate, and a base. The reaction is carried out following the procedure described in Method 3 of Step A3.

Method 4

This method may be used where the protecting group is a lower alkyl group and comprises reacting the unprotected compound with the corresponding alcohol used as a reagent, such as methanol, ethanol, propanol and butanol in a solvent. There is no particular limitation upon the nature of the solvent used, provided that it has no adverse effect upon the reaction and that it can dissolve a starting material, at least to some extent. Examples of preferred solvents include: the same alcohols as used as the reagent; aliphatic hydrocarbons, such as hexane and heptane; aromatic hydrocarbons, such as benzene, toluene and xylene; halogenated hydrocarbons, such as methylene chloride, chloroform, carbon tetrachloride, dichloroethane, chlorobenzene and dichlorobenzene; ethers, such as diethyl ether, diisopropyl ether, tetrahydrofuran, dioxane, dimethoxyethane and diethylene glycol dimethyl ether; ketones, such as acetone, methyl ethyl ketone, methyl isobutyl ketone, isophorone and cyclohexanone; nitriles, such as acetonitrile and isobutyronitrile; and amides, such as formamide, dimethylformamide, dimethylacetamide, N-methyl-2-pyrrolidone, N-methylpyrrolidinone and hexamethylphosphoric triamide. Of these, we prefer to use the same alcohols as are used as the reagent. The reaction is effected in the presence of an acid catalyst. There is no particular limitation upon the nature of the acid catalyst used, and any acid commonly used as a catalyst in conventional reactions of this type may equally be used here. Examples of preferred acid catalysts include: inorganic acids, such as hydrochloric acid, hydrobromic acid, sulfuric acid, perchloric acid and phosphoric acid; Brönsted acids including organic acids, such as acetic acid, formic acid, oxalic acid, methanesulfonic acid, p-toluenesulfonic acid, trifluoroacetic acid and trifluoromethanesulfonic acid; Lewis acids, such as boron trichloride, boron trifluoride and boron tribromide; and acidic ion-exchange resins.

The reaction will take place over a wide range of temperatures, and the precise reaction temperature chosen is not critical to the invention. In general, we find it convenient to carry out the reaction at a temperature in the range of from 0° C. to 100° C., more preferably from 20° C. to 60° C. The time required for the reaction may likewise vary widely, depending on many factors, notably the reaction temperature and the nature of the reagents. However, in most cases, a period of from 1 to 24 hours will normally suffice.

Method 5

This method comprises reacting the unprotected carboxylic acid compound with either:

(i) a halogenating agent, for example phosphorus pentachloride, thionyl chloride or oxalyl chloride, at a suitable temperature, for example about room temperature, for a suitable period, for example a period of from 30 minutes to 5 hours, to produce the corresponding acid halide, or (ii) a chloroformate, such as methyl chloroformate or ethyl chloroformate, in the presence of an organic amine (such as triethylamine), which may be carried out at a similar temperature and for a similar time to those in (i) above, to produce the corresponding acid anhydride;

followed by treating the resulting acid anhydride or acid halide with a suitable alcohol or alkali metal alkoxide to give the desired ester. To prepare the t-butyl ester, the use of potassium t-butoxide is preferred.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: aromatic hydrocarbons, such as benzene, toluene and xylene; halogenated hydrocarbons, such as methylene chloride and chloroform; esters, such as ethyl acetate and propyl acetate; ethers, such as diethyl ether, tetrahydrofuran, dioxane and dimethoxyethane; and nitriles, such as acetonitrile. It is also effected in the presence of a base, the nature of which is not critical, for example triethylamine. The reaction can take place over a wide range of temperatures, and the precise reaction temperature is not critical to the invention. In general, we find it convenient to carry out the reaction at a temperature of from $-10°$ C. to $150°$ C., more preferably at about room temperature. The time required for the reaction may also vary widely, depending on many factors, notably the reaction temperature and the nature of the reagents and solvent employed. However, provided that the reaction is effected under the preferred conditions outlined above, a period of from 10 minutes to 15 hours, more preferably from 30 minutes to 10 hours, will usually suffice.

Method 6

This method comprises reacting the unprotected free carboxylic acid compound with a diazoalkane, such as diazomethane or diazoethane (generally an ethereal solution of the diazoalkane) at a suitable temperature, for example about room temperature, but, if necessary, the reaction is carried out with heating.

Alternatively, a carboxylic acid ester may be used as the starting compound, in which case, the desired compound can be prepared by conventional means, that is by transesterification with a compound of formula $R^{4"}$—OH, wherein $R^{4"}$ is as defined above.

Where the carboxy-protecting group capable of being cleaved in vivo by biological methods is an amide-type group, the protecting reaction may be accomplished by:

Method 7

This method comprises converting a salt of the carboxylic acid or the free carboxylic acid, which may have been prepared as described above, to an acid halide or acid anhydride following the procedure described in Method 5, and then reacting the acid halide or acid anhydride with the corresponding base, for example gaseous ammonia or dimethylamine.

Method 8

This method comprises subjecting a carboxylic acid ester, which may have been prepared as described above in Methods 1 to 6, to a conventional ester-amide interchange reaction.

Preparation of Salts

Reactions which produce a salt of the carboxylic acid may be carried out as follows:

(1) Metal Salts of Carboxylic Acids

The desired salt can be prepared by contacting a free carboxylic acid with a suitable metal compound, for example from a metal hydroxide or a metal carbonate, in an aqueous solvent.

Examples of preferred aqueous solvents include water itself or a mixture of water and an organic solvent such as: an alcohol, for example methanol or ethanol; or a ketone, for example acetone. We especially prefer to use a mixture of water and a hydrophilic organic solvent.

In general, the reaction is preferably carried out at about room temperature or, if necessary, it may optionally be conducted with heating.

(2) Amine Salts of Carboxylic Acids

The desired salt can be prepared by contacting a free carboxylic acid with a suitable amine in an aqueous solvent.

Examples of preferred aqueous solvents include water itself or a mixture of water and an organic solvent such as: an alcohol, for example methanol or ethanol; an ether, for example tetrahydrofuran; or a nitrile, for example acetonitrile. Of these, we particularly prefer aqueous acetone.

In general, the reaction is preferably carried out in the pH range of from 7.0 to 8.5 at a temperature below room temperature, particularly at a temperature from $5°$ C. to $10°$ C. It goes immediately to completion.

Alternatively, the desired salt can be prepared by a salt-amine inter-exchange reaction, that is, by dissolving a metal salt of carboxylic acid, which may have been prepared as described in (i) above, in an aqueous solvent and then adding a mineral acid salt of the desired amine (for example a salt of hydrohalic acid, such as the hydrochloride). The reaction may be effected under the same conditions as described above.

(3) Amino Acid Salts of Carboxylic Acids

The desired salt can be prepared by contacting a free carboxylic acid with the desired amino acid in an aqueous solvent.

Examples of preferred aqueous solvents include water itself or a mixture of water and an organic solvent such as: an alcohol, for example methanol or ethanol; or an ether, such as tetrahydrofuran.

The reaction is normally carried out with heating, preferably at a temperature of from $50°$ C. to $60°$ C.

Preparation of a Lactone

The desired lactone compound can be prepared by contacting the carboxylic acid compound prepared as described above with a catalytic amount of an acid.

The reaction is normally and preferably effected in the presence of a solvent. There is no particular restriction on the nature of the solvent to be employed, provided that it has no adverse effect on the reaction or on the reagents involved and that it can dissolve the reagents, at least to some extent. Examples of suitable solvents include: water; ethers, such as tetrahydrofuran, dioxane, dimethoxyethane and diethylene glycol dimethyl ether; ketones, such as acetone and methyl ethyl ketone; nitriles, such as acetonitrile and isobutyronitrile; amides, such as formamide, dimethylformamide, dimethylacetamide, N-methyl-2-pyrrolidone and hexamethylphosphoric triamide; sulfoxides, such as dimethyl sulfoxide and sulfolane; or a mixture of one or more of these organic solvents with water.

There is no particular limitation upon the nature of the acid catalyst used, and any acid catalyst commonly used in conventional reactions of this type may equally be used here. Examples of preferred acid catalysts include: inorganic acids, such as hydrochloric acid, hydrobromic acid, sulfuric acid, perchloric acid and phosphoric acid; Brönsted acids including organic acids, such as acetic acid, formic acid, oxalic acid, methanesulfonic acid, p-toluenesulfonic acid, trifluoroacetic acid and trifluoromethanesulfonic acid; Lewis acids, such as zinc chloride, tin tetrachloride, boron trichloride, boron trifluoride and boron tribromide; and acidic ion-exchange resins. Of these, we prefer the inorganic acids.

The reaction can take place over a wide range of temperatures, and the precise reaction temperature is not critical to the invention. In general, we find it convenient to carry out the reaction at a temperature of from −20° C. to 170° C., more preferably from 0° C. to 50° C. The time required for the reaction may also vary widely, depending on many factors, notably the reaction temperature and the nature of the reagents and solvent employed. However, provided that the reaction is effected under the preferred conditions outlined above, a period of from 10 minutes to one day will usually suffice.

After completion of the reaction, the resulting compound of formula (X) can be recovered and purified by any suitable combination of various kinds of recovery and purification methods, such as those described and exemplified above, notably the various chromatography techniques. Examples of such techniques include: partition column chromatography through a synthetic absorbent such as Sephadex™ LH-20 (Pharmacia Inc.), Amberlite™ XAD-11 (Rohm and Haas Co.) or Diaion™ HP-20 (Mitsubishi Kasei Corporation); ion-exchange chromatography; gel filtration through a Sephadex column; liquid chromatography through a regular or reverse phase column packed with silica gel or with an alkylated silica gel (preferably high performance liquid chromatography); or any suitable combination of these chromatographic methods; The desired compound may then be eluted with a suitable eluting solvent. Otherwise the product may effectively be extracted with an organic solvent, such as diethyl ether, ethyl acetate or chloroform.

Where the desired compound obtained in the steps described above is produced as a mixture of stereoisomers and the resolution of individual isomers is required, each of the isomers can be separated and purified by conventional methods described above at the end of each reaction or at any desired time after completion of each reaction.

REACTION SCHEME B

An alternative method of preparing compounds of the present invention is shown in Reaction Scheme B:

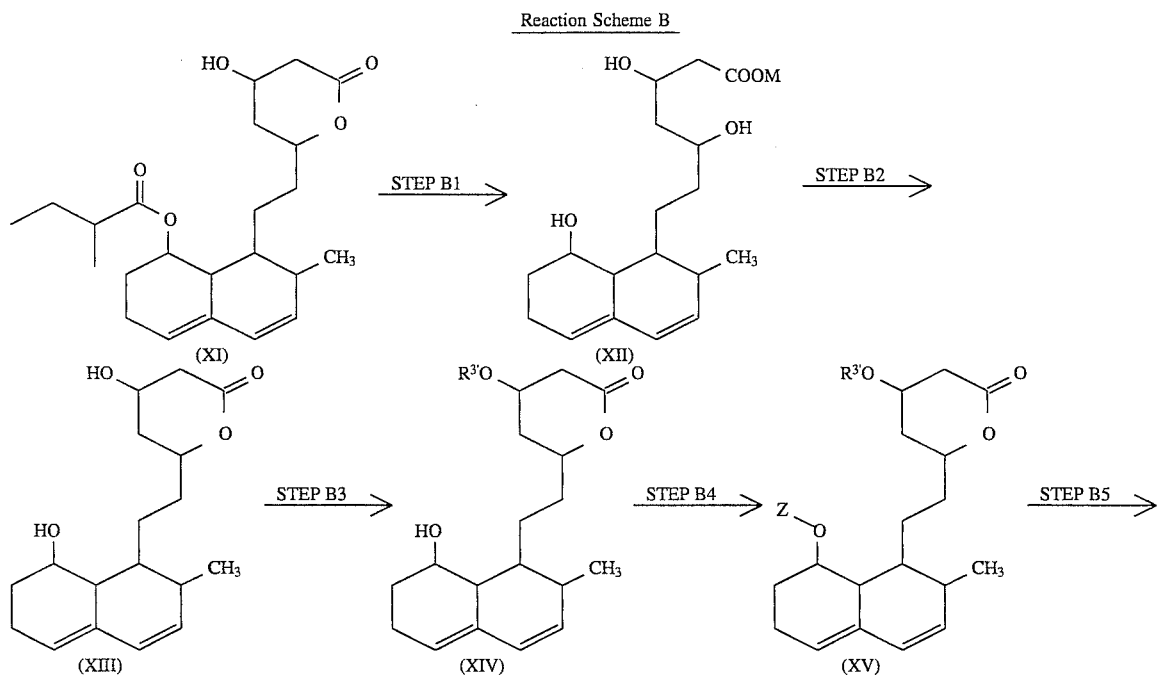

Reaction Scheme B

-continued
Reaction Scheme B

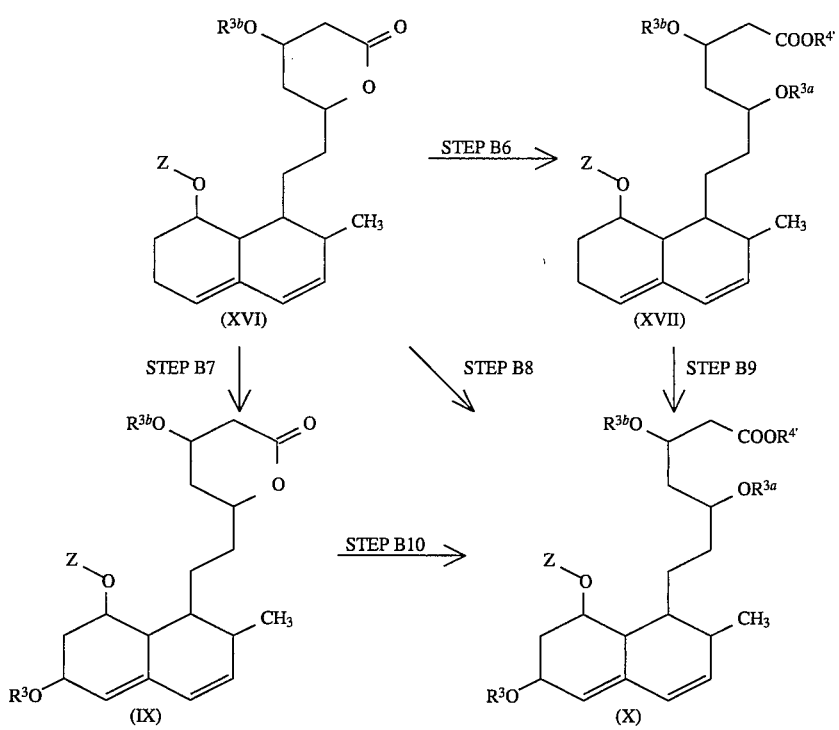

In the above formulae, Z, $R^3$, $R^{3a}$, $R^{3b}$, $R^{3'}$, $R^{4'}$ and M are as defined above.

Reaction Scheme B provides a method of preparing compounds of formulae (XVI) and (XVII), which are compounds of the present invention, and an alternative method of preparing compounds of formulae (IX) and (X), which are also compounds of the present invention.

Step B1

In this Step, a compound of formula (XII) is prepared by hydrolysis of the ester side chain at the 8-position of a starting compound of formula (XI), using a base in a solvent. This reaction is essentially the same as that described in Step A1 of Reaction Scheme A, and may be carried out using the same reagents and reaction conditions.

Step B2

In this Step, a lactone compound of formula (XIII) is prepared by neutralizing the salt of a hydroxy acid of formula (XII), preferably in a solvent with one or more equivalents of an acid, and then ring-closing the resulting free acid. This reaction is essentially the same as that described in Step A2 of Reaction Scheme A, and may be carried out using the same reagents and reaction conditions.

Step B3

In this Step, a compound of formula (XIV) is prepared by selectively protecting a hydroxy group other than the hydroxy group at the 8-position, of the compound of formula (XIII), with a group $R^{3'}$. This reaction is essentially the same as that described in Step A3 of Reaction Scheme A, and may be carried out using the same reagents and reaction conditions.

Step B4

In this Step, a compound of formula (XV) is prepared by acylating the hydroxy group at the 8-position of the compound of formula (XIV) with a group Z. This reaction is essentially the same as that described in Step A4 of Reaction Scheme A, and may be carried out using the same reagents and reaction conditions.

Step B5

In This Step, a compound of formula (XVI), which is a compound of the present invention, is prepared by eliminating the hydroxy-protecting group represented by $R_3{}'$ of the compound of formula (XV) and then, if desired, protecting the resulting hydroxy group with another protecting group, preferably one capable of being cleaved in vivo by biological methods, such as hydrolysis. This reaction is essentially the same as that described in Step A5 of Reaction Scheme A, and may be carried out using the same reagents and reaction conditions.

Step B6

In this Step, a compound of formula (XVII) is prepared by hydrolysis or solvolysis of a lactone ring in a compound of formula (XVI), to produce a salt of a carboxylic acid or a carboxylic acid ester and then, if desired, subjecting the product to any of following reactions:

(1) producing a free carboxylic acid;

(2) protecting some or all of the free hydroxy groups with protecting groups, preferably ones capable of being cleaved in vivo by biological methods, such as hydrolysis;

(3) protecting the resulting carboxy group with a protecting group, preferably one capable of being cleaved in vivo by biological methods, such as hydrolysis, or producing other salts of the carboxylic acid; and/or (4) if desired, producing again a lactone compound by ring-closure. The reaction is carried out following the procedure described in Step 6.

STEPS B7, B8 and B9

In these Steps, compounds of formulae (IX) and (X) are prepared by introducing stereospecifically a hydroxy group into the 6-position of the carboxylic acid compound of formula (XVII), a pharmaceutically acceptable salt or ester thereof, or a lactone compound of formula (XVI) by enzymatic hydrolysis. This may be carried out using the procedure described hereafter under the heading "Preparation by Biological Methods".

Step B10

In this step, a compound of formula (X), which is a compound of the present invention, is prepared by hydrolysis or solvolysis of the lactone ring of the compound of formula (IX) to produce a salt of a carboxylic acid, or a carboxylic acid ester. The reaction can, if desired, be conducted by:

(1) production of a free carboxylic acid;

(2) protecting some or all of the free hydroxy groups with protecting groups, preferably ones capable of being cleaved in vivo by biological methods, such as hydrolysis, which groups may be the same as each other or they may be different from each other;

(3) protecting the resulting carboxy group with a protecting group which is preferably capable of being cleaved in vivo by biological methods, such as hydrolysis, or producing other salts of a carboxylic acid; and/or (4) if desired, subjecting the carboxylic acid compound to ring-closure again, to produce a lactone compound.

These reactions are essentially the same as those described in Step A6 of Reaction Scheme A, and may be carried out using the same reagents and reaction conditions.

REACTION SCHEME C

This provides an alternative method of preparing the compound of formula (IX) used as an intermediate in Reaction Scheme A and the compound of formula (XVI) used as an intermediate in Reaction Scheme B.

Reaction Scheme C

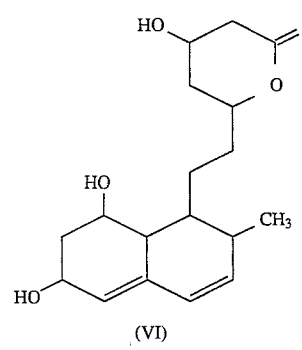

(VI)

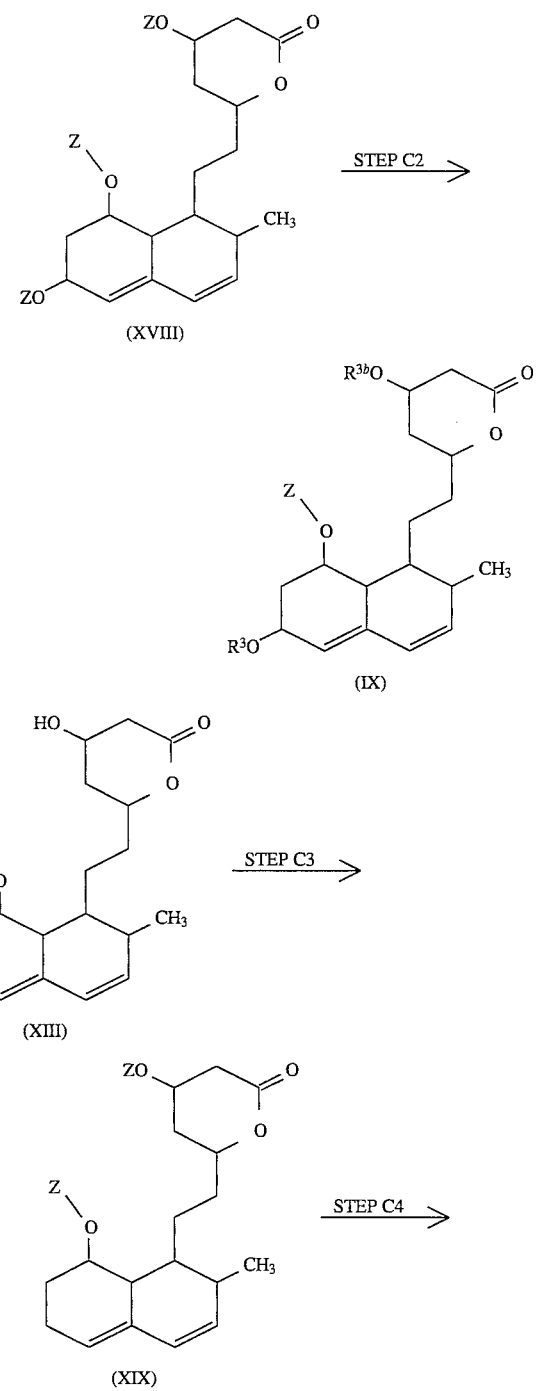

-continued
Reaction Scheme C

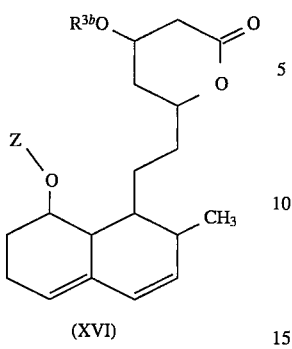

(XVI)

In the above formulae, $R^3$, $R^{3a}$ and Z are as defined above.

The compounds of formulae (IX) and (XVI) used as intermediates can be prepared by acylating all of the hydroxy groups in a compound of formula (VI) or (XIII) with a group of Z to produce a compound of formula (XVIII) or (XIX), respectively. This reaction is essentially the same as that described in Step A4 of Reaction Scheme A, and may be carried out using the same reagents and reaction conditions. One or two protecting groups other than the acylated hydroxy group at the 8-position are then removed selectively following the procedure described in British Patent Specification No. 2,255,974 A, after which, if desired, either or both of the deprotected groups are protected by a protecting group, preferably one capable of being cleaved in vivo by biological methods such as hydrolysis, which groups may be the same as each other or different from each other. This reaction is essentially the same as that described in Step A5 of Reaction Scheme A, and may be carried out using the same reagents and reaction conditions.

The compound of formula (XI) used as a starting material in Reaction Scheme B can be prepared chemically following the procedure described in any one of the following literature references:

(i) D. J. Clive et al., J. Am. Chem. Soc., 112, 3018 (1990);
(2) C. T. Hsu et al., J. Am. Chem. Soc., 105, 593 (1983);
(3) N. N. Girotra et al., Tetrahedron Lett., 23, 5501 (1982); ibid., 24, 3687(1983) and ibid., 25, 5371 (1984);
(4) M. Hirama et al. , J. Am. Chem. Soc., 104, 4251 (1982);
(5) P. A. Grieco et al., J. Am. Chem. Soc., 108, 5908 (1986);
(6) T. Rosen et al., J. Am. Chem. Soc., 107, 3731 (1985);
(7) G. E. Keck et al., J. Org. Chem. 51, 2487 (1986);
(8) A. P. Kozikowski et al., J. Orgo Chem., 52, 3541 (1987);
(9) S. J. Danishefsky et al., J. Am. Chem. Soc., 111, 2599 (1989);

Following the procedures described in Japanese Patent Publication No. Sho 56-12114 and Japanese Patent Application Kokai No. Sho 51-136885, the starting compounds of formulae (XI) and (XIII) employed in Reaction Schemes B and C may be prepared microbiologically.

Pravastatin, which may be used as a starting material, can be prepared enzymatically by stereo-selective hydroxylation of a compound of formula (XI) at the 6-position to produce a compound having a 6β-hydroxy group following the procedure disclosed in Japanese Patent Publication No. 61-13699 or in Steps B7, B8 and B9.

The carboxylic acid of formula Z—OH, which is used as a starting material in the process of the present invention, can easily be prepared by known methods, for example, the method reported by Bettoni et al in Chirality, vol 4, No. 3, (1992) 193.

PREPARATION BY BIOLOGICAL METHODS

Certain of the compounds of the present invention may also be prepared by biological methods, as described in more detail below.

Hydroxylation of a Compound of Formula (Ib) to a Compound of Formula (Ia)

A compound of formula (Ib):

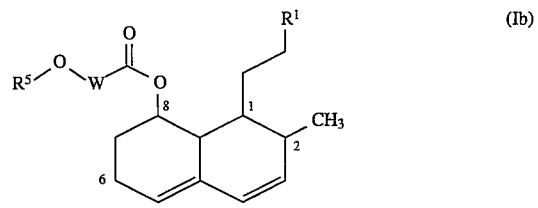

in which $R^1$ is as defined above or a corresponding compound in which reactive groups are protected may be converted to a compound of formula (Ia):

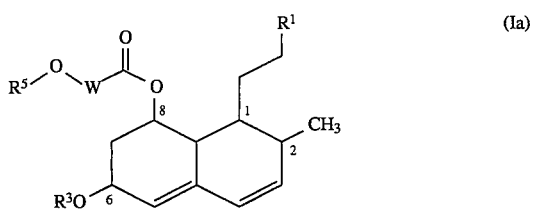

in which $R^1$ is as defined above or a corresponding compound in which reactive groups are protected by means of a hydrolyzing enzyme.

The hydrolyzing enzyme may be derived from a microorganism of a genus selected from the group consisting of Amycolata, Nocardia, Syncephalastrum, Mucor, Rhizopus, Zygorynchus, Circinella, Actinomucor, Gongronella, Phycomyces, Absidia, Cunninghamella, Mortierella, Pychnoporus (old genus name: Trametes), Streptomyces and Rhizoctonia.

This hydrolysis may be effected by any of the following methods:

Method 1: which comprises adding a compound of formula (Ib) to a broth in the course of the cultivation of converting microorganisms, and then continuing the cultivation;

Method 2: which comprises contacting a compound of formula (Ib) with cultured cells collected from a culture broth of the said microorganism; or Method 3: which comprises contacting a compound of formula (Ib) with a cell-free extract prepared from the said microorganism.

In any of these methods, the microorganism is cultivated under conditions suitable to maximize production and efficacy of the enzyme in a suitable culture medium, for example a natural or a synthetic medium. Such media are generally well known in the art, and will frequently be of a type commonly used in the production of other fermentation products.

Typically, it will be necessary for the medium to comprise any combination of a carbon source, a nitrogen source and one or more inorganic salts assimilable by the relevant microorganism. The minimum requirement for the medium will be that it contains those ingredients essential for the growth of the microorganism.

Suitable carbon sources include any carbon-containing material which is assimilable by the microorganism, for example: carbohydrates, such as glucose, fructose, maltose, lactose, sucrose, starch, mannitol, dextrin, glycerin, thick malt syrup, molasses, blackstrap molasses, oat powder, rye powder, corn starch, potato, corn powder, soybean powder, or malt extract; oils or fats, such as soybean oil, cotton seed oil, olive oil, cod-liver oil, or lard oil; organic acids, such as citric acid, sodium ascorbate, malic acid, acetic acid, fumaric acid, tartaric acid, succinic acid or gluconic acid; alcohols, such as methanol, ethanol, propanol, isopropanol, butanol, isobutanol, or t-butanol; and amino acids, such as glutamic acid. These substances can be used alone or a mixture of any two or more of them may be used. Typical amounts will be in a range from about 1 to 10% w/v of the amount of medium, although the amount may be varied as desired and in accordance with the desired result.

Suitable nitrogen sources include any nitrogen-containing material which is assimilable by the microorganism, for example any substance containing a protein, or other readily assimilable source of nitrogen. Representative examples of nitrogen sources are: organic nitrogen sources from animals and plants, and may be extracts from such natural sources as rice meal, soybean meal, wheat bran, wheat germ, peanut meal, cottonseed meal, cottonseed oil, soybean casein, soy protein isolate, casamino acid, casein hydrolysate, fermamine, fish meal, corn steep liquor, peptone, meat extract, yeast, yeast autolysate, yeast extract, malt extract and urea; amino acids, such as aspartic acid, glutamine, cystine, or alanine; ammonium salts, such as ammonium sulfate, ammonium nitrate, ammonium chloride or ammonium phosphate; and inorganic nitrogen compounds, such as sodium nitrate or potassium nitrate. As with the carbon source, these may be employed alone or in any combination. Suitable amounts are typically within a range from about 0.2 to 6% w/v of the amount of medium.

Suitable nutrient inorganic salts are those which provide trace elements as well as the major constituent of the salt. Preferably, salts should provide such ions as sodium, potassium, magnesium, ammonium, calcium, phosphate, sulfate, chloride, or carbonate in an assimilable form, and preferably such trace metals as molybdenum, boron, copper, cobalt, manganese and iron. Examples of suitable compounds include: sodium chloride, manganese chloride, cobalt chloride, potassium chloride, calcium chloride, calcium carbonate, aluminum potassium sulfate, manganese sulfate, cupric sulfate, cobalt sulfate, zinc sulfate, ferrous sulfate, magnesium sulfate, monopotassium phosphate, dipotassium phosphate, disodium phosphate, or ammonium molybdate. In addition, any other additives necessary for the growth of the microorganism and for promoting the formation of a compound of the invention may be used in any suitable combination.

Addition of a sulfur compound assimilable by the microorganism from the medium may sometimes elevate production of the desired compound. Suitable sulfur compounds include inorganic sulfur compounds including: sulfates, such as zinc sulfate, cupric sulfate, ferrous sulfate or ammonium sulfate; thiosulfates, such as ammonium thiosulfate; and sulfites, such as ammonium sulfide; or organic sulfur compounds including: sulfur-containing amino acids, such as cystine, cystein, or L-thiazoline-4-carboxylic acid; sulfur-containing peptides, such as hypotaurin and glutathione; heavy metal sulfate compounds, such as ferrous sulfate or cupric sulfate: vitamins, such as vitamin $B_1$ or biotin; and bacterial growth promoting factors, such as thiamine.

An antifoaming agent such as a silicone oil, a polyalkylene glycol ether, a vegetable oil, an animal oil or suitable surfactant may be added to the medium. Such addition may be particularly appropriate when the microorganism is fermented as a liquid culture.

There is no particular limitation upon the species of the microorganism used, provided that it is a microorganism capable of introducing a hydroxy group am the 6-position of the compound of formula (Ib). Examples of such microorganisms include:

fungi of the class Zygomycetes: genera Syncephalastrum, Mucor, Rhizopus, Zygorynchus, Circinella, Actinomucor, Gongronella, Phycomyces, Absidia, Cunninghamella and Mortierella;

fungi of other classes than Zygomycetes: genera Pychnoporus (former genus name: Trametes) and Rhizoctonia;

actinomycetes: genera Amycolata, Nocardia and Streptomyces; preferably strains belonging to the genus Syncephalastrum, including:
  *Syncephalastrum racemosum* (Cohn) Schroeter SANK 41872 (FERM BP-4107); *Syncephalastrum nigricans* Vuillemin SANK 42372, IFO 4814 (FERM BP-4106); *Syncephalastrum nigricans* SANK 42172 (FERM P-6041); *Syncephalastrum nigricans* SANK 42272 (FERM P-6042); and *Syncephalastrum racemosum* IFO 4828;

strains belonging to the genus Mucor, including:
  *Mucor hiemalis* Wehmer SANK 36372, IFO 5834 (FERM BP-4108); *Mucor hiemalis* f. *hiemalis* IFO 5303; *Mucor hiemalis* f. *hiemalis* IFO 8567; *Mucor hiemalis* f. *hiemalis* IFO 8449; *Mucor hiemalis* f. *hiemalis* IFO 8448; *Mucor hiemalis* f. *hiemalis* IFO 8565; *Mucor hiemalis* f. *hiemalis* CBS 117.08; *Mucor hiemalis* f. *hiemalis* CBS 109.19; *Mucor hiemalis* f. *hiemalis* CBS 200.28; *Mucor hiemalis* f. *hiemalis* CBS 242.35; *Mucor hiemalis*, f. *hiemalis* CBS 110.19; *Mucor hiemalis* f. *hiemalis* CBS 201.65; *Mucor bacilliformis* NRRL 2346; *Mucor circinelloide* f. *circinelloides* IFO 4554; *Mucor circinelloides* f. *circinelloides* IFO 5775; *Mucor hiemalis* f. *corticolus* SANK 34572 (FERM P-5913); *Mucor dimorphosporus* IFO 4556; *Mucor fragillis* CBS 23635; *Mucor genevesis* IFO 4585; *Mucor globosus* SANK 35472 (FERM P-5915); and *Mucor circinelloides* f. *griseocyanus* IFO 4563;

strains belonging to the genus Rhizopus, including:
  *Rhizopus chinonsis* IFO 4772; *Rhizopus circinans* ATCC 1225; and *Rhizopus arrhizus* ATCC 11145;

strains belonging to the genus Zygorynchus, including:
  *Zygorynchus moelleri* IFO 4833;

strains belonging to the genus Circinella, including:
  *Circinella muscae* IFO 4457; *Circinella umbellata* IFO 4452; and *Circinella umbellata* IFO 5842;

strains belonging to the genus Actinomucor, including:
  *Actinomucor elegans* ATCC 6476;

strains belonging to the genus Gongronella, including:
  *Gongronella butleri* IFO 8080;

strains belonging to the genus Phycomyces, including:
  *Phycomyces blakesleeanus* SANK 45172 (FERM P-5914);

strains belonging to the genus Absidia, including:
  *Absidia coerulea* IFO 4423; and *Absidia glauca* var. *paradoxa* IFO 4431;

strains belonging to the genus Cunninghamella, including:
  *Cunninghamella echinulata* IFO 4445; *Cunninghamella echinulata* IFO 4444; and *Cunninghamella echinutata* ATCC 9244;

strains belonging to the genus Mortierella, including:
Mortierella isabellina IFO 6739;

strains belonging to the genus Amycolata, including:
Amycolata autotrophica SANK 62981 (FERM BP-4105); Amycolata autotrophica SANK 62781 (FERM P-6181); Amycolata autotrophica subsp. canberrica subsp. nov SANK 62881 (FERM P-6182); and Amycolata autotrophica IFO 12743;

strains belonging to the genus Nocardia, including:
Nocardia asteroides IFO 3424; Nocardia farcinica ATCC 3318; and Nocardia coeliaca ATCC 17040;

strains belonging to the genus Pychnoporus, including:
Pycnoporus coccineus SANK 11280 (FERM P-5916);

strains belonging to the genus Streptomyces, including:
Streptomyces carbophilus SANK 62585 (FERM BP-4128); Streptomyces roseochromogenus IFO 3363; Streptomyces roseochromogenus IFO 3411; and Streptomyces halstedii IFO 3199;

strains belonging to the genus Rhizoctonia, including:
Rhizoctonia solani SANK 22972 (FERM P-5917).

Of these, the most preferred microorganisms are:

Amycolata autotrophica SANK 62981 (FERM BP-4105);

Syncephalastrum racemosum (Cohn) Schroeter SANK 41872 (FERM BP-4107);

Syncephalastrum nigricans Vuillemin SANK 42372 (FERMBP-4106);

Mucor hiemalis Wehmer SANK 36372 (FERM BP-4108); and

Streptomyces carbophilus SANK 62585 (FERM BP-4128).

The microorganisms described above have been deposited in the culture collection of the Fermentation Research Institute, Agency of Industrial Science and Technology, the Ministry of International Trade and Industry or are available from official agencies (IFO, CBS, NRRL and ATCC) without restriction as to availability. The following Examples using the foregoing more preferred fungi are provided in order that the present invention may be more fully understood.

It will be appreciated that the strains mentioned above, or any other strain capable of similar activity, may be subcultured or biotechnologically altered or modified to produce an organism with different characteristics. The only requirement is that the resulting organism be capable of producing the required compound. Alterations may occur naturally or artificially, by induction.

Such alterations and modifications may take any desired form, or may be consequent on such considerations as culture conditions, for example. Strains may be modified by culture and so selected as to exhibit such characteristics as enhanced growth, or growth at lower/higher temperatures.

Biotechnological modifications will generally be intentional, and may introduce selectable characteristics, such as bacteriostat resistance or susceptibility, or combinations thereof, in order to maintain purity, or to allow purification of cultures, especially seed cultures, from time to time.

Other characteristics which may be introduced by genetic manipulation are any that are permissible in species of which the above are strains. For example, plasmids encoding resistances may be incorporated, or any naturally occurring plasmids may be removed. Advantageous plasmids include those that confer auxotrophy. Plasmids may be obtained from any suitable source, or may be engineered by isolating a naturally occurring plasmid and inserting a desired gene or genes from another source. Natural plasmids may also be modified in any other manner that may be considered desirable.

Any such modified strain may be employed in the process of the present invention, provided only that the strain is capable of the required activity, a matter which can readily be ascertained by simple and routine experimentation.

The mycological properties of these strains are as follows.

Mycological Properties of Amycolata Autotrophica SANK 62981

According to the methods of Shirling and Gottlieb [international Journal of Systematic Bacteriology 16, 313–340 (1968)] and of S. A. Waksman [The Actinomycetes], the strain was observed throughout 14 days at a temperature of 28° C.

(1) Morphological Characteristics

| | |
|---|---|
| The shape of the top of aerial hyphae: | Rectus-flexibilis |
| The mode of hyphal branching: | Simple branching |
| Hyphal division: | Observable |
| Surface structure of hyphal body: (thallic-arthric conidium) | Smooth |
| Other organs: | None |

(2) Properties on Various Kinds of Media for Classification

The strain grows well on any of the media tested.

Strain SANK 62981 grows showing a light brownish white to pale yellowish orange color. As cultivation progresses, light brown to violet spots are observed.

On other media than yeast extract—malt extract agar medium, the formation of light brownish grey aerial hyphae is observed.

No formation of soluble pigment is observed.

TABLE 3

Properties after culture for 14 days at 28° C. on various kinds of media

| Medium | Item | SANK 62981 |
|---|---|---|
| Yeast extract - malt extract agar (ISP 2) | G | Very good, brownish white (2-9-8) to grayish red-brown (4-3-5) |
| | AM | Trace, white |
| | R | Brownish white (2-9-8) to grayish red brown (4-3-5) |
| | SP | Not produced |
| Oatmeal agar (ISP 3) | G | Very good, dark reddish brown (4-3-4) |
| | AM | Ordinary, pale pink (2-8-4) |
| | R | Brownish violet (3-3-2) |
| | SP | Not produced |
| Inorganic salt-starch agar (ISP 4) | G | Very good, brownish violet (3-3-2) |
| | AM | Good, light brownish gray (2-8-2) |
| | R | Dark reddish brown (4-3-4) |
| | SP | Not produced |
| Glycerine aspargine agar (ISP 5) | G | Very good, pale brown (2-9-9) to brownish violet (3-3-2) |
| | AM | Abundant, white |
| | R | Pale yellowish orange (2-9-9) to grayish red brown (4-3-6) |
| | SP | Not produced |

TABLE 3-continued

Properties after culture for 14 days at 28° C. on various kinds of media

| Medium | Item | SANK 62981 |
|---|---|---|
| Tyrosine agar (ISP 7) | G | Good, grayish brown (4-6-6) |
| | AM | Trace, white |
| | R | Pale yellowish orange (2-9-9) to brownish violet (3-3-2) |
| | SP | Not produced |
| Sucrose nitrate agar | G | Not so good, pale yellowish orange (2-9-9) |
| | AM | Ordinary, white |
| | R | Pale yellowish orange (2-9-9) |
| | SP | Not produced |
| Glucose asparagine agar | G | Very good, pale yellowish orange (2-9-9) to brownish violet (3-3-2) |
| | AM | Ordinary, white |
| | R | Pale yellowish orange (2-9-9) to grayish red brown (4-3-6) |
| | SP | Not produced |
| Nutrient agar | G | Good, pale yellowish orange (2-9-9) |
| | AM | Trace, white |
| | R | Pale yellowish orange (2-9-9) |
| | SP | Not produced |
| Water agar | G | Not so good, pale yellowish orange (2-9-9) |
| | AM | Ordinary, white |
| | R | Pale yellowish orange (2-9-9) |
| | SP | Not produced |
| Potato extract - carrot extract agar | G | Not so good, pale yellowish orange (2-9-9) |
| | AM | Ordinary, white |
| | R | Pale yellowish orange (2-9-9) |
| | SP | Not produced |

In the table, G, AM, R and SP mean growth, aerial mycelium, reverse and soluble pigment respectively. The color tones are indicated in the above Table according to the Color Tip Numbers described in [Standard Color Table] published by Nihon Shikisai Kenkyujo.

(3) Physiological Properties

| Reduction of nitrate: | positive |
|---|---|
| Hydrolysis of starch: | Negative |
| Formation of melanoid pigment: | Negative |

Determined on the following 3 media:
Medium 1: Tryprone.yeast extract broth (ISP 1)
Medium 2: Peptone.yeast extract.iron agar (ISP 6)
Medium 3: Tyrosine agar (ISP 7)

(4) Assimilability of Various Kinds of Carbon Sources

By using Pridham-Gottlieb agar medium (ISP 9), assimilation of carbon sources was examined and judged after culture for 14 days at 28° C.

In the following table:

| D-Glucose: | + |
|---|---|
| L-Arabinose: | + |
| D-Xylose: | + |
| D-Fructose: | + |
| L-Rhamnose: | ± |
| Inositol: | + |
| Sucrose: | – |
| Raffinose: | – |
| D-Mannitol: | + |
| Control: | – |

+ means assimilation,
± means a little assimilation and
– means no assimilation.

(5) Intracellular Components

According to the methods of B. Becker et al. [Applied Microbiology 12, 236 (1965)], and M. P. Lechevalier et al. [The Actinomycetales by H. Prauser, p. 311 (1970)], the acid hydrolysates of the cells of these strains were analyzed by paper chromatography. In the cell walls, meso-2,6-diaminopimelic acid was found, and arabinose and galactose were noted as sugar components of the bacterial cells, from which the bacterial components were confirmed to be type IV-A.

The phospholipid component of the cell was found to be of the PII type, containing no mycolic acid, and the peptidoglycan was of the acetyl type.

On the basis of these results, strain SANK 62981 was determined to belong to the species *Amycolata autotrophica*.

However, as the vegetative growth of the strain of SANK 62981 reveals a color tone like amethyst, it is concluded that the species is a subspecies of *Amycolata autotrophica*.

This strain has been deposited under the conditions of the Budapest Treaty in the permanent culture collection of the Fermentation Research Institute, Agency of Industrial Science & Technology, Ministry of International Trade and Industry, Japan, under the Accession Number FERM BP-4105.

This strain was identified according to the standard of the International Streptomyces Project; [Bergey's Manual of Determinative Bacteriology, 8th Ed.]; [The Actinomycetes, Vol. 2] by S. A. Waksman; and recent reports about Actinomycetes. The genus Amycolata was hitherto classified as part of the genus Nocardia. However, because of differences in the components of bacterial cells, Amycolata is now thought to be an independent genus from Nocardia, and each forms a new genus [International Journal of Systematic Bacteriology 36, 29 (1986)].

Mycological Properties of *Syncephalastrum racemosum* (Cohn) Schroeter SANK 41872

This strain was obtained by transfer from a strain deposited at the IFO under the accession number IFO 4814. It was redeposited at the Fermentation Research Institute, Agency of Industrial Science and Technology, the Ministry of International Trade and Industry and assigned the accession number FERM BP-4107.

Mycological Properties of *Syncephalastrum nigricans* Vuillemin SANK 42372

Vegetative hyphae develop well and grow rapidly.

Sporangiophores stand vertically from the hyphae, are pale brown in color with rhizoid and irregular branches, and form septa.

Lateral branches sometimes curve sharply.

At the tops of the main axis and lateral branches, vesicles are formed. Vesicles are sub-spherical or oval, sometimes elliptical in shape, and those formed the top of the main axis are 28 μm to 50 μm in diameter, and those formed at the top of the lateral branches are 15 μm to 25 μm in diameter.

Many merosporangia are formed on the whole surface. Sporangiophores are single rod or finger-like in shape, and frequently from 5 to 10 spores are formed in a line.

Spores are almost colorless with smooth surfaces, unicellular and sub-spherical to oval in shape, from 3.5 μm to 6.5 μm in diameter.

No zygospores are observable.

Comparing these properties with those of known strains, the properties of this strain accorded well with those of *Syncephalastrum nigricans* Vuillemin described in "An Illustrated Book of Fungi" Edited by Keisuke Tsubaki & Shun-ichi Udagawa, Kodansha; p.303–304 (1978).

This strain has been deposited under the conditions of the Budapest Treaty at the Fermentation Research Institute, Agency of Industrial Science & Technology, Ministry of International Trade and Industry under the Accession Number FERM BP-4106.

Mycological Properties of *Mucol hiemalis* Wehmer SANK 36372

This strain was obtained by transfer from a strain deposited at the IFO under the accession number IFO 5834. It was redeposited at the Fermentation Research Institute, Agency of Industrial Science and Technology, the Ministry of International Trade and Industry and assigned the Accession number FERM BP-4108.

Mycological Properties of *Streptomyces carbophilus* SANK 62585

(1) Morphological Characteristics

The morphology of the strain was observed under a microscope after 14 days cultivation at 28° C. on a medium prescribed by International Streptomyces Project (ISP).

Substrate hyphae elongated well and branched and aerial mycelia branched simply. Sporangiophores were straight or curved or sometimes formed spirals and the spore surface was smooth.

No special organs such as whirls, sclerotia, fragmentation of substrate hyphae or sporangia were observed.

(2) Properties on Various Kinds of Media for Classification

The properties of strain SANK 62585 were determined on various media after 14 days incubation at 28° C. The results are shown in Table 4.

TABLE 4

| Medium | Item | Properties of strain SANK 62585 |
|---|---|---|
| Yeast extract malt extract agar (ISP 2) | G: | Very good, yellowish brown (6-7-9) |
| | AM: | Very abundant, powdery, light olive gray (2-8-11) |
| | R: | Yellowish brown (6-5-9) |
| | SP: | Not produced |
| Oatmeal agar (ISP 3) | G: | Very good, grayish yellow brown (4-5-9) |
| | AM: | Very abundant, powdery, light olive gray (2-8-12) |
| | R: | Dark brownish gray (2-3-9) |

TABLE 4-continued

| Medium | Item | Properties of strain SANK 62585 |
|---|---|---|
| | SP: | Not produced |
| Inorganic salt-starch agar (ISP 5) | G: | Very good, brownish gray (2-6-9) |
| | AM: | Abundant, powdery, yellowish gray (1-9-10) to light olive gray (2-8-12) |
| | R: | Pale brown (2-8-9) to brownish gray (2-4-9) |
| | SP: | Not produced |
| Glycerine-asparagine agar (ISP 5) | G: | Not so good, pale yellowish brown (2-7-9) |
| | AM: | Moderate, powdery, grayish white (N-9) |
| | R: | Pale yellowish brown (4-8-9) |
| | SP: | Not produced |
| Tyrosine agar (ISP 7) | G: | Good, dark yellowish brown (4-4-9) |
| | AM: | Very abundant, powdery, yellowish gray (1-9-10) to light olive gray (2-8-11) |
| | R: | Dark brownish gray (2-3-9) |
| | SP: | Not produced |
| Sucrose-nitrate agar | G: | Not so good, pale yellowish orange (2-9-9) |
| | AM: | Moderate, powdery, grayish white (N-9) |
| | R: | Pale yellowish orange (2-9-9) |
| | SP: | Not Produced |
| Glucose-asparagine agar | G: | Not so good, yellowish gray (2-5-9) to brownish gray (1-9-10) |
| | AM: | Poor, grayish white (N-9) |
| | R: | Yellowish gray (2-5-9) to brownish gray (1-9-10) |
| | SP: | Not produced |
| Nutrient agar (Difco) | G: | Not so good, light olive gray (4-8-10) |
| | AM: | None |
| | R: | Light olive gray (4-8-10) |
| | SP: | Not produced |
| Peptone - yeast extract - iron agar (ISP 6) | G: | Good, yellowish brown (4-6-9) |
| | AM: | None |
| | R: | Yellowish brown (4-6-9) |
| | SP: | Not produced |
| Potato extract-carrot extract agar | G: | Poor, yellowish gray (1-9-10) to dull orange (6-8-6) |
| | AM: | Moderate, powdery, pale yellowish orange (2-9-9) |
| | R: | Pale brown (3-8-6) |
| | SP: | Not produced |

In the above Table, the abbreviations used are as defined in Table 3.

The color tones are indicated in the above Table according to the Color Tip Numbers described in [Standard Color Table] published by Nihon Shikisai Kenkyujo.

(3) Physiological Properties

Hydrolysis of starch: positive
Liquefaction of gelatin: negative
Reduction of nitrate: positive
Coagulation of milk: positive
Peptonization of milk: positive
Temperature range for growth
(Medium 1): 4°–45° C.
Temperature range for optimum growth
(Medium 1): 15°–35° C.
Production of melanoid pigments
(Medium 2): negative
(Medium 3): pseudo-positive
(Melanoid pigment is sometimes produced in the latter period of incubation.)

(Medium 4): negative

The media used in the above tests were:

Medium 1: Yeast malt agar (ISP 2)

Medium 2: Tryprone-yeast extract broth (ISP 1)

Medium 3: Peptone-yeast extract-iron agar (ISP 6)

Medium 4: Tyrosine agar (ISP 7)

(4) Assimilability of Carbon Sources

Assimilability of the carbon source which was utilized in Pridham-Gottlieb basal agar (ISP 9) medium was examined by adding D-glucose, L-arabinose, D-xylose, inositol, D-mannitol, D-fructose, L-rhamnose, sucrose, raffinose, cellobiose or trehalose. Fermentation employing this microorganism was conducted at a temperature of 28° C. for 14 days. As the strain grew well in the control medium without the addition of any carbon source, the assimilability of carbon sources remains to be determined. However, the vegetative growth of this strain in media containing D-glucose, D-xylose, innositol, raffinose, cellobiose or trehalose was far superior to that in the control medium.

(5) Intracellular Components

The cell wall components of the strain SANK 62585 was analyzed following the method described by B. Becker et al. [Applied Microbiology, 12, 421–423 (1964)]. L,L-Diaminopimelic acid and glycine were detected. The cell walls of this strain were thus confirmed to be cell wall type 1. The sugar components of the whole cell were analyzed following the method described by M. P. Lechevalier et al. [Journal of Laboratory and Clinical Medicine, 71, 934 (1968)], but no characteristic patterns were found.

On the basis of the foregoing data, it is evident that SANK 62585 belongs to the genus Streptomyces, one of the genera of actinomycetes.

Identification of the strain SANK 62585 was made according to the standard of ISP (The International Streptomyces Project), Bergey's Mannual of Determinative Bacteriology (the 8th edition), S. A. Waksman: The Actinomycetes and recent literature on Actinomycetes. A careful comparison of the foregoing data with published descriptions of known microorganisms reveals significant differences which indicate that SANK 62585 should be classified as a new species belonging to the genus Streptomyces. On this basis, it was designated *Streptomyces carbophilus*. The strain has been deposited in the permanent culture collection of the Fermentation Research Institute, Agency of Industrial Science and Technology, the Ministry of International Trade and Industry, and has been assigned the Accession number FERM BP-4128.

There is no particular limitation upon the method of cultivation employed for the growth of the converting microorganism, and any method commonly used for cultivating microorganisms may equally be used here. Examples of such methods include: solid culture, stationary culture, shaking culture, agitating culture and aerating culture. Of these, an aerobic culture method is preferred, that is, agitating culture, shaking culture or aerating culture, more preferably shaking culture.

Fermentation for industrial purposes is preferably carried out by agitating culture with forced aeration.

The pH of the nutrient medium for the growth of the converting microorganism is normally in the range of from pH 5.0 to 8.0, preferably from pH 6.0 to 7.0.

The fermentation employing the converting microorganism is preferably conducted at temperature ranging from 15° to 35° C., more preferably from 26° to 30° C., and most preferably at 28° C.

Method 1

This method of conducting the enzymatic hydrolysis is effected by incubating a strain of the converting microorganism and by adding a compound of formula (Ib) in the course of the fermentation.

The time at which the compound is added may vary, depending upon the optimum cultivating conditions for the converting microorganism employed, particularly upon the culture apparatus, the composition of the medium, the culture temperature and other conditions, it is preferred to added the compound of formula (Ib) when the hydroxylating ability of the converting microorganism begins to rise. In general, the point of time from 1 to 3 days after begining the incubation of the converting microorganism is preferred.

The amount of the compound of formula (Ib) to be added is normally in a range of from 0.01 to 5.0%, more preferably from 0.05 to 2.0%, based on the volume of the medium.

The time required for the incubation may vary widely, depending upon many factors, including the cultivation conditions and the nature of the microorganism, but, in general, a period of from 3 to 5 days after the addition of the compound of formula (Ib) is appropriate.

Method 2

This method is conducted by incubating the converting microorganism in the presence of a small amount of substrate following the procedure of Method 1, until the hydroxylation by the microorganism reaches to maximum productivity.

The hydroxylating ability will vary, depending upon the type of culture medium, the fermentation temperature and other conditions, but it generally reaches a maximum between 4 and 5 days after beginning of the culture. The culture is normally terminated at this time.

The cells are then collected by subjecting the culture broth to centrifugation, filtration or the like. It is preferred that the cells thus collected should be washed before use with physiological saline or with an appropriate a buffer solution.

The compound of formula (lb) is usually contacted with the cells thus obtained in an aqueous solvent, for example, a phosphate buffer of pH 5 to 9.

The hydrolysis reaction is preferably carried out at a temperature of from 20° to 45° C., more preferably from 25° to 35° C.

The concentration of the compound of formula (Ib) is preferably in a range of from 0.01 to 5.0% based on the volume of the medium.

The time required for the reaction will vary, depending upon many factors, such as the concentration of the compound of formula (Ib), the reaction temperature and other conditions, but the reaction is normally complete within a period of from 1 to 5 days.

Method 3

In this method, a cell-free extract is prepared by disrupting the cells, which may be achieved by physical or chemical means, for example, by grinding or ultrasonic treatment, to make a suspension containing the cellular components, including the enzyme. Alternatively, it may be effected by treating the cells with an organic solvent, a surface active agent or an enzyme to make a cell-free extract. The cells may be obtained as described in Method 2. The extract then is contacted with the compound of formula (Ib).

The conditions employed for contacting the cell-free extract with the compound of formula (Ib) are similar those described in Method 2.

According to the methods described above, a suitable substrate (a hydroxy-acid or a lactone compound) is reacted with the converting microorganism or with a cell-free enzyme-containing extract thereof to introduce stereoselectively a hydroxy group into the 6-position of the substrate. The desired compounds having a 6β-hydroxy group can be prepared selectively by using an appropriate combination, for example:

(1) a lactone compound and a strain of *Mucor hiemalis* Wehmer;
(2) a hydroxy-acid compound and a strain of *Streptomyces carbophilus*; or
(3) a hydroxy-acid compound and a strain of *Amycolata autotrophica*.

The desired compounds having a 6α-hydroxy group can be prepared by using an appropriate combination, for example:

(1) a lactone compound and a strain of *Syncephalastrum nigricans* Vuillemin; or
(2) a lactone compound and a strain of *Syncephalastrum racemosum* (Cohn) Schroeter.

The products prepared by the above methods of the present invention are found in the broth filtrate and mycelia at the end of the fermentation. The compound of the present invention exists in the form of either the hydroxy-acid or the lactone and the forms are interconvertable with each other. An important advantage of a hydroxy-acid compound that it can form a stable salt.

Accordingly the extraction and recovery of the desired product from the whole fermentation broth can, for example, be carried out by the following Method 1 or Method 2.

Method 1

The whole fermentation broth is centrifuged or filtered using a filter aid, such as diatomaceous earth, to separate the supernatant from the mycelia and other solid materials. These are then treated as follows:

(1) Supernatant

When the supernatant contains a lactone compound, it is subjected to hydrolysis under alkaline conditions (preferably at a pH 12 or more) in order to open the lactone ring. The hydrolyzate is then acidified carefully to produce a free hydroxy-acid. This acidified hydrolyzate or the supernatant containing a free hydroxy-acid is then extracted with a water-immiscible organic solvent, and the solvent is removed from the extract, for example by distillation under reduced pressure. Examples of suitable water-immiscible organic solvents include: aliphatic hydrocarbons, such as hexane or heptane; aromatic hydrocarbons, such as benzene, toluene or xylene; halogenated hydrocarbons, such as methylene chloride, chloroform, carbon tetrachloride, dichloroethane, chlorobenzene or dichlorobenzene; ethers, such as diethyl ether or diisopropyl ether; esters, such as ethyl formate, ethyl acetate, propyl acetate, butyl acetate or diethyl carbonate; and mixtures of any two or more of the above solvents.

Micro-organisms

A water-imiscible organic solvent is added to the microorganisms such that the final concentration of the cake is 50 to 90% by volume of the mixture. The resulting mixture is then treated in a similar manner to that described above for the treatment of the supernatant. Examples of suitable water-immiscible organic solvents include: alcohols, such as methanol or ethanol; ketones, such as acetone; nitriles, such as acetonitrile or isobutyronitrile; and amides, such as formamide, dimethylformamide, dimethylacetamide, N-methyl-2-pyrrolidone, N-methypyrrolidinone or hexamethylphosphoric triamide.

Method 2

The fermentation broth is hydrolyzed under alkaline conditions (preferably at pH 12 or more), either with heating or at room temperature, to open the lactone ring at the same time as destroying the mycelia. The whole of the active compounds in the broth are forcedly converted to a salt of the hydroxy-acid compound and the desired free hydroxy-acid may be recovered from the mixture by similar treatment to that described above for the supernatant.

The free hydroxy-acid compound thus obtained can, if desired, be dissolved in an aqueous solution of an alkali metal salt or an alkali metal hydroxide, such as sodium hydroxide, to form a corresponding salt, following the procedure described in Step 6. The hydroxy-acid may then be recovered conveniently in the form of its most stable salt.

Alternatively, in order to recover the desired compound, the free hydroxy-acid compound thus obtained is dehydrated by heating in an organic solvent to produce a compound having a lactone ring, following the procedure described in Step 6.

A mixture consisting of compounds including the free hydroxy-acid, one or more salts of the hydroxy-acid and the lactone compound can normally be separated and recovered by conventional means used in organic chemistry. For example, they may be separated and recovered by the various chromatographic techniques, including: partition column chromatography through a synthetic absorbent such as Sephadex LH-20™ (Pharmacia Inc.), Amberlite™ XAD-11 (Rohm and Haas Co.) or Diaion™ HP-20 (Mitsubishi Kasei Corporation); liquid chromatography through a regular or reverse phase column packed with silica gel or with an alkylated silica gel (preferably high performance liquid chromatography); or an appropriate combination of these techniques; after which the compound may be obtained by eluting with a suitable eluting solvent.

A lactone compound can also be purified by absorption column chromatography through a carrier such as silica gel, alumina or Florisil (containing magnesium and silica gel).

Examples of the preferred solvents used for the elution include: aliphatic hydrocarbons, such as hexane, heptane, ligroin or petreum ethers; aromatic hydrocarbons, such as benzene, toluene or xylene; halogenated hydrocarbons, such as methylene chloride, chloroform, carbon tetrachloride, dichloroethane, chlorobenzene or dichlorobenzene; esters, such as ethyl formate, ethyl acetate, propyl acetate, butyl acetate or diethyl carbonate; and ethers, such as diethyl ether, diisopropyl ether, tetrahydrofuran, dioxane, dimethoxyethane or diethylene glycol dimethyl ether.

Alternatively the extract may be purified by absorption column chromatography to remove inpurities. The desired hydroxy-acid compound can be obtained by absorbing it in an absorption column and then eluting it with an eluting solvent, for example: an aqueous alcohol, such as aqueous methanol, aqueous ethanol, aqueous propanol or aqueous isopropanol; or an aqueous ketone, such as aqueous acetone. Examples of such absorbents include: active charcoal; or an absorption resin, such as Amberlite™ XAD-2 or XAD-4 (Rohm and Haas Co.); or Diaion™ HP-10, HP-20, CHP-20 or HP-50 (Mitsubishi Kasei Corporation).

For the purpose of purification, the desired compound can be utilized in the form of either the free hydroxy-acid or a salt of the hydroxy-acid because both forms are mutually interconvertable following the procedure described in Step 6.

Biological Activity

The compounds of the present invention have a marked ability to reduce the levels of serum cholesterol. Specifically, the compounds inhibit the biosynthesis of chlolesterol in an enzyme system or a culture cell system separated from an experimental animal by inhibiting 3-hydroxy-3-methylglutaryl-CoA reductase (HMG-CoA), the rate limiting enzyme of sterol biosynthesis, by competing with the HMG-CoA. This demonstrates that the compounds will exhibit a powerful serum cholesterol reducing effect when employed in the treatment of humans and other animals.

Experiment 1

Determination of HMG-CoA Reductase Inhibitory Activity

The ability of the preferred test compounds to inhibit the activity of HMG-CoA reductase was determined by the method of Koga et al. [Eur. J. Biochem. 209, 315–319 (1992)], the improved procedure of Kuroda et al. [Biochem. Biophys, Acta, 485, 70–81 (1977)] which a modification of the method of Shapiro et al. [Anal. Biochem. 31, 383–390, (1969)].

A solution of 5 μl of the preferred test compound dissolved in distilled water was added to 45 μl of a reaction mixture containing 100 mM of a potassium phosphate buffer (pH7.4), 0.2 mM of [$^{14}$C]HMG-CoA, 10 mM of ethylenediaminetetraacetic acid disodium salt, 10 mM of dithiothreitol, 10 mM of NADPH (=reduced nicotinamide adenine dinucleotide phosphate) and an enzyme solution (rat liver microsomal fraction). The concentrations are expressed in terms of the final 50 μl of assay mixture. The resulting mixture was incubated for 15 minutes at 37° C. The reaction was then terminated by adding 10 μl of 2N aqueous hydrochloric acid, to lactonize the [$^{14}$C]mevalonate produced. After 15 minutes incubation, 1 ml of a 1:1 by volume aqueous suspension of Biorex-5 was added and the tubes were vigorously mixed using a Vortex mixer. The mixture was then centrifuged at 3,000×g for 10 minutes at 4° C. The supernatant (400 μl) was mixed with 4.5 ml of Optiflow™ in scintillation vials and the activity of the [$^{14}$C]mevalonolactone was determined by a liquid scintillation counter.

The results are shown in the following Table 5.

TABLE 5

| Test Compound | HMG-CoA Reductase Inhibitory Activity IC$_{50}$ (nM) |
|---|---|
| Example 3 | 30.6 |
| Example 6 | 33.5 |

TABLE 5-continued

| Test Compound | HMG-CoA Reductase Inhibitory Activity IC$_{50}$ (nM) |
|---|---|
| Prior Art Compound | 44.9 |

The prior art compound employed has the following formula (XXIII) and is the compound of Example 4 described in Japanese Patent Publication No. Hei 3-33698.

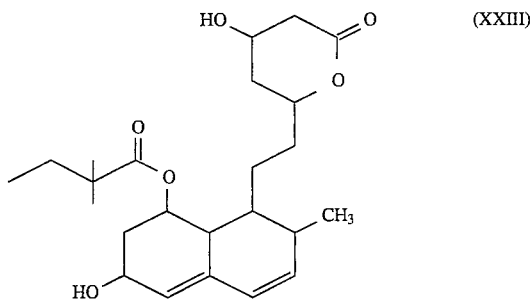

As can clearly be seen from the test results given above, the compounds of the present invention compete with 3-hydroxy-3-methylglutaryl-CoA, which is responsible for the rate-determining step of cholesterol biosynthesis in the the enzyme system separated from laboratory animals or in the liver of mouse. Accordingly the activity of 3-hydroxy-3-methylglutaryl-CoA reductase is inhibited and cholesterol biosynthesis is prevented.

The compounds of the present invention reveal strong cholesterol lowering activity in the blood serum of animals. In addition, their toxicity is very low. Consequently they are useful as a medicament for the treatment of hyperlipemia and the prophylaxis of arteriosclerosis, and also as antifungal or antineoplastic agents.

For this purposes, the compounds of formula (I) can be administered orally in the form of tablets, capsules, granules, powders or syrups, or parenterally by intravenous injection, suppositories or the like. These pharmaceutical formulations can be prepared by mixing the compounds of the present invention with one or more adjuvants, such as excipients (e.g. organic excipients including sugar derivatives, such as lactose, sucrose, glucose, mannitol or sorbitol; starch derivatives, such as cornstarch, mashed potato, α-starch, dextrine or carboxymethyl starch; cellulose derivatives, such as crystalline cellulose, low hydroxypropyl-substituted cellulose, hydroxypropylmethyl cellulose, carboxymethyl cellulose, carboxymethyl cellulose calcium or internally bridged carboxymethyl cellulose sodium; gum arabic; dextran; and Pullulan; inorganic excipients including silicates, such as light silicic acid anhydride, synthetic aluminum silicate or magnesium meta-silicic acid aluminate; phosphates, such as calcium phosphate; carbonates, such as calcium carbonate; and sulfates, such as calcium sulfate); lubricants (e.g. metal stearates, such as stearic acid, calcium stearate or magnesium stearate; talc; colloidal silica; waxes, such as bees wax or spermaceti; boric acid; adipic acid; sulfates, such as sodium sulfate; glycol; fumaric acid; sodium benzoate; DL-leucine; sodium salts of aliphatic acids; lauryl sulfates, such as sodium laurylsulfate or magnesium laurylsulfate; silicates, such as silicic acid anhydride or silicic acid hydrate; and the foregoing starch derivatives); binders (e.g. polyvinyl pyridone, Macrogol; and similar compounds to the excipients described above); disintegrating agents (e.g. similar compounds to the excipients described above; and chemically modified starch-celluloses, such as Crosscarmelose sodium, sodium carboxymethyl starch or bridged polyvinyl pyrrolidone); stabilizers (e.g. p-hydroxybenzoates, such as methylparaben or propylparaben; alcohols, such as chlorobutanol, benzyl alcohol or phenylethyl alcohol; benzalkonium chloride; phenols, such as phenol or cresol; thimerosal; dehydroacetic acid; and sorbic acid); corrigents (e.g. sweeteners, vinegar or perfums, such as those conventionally used); diluents and the like.

The dose varies depending upon the condition and age of the patient and upon the route and type of administration but, for example, the compounds of the present invention can be administered orally in a daily dose of from 0.01 to 1000 mg/kg body weight (preferably 0.05 to 200 mg/kg body weight), either as a single dose or as divided doses.

The preparation of certain of the compounds of the invention is further illustrated by the following Examples. The subsequent Preparations, as well as Examples A and B, illustrate the preparation of certain of the starting materials used in these Examples. The remaining starting materials are either commonly available, disclosed in JCS Perkin I (1977) 1200–1203 or easily obtained following the procedures described in, for example, Bull. Chem. Soc. Japan, 36, No. 3, (1963) 290–295 and Chirality, 4, No. 3, (1992) 193.

These Examples include the preparation of representative compounds of the invention by direct isolation from microorganisms. The processes described in these Examples are purely illustrative, and these may be modified, for example on the basis of the properties of the desired compound, in order to recover the desired compound.

EXAMPLE A (4R,6R)-6-{2-[(1S,2S,6S,8S,8aR)-1,2,6,7,8,8 a-Hexahydro-6,8-dihydroxy-2-methyl-1-naphthyl]-ethyl}tetrehydro-4-hydroxy-2H-pyran-2-one

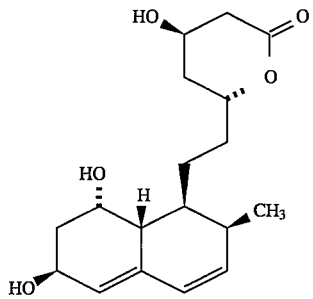

A-(1) Sodium (3R,5R)-3,5-dihydroxy-7-[(1S,2S,6S,8S,8aR)-6,8-dihydrxoy-2-methyl-1,2,6,7,8,8a-hexahydro-1-naphthyl]heptanoate 50 ml (0.24 mol) of a 28% w/v solution of sodium methoxide in methanol were added to a solution of 100 g (0.31 mol) of (3R,5R)-3,5-dihydroxy-7-[(1S,2S,6S,8S,8aR)-6-hydroxy-2-methyl-8-[(S)-2-methyl-butyryloxy]-1,2,6,7,8,8a-hexahydro-1-naphthyl]heptanoate (pravastatin: prepared as described in U.S. Pat. No. 4,346,227) in 900 ml of methanol, and the resulting mixture was heated under reflux for 60 hours. At the end of this time, the mixture was cooled to room temperature, and the methanol was then removed from the reaction mixture by distillation under reduced pressure. The resulting residue was washed with 200 ml of hexane and then dried in vacuo to give 120 g of the title compound.

A-(2) (3R,5R)-3,5-Dihydroxy-7-[(1S,2S,6S,8S,8aR)-6,8-dihydroxy-2-methyl-1,2,6,7,8,8a-hexahydro-1-naphthyl]heptanoic acid The whole of the sodium (3S,5R)-3,5-dihydroxy-7-[(1S,2S,6S,8S,8aR)-6,8-dihydroxy-2-methyl-1,2,6,7,8,8a-hexahydro-1-naphthyl] heptanoate prepared as described in Step 1, above, was dissolved directly and without further purification in 300 ml of water. The pH of the solution was adjusted to pH 4.0 by the addition of a 35% w/v aqueous hydrogen chloride solution. The water was then removed from the mixture by distillation under reduced pressure. The residue was dried in vacuo, after which the dried residue was dissolved in 300 ml of ethanol. Sodium chloride formed during the reaction was then removed by filtration, after which the resulting filtrate was concentrated by evaporation under reduced pressure. The residue obtained was dried to give 94 g of the title compound.

A-(3) (4R,6R)-6-{2-[(1S,2S,6S,8S,8aR)-1,2,6,7,8,8a-Hexahydro- 6,8-dihydroxy-2-methyl-1-naphthyl]ethyl}tetrahydro-4-hydroxy-2H-pyran-2-one The whole of the crude (3R,5R)-3,5-dihydroxy-7-[(1S,1S,6S,8S,8aR)-6,8-dihydroxy-2-methyl-1,2,6,7,8,8a-hexahydro- 1-naphthyl]heptanoic acid, prepared as described in Step 2, above, was mixed with 1000 ml of tetrahydrofuran. 38 ml (0.27 mol) of triethylamine were then added to the mixture, followed by 38 ml (0.25 mol) of diethyl cyanophosphonate, whilst ice-cooling and stirring. The resulting mixture was then stirred at room temperature for 1.5 hours. At the end of this time, the tetrahydrofuran was removed from the reaction mixture by distillation under reduced pressure and the residue was triturated with a mixture of diethyl ether and ethanol to stimulate crystallization. The resulting crystals were collected by filtration to provide 47.7 g of the title compound. This was then recrystallized from a mixture of ethyl acetate and ethanol to produce colorless plates melting at between 161° and 163° C.

Nuclear Magnetic Resonance Spectrum: (270 MHz, hexadeuterated dimethyl sulfoxide) δ ppm: 0.82 (3H, doublet, J=6.8 Hz); 4.07–4.15 (2H, multiplet); 4.29 (1H, doublet, J=4.4 Hz, interchangeable with $D_2O$); 4.23–4.35 (1H, multiplet); 4.52 (1H, doublet, J=6.4 Hz, interchangeable with $D_2O$); 4.51–4.62 (1H, multiplet); 5.15 (1H, doublet, J=2.9 Hz, interchangeable with $D_2O$); 5.40 (1H, broad singlet); 5.84 (1H, doublet of doublets, J=6.2 & 9.8 Hz); 5.90 (1H, doublet, J=9.8 Hz). Elemental Analysis: Calculated for $C_{18}H_{26}O_5$: C: 67.06%; H: 8.13%; Found: C: 66.81%; H: 8.37%. Infrared Absorption Spectrum (KBr) $v_{max}$ $cm^{-1}$; 3436, 3339, 3222, 1730, 1260, 1217, 1042. Mass Spectrum (m/e): 322 ($M^+$), 304, 286, 268. $[\alpha]_D^{25}$ +188.6° (c=0.59, ethanol).

EXAMPLE B (4R,6R)-6-{2-[(1S,2S,6S,8S,8aR)-1,2,6,7,8,8a-Hexahydro-6-t-butyldimethylsiyloxy-8-hydroxy-2-methyl-1-naphthyl]ethyl}tetrahydro-4-t-butyldimethylsilyloxy-2H-pyran-2-one

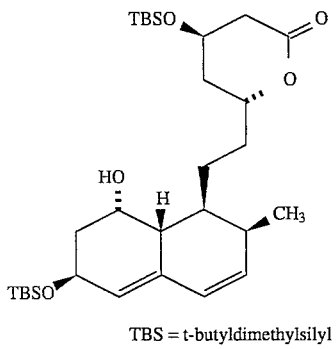

TBS = t-butyldimethylsilyl

A solution of 9.04 g (60.0 mmol) of t-butyldimethylsilyl chloride in 35 ml of dimethylformamide was added dropwise to a solution of 9.65 g (30.0 mmol) of (4R,6R)-6-{2-[(1S,2S,6S,8S,8aR)-1,2,6,7,8,8a-hexahydro-6,8-dihydroxy-2-methyl-1-naphthyl]ethyl}tetrahydro-4-hydroxy-2H-pyran-2-one [prepared as described in Example A, above] and 6.12 g (90.0 mmol) of imidazole in 45 ml of dimethylformamide, whilst ice-cooling and stirring. The resulting mixture was then stirred an room temperature for 5 hours, after which the solvent was removed by distillation under reduced pressure. The resulting residue was dissolved in 500 ml of ethyl acetate, and the solution was then washed first with water and then with a saturated aqueous solution of sodium chloride. The solution was then dried over anhydrous magnesium sulfate, after which the solution was filtered. The resulting filtrate was then concentrated by evaporation under reduced pressure. The concentrate was purified by flash column chromatography through silica gel using a gradient elution method, with mixtures of hexane and ethyl acetate ranging from 2:1 to 1:1 by volume as the eluent, to provide 13.3 g of the title compound as a colorless solid. This was then recrystallized from diisopropyl ether to produce colorless needles, melting at between 132° and 134° C.

Elemental Analysis: Calculated for $C_{30}H_{54}O_5Si_2$: C: 65.40; H: 9.88; Found: C: 65.29; H: 9.96. Nuclear Magnetic Resonance Spectrum: (270 MHz, hexadeuterated dimethyl sulfoxide) δ ppm: 0.79–0.92 (21H, multiplet); 4.07–4.15 (1H, multiplet); 4.27–4.34 (1H, multiplet); 4.38 (1H, doublet, J=3.9 Hz, interchangeable with $D_2O$); 4.48–4.60 (2H, multiplet); 5.33 (1H, broad singlet); 5.82 (1H, doublet of doublets, J=6.2 & 9.8 Hz); 5.92 (1H, doublet, J=9.8 Hz). Infrared Absorption Spectrum (KBr) $v_{max}$ cm$^{-1}$: 3497, 2956, 2929, 2857, 1736, 1711, 1361, 1257, 1071, 837. Mass Spectrum (m/e): 550 (M$^+$), 532, 493, 475, 343, 275 [α]$_D^{25}$+ 89.7° (c=0.50, acetone).

EXAMPLE 1

(4R,6R)-6-([1S,2S,6S,8S,8aR]-2-{1,2,6,7,8,8a-Hexahydro-6-t-butyldimethylsilyloxy-8-[(2RS)}-2-(4-methylphenoxy)butyryloxy]-2-methyl-1-naphthyl}ethyl)tetrahydro-4-t-butyldimethylsilyloxy-2H-pyran-2-one (Compound No. 1-71)

0.84 g of (2RS)-2-(4-methylphenoxy)butyric acid was dissolved in 20 ml of benzene, after which 1.01 ml of triethylamine and 0.78 g of diethyl chlorophosphate, followed by an excess of 4-(1-pyrrolidinyl)pyridine, were added to the resulting solution. The mixture was then stirred at room temperature for 30 minutes. 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above] was then added to the reaction mixture, and the mixture was stirred for a further 30 minutes. At the end of this time, 150 ml of ethyl acetate were added to the reaction mixture, the resulting mixture was washed with each of an aqueous solution of hydrogen chloride, water, a saturated aqueous solution of sodium hydrogencarbonate and an aqueous sodium chloride solution, in that order, and then dried over anhydrous magnesium sulfate. The solvent was then removed by distillation under reduced pressure. The resulting oil was separated and purified by silica gel column chromatography, using a 4:1 by volume mixture of hexane and ethyl acetate as the eluent, to give 1.31 g of the title compound as a colorless foam.

Nuclear Magnetic Resonance Spectrum (270 MHz, CDCl$_3$) δ ppm: 1.12 (3H, triplet, J=7.3 Hz); 2.31 (3H, singlet); 4.16–4.26 (1H, multiplet); 4.45–4.65 (2H, multiplet); 5.46 (1H, broad singlet); 5.52 (1H, broad singlet); 5.83–5.93 (1H, multiplet); 6.00 (1H, doublet, J=9.2 Hz); 6.81 (2H, doublet, J=8.6 Hz); 7.07 (2H, doublet, J=8.6 Hz).

EXAMPLE 2

(4R,6R)-6-([1S,2S,6S,8S,8aR]-2-{1,2,6,7,8.,8a-Hexahydro-6-hydroxy-6-[(2RS)-2-(4-methylphenoxy}butyryloxy]-2-methyl-1-naphthyl}ethyl)tetrahydro-4-hydroxy-2H-pyran-2-one (Compound No. 1-71)

1.31 g of (4R,6R)-6-(1S,2S,6S,8S,8aR)-2-{1,2,6,7,8,8a-hexahydro-6-t-butyldimethylsilyloxy-8 -[(2RS)-2-(4-methylphenoxy)butyryloxy]-2-methyl-1-naphthyl}ethyl)tetrahydro-4-t-butyldimethylsilyloxy-2H-pyran-2-one [prepared as described in Example 1, above] were dissolved in 10 ml of tetrahydrofuran, and the resulting solution was added to a mixture of 2.6 ml of acetic acid and 27.2 ml of a 1.0 molar solution of tetrabutylammonium fluoride in tetrahydrofuran, whilst ice-cooling. The reaction mixture was then stirred at room temperature for 14 hours. At the end of this time, the solvent was removed by distillation under reduced pressure, and 100 ml of ethyl acetate were added to the resulting residue. The mixture was then washed with a saturated aqueous solution of sodium hydrogencarbonate and with an aqueous sodium chloride solution, in that order, and then dried over anhydrous magnesium sulfate. The solvent was then removed by distillation under reduced pressure. The resulting oil was separated and purified by silica gel column chromatography, using a 1 by volume mixture of diethyl ether and hexane and then a 3:1 by volume mixture of ethyl acetate and hexane as the eluent, to give white crystals. These white crystals were recrystallized from a mixture of methylene chloride and diisopropyl ether to give 0.235 g of the title compound, melting at between 128° and 130° C.

Nuclear Magnetic Resonance Spectrum (270 MHz, CDCl$_3$) δ ppm: 0.85 (3H, doublet, J=7.3 Hz); 1.06 (3H, triplet, J=7.3 Hz); 2.26 (3H, singlet); 4.27–4.60 (3H, multiplet); 5.45 (1H, broad singlet); 5.57 (1H, broad singlet); 5.83–5.93 (1H, multiplet); 5.98 (1H, doublet, J=9.9 Hz); 6.77 (2H, doublet, J=8.6 Hz); 7.04 (2H, doublet, J=8.6 Hz).

EXAMPLE 3

Sodium Salt of (3R,5R)-3,5-dihydroxy-7-{(1S,2S,6S,8S,8aR)-1,2,6,7,8,8a-hexahydro-6-hydroxy-8-[(2RS)-2-(4-methylphenoxy)butyryloxy]-2-methyl-1-naphthyl}heptanoic acid (Compound No. 1-71)

30.0 mg of (4R,6R)-6-([1S,2S,6S,8S,8aR]-2-{1,2,6,7,8,8a-hexahydro-6-hydroxy-8-[(2RS.)-2-(4-methylphenoxy)butyryloxy]-2-methyl-1-naphthyl}ethyl)tetrahydro-4-hydroxy-2H-pyran-2-one [prepared as described in Example 2, above] were dissolved in a mixture of 1 ml of dioxane and 0.5 ml of distilled water. 0.60 ml of a 0.1N aqueous sodium hydroxide solution was then added to the mixture, whilst ice-cooling, and the mixture was left to stand at room temperature for 30 minutes. At the end of this time, the solvent was freeze-dried to give 36.0 mg of the title compound as a white foam.

EXAMPLE 4

(4R,6R)-6-([1S,2S,6S,8S,8aR]-2-{1,2,6,7,8,8a-Hexahydro-6-t-butyldimethylsilyloxy-8-[(2RS)-2-(2,6-dimethylphenoxy)butyryloxy]-2-methyl-1-naphthyl}ethyl)tetrahydro-4-t-butyldimethylsilyloxy-2H-pyran-2-one (Compound No. 1-78)

A procedure similar to that described in Example 1, above, was followed, but using 0.76 g of (2RS)-2-(2,6-dimethylphenoxy)butyric acid and 1.0 g of (4R,6R)-6-{(1S,2S,6S,8S,8aR)-2-[1,2,6,7,8,8a-hexahydro-t-butyldimethylsilyloxy-8-hydroxy-2-methyl-1-naphthyl] ethyl}tetrahydro-4-t-butyldimethylsilyloxy-2H-pyran-2-one [prepared as described in Example B, above], to give 1.22 g of the title compound as a colorless foam.

Nuclear Magnetic Resonance Spectrum (270 MHz, CDCl$_3$) δ ppm: 1.03 (3H, triplet, J=7.3 Hz); 2.27 (6H, singlet); 4.23–4.45 (2H, multiplet); 4.47–4.65 (2H, multiplet); 5.44 (1H, broad singlet); 5.47 (1H, broad singlet); 5.79–5.92 (1H, multiplet); 5.97 (1H, doublet, J=9.2 Hz); 6.82–7.05 (3H, multiplet).

EXAMPLE 5

(4R,6R)-6-([1S,2S,6S,8S,8aR]-2-{1,2,6,7,8,8a-Hexahydro-6-hydroxy-8-[(2RS)-2-(2,6-dimethylphenoxy)butyryloxy]-2-methyl-1-naphthyl}ethyl)tetra-hydro-4-hydroxy-2H-pyran-2-one (Compound No. 1-78)

A procedure similar to that described in Example 2, above, was followed, but using 1.17 g of (4R,6R)-6-([1S,2S,6S,8S,8aR]-2-{1,2,6,7,8,8a-hexahydro-6-t-butyldimethylsilyloxy-8-[(2RS)-2-(2,6-dimethylphenoxy)butyryloxy]-2-methyl-1-naphthyl}ethyl)tetrahydro-4-t-butyldimethylsilyloxy-2H-pyran-2-one [prepared as described in Example 4, above] and 23.7 ml of a 1.0 molar solution of tetrabutylammonium fluoride in tetrahydrofuran, to give 0.48 g of the title compound, melting at between 125° and 127° C.

Nuclear Magnetic Resonance Spectrum (270 MHz, CDCl$_3$) δ ppm: 1.00 (3H, triplet, J=7.3 Hz); 2.27 (6H, singlet); 3.98 (1H, broad singlet); 4.34 (1H, broad singlet); 4.47 (1H, triplet, J=5.9 Hz); 4.50–4.65 (1H, multiplet); 5.49 (2H, singlet); 5.81–5.94 (1H, multiplet); 5.97 (1H, doublet, J=9.9 Hz); 6.85–7.02 (2H, multiplet).

EXAMPLE 6

Sodium salt of (3R,5R)-3,5-dihydroxy-7-{(1S,2S,6S,8S,8aR)-1,2,6,7,8,8a-hexahydro-6-hydroxy-8-[(2RS)-2-(2,6-dimethylphenoxy)butyryloxy]-2-methyl-1-naphthyl}heptanoic acid (Compound No. 1-78)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2,6-dimethylphenoxy)butyryloxy]-2-methyl-1-naphthyl}ethyl)tetrahydro-4-hydroxy-2H-pyran-2-one [prepared as described in Example 5, above] and 0.58 ml of a 0.1N aqueous solution of sodium hydroxide, to give 33.9 mg of the title compound, as a colorless hygroscopic powder.

EXAMPLE 7

(4R,6R)-6-([1S,2S,6S,8S,8aR]-2-{2,6,7,8,8a-Hexahydro-6-t-butyldimethylsilyloxy-8-[(2RS)-2-(2-isopropylphenoxy)butyryloxy]-2-methyl-1-naphthyl}ethyl)tetrahydro-4-t-butyldimethylsilyloxy-2H-pyran-2-one (Compound No. 1-82)

A procedure similar to that described in Example 1, above, was followed, but using 0.92 g of (2RS)-2-(isopropylphenoxy)butyric acid and 1.0 g of (4R,6R)-6-{(1S,2S,6S,8S,8aR)-2-[1,2,6,7,8,8a-hexahydro-t-butyldimethylsilyloxy-8-hydroxy-2-methyl-1-naphthyl] ethyl}tetrahydro-4-t-butyldimethylsilyloxy-2H-pyran-2-one [prepared as described in Example B, above], give 0.76 g of the title compound as a colorless foam.

Nuclear Magnetic Resonance Spectrum (270 MHz, CDCl$_3$) δ ppm: 1.15 (3H, triplet, J=7.3 Hz); 1.20–1.28 (6H, multiplet); 3.30–3.48 (1H, multiplet); 4.34 (1H, multiplet); 4.40–4.61 (2H, multiplet); 4.68 (1H, triplet, J=5.9 Hz); 5.43 (1H, broad singlet); 5.49 (1H, broad singlet); 5.76–5.88 (1H, multiplet); 5.97 (1H, doublet, J=9.9 Hz); 6.71 (1H, doublet, J=7.9 Hz); 6.93 (1H, triplet, J=7.9 Hz); 7.09 (1H, triplet, J=7.9 Hz); 7.23 (1H, doublet, J=7.9 Hz).

EXAMPLE 8

(4R,6R)-6-([1S,2S,6S,8S,8aR]-2-{1,2,6,7,8,8a-Hexahydro-6-hydroxy-8-[(2RS)-2-(2-isopropylphenoxy)butyryloxy]-2-methyl-1-naphthyl}ethyl)tetrahydro-4-hydroxy-2H-pyran-2-one (Compound No. 1-82)

A procedure similar to that described in Example 2, above, was followed, but using 700 mg of (4R,6R)-6-([1S,2S,6S,8S,8aR]-2-{1,2,6,7,8,8a-hexahydro-6-t-butyldimethylsilyloxy-8-[(2RS)-2-(2-isopropylphenoxy)butyryloxy]-2-methyl-1-naphthyl}ethyl)tetrahydro-4-t-butyldimethylsilyloxy-2H-pyran-2-one [prepared as described in Example 7, above] and 14.0 ml of a 1.0 molar solution of tetrabutylammonium fluoride in tetrahydrofuran, to give 470 mg of the title compound as a colorless foam.

Nuclear Magnetic Resonance Spectrum (270 MHz, CDCl$_3$) δ ppm: 1.08 (3H, triplet, J=7.3 Hz); 1.14–1.21 (6H, multiplet); 3.20–3.40 (1H, multiplet); 4.30–4.50 (3H, multiplet); 4.62 (1H, triplet, J=5.9 Hz); 5.39 (1H, broad singlet); 5.53 (1H, broad singlet); 5.75–5.85 (1H, multiplet); 5.93 (1H, doublet, J=9.9 Hz); 6.69 (1H, doublet, J=7.9 Hz); 6.89

(1H, triplet, J=7.9 Hz); 7.07 (1H, triplet, J=7.9 Hz); 7.18 (1H, doublet, J=7.9 Hz).

EXAMPLE 9

Sodium salt of (3R,5R)-3,5-dihydroxy-7 -{(1S,2S,6S,8S,8aR)-1,2,6,7,8,8a-hexahydro-6 -hydroxy-8-[(2RS)-2-(2-isopropylphenoxy)butyryloxy]- 2-methyl-1-naphthyl}heptanoic acid (Compound No. 1-82)

A procedure similar to that described in Example 3, above, was followed, but using 30.0 mg of (4R,6R)-6-([1S, 2S,6S,8S,8aR]-2-{1,2,6,7,8,8a-hexahydro-6 -hydroxy-8- [(2RS)-2-(2-isopropylphenoxy)butyryloxy]-2 -methyl-1- naphthyl}ethyl)tetrahydro-4-hydroxy-2H-pyran-2-one [prepared as described in Example 8, above] and 0.57 ml of a 0.1N aqueous sodium hydroxide solution, to give 28.6 mg of the title compound, as a colorless hygroscopic powder.

EXAMPLE 10

(4R,6R)-6-([1S,2S,6S,8S,8aR]-2-{1,2,6,7,8,8a- Hexahydro- 6-t-butyldimethylsilyloxy-8-[(2RS)-2-(2- methylphenoxy)butyryloxy] -2-methyl-1-naphthyl}ethyl)tetrahydro-4-t- butyldimethylsilyloxy-2H-pyran-2-one (Compound No. 1-69)

600 mg of (2RS)-2-(2-methylphenoxy)butyric acid were dissolved in 5 ml of anhydrous methylene chloride, after which 0.53 ml of oxalyl chloride and several droplets of dimethylformamide were added to the mixture, whilst stirring and ice-cooling. The mixture was then stirred at room temperature for 1 hour, after which any excess oxalyl chloride and the solvent were removed by distillation under reduced pressure.

The oily acid chloride product was dissolved in 5 ml of methylene chloride and the resulting solution was added dropwise to a solution of 850 mg of (4R,6R)-6 -{(1S,2S, 6S,8S,8aR)-2-[1,2,6,7,8,8a-hexahydro-6-t-butyldimethylsilyloxy- 8-hydroxy-2-methyl-1-naphthyl]ethyl}tetrahydro-4- t-butyldimethylsilyloxy-2H-pyran-2-one [prepared as described in Example B, above] dissolved in 5 ml of pyridine, whilst ice-cooling. The mixture was then stirred for 30 minutes whilst ice-cooling, after which the mixture was poured into 50 ml of ice water. The resulting mixture was extracted with 200 ml of ethyl acetate, and the extract was washed with an aqueous solution of hydrogen chloride, a saturated aqueous solution of sodium hydrogencarbonate and a saturated aqueous solution of sodium chloride, in that order. The mixture was then dried over anhydrous magnesium sulfate, and the solvent was removed by distillation under reduced pressure. The residue thus obtained was separated and purified by silica gel column chromatography, using a 6:1 by volume mixture of hexane and ethyl acetate as the eluent, to give 671 mg of the title compound as a colorless foam.

Nuclear Magnetic Resonance Spectrum (270 MHz, CDCl$_3$) δ ppm: 1.13 (3H, triplet, J=7.3 Hz); 2.25 & 2.28 (total 3H, each singlet); 4.10–4.60 (3H, multiplet); 4.67 (1H, triplet, J=5.9 Hz); 5.41 (1H, broad singlet); 5.50 & 5.53 (total 1H, each broad singlet); 5.78–6.05 (2H, multiplet); 6.65–6.78 (1H, multiplet); 6.80–6.93 (1H, multiplet); 7.03–7.20 (2H, multiplet).

EXAMPLE 11

(4R,6R)-6-([1S,2S,6S,8S,8aR]-2-{1,2,6,7,8,8a- Hexahydro- 6-hydroxy-8-[(2RS)-2-(2-methylphenoxy)butyryloxy] -2-methyl-1-naphthyl}ethyl)tetrahydro-4-hydroxy- 2H-pyran-2-one (Compound No. 1-69)

A procedure similar to that described in Example 2, above, was followed, but using 590 mg of (4R,6R)-6 -([1S, 2S,6S,8S,8aR]-2-{1,2,6,7,8,8a-hexahydro-6-t-butyldimethylsilyloxy- 8-[(2RS)-2-(2-methylphenoxy)butyryloxy] -2-methyl-1-naphthyl}ethyl)tetrahydro-4-t-butyldimethylsilyloxy-2H-pyran-2-one [prepared as described in Example 10, above] and 11.6 ml of a 1.0 molar solution of tetrabutylammonium fluoride in tetrahydrofuran, to give 220 mg of the title compound, melting between 152° and 155° C.

Nuclear Magnetic Resonance Spectrum (270 MHz CDCl$_3$) δ ppm: 2.20 & 2.23 (total 3H, each singlet); 4.20–4.60 (3H, multiplet); 4.62–4.75 (1H, multiplet); 5.41 (1H, broad singlet); 5.51 & 5.56 (total 1H, each broad singlet); 5.80–6.05 (2H, multiplet); 6.63–6.93 (2H, multiplet); 7.02–7.20 (2H, multiplet).

EXAMPLE 12

Sodium salt of (3R,5R)-3,5-dihydroxy-7 -{(1S,2S,6S,8S,8aR)-8-[(2RS)-2 -(2-methylphenoxy)butyloxy-2-methyl-1- naphthyl}heptanoic acid (Compound No. 1-69)

A procedure similar to that described in Example 3, above, was followed, but using 30.0 mg of (4R,6R)-6 -([1S,2S,6S, 8S,8aR]-2-{1,2,6,7,8,8a-hexahydro-6- hydroxy-8-[(2RS)-2-(2-methylphenoxy)butyryloxy]-2-methyl-1 -naphthyl}ethyl)tetrahydro-4-hydroxy-2H-pyran-2- one prepared as described in Example 11, above] and 0.60 ml of a 0.1N aqueous sodium hydroxide solution, to give 33.6 mg of the title compound, as a colorless hygroscopic powder.

EXAMPLE 13

(4R,6R)-6-([1S,2S,6S,8,8aR]-2-{1,2,6,7,8,8a- Hexahydro- 6-t-butyldimethylsilyloxy-8-[(2RS)-2-(2,6- dichlorophenoxy)butyryloxy] -2-methyl-1-naphthyl}ethyl)tetrahydro-4-t- butyldimethylsilyloxy-2H-pyran-2-one (Compound No. 1-109)

A procedure similar to that described in Example 1, above, was followed, but using 0.78 g of (2RS)-2-(2,6- dichlorophenoxy)butyric acid and 1.0 g of (4R,6R)-6-{(1S, 2S,6S,8S,8aR)-2-[1,2,6,7,8,8 a-hexahydro-t-butyldimethylsilyloxy-8-hydroxy-2-methyl-1-naphthyl] ethyl}tetrahydro- 4-t-butyldimethylsilyloxy-2H-pyan-one [prepared as described in Example B, above], to give 1.56 g of the title compound as a colorless oil.

Nuclear Magnetic Resonance Spectrum (270 MHz, CDCl$_3$) δ ppm: 1.02–1.12 (3H, multiplet); 4.23–4.33 (1H, multiplet); 4.35–4.50 (1H, multiplet); 4.50–4.66 (1H, multiplet); 5.00 (1H, triplet, J=5.3 Hz); 5.40–5.70 (2H; multiplet); 5.76–5.90 (1H, multiplet); 5.96 (1H, doublet, J=9.9 Hz); 6.90–7.05 (1H, multiplet); 7.20–7.35 (2H, multiplet).

EXAMPLE 14

(4R,6R)-6-([1S,2S,6S,8S,8aR]-2-{1,2,6,7,8,8a-Hexahydro-6-hydroxy-8-[(2RS)-2-(2,6-dichlorophenoxy)butyryloxy]-2-methyl-1-naphthyl}ethyl)tetrahydro-4-hydroxy-2H-pyran-2-one (Compound No. 1-109)

A procedure similar to that described in Example 2, above, was followed, but using 1.41 g of (4R,6R)-6 -([S,2S,6S,8S,8aR]-2-{1,2,6,7,8,8a-hexahydro-6-t-butyldimethylsilyloxy- 8-[(2RS)-2-(2,6-dichlorophenoxy)butyryloxy]-2-methyl-1-naphthyl}ethyl)tetrahydro-4-t-butyldimethylsilyloxy-2H-pyran-2-one [prepared as described in Example 13, above] and 43.3 ml of a 1.0 molar solution of tetrabutylammonium fluoride in tetrahydrofuran, to give 0.29 g of the title compound, melting at between 107° and 109° C.

Nuclear Magnetic Resonance Spectrum (270 MHz, CDCl$_3$) δ ppm: 1.07 (3H, triplet, J=7.3 Hz); 4.26–4.43 (2H, multiplet); 4.53–4.65 (1H, multiplet); 4.91 (1H, triplet, J=5.3 Hz); 5.54 (2H, broad singlet); 5.80–6.02 (2H, multiplet); 6.91–7.03 (1H, multiplet); 7.25–7.32 (2H, multiplet).

EXAMPLE 15

Sodium salt of (3R,5R)-3,5-dihydroxy-7-{(1S,2S,6S,8S,8aR)-1,2,6,7,8,8a-hexahydro-6-hydroxy-8-[(2RS)-2-(2,6-dichlorophenoxy)butyryloxy]-2-methyl-1-naphthyl)heptanoic acid (Compound No. 1-109)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2,6-dichlorophenoxy)butyryloxy]-2-methyl-1-naphthyl}ethyl tetrahydro-4-hydroxy-2-H-pyran-2-one [prepared as described in Example 14, above] and 0.54 ml of a 0.1N aqueous solution of sodium hydroxide, to give 33.2 mg of the title compound, as a colorless hygroscopic powder.

EXAMPLE 16

(4R,6R)-6-([1S,2S,6S,8S,8aR]-2-{1,2,6,7,8,8a-Hexahydro-6-t-butyldimethylsilyloxy-8-[(2RS)-2-(3-methylphenoxy)butyryloxy]-2-methyl-1-naphthyl}ethyl)tetrahydro-4-t-butyldimethylsilyloxy-2H-pyran-2-one (Compound No. 1-70)

A procedure similar to that described in Example 1, above, was followed, but using 0.71 g of (2RS)-2-(3-methylphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl} tetrahydro-4-t-butyldimethylsilyloxy-2H-pyran-2-one [prepared as described in Example B, above], to give 1.30 g of the title compound as a colorless foam.

Nuclear Magnetic Resonance Spectrum (270 MHz, CDCl$_3$) δ ppm: 1.07 (3H, triplet, J=7.3 Hz); 2.29 (3H, singlet); 4.26 (! H, multiplet); 4.37–4.55 (2H, multiplet); 4.58 (1H, triplet, J=5.3 Hz); 5.39 (1H, broad singlet); 5.47 (1H, broad singlet); 5.81 (1H, doublet of doublets, J=5.9 & 9.2 Hz); 5.96 (1H, doublet, J=9.2 Hz); 6.62 (1H, multiplet); 6.74 (2H, multiplet); 7.10 (1H, triplet, J=8.6 Hz).

EXAMPLE 17

(4R,6R)-6-([1S,2S,6S,8S,8aR]-2-{1,2,6,7,8,8a-Hexahydro-6-hydroxy-8-[(2RS)-2-(3-methylphenoxy)butyryloxy]-2-methyl-1-naphthyl}ethyl)tetrahydro-4-hydroxy-2H-pyran-2-one (Compound No. 1-70)

A procedure similar to that described in Example 2, above, was followed, but using 1.15 g of (4R,6R)-6 -([1S,2S,6S,8S,8aR]-{1,2,6,7,8,8a-hexahydro-6-t-butyldimethylsilyloxy- 8-[(2RS)-2-(3-methylphenoxy)butyryloxy]-2-methyl-1-naphthyl}ethyl)tetrahydro-4-t-butyldimethylsilyloxy- 2H-pyran-2-one [prepared as described in Example 16, above] and 38.0 ml of a 1.0 molar solution of tetrabutylammonium fluoride in tetrahydrofuran, to give 0.46 g of the title compound, melting at between 147° and 149° C.

Nuclear Magnetic Resonance Spectrum (270 MHz, CDCl$_3$) δ ppm: 1.07 (3H, triplet, J=7.3 Hz); 2.30 (3H, singlet); 4.25–4.53 (3H, multiplet); 4.56 (1H, triplet, J=5.9 Hz); 5.43 (1H, broad singlet); 5.58 (1H, broad singlet); 5.87 (1H, doublet of doublets, J=5.9 & 9.9 Hz); 5.99 (1H, doublet, J=9.9 Hz); 6.60–6.80 (3H, multiplet); 7.13 (1H, triplet, J=7.3 Hz).

EXAMPLE 18

Sodium salt of (3R,5R)-3,5-dihydroxy-7-{(1S,2S,6S,8S,8aR)-1,2,6,7,8,8a-hexahydro-6-hydroxy-8-[(2RS)-2-(3-methylphenoxy)butyryloxy]-2-methyl-1-naphthyl}heptanoic acid (Compound No. 1-70)

A procedure similar to that described in Example 3, above, was followed, but using 30.0 mg of (4R,6R)-6 -([1S,2S,6S,8S,8aR]-2-{1,2,6,7,8,8a-hexahydro-6-hydroxy-8-[(2RS)-2-(3-methylphenoxy)butyryloxy]-2-methyl-1-naphthyl}ethyl)tetrahydro-4-hydroxy-2H-pyan-2-one [prepared as described in Example 17, above] and 0.60 ml of a 0.1N aqueous solution of sodium hydroxide, to give 33.1 mg of the title compound, as a colorless hygroscopic powder.

EXAMPLE 19

(4R,6R)-6-([1S,2S,6S,8S,8aR]-2-{1,2,6,7,8,8a-Hexahydro-6-t-butyldimethylsilyloxy-8-[(2RS)-2-(2-bromophenoxy)butyryloxy]-2-methyl-1-naphthyl}ethyl)tetrahydro-4-t-butyldimethylsilyloxy-2H-pyran-2-one (Compound No. 1-100)

A procedure similar to that described in Example 1, above, was followed, but using 0.94 g of (2RS)-2-(2-bromophenoxy)buryric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]-ethyl}tetrahydro-4-t-butyldimethylsilyloxy-2H-pyran-2-one [prepared as described in Example B, above] to give 1.42 g of the title compound as a colorless foam.

Nuclear Magnetic Resonance Spectrum (270 MHz, CDCl$_3$) δ ppm: 1.12 (3H, triplet, J=7.3 Hz); 4.29 (1H, multiplet); 4.43–4.60 (2H, multiplet); 4.73 (1H, triplet, J=5.3 Hz); 5.43 (2H, broad singlet); 5.77 (1H, doublet of doublets, J=5.9 & 9.2 Hz); 5.93 (1H, doublet, J=9.9 Hz); 6.75–6.85 (2H, multiplet); 7.10–7.22 (1H, multiplet); 7.50 (1H, doublet, J=7.9 Hz).

EXAMPLE 20

(4R,6R)-6-([1S,2S,6S,8S,8aR]-2-{1,2,6,7,8,8a-Hexahydro-6-hydroxy-8-[(2RS)-2-(2-bromophenoxy)butyryloxy]-2-methyl-1-naphthyl}ethyl)tetrahydro-4-hydroxy-2H-pyran-2-one (Compound No. 1-100)

A procedure similar to that described in Example 3, above, was followed, but using 1.33 g of (4R,6R)-6-([1S,2S,6S,8S,8aR]-2-{1,2,6,7,8,8a-hexahydro-6-t-butyldimethylsilyloxy-8-[(2RS)-2-(2-bromophenoxy)butyryloxy]-2-methyl-1-naphthyl}ethyl)tetrahydro-4-t-butyldimethylsilyloxy-2H-pyran-2-one [prepared as described in Example 19, above] and 40.3 ml of a 1.0 molar solution of tetrabutylammonium fluoride in tetrahydrofuran, to give 0.57 g of the title compound, melting at between 160° and 162° C.

Nuclear Magnetic Resonance Spectrum (270 MHz, $CDCl_3$+hexadeuterated dimethyl sulfoxide) δ ppm: 1.11 (3H, triplet, J=7.3 Hz); 4.27 (1H, multiplet); 4.35–4.60 (2H, multiplet); 4.68 (1H, triplet, J=5.9 Hz); 5.43 (1H, broad singlet); 5.57 (1H, broad singlet); 5.81 (1H, doublet of doublets, J=5.9 & 9.9 Hz); 5.95 (1H, doublet, J=9.9 Hz); 6.76–6.90 (2H, multiplet); 7.17–7.28 (1H, multiplet); 7.51 (1H, doublet, J=6.6 Hz).

EXAMPLE 21

Sodium salt of (3R,5R)-3,5-dihyroxy-7-{(1S,2S,6S,8S,8aR)-1,2,6,7,8,8a-hexahydro-6-hydroxy-8-[(2RS)-2-(2-bromophenoxy)butyryloxy]-2-methyl-1-naphthyl}heptanoic acid (Compound No. 1-100)

A procedure similar to that described in Example 1, was followed, but using 30.0 mg of (4R,6R)-6-([1S,2S,6S,8S,8aR]-2-{1,2,6,7,8,8a-hexahydro-6-hydroxy-8-[(2RS)-2-(2-bromophenoxy)butyryloxy]-2-methyl-1-napthyl}ethyl)tetrahydro-4-hydroxy-2H-pyan-2-one [prepared as described in Example 20, above] and 0.53 ml of a 0.1N aqueous sodium hydroxide solution to give 34.1 mg of the title compound, as a colorless hygroscopic powder.

EXAMPLE 22

(4R,6R)-6-([1S,2S,6S,8S,8aR]-2-{1,2,6,7,8,8a-Hexahydro-6-t-butyldimethylsilyloxy-8-[(2RS)-2-(4-fluorophenoxy)butyryloxy]-2-methyl-1-naphthyl}ethyl)tetrahydro-4-t-butyldimethylsilyloxy-2H-pyran-2-one (Compound No. 1-99)

A procedure similar to that described in Example 1, above, was followed, but using 0.72 g of (2RS)-2-(4-fluorophenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.30 g of the title compound as a colorless foam.

Nuclear Magnetic Resonance Spectrum (270 MHz, $CDCl_3$) δ ppm: 1.13 (3H, triplet, J=7.3 Hz); 4.34 (1H, multiplet); 4.43–4.65 (3H, multiplet); 5.44 (1H, broad singlet); 5.51 (1H, broad singlet); 5.87 (1H, doublet of doublets, J=5.9 & 9.9 Hz); 5.96–6.07 (1H, multiplet); 6.83–7.05 (4H, multiplet).

EXAMPLE 23

(4R,6R)-6-([1S,2S,6S,8S,8aR]-2-{1,2,6,7,8,8a-Hexahydro-6-hydroxy-8-[(2RS)-2-(4-fluorophenoxy)butyryloxy]-2-methyl-1-naphthyl}ethyl)tetrahydro-4-hydroxy-2H-pyran-2-one (Compound No. 1-99)

A procedure similar to that described in Example 1, above, was followed, but using 1.20 g of (4R,6R)-6-([1S,2S,6S,8S,8aR]-2-{1,2,6,7,8,8a-hexahydro-6-t-butyldimethylsilyloxy-8-[(2RS)-2-(4-fluorophenoxy)butyryloxy]-2-methyl-1-naphthyl}ethyl)tetrahydro-4-t-butyldimethylsilyloxy-2H-pyan-2-one [prepared as described in Example 22, above] and 24.6 ml of a 1.0 molar solution of tetrabutylammonium fluoride in tetrahydrofuran, to give 0.30 g of the title compound, melting at between 149° and 150° C.

Nuclear Magnetic Resonance Spectrum (270 MHz, $CDCl_3$) δ ppm: 1.07 (3H, triplet, J=7.3 Hz); 4.30–4.52 (3H, multiplet); 4.50 (1H, triplet, J=5.9 Hz); 5.42 (1H, broad singlet); 5.56 (1H, broad singlet); 5.86 (1H, doublet of doublets, J=5.9 & 9.9 Hz); 5.97 (1H, doublet, J=9.9 Hz); 6.75–7.00 (4H, multiplet).

EXAMPLE 24

Sodium salt of (3R,5R)-3,5-dihydroxy-7-{(1S,2S,6S,8S,8aR)-1,2,6,7,8,8a-hexahydro-6-hydroxy-8-[(2RS)-2-(4-fluorophenoxy)butyryloxy]-2-methyl-1-naphthyl}heptanoic acid (Compound No. 1-99)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(4-fluorophenoxy)butyryloxy]-2-methyl-1-naphthyl}ethyl)tetrahydro-4-hydroxy-2H-pyran-2-one [prepared as described in Example 23, above] and 0.59 ml of a 0.1N aqueous solution of sodium hydroxide, to give 35.1 mg of the title compound, as a colorless hygroscopic powder.

EXAMPLE 25

(4R,6R)-6-([1S,2S,6S,8S,8aR]-2-(1,2,6,7,8,8a-Hexadyro-6-t-butyldimethylsilyloxy-8-[(2RS)-2-(2,3-dimethylphenoxy)butyryloxy]-2-methyl-1-naphthyl}ethyl)tetrahydro-4-t-butyldimethylsilyloxy-2H-pyran-2-one (Compound No. 1-75)

A procedure similar to that described in Example 1, above, was followed, but using 708 mg of (2RS)-2-(2,3-dimethylphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.25 g of the title compound as a colorless foam.

Nuclear Magnetic Resonance Spectrum (270 MHz, $CDCl_3$) δ ppm: 1.14 (3H, triplet, J=7.3 Hz); 2.17 & 2.20 (total 3H, each singlet); 2.26 & 2.28 (total 3H, each singlet); 4.00–4.80 (4H, multiplet); 5.41 (1H, broad singlet); 5.50 (1H, broad singlet); 5.78–6.05 (2H, multiplet); 6.60 (1H, multiplet); 6.77 (1H, multiplet); 6.96 (1H, multiplet).

EXAMPLE 26

(4R,6R)-6-([1S,2S,6S,8S,8aR]-2-{1,2,6,7,8,8a-Hexahydro-6-hydroxy-8-[(2RS)-2-(2,3-dimethylphenoxy)butyryloxy]-2-methyl-1-naphthyl}ethyl)tetrahydro-4-hydroxy-2H-pyran-2-one (Compound No. 1-75)

A procedure similar to that described in Example 2, above, was followed, but using 1.25 g of (4R,6R)-6-([1S, 2S,6S,8S,8aR]-2-{1,2,6,7,8,8a-hexahydro-6-t-butyldimethylsilyloxy-8-[(2RS)-2-(2,3-dimethylphenoxy)butyryloxy]-2-methyl-1-naphthyl}ethyl)tetrahydro-4-t-butyldimethylsilyloxy-2H-pyran-2-one [prepared as described in Example 25, above] and 33.8 ml of a 1.0 molar solution of tetrabutylammonium fluoride in tetrahydrofuran, to give 187 mg of the title compound, melting at between 148° and 150° C.

Nuclear Magnetic Resonance Spectrum 270 MHz, $CDCl_3$) δ ppm: 1.09 (3H, triplet, J=7.3 Hz); 2.12 & 2.15 (total 3H, each singlet); 2.22 & 2.26 (total 3H, each singlet); 4.30–4.55 (3H, multiplet); 4.67 (1H, triplet, J=5.9 Hz); 5.40 (1H, broad singlet); 5.55 (1H, broad singlet ); 5.83 (1H, doublet of doublets, J=5.9 & 9.2 Hz); 5.96 (1H, doublet, J=9.9 Hz); 6.60 (1H, doublet, J=7.9 Hz); 6.73 (1H, doublet, J=7.3 Hz); 6.95 (1H, triplet, J=7.3 Hz).

EXAMPLE 27

Sodium salt of (3R,5R)-3,5-dihydroxy-7-{(1S,2S,6S,8S,8aR)-1,2,6,7,8,8a-hexahydro-6-hydroxy-8-[(2RS)-2-(2,3-dimethylphenoxy)butyryloxy]-2-methyl-1-naphthyl}heptanoic acid (Compound No. 1-75)

A procedure similar to that described in Example 3, above, was followed, but using 20.6 mg of (4R,6R)-6-([1S, 2S,6S,8S,8aR]-2-{1,2,6,7,8,8a-hexahydro-6-hydroxy-8-[(2RS)-2-(2,3-dimethylphenoxy)butyryloxy]-2-methyl-1-naphthyl}ethyl)tetrahydro-4-hydroxy-2H-pyran-2-one [prepared as described in Example 26, above] and 0.40 ml of a 0.1N aqueous solution of sodium hydroxide, to give 25.0 mg of the title compound, as a colorless hygroscopic powder.

EXAMPLE 28

(4R,6R)-6-([1S,2S,6S,8S,8aR]-2-{1,2,6,7,8,8a-Hexahydro-6-t-butyldimethylsilyloxy-8-[(2RS)-2-(4-chlorophenoxy)butyryloxy]-2-methyl-1-naphthyl}ethyl)tetrahydro-4-t-butyldimethylsilyloxy-2H-pyran-2-one (Compound No. 1-96)

A procedure similar to that described in Example 1, above, was followed, but using 730 mg of (2RS)-2-(4-chlorophenoxy)butyric acid and 1.0 g of (4R,6R)-6-{(1S, 2S,6S,8S,8aR)-2-[1,2,6,7,8,8a-hexahydro-6-t-butyldimethylsilyloxy-8-hydroxy-2-methyl-1-naphthyl] ethyl}tetrahydro-4-t-butyldimethylsilyloxy-2H-pyran-2-one [prepared as described in Example B, above], to give 1.42 g of the title compound as a colorless foam.

Nuclear Magnetic Resonance Spectrum (270 MHz, $CDCl_3$) δ ppm: 1.12 (3H, triplet, J=7.3 Hz); 4.12–4.66 (4H, multiplet); 5.44 (1H, broad singlet); 5.49 (1H, broad singlet); 5.82–6.06 (2H, multiplet); 6.85 (2H, doublet, J=9.2 Hz); 7.22 (2H, doublet, J=9.2 Hz).

EXAMPLE 29

(4R,6R)-6-([1S,2S,6S,8S,8aR]-2-{1,2,6,7,8,8a-Hexahydro-6-hydroxy-8-[(2RS)-2-(4-chlorophenoxy)butyryloxy]-2-methyl-1-naphthyl}ethyl)tetrahydro-4-hydroxy-2H-pyran-2-one (Compound No. 1-96)

A procedure similar to that described in Example 2, above, was followed, but using 1.42 g of (4R,6R)-6-([1S, 2S,6S,8S,8aR]-2-{1,2,6,7,8,8a-hexahydro-6-t-butyldimethylsilyloxy-8-[(2RS)-2-(4-chlorophenoxy)butyryloxy]-2-methyl-1-naphthyl}ethyl)-4-tetrahydro-4-t-butyldimethylsilyloxy-2H-pyran-2-one [prepared as described in Example 28, above] and 38.0 ml of a 1.0 molar solution of tetrabutylammonium fluoride in tetrahydrofuran, to give 653 mg of the title compound, melting at between 140° and 142° C.

Nuclear Magnetic Resonance Spectrum (270 MHz, $CDCl_3$) δ ppm: 1.06 (3H, triplet, J=7.3 Hz); 4.30–4.50 (3H, multiplet); 4.53 (1H, triplet, J=5.9 Hz); 5.41 (1H, broad singlet); 5.56 (1H, broad singlet); 5.86 (1H, doublet of doublets, J=5.9 & 9.9 Hz); 5.97 (1H, doublet, J=9.9 Hz); 6.83 (2H, doublet, J=9.2 Hz); 7.21 (2H, doublet, J=9.2 Hz).

EXAMPLE 30

Sodium salt of (3R, 5R)-3,5-dihydroxy-7-{(1S,2S,6S,8S,8aR)-1,2,6,7,8,8a-hexahydro-6-hydroxy-8-[(2RS)-2-(4-chlorophenoxy)butyryloxy]-2-methyl-1-naphthyl}heptanoic acid (Compound No. 1-96)

A procedure similar to that described in Example 3, above, was followed, but using 21.7 mg of (4R,6R)-6-([1S, 2S,6S,8S,8aR]-2-{1,2,6,7,8,8a-hexahydro-6-hydroxy-8-[(2RS)-2-(4-chlorophenoxy)butyryloxy]-2-methyl-1-naphthyl}ethyl)tetrahydro-4-hydroxy-2H-pyran-2-one [prepared as described in Example 29, above] and 0.42 ml of a 0.1N aqueous solution of sodium hydroxide, to give 25.3 mg of the title compound, as a colorless hygroscopic powder.

EXAMPLE 31

(4R,6R)-6-([1S,2S,6S,8S,8aR]-2-{1,2,6,7,8,8a-Hexahydro-6-t-butyldimethylsilyloxy-8-[(2RS)-2-(4-methylphenoxy)-2-methylbutyryloxy]-2-methyl-1-naphthyl}ethyl)tetrahydro-4-t-butyldimethylsilyloxy-2H-pyran-2-one (Compound No. 1-279)

A procedure similar to that described in Example 10, above, was followed, but using 600 mg of (2RS)-2-(4-methylphenoxy)-2-methylbutyric acid and 1.32 g of (4R, 6R)-6-{(1S,2S,6S,8S,8aR)-2-[1,2,6,7,8,8a-hexahydro-6-t-butyldimethylsilyloxy-8-hydroxy-2-methyl-1-napthyl] ethyl}tetrahydro-4-t-butyldimethylsilyloxy-2H-pyran-2-one [prepared as described in Example B, above], to give 1.51 g of the title compound as a colorless foam.

Nuclear Magnetic Resonance Spectrum (270 MHz, $CDCl_3$) δ ppm: 1.45 (3H, singlet); 4.25–4.50 (2H, multiplet); 4.52–4.72 (1H, multiplet); 5.47 (1H, broad singlet); 5.53 (1H, broad singlet); 5.82–5.95 (1H, multiplet); 5.99 (1H, doublet, J=9.2 Hz); 6.83 (2H, doublet, J=8.6 Hz); 7.04 (2H, doublet, J=8.6 Hz).

EXAMPLE 32

(4R,6R)-6-([1S,2S,6S,8S,8aR]-2-{1,2,6,7,8,8a-Hexahydro-6-hydroxy-8-[(2RS)-2-(4-methylphenoxy)-2-methylbutyryloxy]-2-methyl-1-naphthyl}ethyl)tetrahydro-4-hydroxy-2H-pyran-2-one (Compound No. 1-279)

A procedure similar to that described in Example 2, above, was followed, but using 1.50 g of (4R,6R)-6-([1S,2S,6S,8S,8aR]-2-{1,2,6,7,8,8a-hexahydro-6-t-butyldimethylsilyloxy-8-[(2RS)-2-(4-methylphenoxy)-2-methylbutyryloxy]-2-methyl-1-naphthyl}ethyl)tetrahydro-4-t-butyldimethylsilyloxy-2H-pyran-2-one [prepared as described in Example 31, above] and 30.4 ml of a 1.0 molar solution of tetrabutylammonium fluoride in tetrahydrofuran, to give 840 mg of the title compound as a colorless foam.

Nuclear Magnetic Resonance Spectrum (270 MHz, CDCl$_3$) δ ppm: 1.40 & 1.46 (total 3H, each singlet); 3.93–4.20 (1H, multiplet); 4.35 (1H, multiplet); 4.50–4.65 (1H, multiplet); 5.51 (2H, broad singlet); 5.80–5.92 (1H, multiplet); 5.98 (1H, doublet, J=9.9 Hz); 6.78 (2H, doublet, J=8.6 Hz); 7.03 (2H, doublet, J=8.6 Hz).

EXAMPLE 33

Sodium salt of (3R,SR)-3,5-dihydroxy-7-{(1S,2S,6S,8S,8aR)-1,2,6,7,8,8a-hexahydro-6-hydroxy-8-[(2RS)-2-(4-methylphenoxy)-2-methylbutyryloxy]-2-methyl-1-naphthyl}heptanoic acid (Compound No. 1-279)

A procedure similar to that described in Example 3, above, was followed, but using 30.1 mg of (4R,6R)-6-([1S,2S,6s,8S,8aR]-2-{1,2,6,7,8,8a-hexahydro-6hydroxy-8-[(2RS)-2-(4-methylphenoxy)-2-methylbutyryloxy]-2-methyl-1-naphthyl}ethyl)tetrahydro-4-hydroxy-2H-pyran-2-one [prepared as described in Example 32, above] and 0.59 ml of a 0.1N aqueous solution of sodium hydroxide, to give 29.7 mg of the title compound, as a colorless hygroscopic powder.

EXAMPLE 34

(4R,6R)-6-([1S,2S,6S,8S,8aR]-2-{1,2,6,7,8,8a-Hexahydro-6-t-butyldimethylsilyloxy-8-[(2RS)-2-(2-methyl-1-naphthyloxy)butyryloxy]-2-methyl-1-naphthyl}ethyl)tetrahydro-4-t-butyldimethylsilyloxy-2H-pyran-2-one (Compound No. 1-369)

A procedure similar to that described in Example 1, above, was followed, but using 830 mg of (2RS)-2-(2-methyl-1-naphthyloxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-napthyl]ethyl}tetrahydro-4-t-butyldimethylsilyloxy-2H-pyran-2-one [prepared as described in Example B, above], to give 1.52 g of the title compound as a colorless foam.

Nuclear Magnetic Resonance Spectrum (270 MHz, CDCl$_3$) δ ppm: 1.05 (3H, triplet, J=7.3 Hz); 2.48 (3H, singlet); 4.23 (1H, multiplet); 4.37 (1H, multiplet); 4.57 (1H, multiplet); 4.72 (1H, multiplet); 5.45 (1H, broad singlet); 5.51 (1H, broad singlet); 5.85 (1H, doublet of doublets, J=5.9 & 9.9 Hz); 5.98 (1H, doublet, J=9.9 Hz); 7.20–7.33 (1H, multiplet); 7.37–7.60 (3H, multiplet); 7.75–7.82 (1H, multiplet); 8.10–8.23 (1H, multiplet).

EXAMPLE 35

(4R,6R)-6-([1S,2S,6S,8S,8aR]-2-{1,2,6,7,8,8a-Hexahydro-6-hydroxy-8-[(2RS)-2-(2-methyl-1-naphthyloxy)butyryloxy]-2-methyl-1-naphthyl}ethyl)tetrahydro-4-hydroxy-2H-pyran-2-one (Compound No. 1-369 )

A procedure similar to that described in Example 2, above, was followed, but using 1.52 g of (4R,6R)-6-([1S,2S,6S,8S,8aR]-2-{1,2,6,7,8,8a-hexahydro-6-t-butyldimethylsilyloxy-8-[(2RS)-2-(2-methyl-1-naphthyloxy)butyryloxy]-2-methyl-1-naphthyl}ethyl)tetrahydro-4-t-butyldimethylsilyloxy-2H-pyran-2-one [prepared as described in Example 34, above] and 36.0 ml of a 1.0 molar solution of tetrabutylammonium fluoride in tetrahydrofuran, to give 0.79 g of the title compound as a foam.

Nuclear Magnetic Resonance Spectrum (270 MHz, CDCl$_3$) δ ppm: 1.01 (3H, triplet, J=7.3 Hz); 2.44 (3H, singlet); 3.53 (1H, multiplet); 4.27 (1H, multiplet); 4.46–4.64 (2H, multiplet); 5.36 (1H, broad singlet); 5.41 (1H, broad singlet); 5.76–6.03 (2H, multiplet); 7.25 (1H, multiplet); 7.36–7.60 (1H, multiplet); 7.77 (1H, doublet, J=9.3 Hz); 8.16 (1H, doublet, J=7.9 Hz).

EXAMPLE 36

Sodium salt of (3R,5R)-3,5-dihydroxy-7-{(1S,2S,6S,8S,8aR)-1,2,6,7,8,8a-hexahydro-6-hydroxy-8-[(2RS)-2-(2-methyl-1-naphthyloxy)butyryloxy]-2methyl-1-naphthyl}heptanoic acid (Compound No. 1-369)

A procedure similar to that described in Example 3, above, was followed, but using 25.3 mg of (4R,6R)-6-([1S,2S,6S,8S,8aR]-2-{1,2,6,7,8,8a-hexahydro-6-hydroxy-8-[(2RS)-2-(2-methyl-1-naphthyloxy)butyryloxy]-2-methyl-1-naphthyl}ethyl)tetrahydro-4-hydroxy-2H-pyran-2-one [prepared as described in Example 35, above] and 0.46 ml of a 0.1N aqueous solution of sodium hydroxide, to give 29.8 mg of the title compound, as a colorless hygroscopic powder.

EXAMPLE 37

(4R,6R)-6-([1S,2S,6S,8S,8aR]-2-{1,2,6,7,8,8a-Hexahydro-6-t-butyldimethylsilyloxy-8-[(2RS)-2-phenoxybutyryloxy]-2-methyl-1-naphthyl}ethyl)tetrahydro-4-t-butyldimethylsilyloxy-2H-pyran-2-one (Compound No. 1-65)

A procedure similar to that described in Example 10, above, was followed, but using 0.66 g of (2RS)-2-phenoxybutyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as describe in Example B, above], to give 1.20 g of the title compound as a colorless foam.

Nuclear Magnetic Resonance Spectrum (270 MHz, CDCl$_3$) δ ppm: 1.12 (3H, triplet, J=7.3 Hz); 4.15–4.70 (4H, multiplet); 5.44 (1H, broad singlet); 5.48–5.60 (1H, multiplet); 5.80–6.05 (1H, multiplet); 6.85–7.05 (3H, multiplet); 7.27 (2H, triplet, J=7.3 Hz).

EXAMPLE 38

(4R,6R)-6-([1S,2S,6S,8S,8aR]-2-{1,2,6,7,8,8a-Hexahydro-6-hydroxy-8-[(2RS)-2-phenoxybutyryloxy]-2-methyl-1-naphthyl}ethyl)tetrahydro-4-hydroxy-2H-pyran-2-one (Compound No. 1-65)

A procedure similar to that described in Example above, was followed, but using 1.10 g of (4R,6R)-6-([1S,2S,6S,8S,8aR]-2-{1,2,6,7,8,8a-hexahydro-6-t-butyldimethylsilyloxy-8-[(2RS)-2-phenoxybutyryloxy]-2-methyl-1-naphthyl}ethyl)tetrahydro-4-t-butyldimethylsilyloxy-2H-pyran-2-one [prepared as described in Example 37, above] and 37.7 ml of a 1.0 molar solution of tetrabutylammonium fluoride in tetrahydrofuran, to give 0.29 g of the title compound as white crystals, melting at between 120° and 122° C.

Nuclear Magnetic Resonance Spectrum (270 MHz, $CDCl_3$+hexadeuterated dimethyl sulfoxide) δ ppm: 3.85–4.65 (4H, multiplet); 5.35–5.63 (2H, multiplet); 5.78–6.03 (2H, multiplet); 6.87 (2H, doublet, J=7.3 Hz); 6.95 (1H, triplet, J=7.3 Hz); 7.26 (1H, triplet, J=7.3 Hz).

EXAMPLE 39

Sodium salt of (3R,5R)-3,5-dihydroxy-7-{(1S,2S,6S,8S,8aR)-1,2,6,7,8,8a-hexahydro-6-hydroxy-8-[(2RS)-2-phenoxybutyryloxy]-2-methyl-1-naphthyl}heptanoic acid (Compound No. 1-65)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-phenoxybutyryloxy]-2-methyl-1-naphthyl}ethyl)tetrahydro-4-hydroxy-2H-pyran-2-one [prepared as described in Example 38, above] and 0.62 ml of a 0.1N aqueous solution of sodium hydroxide, to give 32.5 mg of the title compound, as a colorless hygroscopic powder.

EXAMPLE 40

(4R,6R)-6-([1S,2S,6S,8S,8aR]-2-{1,2,6,7,8,8a-Hexahydro-6-t-butyldimethylsilyloxy-8-[(2RS)-2-(3,4-dimethylphenoxy)butyryloxy]-2-methyl-1-naphthyl}ethyl)tetrahydro-4-t-butyldimethylsilyloxy-2H-pyran-2-one (Compound No. 1-79)

A procedure similar to that described in Example 1, above, was followed, but using 0.76 g of (2RS)-2-(3,4-dimethylphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.38 g of the title compound as a colorless foam.

Nuclear Magnetic Resonance Spectrum (270 MHz, $CDCl_3$) δ ppm: 1.06 (3H, triplet, J=7.3 Hz); 2.16 (3H, singlet); 2.17 (3H, singlet); 4.27 (1H, multiplet); 4.40–4.62 (2H, multiplet); 5.40 (1H, broad singlet); 5.47 (1H, broad singlet); 5.82 (1H, doublet of doublets, J=5.9 & 9.9 Hz); 5.96 (1H, doublet, J=9.9 Hz); 6.55 (1H, doublet of doublets, J=2.6 & 7.9 Hz); 6.73 (1H, doublet, J=2.6 Hz); 6.95 (1H, doublet, J=7.9 Hz).

EXAMPLE 41

(4R,6R)-6-([1S,2S,6S,8S,8aR]-2-{1,2,6,7,8,8a-Hexahydro-6-hydroxy-8-[(2RS)-2-(3,4-dimethylphenoxy)butyryloxy]-2-methyl-1-naphthyl}ethyl)tetrahydro-4-hydroxy-2H-pyran-2-one (Compound No. 1-79)

A procedure similar to that described in Example 2, above, was followed, but using 0.94 g of (4R,6R)-6-([1S,2S,6S,8S,8aR]-2-{1,2,6,7,8,8a-hexahydro-6-t-butyldimethylsilyloxy-8-[(2RS)-2-(3,4-dimethylphenoxy)butyryloxy]-2-methyl-1-naphthyl}ethyl)tetrahydro-4-t-butyldimethylsilyloxy-2H-pyran-2-one [prepared as described in Example 40, above] and 31.0 ml of a 1.0 molar solution of tetrabutylammonium fluoride in tetrahydrofuran, to give 0.26 g of the title compound as white crystals, melting at between 137° and 139° C.

Nuclear Magnetic Resonance Spectrum (270 MHz, $CDCl_3$) δ ppm: 1.06 (3H, triplet, J=7.3 Hz); 2.16 (3H, singlet); 2.19 (3H, singlet); 4.33 (1H, multiplet); 4.38–4.65 (2H, multiplet); 4.54 (1H, triplet, J=5.9 Hz); 5.45 (1H, broad singlet); 5.58 (1H, broad singlet); 5.86 (1H, doublet of doublets, J=5.9 & 9.9 Hz); 5.98 (1H, doublet, J=9.9 Hz); 6.59 (1H, doublet of doublets, J=2.6 & 7.9 Hz); 6.70 (1H, doublet, J=2.6 Hz); 6.98 (1H, doublet, J=7.9 Hz).

EXAMPLE 42

Sodium salt of (3R,5R)-3,5-dihydroxy-7-{(1S,2S,6S,8S,8aR)-1,2,6,7,8,8a-hexahydro-6-hydroxy-8-[(2RS)-2-(3,4-dimethylphenoxy)butyryloxy]-2-methyl-1-naphthyl}heptanoic acid (Compound No. 1-79)

A procedure similar to that described in Example above, was followed, but using 30.0 mg of (4R,6R)-6-([1S,2S,6S,8S,8aR]-2-{1,2,6,7,8,8a-hexahydro-6-hydroxy-8-[(2RS)-2-(3,4-dimethylphenoxy)butyryloxy]-2-methyl-1-naphthyl}ethyl)tetrahydro-4-hydroxy-2H-pyran-2-one [prepared as described in Example 41, above] and 0.59 ml of a 0.1N aqueous solution of sodium hydroxide, to give 34.9 mg of the title compound, as a colorless hygroscopic powder.

EXAMPLE 43

(4R,6R)-6-([1S,2S,6S,8S,8aR]-2-{1,2,6,7,8,8a-Hexahydro-6-t-butyldimethylsilyloxy-8-[(2RS)-2-(2,6-dibromophenoxy)butyryloxy]-2-methyl-1-naphthyl}ethyl)tetrahydro-4-t-butyldimethylsilyloxy-2H-pyran-2-one (Compound No. 1–121)

A procedure similar to that described in Example 1, above, was followed, but using 1.23 g of (2RS)-2-(2,6-dibromophenoxy)butyric acid and 1.0 g of (4R,6R)-6-{(1S,2S,6S,8S,8aR-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.46 g of the title compound as a colorless foam.

Nuclear Magnetic Resonance Spectrum (270 MHz, $CDCl_3$) δ ppm: 1.08 (3H, triplet, J=7.3 Hz); 4.28 multiplet); 4.40–4.65 (2H, multiplet); 5.08 (1H, triplet, J=5.3 Hz); 5.45 (1H, broad singlet); 5.49 (1H, broad singlet); 5.82 (1H, doublet of doublets, J=5.9 & 9.9 Hz); 5.96 (1H, doublet, J=9.9 Hz); 6.82 (1H, triplet, J=7.9 Hz); 7.47 (2H, doublet, J=7.9 Hz).

EXAMPLE 44

(4R,6R)-6-([1S,2S,6S,8S,8aR]-2-{1,2,6,7,8,8a-Hexahydro-6-hydroxy-8-[(2RS)-2-(2,6-dibromophenoxy)butyryloxy]-2-methyl-1-naphthyl}ethyl)tetrahydro-4-hydroxy-2H-pyran-2-one (Compound No. 1-121)

A procedure similar to that described in Example 2, above, was followed, but using 1.36 g of ([1S,2S,6S,8S,8aR]-2-{1,2,6,7,8,8a-hexahydro-6-t-butyldimethylsilyloxy-8-[(2RS)-2-(2,6-dibromophenoxy)butyryloxy]-2-methyl-1-naphthyl}ethyl)tetrahydro-4-t-butyldimethylsilyloxy-2H-pyran-2-one [prepared as described in Example 43, above] and 37.5 ml of a 1.0 molar solution of tetrabutylammonium fluoride in tetrahydrofuran, to give 0.37 g of the title compound as white crystals, melting at between 114° and 116° C.

Nuclear Magnetic Resonance Spectrum (270 MHz, CDCl$_3$) δ ppm: 1.13 (3H, triplet, J=7.3 Hz); 4.43 (2H, multiplet); 4.60–4.75 (1H, multiplet); 5.05 (1H, triplet, J=5.3 Hz); 5.61 (2H, broad singlet); 5.93 (1H, doublet of doublets, J=5.9 & 9.9 Hz); 6.04 (1H, doublet, J=9.9 Hz); 6.90 (1H, triplet, J=7.9 Hz); 7.55 (2H, doublet, J=7.9 Hz).

EXAMPLE 45

Sodium salt of (3R,5R)-3,5-dihydroxy-7-{(1S,2S,6S,8S,8aR]-1,2,6,7,8,8a-hexahydro-6-hydroxy-8-[(2RS)-2-(2,6-dibromophenoxy)butyryloxy]-2-methyl-1-naphthyl}heptanoic acid (Compound No. 1-121)

A procedure similar to that described in Example 3, above, was followed, but using 30.0 mg of (4S,6R)-6-([1S,2S, 6S,8S,8aR]-2-{1,2,6,7,8,8a-hexahydro-6-hydroxy-8-[(2RS)-2-(2,6-dibromophenoxy)butyryloxy]-2-methyl-1-naphthyl}ethyl)tetrahydro-4-hydroxy-2H-pyran-2-one [prepared as described in Example 44, above] and 0.47 ml of a 0.1N aqueous solution of sodium hydroxide, to give 34.1 mg of the title compound, as a colorless hygroscopic powder.

EXAMPLE 46

(4R,6R)-6-([1S,2S,6S,8S,8aR]-2-{1,2,6,7,8,8a-Hexahydro-6-t-butyldimethylsilyloxy-8-[(2RS)-2-(1-naphthyloxy)butyryloxy]-2-methyl-1-naphthyl}ethyl)tetrahydro-4-t-butyldimethylsilyloxy-2H-pyran-2-one (Compound No. 1-67)

A procedure similar to that described in Example 1, above, was followed, but using 829 mg of (2RS)-2-(1-naphthyloxy)butyric acid and 1.0 g of (4R,6R)-6-{(1S,2S, 6S,8S,8aR]-2-[1,2,6,7,8,8a-hexahydro-6 -t-butyldimethysilyloxy-2H-pyran-2-one [prepared as described in Example B, above], to give 719 mg of the title compound as a colorless foam.

Nuclear Magnetic Resonance Spectrum (270 MHz, CDCl$_3$) δ ppm: 1.26 (3H, triplet, J=7.3 Hz); 3.90–4.65 (3H, multiplet); 4.94 (1H, triplet, J=5.9 Hz); 5.45 (2H, broad singlet); 5.70–6.06 (2H, multiplet); 6.81 (1H, doublet, J=7.3 Hz); 7.30–7.63 (4H, multiplet); 7.83 (1H, doublet, J=7.9 Hz); 8.37 (1H, doublet, J=9.2 Hz).

EXAMPLE 47

(4R,6R)-6-([1S,2S,6S,8S,8aR]-2-{1.2,6,7,8,8a-Hexahydro-6-hydroxy-8-[(2RS)-2-(1-naphthyloxy)butyryloxy]-2-methyl-1-naphthyl}ethyl)tetrahydro-4-hydroxy-2H-pyran-2-one (Compound No. 1-67)

A procedure similar to that described in Example 2, above, was followed, but using 719 mg of (4R,6R)-6-([1S,2S,6S,8S,8aR]-2-{1,2,6,7,8,8a-hexahydro-6-t-butyldimethylsilyloxy-8-[(2RS)-2-(1-naphthyloxy)butyryloxy]-2-methyl-1-naphthyl}ethyl)tetrahydro-4-t-butyldimethylsilyloxy-2H-pyran-2-one [prepared as described in Example 46, above] and 18.8 ml of a 1.0 molar solution of tetrabutylammonium fluoride in tetrahydrofuran, to give 272 mg of the title compound as white crystals, melting at between 138° and 140° C.

Nuclear Magnetic Resonance Spectrum (270 MHz, CDCl$_3$) δ ppm: 1.20 (3H, triplet, J=7.3 Hz); 4.31 (2H, multiplet); 4.49 (1H, multiplet); 4.89 (1H, triplet, J=5.9 Hz); 5.43 (1H, broad singlet); 5.52 (1H, broad singlet); 5.76 (1H, doublet of doublets, J=5.9 & 9.9 Hz); 5.87 (1H, doublet, J=9.9 Hz); 6.83 (1H, doublet, J=7.3 Hz); 7.25–7.60 (4H, multiplet); 7.80 (1H, doublet, J=7.3 Hz); 8.33 (1H, doublet, J=9.2 Hz).

EXAMPLE 48

Sodium salt of (3R,5R)-3,5-dihydroxy-7-{(1S,2S,6S,8S,8aR)-1,2,6,7,8,8a-hexahydro-6-hydroxy-8-[(2RS)-2-(1-naphthyloxy)butyryloxy]-2-methyl-1-naphthyl}heptanoic acid (Compound No. 1-67)

A procedure similar to that described in Example 3, above, was followed, but using 30.1 mg of (4R,6R)-6-([1S, 2S,6S,8S,8aR]-2-{1,2,6,7,8,8a-hexahydro-6-hydroxy-8-[(2RS)-2-(1-naphthyloxy)butyryloxy]-2-methyl-1-naphthyl}ethyl)tetrahydro-4-hydroxy-2H-pyran-2-one [prepared as described in Example 47, above] and 0.58 ml of a 0.1N aqueous solution of sodium hydroxide, to give 33.1 mg of the title compound, as a colorless hygroscopic powder.

EXAMPLE 49

(4R,6R)-6-([1S,2S,6S,8S,8aR]-2-{1,2,6,7,8,8a-Hexahydro-6-t-butyldimethylsilyloxy-8-[(2RS)-2-(2,4-difluorophenoxy)butyryloxy]-2-methyl-1-naphthyl}ethyl)tetrahydro-4-t-butyldimethylsilyloxy-2H-pyran-2-one (Compound No. 1-113)

A procedure similar to that described in Example 1, above, was followed, but using 0.79 g of (2RS)-2-(2,4-difluorophenoxy)butyric acid and 1.0 g of (4R,6R)-6-{(1S, 2S,6S,8S,8aR)-2-[1,2,6,7,8,8a-hexahydro-6-t-butyldimethylsilyloxy-8-hydroxy-2-methyl-1-naphthyl] ethyl}tetrahydro-4-t-butyldimethylsilyloxy-2H-pyran-2-one [prepared as described in Example B, above], to give 1.26 g of the title compound as a colorless foam.

Nuclear Magnetic Resonance Spectrum (270 MHz, CDCl$_3$) δ ppm: 1.14 (3H, triplet, J=7.3 Hz); 4.10–4.73 (4H, multiplet); 5.40–5.55 (2H, multiplet); 5.80–6.05 (2H, multiplet); 6.70–7.05 (3H, multiplet).

EXAMPLE 50

(4R,6R)-6-([1S,2S,6S,8S,8aR]-2-{1,2,6,7,8,8a-Hexahydro-6-hydroxy-8-[(2RS)-2-(2,4-difluorophenoxy)butyryloxy]-2-methyl-1-naphthyl}ethyl)tetrahydro-4-hydroxy-2H-pyran-2-one (Compound No. 1-113)

A procedure similar to that described in Example 2, above, was followed, but using 1.24 g of (4R,6R)-6-([1S,2S,6S,8S,8aR]-2-{1,2,6,7,8,8a-hexahydro-6-t-butyldimethylsilyloxy-8-[(2RS)-2-(2,4-difluorophenoxy)butyryloxy]-2-methyl-1-naphthyl}ethyl)tetrahydro-4-t-butyldimethylsilyloxy-2H-pyran-2-one [prepared as described in Example 49, above] and 24.8 ml of a 1.0 molar solution of tetrabutylammonium fluoride in tetrahydrofuran, to give 163 mg of the title compound as white crystals, melting at between 153° and 155° C.

Nuclear Magnetic Resonance Spectrum (270 MHz, $CDCl_3$) δ ppm: 1.09 (3H, triplet, J=7.3 Hz); 4.38 (2H, multiplet); 4.45–4.60 (1H, multiplet); 4.61 (1H, triplet, J=5.3 Hz); 5.48 (1H, broad singlet); 5.56 (1H, broad singlet); 5.86 (1H, doublet of doublets, J=5.9 & 9.9 Hz); 5.97 (1H, doublet, J=9.2 Hz); 6.70–7.03 (3H, multiplet).

EXAMPLE 51

Sodium salt of (3R,5R)-3,5-dihydroxy-7-{(1S,2S,6S,8S,8aR)-1,2,6,7,8,8a-hexahydro-6-hydroxy-8-[(2RS)-2-(2,4-difluorophenoxy)butyryloxy]-2-methyl-1-naphthyl}heptanoic acid (Compound No. 1-113)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2,4-difluorophenoxy)butyryloxy]-2-methyl-1-naphthyl}ethyl)tetrahydro-4-hydroxy-2H-pyran-2-one [prepared as described in Example 50, above] and 0.58 ml of a 0.1N aqueous solution of sodium hydroxide, to give 35.2 mg of the title compound, as a colorless hygroscopic powder.

EXAMPLE 52

(4R,6R)-6-([1S,2S,6S,8S,8aR]-2-{1,2,6,7,8,8a-Hexahydro-6-t-butyldimethylsilyloxy-8-[(2RS)-2-(2,5-dimethylphenoxy)butyryloxy]-2-methyl-1-naphthyl}ethyl)tetrahydro-4-t-butyldimethylsilyloxy-2H-pyran-2-one (Compound No. 1-77)

A procedure similar to that described in Example 1, above, was followed, but using 0.76 g of (2RS)-2-(2,5-dimethylphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.38 g of the title compound as a colorless foam.

Nuclear Magnetic Resonance Spectrum (270 MHz, $CDCl_3$) δ ppm: 1.08 (3H, triplet, J=7.3 Hz); 2.16 (3H, singlet); 2.25 (3H, singlet); 4.26 (1H, multiplet); 4.45 (2H, multiplet); 4.69 (1H, triplet, J=5.3 Hz); 5.38 (1H, broad singlet); 5.44 (1H, broad singlet); 5.80 (1H, doublet of doublets, J=5.9 & 9.9 Hz); 5.94 (1H, doublet, J=9.9 Hz); 6.56 (1H, singlet); 6.64 (1H, doublet, J=7.3 Hz); 6.96 (1H, doublet, J=7.3 Hz).

EXAMPLE 53

(4R,6R)-6-([1S,2S,6S,8S,8aR]-2-{1,2,6,7,8,8a-Hexahydro-6-hydroxy-8-[(2RS)-2-(2,5-dimethylphenoxy)butyryloxy]-2-methyl-1-naphthyl}ethyl)tetrahydro-4-hydroxy-2H-pyran-2-one (Compound No. 1-77)

A procedure similar to that described in Example 2, above, was followed, but using 1.32 g of (4R,6R)-6-([1S,2S,6S,8S,8aR]-2-{1,2,6,7,8,8a-hexahydro-6-t-butyldimethylsilyloxy-8-[(2RS)-2-(2,5-dimethylphenoxy)butyryloxy]-2-methyl-1-naphthyl}ethyl)tetrahydro-4-t-butyldimethylsilyloxy-2H-pyran-2-one [prepared as described in Example 52, above] and 43.0 ml of a 1.0 molar solution of tetrabutylammonium fluoride in tetrahydrofuran, to give 0.20 g of the title compound as white crystals, melting at between 138° and 140° C.

Nuclear Magnetic Resonance Spectrum (270 MHz, $CDCl_3$) δ ppm: 1.07 (3H, triplet, J=7.3 Hz); 2.16 (3H, singlet); 2.26 (3H, singlet); 4.30–4.52 (3H, multiplet); 4.63 (1H, triplet, J=5.9 Hz); 5.42 (1H, broad singlet); 5.56 (1H, broad singlet); 5.85 (1H, doublet of doublets, J=5.9 & 9.9 Hz); 5.97 (1H, doublet, J=9.9 Hz); 6.55 (1H, singlet); 6.65 (1H, doublet, J=7.9 Hz); 6.97 (1H, doublet, J=7.9 Hz).

EXAMPLE 54

Sodium salt of (3R,5R)-3,5-dihydroxy-7-{(1S,2S,6S,8S,8aR)-1,2,6,7,8,8a-hexahydro-6-hydroxy-8-[(2RS)-2-(2,5-dimethylphenoxy)butyryloxy]-2-methyl-1-naphthyl}heptanoic acid (Compound No. 1-77)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2,5-dimethylphenoxy)butyryloxy]-2-methyl-1-naphthyl}ethyl)tetrahydro-4-hydroxy-2H-pyran-2-one [prepared as described in Example 53, above] and 0.59 ml of a 0.1N aqueous solution of sodium hydroxide, to give 34.4 mg of the title compound, as a colorless hygroscopic powder.

EXAMPLE 55

(4R,6R)-6-([1S,2S,6S,8S,8aR]-2-{1,2,6,7,8,8a-Hexahydro-6-t-butyldimethylsilyloxy-8-[(2RS)-2-(2-fluorophenoxy)butyryloxy]-2-methyl-1-naphthyl}ethyl)tetrahydro-4-t-butyldimethylsilyloxy-2H-pyran-2-one (Compound No. 1-97)

A procedure similar to that described in Example 1, above, was followed, but using 0.72 g of (2RS)-2-(2-fluorophenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.30 g of the title compound as a colorless foam.

Nuclear Magnetic Resonance Spectrum (270 MHz, $CDCl_3$) δ ppm: 1.10 (3H, triplet, J=7.3 Hz); 4.15–4.60 (3H, multiplet); 4.66 (1H, triplet, J=5.9 Hz); 5.35–5.55 (2H, multiplet); 5.76–6.03 (2H, multiplet); 6.85–7.12 (4H, multiplet).

EXAMPLE 56

(4R,6R)-6-([1S,2S,6S,8S,8aR]-2-{1,2,6,7,8,8a-Hexahydro-6-hydroxy-8-[(2RS)-2-(2-fluorophenoxy)butyryloxy]-2-methyl-1-naphthyl}ethyl)tetrahydro-4-hydroxy-2H-pyran-2-one (Compound No. 1-97)

A procedure similar to that described in Example 2, above, was followed, but using 1.26 g of (4R,6R)-6-([1S, 2S,6S,8S,8aR]-2-{1,2,6,7,8,8a-hexahydro-6-t-butyldimethylsilyloxy-8-[(2RS)-2-(2-fluorophenoxy)butyryloxy]-2-methyl-1-naphthyl}ethyl)tetrahydro-4-t-butyldimethylsilyloxy-2H-pyran-2-one [prepared as described in Example 55, above] and 25.9 ml of a 1.0 molar solution of tetrabutylammonium fluoride in tetrahydrofuran, to give 635 mg of the title compound as white crystals, melting at between 136° and 138° C.

Nuclear Magnetic Resonance Spectrum (270 MHz, CDCl$_3$) δ ppm: 1.09 (3H, triplet, J=7.3 Hz); 4.30–4.60 (3H, multiplet); 4.64 (1H, triplet, J=5.9 Hz); 5.47 (1H, broad singlet); 5.56 (1H, broad singlet); 5.80–5.93 (1H, multiplet); 5.97 (1H, doublet, J=9.9 Hz); 6.85–7.15 (4H, multiplet).

EXAMPLE 57

Sodium salt of (3R,5R)-3,5-dihydroxy-7-{(1S,2S,6S,8S,8aR)-1,2,6,7,8,8a-hexahydro-6-hydroxy-8-[(2RS)-2-(2-fluorophenoxy)butyryloxy]-2-methyl-1-naphthyl}heptanoic acid (Compound No. 1-97)

A procedure similar to that described in Example 3, above, was followed, but using 30.0 mg of (4R,6R)-6-([1S, 2S,6S,8S,8aR]-2-{1,2,6,7,8,8a-hexahydro-6-hydroxy-8-[(2RS)-2-(2-fluorophenoxy)butyryloxy]-2-methyl-1-naphthyl}ethyl)tetrahydro-4-hydroxy-2H-pyran-2-one [prepared as described in Example 56, above] and 0.60 ml of a 0.1N aqueous solution of sodium hydroxide, to give 33.0 mg of the title compound, as a colorless hygroscopic powder.

EXAMPLE 58

(4R,6R)-6-([1S,2S,6S,8S,8aR]-2-{1,2,6,7,8,8a-Hexahydro-6-t-butyldimethylsilyloxy-8-[(2RS)-2-(2,4,6-trimethylphenoxy)butyryloxy]-2-methyl-1-naphthyl}ethyl)tetrahydro-4-t-butyldimethylsilyloxy-2H-pyran-2-one (Compound No. 1-81)

A procedure similar to that described in Example 1, above, was followed, but using 800 mg of (2RS)-2-(2,4,6-trimethylphenoxy)butyric acid and 1.0 g of (4R,6R)-6-{(1S, 2S,6S,8S,8aR)-2-[1,2,6,7,8,8a-hexahydro-6-t-butyldimethylsilyloxy-8-hydroxy-2-methyl-1-naphthyl)ethyl}tetrahydro-4-t-butyldimethylsilyloxy-2H-pyran-2-one [prepared as described in Example B, above], to give 1.44 g of the title compound as a colorless foam.

Nuclear Magnetic Resonance Spectrum (270 MHz, CDCl$_3$) δ ppm: 1.02 (3H, triplet, J=7.3 Hz); 2.20 & 2.23 (total 9H, each singlet); 4.28 (1H, multiplet); 4.30–4.41 (1H, multiplet); 4.49 (1H, triplet, J=5.9 Hz); 4.50–4.63 (1H, multiplet); 5.40–5.52 (2H, multiplet); 5.84 (1H, doublet of doublets, J=5.9 & 9.9 Hz); 5.97 (1H, doublet, J=9.2 Hz); 6.75 (2H, singlet).

EXAMPLE 59

(4R,6R)-6-([1S,2S,6S,8S,8aR]-2-{1,2,6,7,8,8a-Hexahydro-6-hydroxy-8-[(2RS)-2-(2,4,6-trimethylphenoxy)butyryloxy]-2-methyl-1-naphthyl}ethyl)tetrahydro-4-hydroxy-2H-pyran-2-one (Compound No. 1-81)

A procedure similar to that described in Example 2, above, was followed, but using 1.44 g of ([1S,2S,6S,8S, 8aR]-2-{1,2,6,7,8,8a-hexahydro-6-t-butyldimethylsilyloxy-8-[(2RS)-2-(2,4,6-trimethylphenoxy)butyryloxy]-2-methyl-1-naphthyl}ethyl)tetrahydro-4-t-butyldimethylsilyloxy-2H-pyran-2-one [prepared as described in Example 58, above] and 38.0 ml of a 1.0 molar solution of tetrabutylammonium fluoride in tetrahydrofuran, to give 694 mg of the desired compound as white crystals, melting at between 134° and 136° C.

Nuclear Magnetic Resonance Spectrum (270 MHz, CDCl$_3$) δ ppm: 0.99 (3H, triplet, J=7.3 Hz); 2.22 (9H, singlet); 4.05 (1H, broad singlet); 4.34 (1H, broad singlet); 4.44 (1H, triplet, J=5.9 Hz); 5.50–5.62 (1H, multiplet); 5.50 (2H, broad singlet); 5.87 (1H, doublet of doublets, J=5.9 & 9.9 Hz); 5.97 (1H, doublet, J=9.9 Hz); 6.77 (2H, singlet).

EXAMPLE 60

Sodium salt of (3R,5R)-3,5-dihydroxy-7-{(1S,2S,6S,8S,8aR)-1,2,6,7,8,8a-hexahydro-6-hydroxy-8-[(2RS)-2-(2,4,6-trimethylphenoxy)butyryloxy]-2-methyl-1-naphthyl}heptanoic acid (Compound No. 1-81)

A procedure similar to that described in Example 3, above, was followed, but using 30.0 mg of (4R,6R)-6-([1S, 2S,6S,8S,8aR]-2-{1,2,6,7,8,8a-hexahydro-6-hydroxy-8-[(2RS)-2-(2,4,6-trimethylphenoxy)butyryloxy]-2-methyl-1-naphthyl}ethyl)tetrahydro-4-hydroxy-2H-pyran-2-one [prepared as described in Example 59, above] and 0.57 ml of a 0.1N aqueous solution of sodium hydroxide, to give 33.3 mg of the title compound, as a colorless hygroscopic powder.

EXAMPLE 61

(4R,6R)-6-([1S,2S,6S,8S,8aR]-2-{1,2,6,7,8,8a-Hexahydro-6-t-butyldimethylsilyloxy-8-[(2RS)-2-phenoxyvaleryloxy]-2-methyl-1-naphthyl}ethyl)tetrahydro-4-t-butyldimethylsilyloxy-2H-pyran-2-one (Compound No. 1-129)

A procedure similar to that described in Example 10, above, was followed, but using 0.70 g of (2RS)-2-phenoxyvaleric acid and 1.0 g of (4S,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.34 g of the title compound as a colorless foam.

Nuclear Magnetic Resonance Spectrum (270 MHz, CDCl$_3$) δ ppm: 4.15–4.33 (1H, multiplet); 4.35–4.55 (2H, multiplet); 4.60–4.70 (1H, multiplet); 5.35–5.60 (2H, multiplet); 5.86–6.05 (2H, multiplet); 6.85–7.02 (3H, multiplet); 7.25 (2H, doublet, J=8.6 Hz).

EXAMPLE 62

(4R,6R)-6-[1S,2S,6S,8S,8aR]-2-{1,2,6,7,8,8a-Hexahydro-6-hydroxy-8-[(2RS)-2-phenoxyvaleryloxy]-2-methyl-1-naphthyl}ethyl)tetrahydro-4-hydroxy-2H-pyran-2-one (Compound No. 1-129)

A procedure similar to that described in Example 2, above, was followed, but using 1.20 g of ([1S,2S,6S,8S,8aR]-2-{1,2,6,7,8,8a-hexahydro-6-t-butyldimethylsilyloxy-8-[(2RS)-2-phenoxyvaleryloxy]-2-methyl-1-naphthyl}ethyl)tetrahydro-4-t-butyldimethylsilyloxy-2H-pyran-2-one [prepared as described in Example 61, above] and 9.7 ml of a 1.0 molar solution of tetrabutylammonium fluoride in tetrahydrofuran, to give 0.27 g of the title compound as white crystals, melting at between 134° and 136° C.

Nuclear Magnetic Resonance Spectrum (270 MHz, $CDCl_3$) δ ppm: 3.80–4.70 (4H, multiplet); 5.35–5.65 (2H, multiplet); 5.78–6.04 (2H, multiplet); 6.85 (2H, doublet, J=7.3 Hz); 6.95 (1H, triplet, J=7.3 Hz); 7.26 (2H, triplet, J=7.3 Hz).

EXAMPLE 63

Sodium salt of (3R,5R)-3,5-dihydroxy-7-{(1S,2S,6S,8S,8aR)-1,2,6,7,8,8a-hexahydro-6-hydroxy-8-[(2RS)-2-phenoxyvaleryloxy]-2-methyl-1-naphthyl}heptanoic acid (Compound No. 1-129)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-phenoxyvaleryloxy]-2-methyl-1-naphthyl}ethyl)tetrahydro-4-hydroxy-2H-pyran-2-one [prepared as described in Example 62, above] and 0.60 ml of a 0.1N aqueous solution of sodium hydroxide, to give 34.3 mg of the title compound, as a colorless hygroscopic powder.

EXAMPLE 64

(4R,6R)-6-([1S,2S,6S,8S,8aR]-2-{1,2,6,7,8,8a-Hexahydro-6-t-butyldimethylsilyloxy-8-[(2RS)-2-(2-allylphenoxy)butyryloxy]-2-methyl-1-naphthyl}ethyl)tetrahydro-4-t-butyldimethylsilyloxy-2H-pyran-2-one (Compound No. 1-89)

A procedure similar to that described in Example 1, above, was followed, but using 0.80 g of (2RS)-2-(2-allylphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.30 g of the title compound as a colorless foam.

Nuclear Magnetic Resonance Spectrum (270 MHz, $CDCl_3$) δ ppm: 3.44 (2H, multiplet); 4.33 (1H, multiplet); 4.40–4.60 (2H, multiplet); 4.70 (1H, triplet, J=5.9 Hz); 5.00–5.15 (2H, multiplet); 5.42 (1H, broad singlet); 5.51 (1H, broad singlet); 5.78–6.10 (3H, multiplet); 6.75 (1H, doublet, J=7.9 Hz); 6.91 (1H, triplet, J=7.3 Hz); 7.08–7.22 (2H, multiplet).

EXAMPLE 65

(4R,6R)-6-([1S,2S,6S,8S,8aR]-2-{1,2,6,7,8,8a-Hexahydro-6-hydroxy-8-[(2RS)-2-(2-allylphenoxy)butyryloxy]-2-methyl-1-naphthyl}ethyl)tetrahydro-4-hydroxy-2H-pyran-2-one (Compound No. 1-89)

A procedure similar to that described in Example 2, above, was followed, but using 1.12 g of (4R,6R)-6-([1S,2S,6S,8S,8aR]-2-{1,2,6,7,8,8a-hexahydro-6-t-butyldimethylsilyloxy-8-[(2RS)-2-(2-allylphenoxy)butyryloxy]-2-methyl-1-naphthyl}ethyl)tetrahydro-4-t-butyldimethylsilyloxy-2H-pyran-2-one [prepared as described in Example 24, above] and 22.3 ml of a 1.0 molar solution of tetrabutylammonium fluoride in tetrahydrofuran, to give 0.27 g of the title compound as white crystals, melting at between 143° and 145° C.

Nuclear Magnetic Resonance Spectrum (270 MHz $CDCl_3$) δ ppm: 3.37 (2H, multiplet); 4.30–4.50 (3H, multiplet); 4.65 (1H, triplet, J=5.9 Hz); 4.95–5.12 (2H, multiplet); 5.40 (1H, broad singlet); 5.56 (1H, broad singlet); 5.78–6.05 (3H, multiplet); 6.74 (1H, doublet, J=7.9 Hz); 6.87 (1H, triplet, J=7.9 Hz); 7.05–7.16 (2H, multiplet).

EXAMPLE 66

Sodium salt of (3R,5R)-3,5-dihydroxy-7-{(1S,2S,6S,8S,8aR)-1,2,6,7,8,8a-hexahydro-6-hydroxy-8-[(2RS)-2-(2-allylphenoxy)butyryloxy]-2-methyl-1-naphthyl]heptanoic acid (Compound No. 1-89)

A procedure similar to that described in Example 3, above, was followed, but using 30.0 mg of (4R, 6R)-6-([1S,2S,6S,8S,8aR]-2-{1,2,6,7,8,8a-hexahydro-6-hydroxy-8-[(2RS)-2-(2-allylphenoxy)butyryloxy]-2-methyl-1-naphthyl}ethyl)tetrahydro-4-hydroxy-2H-pyran-2-one [prepared as described in Example 65, above] and 0.57 ml of a 0.1N aqueous solution of sodium hydroxide, to give 33.0 mg of the title compound, as a colorless hygroscopic powder.

EXAMPLE 67

(4R,6R)-6-([1S,2S,6S,8S,8aR]-2-{1,2,6,7,8,8a-Hexahydro-6-t-butyldimethylsilyloxy-8-[(2RS)-2-(4-ethylphenoxy)butyryloxy]-2-methyl-1-naphthyl}ethyl)tetrahydro-4-t-butyldimethylsilyloxy-2H-pyran-2-one (Compound No. 1-74)

A procedure similar to that described in Example 1, above, was followed, but using 416 mg of (2RS)-2-(4-ethylphenoxy)butyric acid and 551 mg of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl)tetrahydro-4-t-butyldimethylsilyloxy-2H-pyran-2-one [prepared as described in Example B, above], to give 850 mg of the title compound as a colorless foam.

Nuclear Magnetic Resonance Spectrum (270 MHz, $CDCl_3$) δ ppm: 1.07 (3H, triplet, J=7.3 Hz); 1.19 (3H, triplet, J=7.3 Hz); 4.27 (1H, multiplet); 4.45–4.60 (2H, multiplet); 4.56 (1H, triplet, J=5.9 Hz); 5.42 (1H, broad singlet); 5.47 (1H, broad singlet); 5.82 (1H, doublet of doublets, J=5.9, 9.2 Hz); 5.97 (1H, doublet, J=9.9 Hz); 6.77 (2H, doublet, J=8.6 Hz); 7.05 (2H, doublet, J=8.6 Hz).

EXAMPLE 68

(4R,6R)-6-([1S,2S,6S,8S,8aR]-2-{1,2,6,7,8,8a-Hexahydro-6-hydroxy-8-[(2RS)-2-(4-ethylphenoxy)butyryloxy]-2-methyl-1-naphthyl}ethyl)tetrahydro-4-hydroxy-2H-pyran-2-one (Compound No. 1-74)

A procedure similar to that described in Example 2, above, was followed, but using 850 mg of (4R,6R)-6-([1S,2S,6S,8S,8aR]-2-{1,2,6,7,8,8a-hexahydro-6-t-butyldimethylsilyloxy-8-[(2RS)-2-(4-ethylphenoxy)butyryloxy]-2-methyl-1-naphthyl}ethyl)tetrahydro-4-t-butyldimethylsilyloxy-2H-pyran-2-one [prepared as described in Example 67, above] and 20.0 ml of a 1.0 molar solution of tetrabutylammonium fluoride in tetrahydrofuran, to give 84 mg of the title compound as white crystals, melting at between 139° and 140° C.

Nuclear Magnetic Resonance Spectrum (270 MHz, $CDCl_3$) δ ppm: 1.07 (3H, triplet, J=7.3 Hz); 1.19 (3H, triplet, J=7.3 Hz); 4.34 (1H, multiplet); 4.40–4.60 (2H, multiplet); 4.55 (1H, triplet, J=5.9 Hz); 5.47 (1H, broad singlet); 5.57 (1H, broad singlet); 5.86 (1H, doublet of doublets, J=5.9 & 9.2 Hz); 5.98 (1H, doublet, J=9.2 Hz); 6.79 (2H, doublet, J=8.6 Hz); 7.07 (2H, doublet, J=8.6 Hz).

EXAMPLE 69

Sodium salt of (3R,5R)-3,5-dihydroxy-7-{(1S,2S,6S,8S,8aR)-1,2,6,7,8,8a-hexahydro-6-hydroxy-8-[(2RS)-2-(4-ethylphenoxy)butyryloxy]-2-methyl-1-naphthyl}heptanoic acid (Compound No. 1-74)

A procedure similar to that described in Example 3, above, was followed, but using 20.7 mg of (4R,6R)-6-([1S,2S,6S,8S,8aR]-2-{1,2,6,7,8,8a-hexahydro-6-hydroxy-[(2RS)-2-(4-ethylphenoxy)butyryloxy]-2-methyl-1-naphthyl}ethyl)tetrahydro-4-hydroxy-2H-pyran-2-one prepared as described in Example 68, above] and 0.40 ml of a 0.1N aqueous solution of sodium hydroxide, to give 22.7 mg of the title compound, as a colorless hygroscopic powder.

EXAMPLE 70

(4R,6R)-6-([1S,2S,6S,8S,8aR]-2-{1,2,6,7,8,8a-Hexahydro-6-t-butyldimethylsilyloxy-8-[(2RS)-2-(2,4-dimethylphenoxy)butyryloxy]-2-methyl-1-naphthyl}ethyl)tetrahydro-4-t-butyldimethylsilyloxy-2H-pyran-2-one (Compound No. 1-76)

A procedure similar to that described in Example 1, above, was followed, but using 0.46 g of (2RS)-2-(2,4-dimethylphenoxy)butyric acid and 0.81 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.16 g of the title compound as a colorless foam.

Nuclear Magnetic Resonance Spectrum (270 MHz, $CDCl_3$) δ ppm: 1.08 (3H, triplet, J=7.3 Hz); 2.18 (3H, singlet); 2.21 (3H, singlet); 4.28 (1H, multiplet); 4.45–4.60 (2H, multiplet); 4.64 (1H, triplet, j=5.9 Hz); 5.39 (1H, broad singlet); 5.46 (1H, broad singlet); 5.80 (1H, doublet of doublets, J=5.9 & 9.2 Hz); 5.94 (1H, doublet, J=9.9 Hz); 6.57 (1H, doublet, J=8.6 Hz); 6.81 (1H, doublet, J=8.6 Hz); 6.90 (1H, singlet).

EXAMPLE 71

(4R,6R)-6-([1S,2S,6S,8S,8aR]-2-{1,2,6,7,8,8a-Hexahydro-6-hydroxy-8-[(2RS)-2-(2,4-dimethylphenoxy)butyryloxy]-2-methyl-1-naphthyl}ethyl)tetrahydro-4-hydroxy-2H-pyran-2-one (Compound No. 1-76)

A procedure similar to that described in Example 2, above, was followed, but using 1.16 g of (4R,6R)-6-([1S,2S,6S,8S,8aR]-2-{1,2,6,7,8,8a-hexahydro-6-t-butyldimethylsilyloxy-8-[(2RS)-2-(2,4-dimethylphenoxy)butyryloxy]-2-methyl-1-naphthyl}ethyl)tetrahydro-4-t-butyldimethylsilyloxy-2H-pyran-2-one [prepared as described in Example 70, above] and 37.6 ml of a 1.0 molar solution of tetrabutylammonium fluoride in tetrahydrofuran, to give 180 mg of the title compound as white crystals, melting at between 159° and 160° C.

Nuclear Magnetic Resonance Spectrum (270 MHz, $CDCl_3$) δ ppm: 1.07 (3H, triplet, J=7.3 Hz); 2.16 (3H, singlet); 2.22 (3H, singlet); 4.35 (1H, multiplet); 4.44 (2H, multiplet); 4.62 (1H, triplet, J=5.9 Hz); 5.43 (1H, broad singlet); 5.55 (1H, broad singlet); 5.84 (1H, doublet of doublets, J=5.9 & 9.9 Hz); 5.96 (1H, doublet, J=9.2 Hz); 6.60 (1H, doublet, J=8.6 Hz); 6.85 (1H, doublet, J=8.6 Hz); 6.90 (1H, singlet).

EXAMPLE 72

Sodium salt of (3R,5R)-3,5-dihydroxy-7-{(1S,2S,6S,8S,8aR)-1,2,6,7,8,8a-hexahydro-6-hydroxy-8-[(2RS)-2-(2,4-dimethylphenoxy)butyryloxy]-2-methyl-1-naphthyl}heptanoic acid (Compound No. 1-76)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2,4-dimethylphenoxy)butyryloxy]-2-methyl-1-naphthyl}ethyl)tetrahydro-4-hydroxy-2H-pyran-2-one [prepared as described in Example 71, above] and 0.59 ml of a 0.1N aqueous solution of sodium hydroxide, to give 33.6 mg of the title compound, as a colorless hygroscopic powder.

EXAMPLE 73

(4R,6R)-6-([1S,2S,6S,8S,8aR]-2-{1,2,6,7,8,8a-Hexahydro-6-t-butyldimethylsilyloxy-8-[(2RS)-2-(2-ethylphenoxy)butyryloxy]-2-methyl-1-naphthyl}ethyl)tetrahydro-4-t-butyldimethylsilyloxy-2H-pyran-2-one (Compound No. 1-72)

A procedure similar to that described in Example 1, above, was followed, but using 416 mg of (2RS)-2-(2-ethylphenoxy)butyric acid and 551 mg of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 900 mg of the title compound as a colorless foam.

Nuclear Magnetic Resonance Spectrum (270 MHz, $CDCl_3$) δ ppm: 1.10 (3H, triplet, J=7.3 Hz); 1.17 (3H, triplet, J=7.3 Hz); 4.28 (1H, multiplet); 4.45–4.60 (2H, multiplet); 4.65 (1H, triplet, J=5.9 Hz); 5.38 (1H, broad singlet); 5.44 (1H, broad singlet); 5.76 (1H, doublet of doublets, J=5.9 & 9.2 Hz); 5.92 (1H, doublet, J=9.9 Hz); 6.68 (1H, doublet, J=8.6 Hz); 6.84 (1H, triplet, J=7.9 Hz); 7.02–7.15 (2H, multiplet).

EXAMPLE 74

(4R,6R)-6-([1S,2S,6S,8S,8aR]-2-{1,2,6,7,8,8a-Hexahydro-6-hydroxy-8-[(2RS)-2-(2-ethylphenoxy)butyryloxy]-2-methyl-1-naphthyl}ethyl)tetrahydro-4-hydroxy-2H-pyran-2-one (Compound No. 1-72)

A procedure similar to that described in Example 2, above, was followed, but using 900 mg of (4R,6R)-6-([1S,2S,6S,8S,8aR]-2-{1,2,6,7,8,8a-hexahydro-6-t-butyldimethylsilyloxy-8-[(2RS)-2-(2-ethylphenoxy)butyryloxy]-2-methyl-1-naphthyl}ethyl)tetrahydro-4-t-butyldimethylsilyloxy-2H-pyran-2-one [prepared as described in Example 73, above] and 20.0 ml of a 1.0 molar solution of tetrabutylammonium fluoride in tetrahydrofuran, to give 304 mg of the desired compound as white crystals, melting at between 108° and 110° C.

Nuclear Magnetic Resonance Spectrum (270 MHz, CDCl$_3$) δ ppm: 1.08 (3H, triplet, J=7.3 Hz); 1.16 (3H, triplet, J=7.3 Hz); 4.30–4.50 (3H, multiplet); 4.66 (1H, triplet, J=5.9 Hz); 5.40 (1H, broad singlet); 5.54 (1H, broad singlet); 5.81 (1H, doublet of doublets, J=5.9 & 9.2 Hz); 5.94 (1H, doublet, J=9.2 Hz); 6.72 (1H, doublet, J=7.9 Hz); 6.87 (1H, triplet, J=8.6 Hz); 7.00–7.20 (2H, multiplet).

EXAMPLE 75

Sodium salt of (3R,5R)-3,5-dihydroxy-7-{(1S,2S,6S,8S,8aR)-1,2,6,7,8,8a-hexahydro-6-hydroxy-8-[(2RS)-2-(2-ethylphenoxy)butyryloxy]-2-methyl-1-naphthyl}heptanoic acid (Compound No. 1-72)

A procedure similar to that described in Example 3, above, was followed, but using 27.8 mg of (4R,6R)-6-([1S,2S,6S,8S,8aR]-2-{1,2,6,7,8,8a-hexahydro-6-hydroxy-8-[(2RS)-2-(2-ethylphenoxy)butyryloxy]-2-methyl-1-naphthyl}ethyl)tetrahydro-4-hydroxy-2H-pyran-2-one [prepared as described in Example 74, above] and 0.54 ml of a 0.1N aqueous solution of sodium hydroxide, to give 28.6 mg of the title compound, as a colorless hygroscopic powder.

EXAMPLE 76

(4R,6R)-6-([1S,2S,6S,8S,8aR]-2-{1,2,6,7,8,8a-Hexahydro-6-t-butyldimethylsilyloxy-8-[(2RS)-2-(2-methylphenoxy)-2-methylvaleryloxy]-2-methyl-1-naphthyl}ethyl)tetrahydro-4-t-butyldimethylsilyloxy-2H-pyran-2-one (Compound No. 1-341)

A procedure similar to that described in Example 10, above, was followed, but using 0.35 g of (2RS)-2-(2-methylphenoxy)-2-methylvaleric acid and 0.46 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 0.36 g of the title compound as a colorless foam.

Nuclear Magnetic Resonance Spectrum (270 MHz, CDCl$_3$) δ ppm: 2.20 (3H, singlet); 4.28 (1H, multiplet); 4.35–4.45 (1H, multiplet); 4.45–4.70 (1H, multiplet); 5.43 (1H, broad singlet); 5.47 (1H, broad singlet); 5.80–5.90 (1H, multiplet); 5.96 (1H, doublet, J=9.9 Hz); 6.72 (1H, doublet, J=7.9 Hz); 6.84 (1H, triplet, J=7.3 Hz); 7.00 (1H, triplet, J=5.9 Hz); 7.11 (1H, doublet, J=7.3 Hz).

EXAMPLE 77

(4R,6R)-6-([1S,2S,6S,8S,8aR]-2-{1,2,6,7,8,8a-Hexahydro-6-hydroxy-8-[(2RS)-2-(2-methylphenoxy)-2-methylvaleryloxy]-2-methyl-1-naphthyl}ethyl)tetrahydro-4-hydroxy-2H-pyran-2-one (Compound No. 1-341)

A procedure similar to that described in Example 2, above, was followed, but using 0.35 g of (4R,6R)-6-([1S,2S,6S,8S,8aR]-2-{1,2,6,7,8,8a-hexahydro-6-t-butyldimethylsilyloxy-8-[(2RS)-2-(2-methylphenoxy)-2-methylvaleryloxy]-2-methyl-1-naphthyl}ethyl)tetrahydro-4-t-butyldimethylsilyloxy-2H-pyran-2-one [prepared as described in Example 76, above] and 11.1 ml of a 1.0 molar solution of tetrabutylammonium fluoride in tetrahydrofuran, to give 0.16 g of the title compound as white crystals, melting at between 161° and 163° C.

Nuclear Magnetic Resonance Spectrum (270 MHz, CDCl$_3$) δ ppm: 2.19 (3H, singlet); 4.07 (1H, multiplet); 4.35 (1H, multiplet); 4.53 (1H, multiplet); 5.49 (2H, broad singlet); 5.86 (1H, doublet of doublets, J=5.9 & 9.9 Hz); 5.97 (1H, doublet, J=9.9 Hz); 6.73 (1H, doublet, J=7.9 Hz); 6.87 (1H, triplet, J=8.6 Hz); 7.04 (1H, triplet, J=9.2 Hz); 7.12 (1H, doublet, J=6.6 Hz).

EXAMPLE 78

Sodium salt of (3R,5R)-3,5-dihydroxy-7-{(1S,2S,6S,8S,8aR)-1,2,6,7,8,8a-hexahydro-6-hydroxy-8-[(2RS)-2-(2-methylphenoxy)-2-methylvaleryloxy]-2-methyl-1-naphthyl}heptanoic acid (Compound No. 1-341)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2-methylphenoxy)-2-methylvaleryloxy]-2-2methyl-1-naphthyl}ethyl)tetrahydro-4-hydroxy-2H-pyran-2-one [prepared as described in Example 28b and 0.57 ml of a 0.1N aqueous solution of sodium hydroxide, to give 32.1 mg of the title compound, as a colorless hygroscopic powder.

EXAMPLE 79

(4R,6R)-6-([1S,2S,6S,8S,8aR]-2-{1,2,6,7,8,8a-Hexahydro-6-t-butyldimethylsilyloxy-8-[2-(4-chlorophenoxy)-2-methylpropionyloxy]-2-methyl-1-naphthyl}ethyl)tetrahydro-4-t-butyldimethylsilyloxy-2H-pyran-2-one (Compound No. 1-240)

A procedure similar to that described in Example 10, above, was followed, but using 0.78 g of 2-(4-chlorophenoxy)-2-methylpropionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl}ethyl)tetrahydro-4-t-butyldimethylsilyloxy-2H-pyran-2-one [prepared as described in Example B, above], to give 1.08 g of the title compound as a colorless foam.

Nuclear Magnetic Resonance Spectrum (270 MHz, CDCl$_3$) δ ppm: 1.56 (3H, singlet); 1.59 (3H, singlet); 4.20–4.38 (2H, multiplet); 4.55–4.68 (1H, multiplet); 5.43 (1H, broad singlet); 5.49 (1H, broad singlet); 5.84 (1H, doublet of doublets, J=5.9 & 9.9 Hz); 5.97 (1H, doublet, J=9.9 Hz); 6.84 (2H, doublet, J=8.6 Hz); 7.19 (2H, doublet, J=8.6 Hz).

EXAMPLE 80

(4R,6R)-6-([1S,2S,6S,8S,8aR]-2-{1,2,6,7,8,8a-Hexahydro-6-hydroxy.-8-[2-(4-chlorophenoxy)-2-methylpropionyloxy]-2-methyl-1-naphthyl}ethyl)tetrahydro-4-hydroxy-2H -pyran-2-one (Compound No. 1-240)

A procedure similar to that described in Example 2, above, was followed, but using 0.98 g of (4R,6R)-6-([1S, 2S,6S,8S,8aR]-2-{1,2,6,7,8,8a-hexahydro-6-t-butyldimethylsilyloxy-8-[2-(4-chlorophenoxy)-2-methylpropionloxy]-2-methyl-1-naphthyl}ethyl)tetrahydro-4-t-butyldimethylsilyloxy-2H-pyran-2-one [prepared as described in Example 79, above] and 31.5 ml of a 1.0 molar solution of tetrabutylammonium fluoride in tetrahydrofuran, to give 0.46 g of the title compound as white crystals, melting at between 140° and 142° C.

Nuclear Magnetic Resonance Spectrum (270 MHz, CDCl$_3$) δ ppm: 1.53 (3H, singlet); 1.55 (3H, singlet); 4.00–4.13 (1H, multiplet); 4.30 (1H, multiplet); 4.55–4.70 (1H, multiplet); 5.47 (1H, broad singlet); 5.52 (1H, broad singlet);

5.85 (1H, doublet of doublets, J=5.9 & 9.9 Hz);

5.97 (1H, doublet, J=9.9 Hz);

6.82 (2H, doublet, J=9.2 Hz);

7.21 (2H, doublet, J=9.2 Hz).

EXAMPLE 81

Sodium salt of (3R,5R)-3,5-dihydroxy-7-{(1S,2S,6S,8S,8aR)-1,2,6,7,8,8a-hexahydro-6-hydroxy-8-[2-(4-chlorophenoxy)-2-methylpropionyloxy]-2-methyl-1-naphthyl}heptanoic acid (Compound No. 1-240)

A procedure similar to that described in Example 3, above, was followed, but using 30.0 mg of (4R,6R)-6-([1S, 2S,6S,8S,8aR]-2-{1,2,6,7,8,8a-hexahydro-6-hydroxy- 8-2-(4-chlorophenoxy)-2-methylpropionyloxy]-2-methyl-1-naphthyl}ethyl)tetrahydro-4-hydroxy-2H-pyran-2-one [prepared as described in Example 80, above] and 0.58 ml of a 0.1N aqueous solution of sodium hydroxide, to give 30.7 mg of the title compound, as a colorless hygroscopic powder.

EXAMPLE 82

(4R,6R)-6-([1S,2S,6S,8S,8aR]-2-(1,2,6,7,8,8a-Hexahydro-6-t-butyldimethylsilyloxy-8-[(2RS)-2-(4-bromophenoxy)butyryloxy]-2-methyl-1-naphthyl}ethyl)tetrahydro-4-t-butyldimethylsilyloxy-2H-pyran-2-one (Compound No. 1-102)

A procedure similar to that described in Example 1, above, was followed, but using 0.94 g of (2RS)-2-(4-bromophenoxy)butyric acid and 1.0 g of (4R,6R)-6-{(1S, 2S,6S,8S,8aR)-2-[1,2,6,7,8,8a-hexahydro-6-t-butyldimethylsilyloxy-8-hydroxy-2-methyl-1-naphthyl] ethyl}tetrahydro-4-t-butyldimethylsilyloxy-2H-pyran-2-one [prepared as described in Example B, above], to give 1.38 g of the title compound as a colorless foam.

Nuclear Magnetic Resonance Spectrum (270 MHz CDCl$_3$) δ ppm: 1.07 (3H, triplet, J=7.3 Hz); 4.29 (1H, multiplet); 4.40–4.68 (2H, multiplet); 4.58 (1H, triplet, J=5.9 Hz); 5.40 (1H, broad singlet); 5.44 (1H, broad singlet); 5.82 (1H, doublet of doublets, J=5.9 & 9.2 Hz); 5.94 (1H, doublet, J=9.9 Hz); 6.76 (2H, doublet, J=8.6 Hz); 7.31 (2H, doublet, J=8.6 Hz).

EXAMPLE 83

(4R,6R)-6-([1S,2S,6S,8S,8aR]-2-{1,2,6,7,8,8a-Hexahydro-6-hydroxy-8-[(2RS)-2-(4-bromophenoxy)butyryloxy]-2-methyl-1-naphthyl}ethyl)tetrahydro-4-hydroxy-2H-pyran-2-one (Compound No. 1-102)

A procedure similar to that described in Example 2, above, was followed, but using 1.34 g of (4R,6R)-6-([1S, 2S,6S,8S,8aR]-2-{1,2,6,7,8,8a-hexahydro-6-t-butyldimethylsilyloxy-8-[(2RS)-2-(4-bromophenoxy)butyryloxy]-2-methyl-1-naphthyl}ethyl)tetrahydro-4-t-butyldimethylsilyloxy-2H-pyran-2-one [prepared as described in Example 82, above, and 40.6 ml of a 1.0 molar solution of tetrabutylammonium fluoride in tetrahydrofuran, to give 0.49 g of the title compound as white crystals, melting at between 118° and 120° C.

Nuclear Magnetic Resonance Spectrum (270 MHz, CDCl$_3$) δ ppm: 1.06 (3H, triplet, J=7.3 Hz); 4.30–4.50 (3H, multiplet); 4.54 (1H, triplet, J=5.9 Hz); 5.41 (1H, broad singlet); 5.55 (1H, broad singlet); 5.86 (1H, doublet of doublets, J=5.9 & 9.2 Hz); 5.96 (1H, doublet, J=9.9 Hz); 6.78 (2H, doublet, J=8.6 Hz); 7.34 (2H, doublet, J=8.6 Hz).

EXAMPLE 84

Sodium salt of (3R,5R)-3,5-dihydroxy-7-{(1S,2S,6S,8S,8aR)-1,2,6,7,8,8a-hexahydro-6-hydroxy-8-[(2RS)-2-(4-bromophenoxy)butyryloxy]-2-methyl-1-naphthyl}heptanoic acid (Compound No. 1-102)

A procedure similar to that described in Example 3, above, was followed, but using 30.0 mg of (4R,6R)-6-([1S, 2S,6S,8S,8aR]-2-{1,2,6,7,8,8a-hexahydro-6-hydroxy-8-[(2RS)-2-(4-bromophenoxy)butyryloxy]-2-methyl-1-naphthyl}ethyl)tetrahydro-4-hydroxy-2H-pyran-2-one [prepared as described in Example 83, above] and 0.53 ml of a 0.1N aqueous solution of sodium hydroxide, to give 33.4 mg of the title compound, as a colorless hygroscopic powder.

EXAMPLE 85

(4R,6R)-6-([1S,2S,6S,8S,8aR]-2-{1,2,6,7,8,8a-Hexahydro-6-t-butyldimethylsilyloxy-8-[(2RS)-2-(2-chlorophenoxy)butyryloxy]-2-methyl-1-naphthyl}ethyl)tetrahydro-4-t-butyldimethylsilyloxy-2H-pyran-2-one (Compound No. 1-94)

A procedure similar to that described in Example 1, above, was followed, but using 0.78 g of (2RS)-2-(2-chlorophenoxy)butyric acid and 1.0 g of (4R,6R)-6-{(1S, 2S,6S,8S,8aR)-2-[1,2,6,7,8,8a-hexahydro -t-butyldimethylsilyloxy-8-hydroxy-2-methyl-1-naphthyl] ethyl}tetrahydro-4-t-butyldimethylsilyloxy-2H-pyran-2-one [prepared as described in Example B, above], to give 1.34 g of the title compound as a colorless foam.

Nuclear Magnetic Resonance Spectrum (270 MHz, CDCl$_3$) δ ppm: 1.12 (3H, triplet, J=7.3 Hz); 4.29 (1H, multiplet); 4.42–4.58 (2H, multiplet); 4.72 (1H, triplet, J=5.9 Hz); 5.44 (2H, broad singlet); 5.76 (1H, doublet of doublets, J=5.9 & 9.2 Hz); 5.93 (1H, doublet, J=9.2 Hz); 6.86 (2H, multiplet); 7.06–7.15 (1H, multiplet); 7.33 (1H, doublet, J=8.6 Hz).

EXAMPLE 86

(4R,6R)-6-([1S,2S,6S,8S,8aR]-2-{1,2,6,7,8,8a-Hexahydro-6-hydroxy-8-[(2RS)-2-(2-chlorophenoxy)butyryloxy]-2-methyl-1-naphthyl}ethyl)tetrahydro-4-hydroxy-2H-pyran-2-one (Compound No. 1-94)

A procedure similar to that described in Example 2, above, was followed, but using 1.27 g of (4R,6R)-6-([1S,2S,6S,8S,8aR]-2-{1,2,6,7,8,8a-hexahydro-6-t-butyldimethylsilyloxy-8-[(2RS)-2-(2-chlorophenoxy)butyryloxy]-2-methyl-1-naphthyl}ethyl)tetrahydro-4-t-butyldimethylsilyloxy-2H-pyran-2-one [prepared as described in Example 85, above] and 40.8 ml of a 1.0 molar solution of tetrabutylammonium fluoride in tetrahydrofuran, to give 0.54 g of the title compound as white crystals, melting at between 145° and 147° C.

Nuclear Magnetic Resonance Spectrum (270 MHz, CDCl$_3$) δ ppm: 1.11 (3H, triplet, J=7.3 Hz); 4.30–4.55 (3H, multiplet); 4.69 (1H, triplet, J=5.9 Hz); 5.46 (1H, broad singlet); 5.55 (1H, broad singlet); 5.83 (1H, doublet of doublets, J=5.9 & 9.9 Hz); 5.96 (1H, doublet, J=9.2 Hz); 6.89 (2H, multiplet); 7.16 (1H, multiplet); 7.33 (1H, doublet, J=7.9 Hz).

EXAMPLE 87

Sodium salt of (3R,5R)-3,5-dihydroxy-7-{(1S,2S,6S,8S,8aR)-1,2,6,7,8,8a-hexahydro-6-hydroxy-8-[(2RS)-2-(2-chlorophenoxy)butyryloxy]-2-methyl-1-naphthyl}heptanoic acid (Compound No. 1-94)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2-chlorophenoxy)butyryloxy]-2-methyl-1-naphthyl}ethyl)tetrahydro-4-hydroxy-2H-pyran-2-one [prepared as described in Example 86, above] and 0.58 ml of a 0.1N aqueous solution of sodium hydroxide, to give 33.8 mg of the title compound, as a colorless hygroscopic powder.

EXAMPLE 88

(4R,6R)-6-([1S,2S,6S,8S,8aR]-2-{1,2,6,7,8,8a-Hexahydro-6-t-butyldimethylsilyloxy-8-[(2RS)-2-phenoxy-2-methylvaleryloxy]-2-methyl-1-naphthyl}ethyl)tetrahdyro-4-t-butyldimethylsilyloxy-2H-pyran-2-one (Compound No. 1-337)

A procedure similar to that described in Example 10, above, was followed, but using 0.30 g of (2RS)-2-phenoxy-2-methylvaleric acid and 0.64 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], give 0.34 g of the title compound as a colorless foam.

Nuclear Magnetic Resonance Spectrum (270 MHz, CDCl$_3$) δ ppm: 1.46 (3H, singlet); 4.20–4.65 (3H, multiplet); 5.40–5.65 (2H, multiplet); 5.85 (1H, doublet of doublets, J=5.9 & 9.2 Hz); 5.97 (1H, doublet, J=9.2 Hz); 6.80–7.03 (3H, multiplet); 7.18–7.30 (2H, multiplet).

EXAMPLE 89

(4R,6R)-6-([1S,2S,6S,8S,8aR]-2-{1,2,6,7,8,8a-Hexahydro-6-hydroxy-8-[(2RS)-2-phenoxy-2-methylvaleryloxy]-2-methyl-1-naphthyl}ethyl)tetrahydro-4-hydroxy-2H-pyran-2-one (Compound No. 1-337)

A procedure similar to that described in Example 2, above, was followed, but using 0.32 g of (4R,6R)-6-([1S,2S,6S,8S,8 aR]-2-{1,2,6,7,8,8a-hexahydro-6-t-butyldimethylsilyloxy-8-[(2RS)-2-phenoxy-2-methylvaleryloxy]-2-methyl-1-naphthyl}ethyl)tetrahydro-4-t-butyldimethylsilyloxy-2H-pyran-2-one [prepared as described in Example 88, above] and 6.48 ml of a 1.0 molar solution of tetrabutylammonium fluoride in tetrahydrofuran, to give 0.11 g of the title compound as white crystals, melting at between 151° and 153° C.

Nuclear Magnetic Resonance Spectrum (270 MHz, CDCl$_3$) δ ppm: 1.45 (3H, singlet); 3.83 & 4.07 (total 1H, each broad singlet); 4.35 (1H, broad singlet); 4.56 (1H, multiplet); 5.50 (2H, broad singlet); 5.86 (1H, doublet of doublets, J=5.3 & 9.9 Hz); 5.97 (lH, doublet, J=9.9 Hz); 6.88 (2H, doublet, J=7.9 Hz); 6.99 (1H, triplet, J=7.9 Hz); 7.24 (2H, triplet, J=8.6 Hz).

EXAMPLE 90

Sodium salt of (3R,5R)-3,5-dihydroxy-7-{(1S,2S,6S,8S,8aR)-1,2,6,7,8,8a-hexahydro-6-hydroxy-8-[(2RS)-2-phenoxy-2-methylvaleryloxy]-2-methyl-1-naphthyl}heptanoic acid (Compound No. 1-337)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-phenoxy-2-methylvaleryloxy]-2-methyl-1-naphthyl}ethyl)tetrahydro-4-hydroxy-2H-pyran-2-one [prepared as described in Example 89, above] and 0.58 ml of a 0.1N aqueous solution of sodium hydroxide, to give 32.0 mg of the title compound, as a colorless hygroscopic powder.

EXAMPLE 91

(4R,6R)-6-([1S,2S,6S,8S,8aR]-2-{1,2,6,7,8,8a-Hexahydro-6-t-butyldimethylsilyloxy-8-[(2RS)-2-(2-methoxyphenoxy]butyryloxy]-2-methyl-1-naphthyl}ethyl)tetrahydro-4-t-butyldimethylsilyloxy-2H-pyran-2-one (Compound No. 1-90)

A procedure similar to that described in Example 1, above, was followed, but using 0.42 g of (2RS)-2-(2-methoxyphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.30 g of the title compound as a colorless foam.

Nuclear Magnetic Resonance Spectrum (270 MHz, CDCl$_3$) δ ppm: 1.10 (3H, triplet, J=7.3 Hz); 3.82 (3H, singlet); 4.18–4.35 (1H, multiplet); 4.42–4.58 (2H, multiplet); 4.62 (1H, triplet, J=5.9 Hz); 5.40–5.55 (1H, multiplet); 5.80–6.05 (2H, multiplet); 6.80–7.00 (4H, multiplet).

EXAMPLE 92

(4R,6R)-6-([1S,2S,6S,8S,8aR]-2-{1,2,6,7,8,8a-Hexahydro-6-hydroxy-8-[(2RS)-2-(2-methoxyphenoxy)butyryloxy]-2-methyl-1-naphthyl}ethyl)tetrahydro-4-hydroxy-2H-pyran-2-one (Compound No. 1-90)

A procedure similar to that described in Example 2, above, was followed, but using 1.30 g of (4R,6R)-6-([1S,2S,6S,8S,8aR]-2-{1,2,6,7,8,8a-hexahydro-6-t-butyldimethylsilyloxy-8-[(2RS)-2-(2-methoxyphenoxy)butyryloxy]-2-methyl-1-naphthyl}ethyl)tetrahydro-4-t-butyldimethylsilyloxy-2H-pyran-2-one [prepared as described in Example 91, above] and 36.0 ml of a 1.0 molar solution of tetrabutylammonium fluoride in tetrahydrofuran, to give 0.25 g of the title compound as white crystals, melting at between 116° and 117° C.

Nuclear Magnetic Resonance Spectrum (270 MHz, CDCl$_3$) δ ppm: 1.08 (3H, triplet, J=7.3 Hz); 3.81 (3H, singlet); 3.92 –4.70 (4H, multiplet); 5.44 (1H, broad singlet); 5.54 (1H, broad singlet); 5.84 (1H, doublet of doublets, J=5.9 & 9.9 Hz); 5.96 (1H, doublet, J=9.9 Hz); 6.78–7.00 (4H, multiplet).

EXAMPLE 93

Sodium salt of (3R,5R)-3,5-dihydroxy-7-{(1S,2S,6S,8S,8aR)-1,2,6,7,8,8a-hexahydro-6-hydroxy-8-[(2RS)-2-(2-methoxyphenoxy)butyryloxy]-2-methyl-1-naphthyl}heptanoic acid (Compound No. 1-90)

A procedure similar to that described in Example 3, above, was followed, but using 23.2 mg of (4R,6R)-6-([1S,2S,6S,8S,8aR]-2-{1,2,6,7,8,8a-hexahydro-6-hydroxy-8-[(2RS)-2-(2-methoxyphenoxy)butyryloxy]-2-methyl-1-naphthyl}ethyl)tetrahydro-4-hydroxy-2H-pyran-2-one [prepared as described in Example 92, above] and 0.45 ml of a 0.1N aqueous solution of sodium hydroxide, to give 23.8 mg of the title compound, as a colorless hygroscopic powder.

EXAMPLE 94

(4R,6R)-6-([1S,2S,6S,8S,8aR]-2-{1,2.6,7,8,8a-Hexahydro-6-t-butyldimethylsilyloxy-8-[(2RS)-2-(2-cyanophenoxy)butyryloxy]-2-methyl-1-naphthyl}ethyl)tetrahydro-4-t-butyldimethylsilyloxy-2H-pyran -2-one (Compound No. 1-91)

A procedure similar to that described in Example 1, above, was followed, but using 739 mg of (2RS)-2-(2-cyanophenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.08 g of the title compound as a colorless foam.

Nuclear Magnetic Resonance Spectrum (270 MHz, CDCl$_3$) δ ppm: 1.14 (3H, triplet, J=7.3 Hz); 4.32 (1H, multiplet); 4.45–4.70 (2H, multiplet); 4.89 (1H, triplet, J=5.9 Hz); 5.47 (2H, broad singlet); 5.73 (1H, doublet of doublets, J=5.9 & 9.9 Hz); 5.91 (1H, doublet, J=9.9 Hz); 6.97 (2H, multiplet); 7.40–7.60 (2H, multiplet).

EXAMPLE 95

(4R,6R)-6-([1S,2S,6S,8S,8aR]-2-{1,2,6,7,8,8a-Hexahydro-6-hydroxy-8-[(2RS)-2-(2-cyanophenoxy)butyryloxy]-2-methyl-1-naphthyl}ethyl)tetrahydro-4-hydroxy-2H-pyran-2-one (Compound No. 1-91)

A procedure similar to that described in Example 2, above, was followed, but using 1.08 g of (4R,6R)-6-([1S,2S,6S,8S,8aR]-2-{1,2,6,7,8,8a-hexahydro-6-t-butyldimethylsilyloxy-8-[(2RS)-2-(2-cyanophenoxy)butyryloxy]-2-methyl-1-naphthyl}ethyl)tetrahydro-4-t-butyldimethylsilyloxy-2H-pyran-2-one [prepared as described in Example 94, above] and 29.4 ml of a 1.0 molar solution of tetrabutylammonium fluoride in tetrahydrofuran, to give 0.40 g of the title compound as white crystals, melting at between 95° and 97° C.

Nuclear Magnetic Resonance Spectrum (270 MHz, CDCl$_3$) δ ppm: 4.40 (1H, multiplet); 4.45–4.65 (2H, multiplet); 4.87 (1H, triplet, J=5.3 Hz); 5.50 (1H, broad singlet); 5.57 (1H, broad singlet); 5.79 (1H, doublet of doublets, J=5.3 & 9.2 Hz); 5.93 (1H, doublet, J=9.2 Hz); 6.95–7.05 (2H, multiplet); 7.43–7.60 (2H, multiplet).

EXAMPLE 96

Sodium salt of (3R,5R)-3,5-dihydroxy-7-{(1S,2S,6S,8S,8aR)-1,2,6,7,8,8a-hexahydro-6-hydroxy-8-[(2RS)-2-(2-cyanophenoxy)butyryloxy]-2-methyl-1-naphthyl}heptanoic acid (Compound No. 1-91)

A procedure similar to that described in Example 3, above, was followed, but using 29.9 mg of ([1S,2S,6S,8S,8aR]-2-{1,2,6,7,8,8a-hexahydro-6-hydroxy-8-[(2RS)-2-(2-cyanophenoxy)butyryloxy]-2-methyl-1-naphthyl}ethyl)tetrahydro-4-hydroxy-2H-pyran-2-one [prepared as described in Example 95, above] and 0.59 ml of a 0.1N aqueous solution of sodium hydroxide, to give 34.1 mg of the title compound, as a colorless hygroscopic powder.

EXAMPLE 97

(4R,6R)-6-([1S,2S,6S,8S,8aR]-2-{1,2,6,7,8,8a-Hexahydro-6-t-butyldimethylsilyloxy-8-[(2RS)-2-(2-acetylphenoxy)butyryloxy]-2-methyl-1-naphthyl}ethyl)tetrahydro-4-t-butyldimethylsilyloxy-2H-pyran-2-one (Compound No. 1-364)

A procedure similar to that described in Example 1, above, was followed, but using 0.81 g of (2RS)-2-(2-acetylphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2 H-pyran-2-one [prepared as described in Example B, above], to give 1.22 g of the title compound as a colorless foam.

Nuclear Magnetic Resonance Spectrum (270 MHz, CDCl$_3$) δ ppm: 1.11 (3H, triplet, J=7.3 Hz); 2.63 (3H, singlet); 4.30 (1H, multiplet); 4.40–4.55 (2H, multiplet); 4.83 (1H, triplet, J=5.9 Hz); 5.42 (2H, broad singlet); 5.77 (1H, doublet of doublets, J=5.9 & 9.2 Hz); 5.91 (1H, doublet, J=9.2 Hz); 6.84 (1H, doublet, J=7.9 Hz); 6.98 (1H, triplet, J=7.9 Hz); 7.36 (1H, triplet, J=8.6 Hz); 7.73 (1H, doublet, J=7.9 Hz).

EXAMPLE 98

(4R,6R)-6-([1S,2S,6S,8S,8aR]-2-{1,2,6,7,8,8a-Hexahydro-6-hydroxy-8-[(2RS)-2-(2-acetylphenoxy)butyryloxy]-2-methyl-1-naphthyl}ethyl)tetrahydro-4-hydroxy-2H-pyran-2-one (Compound No. 1-364)

A procedure similar to that described in Example 2, above, was followed, but using 1.11 g of (4R,6R)-6-([1S,2S,6S,8S,8aR]-2-{1,2,6,7,8,8a-hexahydro-6-t-butyldimethylsilyloxy-8-[(2RS)-2-(2-acetylphenoxy)butyryloxy]-2-methyl-1-naphthyl}ethyl)tetrahydro-4-t-butyldimethylsilyloxy-2H-pyran-2-one [prepared as described in Example 97, above] and 35.3 ml of a 1.0 molar solution of tetrabutylammonium fluoride in tetrahydrofuran, to give 0.34 g of the title compound as white crystals, melting at between 148° and 150° C. Nuclear Magnetic Resonance Spectrum (270 MHz CDCl$_3$) δ ppm: 1.10 (3H, triplet, J=7.3 Hz); 2.62 (3H, singlet); 4.32–4.52 (3H, multiplet); 4.81 (1H, triplet, J=5.9 Hz); 5.44 (1H, broad singlet); 5.52 (1H, broad singlet); 5.82 (1H, doublet of doublets, J=5.9 & 9.9 Hz); 5.93 (1H, doublet, J=9.9 Hz); 6.88 (1H, doublet, J=7.9 Hz); 7.00 (1H, triplet, J=8.6 Hz); 7.41 (1H, triplet, J=8.6 Hz); 7.72 (1H, doublet, J=7.9 Hz).

EXAMPLE 99

Sodium salt of (3R,5R)-3,5-dihydroxy-7-{(1S,2S,6S,8S,8aR)-1,2,6,7,8,8a-hexahydro-6-hydroxy-8-[(2RS)-2-(2-acetylphenol)butyryloxy]-2-methyl-1-naphthyl}heptanoic acid (Compound No. 1-364)

A procedure similar to that described in Example 3, above, was followed, but using 30.0 mg of ([1S,2S,6S,8S,8aR]-2-{1,2,6,7,8,8a-hexahydro-6-hydroxy-8-[(2RS)-2-(2-acetylphenoxy)butyryloxy]-2-methyl-1-naphthyl}ethyl)tetrahydro-4-hydroxy-2H-pyran-2-one [prepared as described in Example 98, above] and 0.57 ml of a 0.1N aqueous solution of sodium hydroxide, to give 33.8 mg of the title compound, as a colorless hygroscopic powder.

EXAMPLE 100

(4R,6R)-6-([1S,2S,6S,8S,8aR]-2-{1,2,6,7,8,8a-Hexahydro-6-t-butyldimethylsilyloxy-8-[(2RS)-2-(2-naphthyloxy)butyryloxy]-2-methyl-1-naphthyl]ethyl}tetrahydro-4-t-butyldimethylsilyloxy-2H-pyran-2-one (Compound No. 1-68)

A procedure similar to that described in Example 1, above, was followed, but using 0.84 g of (2RS)-2-(2-naphthyloxy)butyric acid and 1.0 g of (4R,6R)-6-{([1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.31 g of the title compound as a colorless foam. Nuclear Magnetic Resonance Spectrum (270 MHz, CDCl$_3$) δ ppm: 4.03–4.70 (3H, multiplet); 4.93 (1H, triplet, J=6.6 Hz); 5.45–5.76 (2H, multiplet); 5.85–5.95 (1H, multiplet); 6.01–6.20 (1H, multiplet); 7.00–7.92 (7H, multiplet).

EXAMPLE 101

(4R,6R)-6-([1S,2S,6S,8S,8aR]-2-{1,2,6,7,8,8a-Hexahydro-6-hydroxy-8-[(2RS)-2-(2-naphthyloxy)butyryloxy]-2-methyl-1-naphthyl}ethyl)tetrahydro-4-hydroxy-2H-pyran-2-one (Compound No. 1-68)

A procedure similar to that described in Example 2, above, was followed, but using 1.25 g of (4R,6R)-6-([1S,2S,6S,8S,8aR]-2-{1,2,6,7,8,8a-hexahydro-6-t-butyldimethylsilyloxy-8-[(2RS)-2-(2-naphthyloxy)butyryloxy]-2-methyl-1-naphthyl}ethyl)tetrahydro-4-t-butyldimethylsilyloxy-2H-pyran-2-one [prepared as described in Example 100, above] and 24.6 ml of a 1.0 molar solution of tetrabutylammonium fluoride in tetrahydrofuran, to give 0.25 g of the title compound as white crystals, melting at between 124° and 127° C.

Nuclear Magnetic Resonance Spectrum (270 MHz, CDCl$_3$) δ ppm: 1.11 (3H, triplet, J=7.3 Hz); 3.72 (1H, multiplet); 4.13 (1H, multiplet); 4.26–4.56 (2H, multiplet); 4.75 (1H, triplet, J=5.9 Hz); 5.40 (1H, broad singlet); 5.61 (1H, broad singlet); 5.78 (1H, doublet of doublets, J=5.9 & 9.9 Hz); 5.96 (1H, doublet, J=9.9 Hz); 7.05–7.20 (2H, multiplet); 7.26–7.58 (2H, multiplet); 7.65–7.80 (3H, multiplet).

EXAMPLE 102

Sodium salt of (3R,5R)-3,5-dihydroxy-7-{(1S,2S,6S,8S,8aR)-1,2,6,7,8,8a-hexahydro-6-hydroxy-8-[(2RS)-2-(2-naphthyloxy)-butyryloxy]-2-methyl-1-naphthyl}heptanoic acid (Compound No. 1-68)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2-naphthyloxy)butyryloxy]-2-methyl-1-naphthyl}ethyl)tetrahydro-4-hydroxy-2H-pyran-2-one [prepared as described in Example 101, above] and 0.56 ml of a 0.1N aqueous solution of sodium hydroxide, to give 34.2 mg of the title compound, as a colorless hygroscopic powder.

EXAMPLE 103

(4R,6R)-6-([1S,2S,6S,8S,8aR]-2-{1,2,6,7,8,8a-Hexahydro-6-t-butyldimethylsilyloxy-8-[(2RS)-2-(2,6-dimethylphenoxy)propionyloxy]-2-methyl-1-naphthyl}ethyl)tetrahydro-4-t-butyldimethylsilyloxy-2H-pyran-2-one (Compound No. 1-14)

A procedure similar to that described in Example 10, above, was followed, but using 0.81 g of (2RS)-2-(2,6-dimethylphenoxy)propionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl] ethyl}tetrahydro-4-t-butyldimethylsilyloxy-2H-pyran-2-one [prepared as described in Example B, above], to give 1.25 g of the title compound as a colorless foam.

Nuclear Magnetic Resonance Spectrum (270 MHz, CDCl$_3$) δ ppm: 2.26 (6H, singlet); 4.22–4.32 (1H, multiplet); 4.32–4.47 (1H, multiplet); 4.47–4.68 (2H, multiplet); 5.46 (2H, broad singlet); 5.84 (1H, doublet of doublets, J=5.9 & 9.9 Hz); 5.97 (1H, doublet, J=9.9 Hz); 6.85–7.05 (3H, multiplet).

EXAMPLE 104

(4R,6R)-6-([1S,2S,6S,8S,8aR]-2-{1,2,6,7,8,8a-Hexahydro-6-hydroxy-8-[(2RS)-2-(2,6-dimethylphenoxy)propionyloxy]-2-methyl-1-naphthyl}ethyl)tetrahydro-4-hydroxy-2H-pyran-2-one (Compound No. 1-14)

A procedure similar to that described in Example 2, above, was followed, but using 1.21 g of (4R,6R)-6-([1S,2S,6S,8S,8aR]-2-{1,2,6,7,8,8a-hexahydro-6-t-butyldimethylsilyloxy-8-[(2RS)-2-(2,6-dimethylphenoxy)propionyloxy]-2-methyl-1-naphthyl}ethyl)tetrahydro-4-t-butyldimethylsilyloxy-2H-pyran-2-one [prepared as described in Example 103, above] and 23.8 ml of a 1.0 molar solution of tetrabutylammonium fluoride in tetrahydrofuran, to give 0.50 g of the title compound as white crystals, melting at between 85° and 88° C.

Nuclear Magnetic Resonance Spectrum (270 MHz, $CDCl_3$) δ ppm: 1.46 (3H, doublet, J=6.6 Hz); 2.26 (6H, singlet); 4.08–4.40 (2H, multiplet); 4.50–4.70 (2H, multiplet); 5.50 (1H, broad singlet); 5.55 (1H, broad singlet); 5.82–5.90 (1H, multiplet); 5.98 (1H, doublet, J=9.9 Hz); 6.86–7.03 (3H, multiplet).

EXAMPLE 105

Sodium salt of (3R,5R)-3,5-dihydroxy-7-{(1S,2S,6S,8S,8aR)-1,2,6,7,8,8a-hexahydro-6-hydroxy-8-[(2RS)-2-(2,6-dimethylphenoxy)propionyloxy]-2-methyl-1-naphthyl}heptanoic acid (Compound No. 1-14)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2,6-dimethylphenoxy)propionyloxy]-2-methyl-1-naphthyl}ethyl)tetrahydro-4-hydroxy-2H-pyran-2-one [prepared as described in Example 104, above] and 0.60 ml of a 0.1N aqueous solution of sodium hydroxide, to give 35.5 mg of the title compound, as a colorless hygroscopic powder.

EXAMPLE 106

(4R,6R)-6-([1S,2S,6S,8S,8aR]-2-{1.2,6,7,8,8a-Hexahydro-6-t-butyldimethylsilyloxy-8-[(2RS)-2-(3-trifluoromethylphenoxy)butyryloxy]-2-methyl-1-naphthyl}ethyl)tetrrahydro-4-t-butyldimethylsilyloxy-2H-pyran-2-one (Compound No. 1-92)

A procedure similar to that described in Example 1, above, was followed, but using 0.90 g of (2RS)-2-(3-trifluoromethylphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.51 g of the title compound as a colorless foam.

Nuclear Magnetic Resonance Spectrum (270 MHz, $CDCl_3$) δ ppm: 1.08 (3H, triplet, J=7.3 Hz); 4.15–4.65 (3H, multiplet); 4.72–4.86 (1H, multiplet); 5.48 (2H, broad singlet); 5.80 –6.08 (2H, multiplet); 7.03–7.45 (4H, multiplet).

EXAMPLE 107

(4R,6R)-6-([1S,2S,6S,8S,8aR]-2-{1,2,6,7,8,8a-Hexahydro-6-hydroxy-8-[(2RS)-2-(3-trifluoromethylphenoxy)butyryloxy]-2-methyl-1-naphthyl}ethyl)tetrahydro-4-hydroxy-2H-pyran-2-one (Compound No. 1-92)

A procedure similar to that described in Example 2, above, was followed, but using 1.40 g of ([1S,2S,6S,8S,8aR]-2-(1,2,6,7,8,8a-hexahydro-6-t-butyldimethylsilyloxy-8-[(2RS)-2-(3-trifluoromethylphenoxy)butyryloxy]-2-methyl-1-naphthyl}ethyl)tetrahydro-4-t-butyldimethylsilyloxy-2H-pyran-2-one [prepared as described in Example 106, above] and 43.0 ml of a 1.0 molar solution of tetrabutylammonium fluoride in tetrahydrofuran, to give 0.37 g of the title compound as white crystals, melting at between 135° and 137° C.

Nuclear Magnetic Resonance Spectrum (270 MHz, $CDCl_3$) δ ppm: 1.09 (3H, triplet, J=7.3 Hz); 4.30–4.58 (3H, multiplet); 4.67 (1H, triplet, J=5.9 Hz); 5.46 (1H, broad singlet); 5.55 (1H, broad singlet); 5.85 (1H, doublet of doublets, J=5.9 & 9.9 Hz); 5.96 (1H, doublet, J=9.9 Hz); 7.02–7.44 (4H, multiplet).

EXAMPLE 108

Sodium salt of (3R,5R)-3,5-dihydroxy-7-{(1S,2S,6S,8S,8aR)-1,2,6,7,8,8a-hexahydro-6-hydroxy-8-[(2RS)-2-(3-trifluoromethylphenoxy)butyryloxy]-2-methyl-1-naphthyl}heptanoic acid (Compound No. 1-92)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(3-trifluoromethylphenoxy)butyryloxy]-2-methyl-1-naphthyl}ethyl)tetrahydro-4-hydroxy-2H-pyran-2-one [prepared as described in Example 107, above] and 0.54 ml of a 0.1N aqueous solution of sodium hydroxide, to give 33.9 mg of the title compound, as a colorless hygroscopic powder.

EXAMPLE 109

(4R,6R)-6-([1S,2S,6S,8S,8aR]-2-{1,2,6,7,8,8a-Hexahydro-6-t-bytyldimethylsilyloxy-8-[(2RS)-3-methyl-2-phenoxybutyryloxy]-2-methyl-1-naphthyl}ethyl)tetrahydro-4-t-butyldimethylsilyloxy-2H-pyran-2-one (Compound No. 1-370)

A procedure similar to that described in Example 1, above, was followed, but using 0.71 g of (2RS)-3-methyl-2-phenoxybutyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.33 g of the title compound as a colorless foam.

Nuclear Magnetic Resonance Spectrum (270 MHz, $CDCl_3$) δ ppm: 1.07 (3H, triplet, J=7.3 Hz); 4.26 (1H, multiplet); 4.41 (1H, doublet, J=5.9 Hz); 4.30–4.50 (2H, multiplet); 5.41 (1H, broad singlet); 5.46 (1H, broad singlet); 5.81 (1H, doublet of doublets, J=5.9 & 9.9 Hz); 5.95 (1H, doublet, J=9.9 Hz); 6.82–6.95 (3H, multiplet); 7.15–7.28 (2H, multiplet).

EXAMPLE 110

(4R,6R)-6-([1S,2S,6S,8S,8aR]-2-{1,2,6,7,8,8a-Hexahydro-6-hydroxy-8-[(2RS)-3-methyl-2-phenoxybutyryloxy]-2-methyl-1-naphthyl}ethyl)tetrahydro-4-hydroxy-2H-pyran-2-one (Compound No. 1-370)

A procedure similar to that described in Example 2, above, was followed, but using 1.20 g of ([1S,2S,6S,8S,8aR]-2-{1,2,6,7,8,8a-hexahydro-6-t-butyldimethylsilyloxy-8-[(2RS)-3-methyl-2-phenoxybutyryloxy]-2-methyl-1-naphthyl}ethyl)tetrahydro-4-t-butyldimethylsilyloxy-2H-pyran-2-one [prepared as described in Example 109, above] and 39.6 ml of a 1.0 molar solution of tetrabutylammonium fluoride in tetrahydrofuran, to give 0.62 g of the title compound as white crystals, melting at between 143° and 145° C.

Nuclear Magnetic Resonance Spectrum (270 MHz, CDCl$_3$) δ ppm: 1.06(6H, doublet of doublets, J=4.0 & 6.6 Hz); 2.26 (1H, multiplet); 4.34 (1H, doublet, J=5.9 Hz); 4.35–4.50 (2H, multiplet); 5.42 (1H, broad singlet); 5.58 (1H, broad singlet); 5.83 (1H, doublet of doublets, J=5.9 & 9.9 Hz); 5.97 (1H, doublet, J=9.9 Hz); 6.80–7.00 (3H, multiplet); 7.25 (2H, triplet, J=8.6 Hz).

EXAMPLE 111

Sodium salt of (3R,5R)-3,5-dihydroxy-7-{(1S,2S,6S,8S,8aR)-1,2,6,7,8,8a-hexahydro-6-hydroxy-8-[(2RS)-3-methyl-2-phenoxybutyryloxy]-2-methyl-1-naphthyl}heptanoic acid (Compound No. 1-370)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-3-methyl-2-phenoxybutyryloxy]-2-methyl-1-naphthyl}ethyl)tetrahydro-4-hydroxy-2H-pyran-2-one [prepared as described in Example 110, above] and 0.60 ml of a 0.1N aqueous solution of sodium hydroxide to give 33.8 mg of the title compound, as a colorless hygroscopic powder.

EXAMPLE 112

(4R,6R)-6-([1S,2S,6S,8S,8aR]-2-{.1,2 6,7,8,8a-Hexahydro-6-t-butyldimethylsilyloxy-8-[(2RS)-2-(2,6-diisopropylphenoxy)butyryloxy]-2-methyl-1-naphthyl}ethyl)tetrahydro-4-t-bytyldimethylsilyloxy-2H-pyran-2-one (Compound No. 1–88)

A procedure similar to that described in Example 1, above, was followed, but using 0.36 g of (2RS)-2-(2,6-diisopropylphenoxy)butyric acid and 0.5 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 0.12 g of the title compound as a colorless foam.

Nuclear Magnetic Resonance Spectrum (270 MHz, CDCl$_3$) δ ppm: 4.30–4.53 (3H, multiplet); 4.62–4.75 (1H, multiplet); 5.54 (1H, broad singlet); 5.58 (1H, broad singlet); 5.90–6.00 (1H, multiplet); 6.08 (1H, doublet, J=9.9 Hz); 7.17 (3H, singlet).

EXAMPLE 113

(4R,6R)-6-([1S,2S,6S,8S,8aR]-2-{1,2,6,7,8,8a-Hexahydro-6-hydroxy-8-[(2RS)-2-(2,6-diisopropylphenoxy)butyryloxy]-2-methyl-1-naphthyl}ethyl)tetrahydro-4-hydroxy-2 H -pyran-2-one (Compound No. 1-88)

A procedure similar to that described in Example 2, above, was followed, but using 0.11 g of (4R,6R)-6-([1S,2S,6S,8S,8aR]-2-{1,2,6,7,8,8a-hexahydro-6-t-butyldimethylsilyloxy-8-[(2RS)-2-(2,6-diisopropylphenoxy)butyryloxy]-2-methyl-1-naphthyl}ethyl)tetrahydro-4-t-butyldimethylsilyloxy-2H-pyran-2-one [prepared as described in Example 112, above] and 7.07 ml of a 1.0 molar solution of tetrabutylammonium fluoride in tetrahydrofuran, to give 28 mg of the title compound as white crystals, melting at between 119° and 121° C.

Nuclear Magnetic Resonance Spectrum (270 MHz, CDCl$_3$) δ ppm: 0.95 (3H, triplet, J=7.3 Hz); 1.18 (6H, multiplet); 3.39 (2H, multiplet); 3.65 (1H, multiplet); 4.30–4.42 (2H, multiplet); 4.53–4.68 (1H, multiplet); 5.43 (2H, broad singlet); 5.85 (1H, multiplet); 5.96 (! H, doublet, J=9.9 Hz); 7.09 (3H, singlet).

EXAMPLE 114

Sodium salt of (3R,5R)-3,5-dihydroxy-7-{(1S,2S,6S,8S,8aR)-1,2,6,7,8,8a-hexahydro-6-hydroxy-8-[(2RS)-2-(2,6-diisopropylphenoxy)butyryloxy]-2-methyl-1-naphthyl}heptanoic acid (Compound No. 1-88)

A procedure similar to that described in Example 3, above, was followed, but using 11.4 mg of (4R,6R)-6-([1S,2S,6S,8S,8aR]-2-{1,2,6,7,8,8a-hexahydro-6-hydroxy-8-[(2RS)-2-(2,6-diisopropylphenoxy)butyryloxy]-2-methyl-1-naphthyl}ethyl)tetrahydro-4-hydroxy-2H-pyran-2-one [prepared as described in Example 113, above] and 0.20 ml of a 0.1N aqueous solution of sodium hydroxide, to give 12.7 mg of the title compound, as a colorless hygroscopic powder.

EXAMPLE 115

(4R,6R)-6-([1S,2S,6S,8S,8aR]-2-{1,2,6,7,8,8a-Hexahydro-6-t-butyldimethylsilyloxy-8-[(2RS)-2-(4-isopropylphenoxy)butyryloxy]-2-methyl-1-naphthyl}ethyl)tetrahydro-4-t-butyldimethylsilyloxy-2H-pyran-2-one (Compound No. 1-84)

A procedure similar to that described in Example 1, above, was followed, but using 756 mg of (2RS)-2-(4-isopropylpheoxy)butyric acid and 1.0 g of (4R,6R)-6-{(1S,2S,6S,8S,8aR)-2-[1,2,6,7,8,8a-Hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.42 g of the title compound as a colorless foam.

Nuclear Magnetic Resonance Spectrum (270 MHz, CDCl$_3$) δ ppm: 1.07 (3H, triplet, J=7.3 Hz); 1.20 (6H, doublet, J=5.9 Hz); 2.83 (1H, multiplet); 4.28 (1H, multiplet); 4.48–4.66 (3H, multiplet); 5.44 (1H, broad singlet); 5.48 (1H, broad singlet); 5.82 (1H, doublet of doublets, J=5.9 & 9.2 Hz); 5.97 (1H, doublet, J=9.2 Hz); 6.78 (2H, doublet, J=9.2 Hz); 7.08 (2H, doublet, J=8.6 Hz).

EXAMPLE 116

(4R,6R),-6-([1S,2S,6S,8S,8aR]-2-{1,2,6,7,8,8a-Hexahydro-6-hydroxy-8-[(2RS)-2-(4-isopropylphenoxy)butyryloxy]-2-methyl-1-naphthyl]ethyl}tetrahydro-4-hydroxy-2 H-pyran-2-one (Compound No. 1-84)

A procedure similar to that described in Example 2, above, was followed, but using 1.42 g of (4R,6R)-6-([1S,2S,6S,8S,8aR]-2-{1,2,6,7,8,8a-hexahydro-6-t-butyldimethylsilyloxy-8-[(2RS)-2-(4-isopropylphenoxy)butyryloxy]-2-methyl-1-naphthyl}ethyl)tetrahydro-4-t-butyldimethylsilyloxy-2H-pyran-2-one [prepared as described in Example 115, above] and 38.0 ml of a 1.0 molar solution of tetrabutylammonium fluoride in tetrahydrofuran, to give 80 mg of the title compound as a pale yellow powder.

Nuclear Magnetic Resonance Spectrum (270 MHz $CDCl_3$) δ ppm: 1.06 (3H, triplet, J=7.3 Hz); 1.20 (6H, doublet, J=5.9 Hz); 2.83 (1H, multiplet); 4.33 (1H, multiplet); 4.40–4.62 (3H, multiplet); 5.48 (1H, broad singlet); 5.57 (1H, broad singlet); 5.85 (1H, doublet of doublets, J=5.9 &9.2 Hz); 5.98 (1H, doublet, J=9.2 Hz); 6.78 (2H, doublet, j=9.2 Hz); 7.10 (2H, doublet, J=8.6 Hz).

EXAMPLE 117

Sodium salt of (3R,5R)-3,5-dihydroxy-7-{(1S,2S,6S,8S,8aR)-1,2,6,7,8,8a-hexahydro-6-hydroxy-8-[(2RS)-2-(4-isopropylphenoxy)butyryloxy]-2-methyl-1-naphthyl}heptanoic acid (Compound No. 1-84)

A procedure similar to that described in Example 3, above, was followed, but using 24.5 mg of (4R,6R)-6-([1S,2S,6S,8S,8aR]-2-{1,2,6,7,8,8a-hexahydro-6-hydroxy-8-[(2RS)-2-(4-isopropylphenoxy)butyryloxy]-2-methyl-1-naphthyl]ethyl}tetrahydro-4-hydroxy-2H-pyran-2-one [prepared as described in Example 116, above] and 0.47 ml of a 0.1N aqueous solution of sodium hydroxide, to give 26.3 mg of the title compound, as a yellow hygroscopic powder.

EXAMPLE 118

(4R,6R)-6-([1S,2S,6S,8S,8aR]-2-{1,2,6,7,8,8a-Hexahydro-6-t-butyldimethylsilyloxy-8-[(2RS)-2-(2-chlorophenoxy)propionyloxy]-2-methyl-1-naphthyl}ethyl)tetrahydro-4-t-butyldimethylsilyloxy-2H-pyran-2-one (Compound No. 1-30)

A procedure similar to that described in Example 1, above, was followed, but using 0.72 g of (2RS)-2-(2-chlorophenoxy)propionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.29 g of the title compound as a colorless foam.

Nuclear Magnetic Resonance Spectrum (270 MHz, $CDCl_3$) 6 ppm: 4.10–4.35 (1H, multiplet); 4.42-4.65 (2H, multiplet); 4.87 (1H, multiplet); 5.35–5.55 (2H, broad singlet); 5.75–6.02 (2H, multiplet); 6.90 (2H, multiplet); 7.15 (1H, multiplet); 7.37 (1H, multiplet).

EXAMPLE 119

(4R,6R)-6-([1S,2S,6S,8S,8aR]-2-{1,2,6,7,8,8a-Hexahydro-6-hydroxy-8-[(2RS)-2-(2-chlorophenoxy)propionyloxy]-2-methyl-1-naphthyl}ethyl)tetrahydro-4-hydroxy-2H-pyran-2-one (Compound No. 1-30)

A procedure similar to that described in Example 2, above, was followed, but using 1.0 g of (4R,6R)-6-([1S,2S,6S,8S,8aR]-2-{1,2,6,7,8,8a-hexahydro-6-t-butyldimethylsilyloxy-8-[(2RS)-2-(2-chlorophenoxy)propionyloxy]-2-methyl-1-naphthyl}ethyl)tetrahydro-4-t-butyldimethylsilyloxy-2H-pyran-2-one [prepared as described in Example 118, above] and 29.4 ml of a 1.0 molar solution of tetrabutylammonium fluoride in tetrahydrofuran, to give 0.14 g of the title compound as white crystals, melting at between 152° and 155° C.

Nuclear Magnetic Resonance Spectrum (270 MHz, $CDCl_3$) δ ppm: 3.85 (1H, multiplet); 4.20–4.58 (2H, multiplet); 4.80 (1H, quartet, J=6.6 Hz); 5.32–5.52 (2H, multiplet); 5.72–5.96 (2H, multiplet); 6.72–6.92 (2H, multiplet); 7.10 (1H, multiplet); 7.29 (1H, multiplet).

EXAMPLE 120

Sodium salt of (3R,5R)-3,5-dihydroxy-7-{S,2S,6S,8S,8aR)-1,2,6,7,8,8a-hexahydro-6-hydroxy-8-[(2RS)-2-(2-chlorophenoxy)butyryloxy]-2-methyl-1-naphthyl}heptanoic acid (Compound No. 1-30)

A procedure similar to that described in Example 3, above, was followed, but using 21.3 mg of (4R,6R)-6-([1S,2S,6S,8S,8aR]-2-{1,2,6,7,8,8a-hexahydro-6-hydroxy-8-[(2RS)-2-(2-chlorophenoxy)propionyloxy]-2-methyl-1-naphthyl}ethyl)tetrahydro-4-hydroxy-2H-pyran-2-one [prepared as described in Example 119, above] and 0.42 ml of a 0.1N aqueous solution of sodium hydroxide, to give 22.0 mg of the title compound, as a colorless hygroscopic powder.

EXAMPLE 121

(4R,6R)-6-([1S,2S,6S,8S,8aR]-2-{1,2,6,7,8,8a-Hexahydro-6-t-butyldimethylsilyloxy-8-[(2RS)-2-(2-methylphenoxy)propionyloxy]-2-methyl-1-naphthyl}ethyl)tetrahydro-4-t-butyldimethylsilyloxy-2H-pyran -2-one (Compound No. 1-5)

A procedure similar to that described in Example 1, above, was followed, but using 0.65 g of (2RS)-2-(2-methylphenoxy)propionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.04 g of the title compound as a colorless foam.

Nuclear Magnetic Resonance Spectrum (270 MHz, $CDCl_3$) δ ppm: 2.24 (3H, singlet); 4.05–4.60 (3H, multiplet); 4.85 (1H, quartet, J=6.6 Hz); 5.40 (1H, broad singlet); 5.50 (1H, broad singlet); 5.80–6.05 (2H, multiplet); 6.68–6.73 (1H, multiplet); 6.81–6.91 (1H, multiplet); 7.03–7.20 (2H, multiplet).

EXAMPLE 122

(4R,6R)-6-([1S,2S,6S,8S,8aR]-2-{1,2,6,7,8,8a-Hexahydro-6-hydroxy-8-[(2RS)-2-(2-methylphenoxy)propionyloxy]-2-methyl-1-naphthyl}ethyl)tetrahydro-4-hydroxy-2H-pyran-2-one (Compound No. 1-5)

A procedure similar to that described in Example 2, above, was followed, but using 1.03 g of (4R,6R)-6-([1S,2S,6S,8S,8aR]-2-{1,2,6,7,8,8a-hexahydro-6-t-butyldimethylsilyloxy-8-[(2RS)-2-(2-methylphenoxy)propionyloxy]-2-methyl-1-naphthyl}ethyl)tetrahydro-4-t-butyldimethylsilyloxy-2H-pyran-2-one [prepared as described in Example 121, above] and 30.9 ml of a 1.0 molar solution of tetrabutylammonium fluoride in tetrahydrofuran, to give 434 mg of the title compound as white crystals, melting at between 85° and 87° C.

Nuclear Magnetic Resonance Spectrum (270 MHz, $CDCl_3$) δ ppm: 2.20 (3H, singlet); 4.30–4.55 (3H, multiplet); 4.83 (1H, quartet, J=6.6 Hz); 5.40 (1H, broad singlet); 5.56 (1H, broad singlet); 5.84 (1H, doublet of doublets, J=5.9 & 9.9 Hz); 5.97 (1H, doublet, J=9.9 Hz); 6.74 (1H, doublet, J=7.9 Hz); 6.84 (1H, multiplet); 7.03–7.20 (2H, multiplet).

EXAMPLE 123

Sodium salt of (3R,5R)-3,5-dihydroxy-7-{1S,2S,6S,8S,8aR)-1,2,6,7,8,8a-hexahydro-6-hydroxy-8-[(2RS)-2-(2-methylphenoxy)propionyloxy]-2-methyl-1-naphthyl}heptanoic acid (Compound No. 1-5)

A procedure similar to that described in Example 3, above, was followed, but using 25.6 mg of ([1S,2S,6S,8S,8aR]-2-(1,2,6,7,8,8a-hexahydro-6-hydroxy-8-[(2RS)-2-(2-methylphenoxy)propionyloxy]-2-methyl-1-naphthyl}ethyl)tetrahydro-4-hydroxy-2H-pyran-2-one [prepared as described in Example 122, above] and 0.58 ml of a 0.1N aqueous solution of sodium hydroxide, to give 29.4 mg of the title compound, as a colorless hygroscopic powder.

EXAMPLE 124

(4R,6R)-6-([1S,2S,6S,8S,8aR]-2-{1,2,6,7,8,8a-Hexahydro-6-t-butyldimethylsilyloxy-8-[(2RS)-2-phenoxyhexanoyloxy]-2-methyl-1-naphthyl}ethyl)tetrahydro-4-t-butyldimethylsilyloxy-2H-pyran-2-one (Compound No. 1-193)

A procedure similar to that described in Example 10, above, was followed, but using 0.71 g of (2RS)-2-phenoxyhexanoic acid and 1.0 g of (4R,6R)-6-{([1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.04 g of the title compound as a colorless foam.

Nuclear Magnetic Resonance Spectrum (270 MHz, $CDCl_3$) δ ppm: 4.14–4.70 (4H, multiplet); 5.35–5.60 (2H, broad singlet); 5.80–6.05 (2H, multiplet); 6.84–7.00 (3H, multiplet); 7.20–7.34 (2H, multiplet).

EXAMPLE 125

(4R,6R)-6-([1S,2S,6S,8S,8aR]-2-{1,2,6,7,8,8a-Hexahydro-6-hydroxy-8-[(2RS)-2-phenoxyhexanoyloxy]-2-methyl-1-naphthyl}ethyl)tetrahydro-4-hydroxy-2H-pyran-2-one (Compound No. 1-193)

A procedure similar to that described in Example above, was followed, but using 1.03 g of (4R,6R)-6-([1S,2S,6S,8S,8aR]-2-{1,2,6,7,8,8a-hexahydro-6-t-butyldimethylsilyloxy-8-[(2RS)-2-phenoxyhexanoyloxy]-2-methyl-1-naphthyl}ethyl)tetrahydro-4-t-butyldimethylsilyloxy-2H-pyran-2-one [prepared as described in Example 124, above] and 20.8 ml of a 1.0 molar solution of tetrabutylammonium fluoride in tetrahydrofuran, to give 0.7 g of the title compound as white crystals, melting at between 139° and 141° C.

Nuclear Magnetic Resonance Spectrum (270 MHz, $CDCl_3$) δ ppm: 0.91 (3H, triplet, J=7.3 Hz); 3.85–4.70 (4H, multiplet); 5.35–5.65 (2H, multiplet); 5.78–6.04 (2H, multiplet); 6.85 (2H, doublet, J=7.9 Hz); 6.95 (1H, triplet, J=7.3 Hz); 7.26 (2H, triplet, J=7.3 Hz).

EXAMPLE 126

Sodium salt of (3R,5R)-3,5-dihydroxy-7-{(1S,2S,6S,8S,8aR)-1,2,6,7,8,8a-hexahydro-6-hydroxy-8-[(2RS)-2-phenoxyhexanoyloxy]-2-methyl-1-naphthyl}heptanoic acid (Compound No. 1-193)

A procedure similar to that described in Example 3, above, was followed, but using 30.2 mg of (4R,6R)-6-([1S,2S,6S,8S,8aR]-2-{1,2,6,7,8,8a-hexahydro-6-hydroxy-8-[(2RS)-2-phenoxyhexanoyloxy]-2-methyl-1-naphthyl}ethyl)tetrahydro-4-hydroxy-2H-pyran-2-one [prepared as described in Example 125, above] and 0.62 ml of a 0.1N aqueous solution of sodium hydroxide, to give 33.9 mg of the title compound, as a colorless hygroscopic powder.

EXAMPLE 127

(4R,6R)-6-([1S,2S,6S,8S,8aR]-2-{1,2,6,7,8,8a-Hexahydro-6-t-butyldimethylsilyloxy-8-[(2RS)-2-phenoxypropionyloxy]-2-methyl-1-naphthyl}ethyl)tetrahydro-4-t-butyldimethylsilyloxy-2H-pyran-2-one (Compound No. 1-1)

A procedure similar to that described in Example 1, above, was followed, but using 598 mg of (2RS)-2-phenoxypropionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 944 mg of the title compound as a colorless foam.

Nuclear Magnetic Resonance Spectrum (270 MHz, $CDCl_3$) δ ppm: 4.15–4.60 (3H, multiplet); 4.81 (1H, quartet, J=6.6 Hz); 5.42 (1H, broad singlet); 5.51 (1H, broad singlet); 5.80–5.93 (1H, multiplet); 6.00 (1H, doublet, J=9.2 Hz); 6.88 (2H, doublet, J=7.9 Hz); 6.96 (1H, triplet, J=7.3 Hz); 7.20–7.35 (2H, multiplet).

EXAMPLE 128

(4R,6R)-6-([1S,2S,6S,8S,8aR]-2-{1,2,6,7,8,8a-Hexahydro-6-hydroxy-8-[(2RS)-2-phenoxypropionyloxy]-2-methyl-1-naphthyl}ethyl)tetrahydro-4-hydroxy-2H-pyran-2-one (Compound No. 1-1)

A procedure similar to that described in Example 2, above, was followed, but using 800 mg of (4R,6R)-6-([1S,2S,6S,8S,8aR]-2-{1,2,6,7,8,8a-hexahydro-6-t-butyldimethylsilyloxy-8-[(2RS)-2-phenoxypropionyloxy]-2-methyl-1-naphthyl}ethyl)tetrahydro-4-t-butyldimethylsilyloxy-2H-pyran-2-one [prepared as described in Example 127, above] and 24.7 ml of a 1.0 molar solution of tetrabutylammonium fluoride in tetrahydrofuran, to give 324 mg of the title compound as a white powder.

Nuclear Magnetic Resonance Spectrum (270 MHz, CDCl$_3$) δ ppm: 4.35 (1H, multiplet); 4.44 (2H, multiplet); 4.78 (1H, quartet, J=6.6 Hz); 5.43 (1H, broad singlet); 5.57 (1H, broad singlet); 5.86 (1H, doublet of doublets, J=5.9 & 9.9 Hz); 5.98 (1H, doublet, J=9.9 Hz); 6.87 (2H, doublet, J=8.6 Hz); 6.95 (1H, triplet, J=7.3 Hz); 7.20–7.32 (2H, multiplet).

EXAMPLE 129

Sodium salt of (3R,5R)-3,5-dihydroxy-7-{(1S,2S,6S,8S,8aR)-1,2,6,7,8,8a-hexahydro-6-hydroxy-8-[(2RS)-2-phenoxypropionyloxy]-2-methyl-1-naphthyl}heptanoic acid (Compound No. 1-1)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-phenoxypropionyloxy]-2-methyl-1-naphthyl}ethyl)tetrahydro-4-hydroxy-2H-pyran-2-one [prepared as described in Example 128, above] and 0.69 ml of a 0.1N aqueous solution of sodium hydroxide, to give 33.0 mg of the title compound, as a colorless hygroscopic powder.

EXAMPLE 130

(4R,6R)-6-([1S,2S,6S,8S,8aR]-2-{1,2,6,7,8,8a-Hexahydro-6-t-butyldimethylsilyloxy-8-[(2RS)-2-(2-isopropylphenoxy)propionyloxy]-2-methyl-1-naphthyl}ethyl)tetrahydro-4-t-butyldimethylsilyloxy-2H-pyran-2-one (Compound No. 1-18)

A procedure similar to that described in Example 1, above, was followed, but using 749 mg of (2RS)-2-(2-isopropylphenoxy)propionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], give 1.31 g of the title compound as a colorless foam.

Nuclear Magnetic Resonance Spectrum (270 MHz, CDCl$_3$) δ ppm: 3.25–3.45 (1H, multiplet); 4.28 (1H, multiplet); 4.42–4.60 (2H, multiplet); 4.80–4.90 (1H, multiplet); 5.42 (1H, broad singlet); 5.50 (1H, broad singlet); 5.83 (1H, doublet of doublets, J=5.9 & 9.9 Hz); 5.97 (1H, doublet, J=9.9 Hz); 6.71 (1H, doublet, J=7.9 Hz); 6.93 (1H, doublet, J=7.9 Hz); 7.10 (1H, triplet, J=7.9 Hz); 7.24 (1H, doublet, J=6.6 Hz).

EXAMPLE 131

(4R,6R)-6-([1S,2S,6S,8S,8aR]-2-{1,2,6,7,8,8a-Hexahydro-6-hydroxy-8-[(2RS)-2-(2-isopropylphenoxy)propionyloxy]-2-methyl-1-naphthyl}ethyl)tetrahydro-4-hydroxy,2H-pyran-2-one (Compound No. 1-18)

A procedure similar to that described in Example 2, above, was followed, but using 1.31 g of (4R,6R)-6-([1S,2S,6S,8S,8aR]-2-{1,2,6,7,8,8a-hexahydro-6-t-butyldimethylsilyloxy-8-[(2RS)-2-(2-isopropylphenoxy)propionyloxy]-2-methyl-1-naphthyl}ethyl)tetrahydro-4-t-butyldimethylsilyloxy-2H-pyran-2-one [prepared as described in Example 130, above] and 35.4 ml of a 1.0 molar solution of tetrabutylammonium fluoride in tetrahydrofuran, to give 488 mg of the title compound as white crystals, melting at between 138° and 141° C.

Nuclear Magnetic Resonance Spectrum (270 MHz, CDCl$_3$) δ ppm: 1.60 (6H, doublet, J=6.6 Hz); 3.20–3.40 (1H, multiplet); 4.20–4.60 (3H, multiplet); 4.79 (1H, quartet, J=6.6 Hz); 5.32–5.57 (2H, multiplet); 5.77–5.98 (2H, multiplet); 6.70 (1H, doublet, J=8.6 Hz); 6.90 (1H, triplet, J=7.9 Hz); 7.07 (1H, triplet, J=7.3 Hz); 7.18 (1H, doublet, J=7.9 Hz).

EXAMPLE 132

Sodium salt of (3R,5R)-3,5-dihydroxy-7-{(1S,2S,6S,8S,8aR)-1,2,6,7,8,8a-hexahydro-6-hydroxy-8-[(2RS)-2-(2-isopropylphenoxy)propionyloxy]-2-methyl-1-naphthyl}heptanoic acid (Compound No. 1-18)

A procedure similar to that described in Example 3, above, was followed, but using 29.9 mg of (4R,6R)-6-([1S,2S,6S,8S,8aR]-2-{1,2,6,7,8,8a-hexahydro-6-hydroxy-8-[(2RS)-2-(2-isopropylphenoxy)propionyloxy]-2-methyl-1-naphthyl}ethyl)tetrahydro-4-hydroxy-2H-pyran-2-one [prepared as described in Example 131, above] and 0.59 ml of a 0.1N aqueous solution of sodium hydroxide, to give 34.1 mg of the title compound, as a colorless hygroscopic powder.

EXAMPLE 133

(4R,6R)-6-([1S,2S,6S,8S,8aR]-2-{1,2,6,7,8,8a-Hexahydro-6-t-butyldimethylsilyloxy-8-[(2RS)-2-(2-t-butylphenoxy)butyryloxy]-2-methyl-1-naphthyl}ethyl)tetrahydro-4-t-butyldimethylsilyloxy-2H-pyran-2-one (Compound No. 1-85)

A procedure similar to that described in Example 1, above, was followed, but using 0.86 g of (2RS)-2-(2-t-butylphenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.46 g of the title compound as a colorless foam.

Nuclear Magnetic Resonance Spectrum (270 MHz, CDCl$_3$) δ ppm: 1.13 (3H, triplet, J=7.3 Hz); 4.29 (1H, multiplet); 4.35–4.54 (2H, multiplet); 4.67 (1H, doublet, J=5.9 Hz); 5.41 (2H, broad singlet); 5.75 (1H, doublet of doublets, J=5.9 & 9.2 Hz); 5.89 (1H, doublet, J=9.2 Hz); 6.65 (1H, doublet, J=7.3 Hz); 6.86 (1H, triplet, J=7.3 Hz); 7.05 (1H, triplet, J=7.9 Hz); 7.27 (1H, doublet, J=7.9 Hz).

EXAMPLE 134

(4R,6R)-6-([1S,2S,6S,8S,8aR]-2-{1,2,6,7,8,8a-Hexahydro-6-hydroxy-8-[(2RS)-2-(2-t-butylphenoxy)butyryloxy]-2-methyl-1-naphthyl}ethyl)tetrahydro-4-hydroxy-2H-pyran-2-one (Compound No. 1-85)

A procedure similar to that described in Example 2, above, was followed, but using 1.40 g of (4R,6R)-6-([1S,2S,6S,8S,8aR]-2-{1,2,6,7,8,8a-hexahydro-6-t-butyldimethylsilyloxy-8-[(2RS)-2-(2-t-butylphenoxy)butyryloxy]-2-methyl-1-naphthyl}ethyl)tetrahydro-4-t-butyldimethylsilyloxy-2H-pyran-2-one [prepared as described in Example 133, above] and 43.7 ml of a 1.0 molar solution of tetrabutylammonium fluoride in tetrahydrofuran, to give 0.40 g of the title compound as white crystals, melting at between 176° and 178° C.

Nuclear Magnetic Resonance Spectrum (270 MHz, $CDCl_3$) δ ppm: 1.12 (3H, triplet, J=7.3 Hz); 4.30–4.50 (3H, multiplet); 4.65 (1H, triplet, J=5.9 Hz); 5.41 (1H, broad singlet); 5.51 (1H, broad singlet); 5.79 (1H, doublet of doublets, J=5.9 & 9.9 Hz); 5.91 (1H, doublet, J=9.9 Hz); 6.69 (1H, doublet, J=7.3 Hz); 6.87 (1H, triplet, J=7.3 Hz); 7.08 (1H, triplet, J=6.6 Hz); 7.27 (1H, doublet, J=7.9 Hz).

EXAMPLE 135

Sodium salt of (3R,5R)-3,5-dihydroxy-7-{(1S,2S,6S,8S,8aR)-1,2,6,7,8,8a-hexahydro-6-hydroxy-8-[(2RS)-2-(2-t-butylphenoxy)butyryloxy]-2-methyl-1-naphthyl}heptanoic acid (Compound No. 1-85)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(2-t-butylphenoxy)butyryloxy]-2-methyl-1-naphthyl}ethyl)tetrahydro-4-hydroxy-2H-pyran-2-one [prepared as described in Example 134, above] and 0.55 ml of a 0.1N aqueous solution of sodium hydroxide, to give 32.9 mg of the title compound, as a colorless hygroscopic powder.

EXAMPLE 136

(4R,6R)-6-([1S,2S,6S,8S,8aR]-2-{1,2,6,7,8,8a-Hexahydro-6-t-butyldimethylsilyloxy-8-[(2RS)-2-(3-dimethylaminophenoxy)butyryloxy]-2-methyl-1-naphthyl}ethyl)tetrahydro-4-t-butyldimethylsilyloxy-2H-pyran-2-one (Compound No. 1-93)

A procedure similar to that described in Example 1, above, was followed, but using 766 mg of (2RS)-2-(3-dimethylaminophenoxy)butyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.26 g of the title compound as a pale yellow foam.

Nuclear Magnetic Resonance Spectrum (270 MHz $CDCl_3$) δ ppm: 1.08 (3H, triplet, J=7.3 Hz); 2.90 (6H, singlet); 4.10–4.65 (4H, multiplet); 5.37–5.63 (2H, multiplet); 5.80–6.04 (2H, multiplet); 6.15 (1H, doublet, J=9.2 Hz); 6.31 (2H, multiplet); 7.04 (1H, triplet, J=9.2 Hz).

EXAMPLE 137

(4R,6R)-6-([1S,2S,6S,8S,8aR]-2-{1,2,6,7,8,8a-Hexahydro-6-hydroxy-8-[(2RS)-2-(3-dimethylaminophenoxy)butyryloxy]-2-methyl-1-naphthyl}tetrahydro-4-hydroxy-2 H-pyran-2-one (Compound No. 1-93)

A procedure similar to that described in Example 2, above, was followed, but using 1.26 g of (4R,6R)-6-([1S,2S,6S,8S,8aR]-2-{1,2,6,7,8,8a-hexahydro-6-t-butyldimethylsilyloxy-8-[(2RS)-2-(3-dimethylaminophenoxy)butyryloxy]-2-methyl-1-naphthyl}ethyl)tetrahydro-4-t-butyldimethylsilyloxy-2H-pyran-2-one [prepared as described in Example 136, above] and 33.4 ml of a 1.0 molar solution of tetrabutylammonium fluoride in tetrahydrofuran, to give 156 mg of the title compound as yellow crystals, melting at between 124° and 126° C.

Nuclear Magnetic Resonance Spectrum (270 MHz, $CDCl_3$) δ ppm: 1.06 (3H, triplet, J=7.3 Hz); 2.90 (6H, singlet); 4.24–4.48 (3H, multiplet); 4.56 (1H, triplet, J=5.9 Hz); 5.41 (1H, broad singlet); 5.57 (1H, broad singlet); 5.85 (1H, doublet of doublets, J=5.9 & 9.2 Hz); 5.98 (1H, doublet, J=9.2 Hz); 6.24 (1H, doublet, j=7.9 Hz); 6.30 (1H, singlet); 6.37 (1H, doublet of doublets, J=2.0 & 7.9 Hz); 7.09 (1H, triplet, J=7.9 Hz).

EXAMPLE 138

Sodium salt of (3R,5R)-3,5-dihydroxy-7-{(1S,2S,6S,8S,8aR)-1,2,6,7,8,8a-hexahydro-6-hydroxy-8-[(2RS)-2-(3-dimethylaminophenoxy)butyryloxy]-2-methyl-1-naphthyl}heptanoic acid (Compound No. 1-93)

A procedure similar to that described in Example 3, above, was followed, but using 25.0 mg of (4R,6R)-6-([1S,2S,6S,8S,8aR]-2-{1,2,6,7,8,8a-hexahydro-6-hydroxy-8-[(2RS)-2-(3-dimethylaminophenoxy)butyryloxy]-2-methyl-1-naphthyl}ethyl)tetrahydro-4-hydroxy-2H-pyran-2-one [prepared as described in Example 137, above] and 0.47 ml of a 0.1N aqueous solution of sodium hydroxide, to give 27.5 mg of the title compound, as a yellow hygroscopic powder.

EXAMPLE 139

(4R,6R)-6-([1S,2S,6S,8S,8aR]-2-{1,2,6,7,8,8a-Hexahydro-6-t-butyldimethylsilyloxy-8-[(2RS)-2-(4-t-butylphenoxy)butyryloxy]-2-methyl-1-naphthyl}ethyl)tetrahydro-4-t-butyldimethylsilyloxy-2H-pyran-2-one (Compound No. 1-87)

A procedure similar to that described in Example 1, above, was followed, but using 803 mg of (2RS)-2-(4-t-butylphenoxy)butyric acid and 1.0 g of (4R,6R)-6-{(1S,2S,6S,8S,8aR)-2-[1,2,6,7,8,8a-hexahydro-6-t-butyldimethylsiloxy-8-hydroxy-2-methyl-1-naphthyl]ethyl}tetrahydro-4-t-butyldimethylsilyloxy-2H-pyran-2-one [prepared as described in Example B, above], to give 1.41 g of the title compound as a colorless foam.

Nuclear Magnetic Resonance Spectrum (270 MHz, $CDCl_3$) δ ppm: 1.07 (3H, triplet, J=7.3 Hz); 4.13–4.34 (1H, multiplet); 4.45–4.62 (3H, multiplet); 5.37–5.58 (2H, multiplet); 5.76–6.02 (2H, multiplet); 6.78 (2H, doublet, J=9.2 Hz); 7.24 (2H, doublet, J=9.2 Hz).

EXAMPLE 140

(4R,6R)-6-([1S,2S,6S,8S,8aR]-2-{1,2,6,7,8,8a-Hexahydro-6-hydroxy-8-[(2RS)-2-(4-t-butylphenoxy)butyryloxy]-2-methyl-1-naphthyl}ethyl)tetrahydro-4-hydroxy-2H-pyran-2-one (Compound No. 1-87)

A procedure similar to that described in Example 2, above, was followed, but using 1.39 g of (4R,6R)-6-([1S,2S,6S,8S,8aR]-2-{1,2,6,7,8,8a-hexahydro-6-t-butyldimethylsilyloxy-8-[(2RS)-2-(4-t-butylphenoxy)butyryloxy]-2-methyl-1-naphthyl}ethyl)tetrahydro-4-t-butyldimethylsilyloxy-2H-pyran-2-one [prepared as described in Example 139, above] and 36.0 ml of a 1.0 molar solution of tetrabutylammonium fluoride in tetrahydrofuran, to give 647 mg of the title compound as white powder.

Nuclear Magnetic Resonance Spectrum (270 MHz, CDCl$_3$) δ ppm: 3.90–4.70 (4H, multiplet); 5.45–5.70 (2H, multiplet); 5.82–6.10 (2H, multiplet); 6.78 (2H, doublet, J=8.6 Hz); 7.25 (2H, doublet, J=8.6 Hz).

EXAMPLE 141

Sodium salt of (3R,5R)-3,5-dihydroxy-7-{(1S,2S,6S,8S,8aR)-1,2,6,7,8,8a-hexahydro-6-hydroxy-8-[(2RS)-2-(4-t-butylphenoxy)butyryloxy]-2-methyl-1-naphthyl}heptanoic acid (Compound No. 1-87)

A procedure similar to that described in Example 3, above, was followed, but using 24.7 mg of (4R,6R)-6-([1S,2S,6S,8S,8aR]-2-{1,2,6,7,8,8a-hexahydro-6-hydroxy-8-[(2RS)-2-(4-t-butylphenoxy)butyryloxy]-2-methyl-1-naphthyl}ethyl)tetrahydro-4-hydroxy-2H-pyran-2-one [prepared as described in Example 140, above] and 0.46 ml of a 0.1N aqueous solution of sodium hydroxide, to give 27.0 mg of the title compound, as a colorless hygroscopic powder.

EXAMPLE 142

(4R,6R)-6-([1S,2S,6S,8S,8aR]-2-{1,2,6,7,8,8a-Hexahydro-6-t-butyldimethylsilyloxy-8-[(2RS)-2-(4-methylphenoxy)-2-phenylacetoxy]-2-methyl-1-naphthyl}ethyl)tetrahyro-4-t-butyldimethylsilyloxy-2H-pyran-2-one (Compound No. 1-357)

A procedure similar to that described in Example 10, above, was followed, but using 0.32 g of (2RS)-2-(4-methylphenoxy)-2-phenylacetic acid and 0.61 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 0.42 g of the title compound as a colorless foam.

Nuclear Magnetic Resonance Spectrum (270 MHz, CDCl$_3$) δ ppm: 2.20 (3H, singlet); 3.85–4.40 (3H, multiplet); 5.36 (1H, broad singlet); 5.46 (1H, broad singlet); 5.60 (1H, singlet); 5.82–5.92 (1H, multiplet); 6.02 (1H, doublet, J=9.2 Hz); 6.86 (2H, doublet, J=8.6 Hz); 7.10 (2H, doublet, J=8.6 Hz); 7.52 (3H, multiplet); 7.76 (2H, doublet, J=6.6 Hz).

EXAMPLE 143

(4R,6R)-6-([1S,2S,6S,8S,8aR]-2-{1,2,6,7,8,8a-Hexahydro-6-hydroxy-8-[(2RS)-2-(4-methylphenoxy)-2-phenylacetoxy]-2-methyl-1-naphthyl}ethyl)tetrahydro-4-hydroxy-2H-pyran-2-one (Compound No. 1-357)

A procedure similar to that described in Example 2, above, was followed, but using 0.42 g of (4R,6R)-6-([1S,2S,6S,8S,8aR]-2-{1,2,6,7,8,8a-hexahydro-6-t-butyldimethylsilyloxy-8-[(2RS)-2-(4-methylphenoxy)-2-phenylacetoxy]-2-methyl-1-naphthyl}ethyl)tetrahydro-4-t-butyldimethylsilyloxy-2H-pyran-2-one [prepared as described in Example 142, above] and 8.1 ml of a 1.0 molar solution of tetrabutylammonium fluoride in tetrahydrofuran, to give 220 mg of the title compound as a white powder, melting at between 130° and 133° C.

Nuclear Magnetic Resonance Spectrum. (270 MHz, CDCl$_3$) δ ppm: 2.30 (3H, singlet); 4.10–4.50 (3H, multiplet); 5.40–5.75 (3H, multiplet); 5.85–6.10 (2H, multiplet); 6.88 (2H, multiplet); 7.10 (2H, multiplet); 7.39 (3H, multiplet); 7.61 (2H, multiplet).

EXAMPLE 144

Sodium salt of (3R,5R)-3,5-dihydroxy-7-{(1S,2S,6S,8S,8aR)-1,2,6,7,8,8a-hexahydro-6-hydroxy-8-[(2RS)-2-(4-methylphenoxy)-2-phenylacetoxy]-2-methyl-1-naphthyl}heptanoic acid (Compound No. 1-357)

A procedure similar to that described in Example 3, above, was followed, but using 30.0 mg of (4R,6R)-6-([1S,2S,6S,8S,8aR]-2-{1,2,6,7,8,8a-hexahydro-6-hydroxy-8-[(2RS)-2-(4-methylphenoxy)-2-phenylacetoxy]-2-methyl-1-naphthyl}ethyl)tetrahydro-4-hydroxy-2H-pyran-2-one [prepared as described in Example 143, above] and 0.55 ml of a 0.1N aqueous solution of sodium hydroxide, to give 33.7 mg of the title compound, as a colorless hygroscopic powder.

EXAMPLE 145

(4R,6R)-6-([1S,2S,6S,8S,8aR]-2-{1,2,6,7,8,8a-Hexahydro-6-t-butyldimethylsilyloxy-8-[2-(4-trifluoromethylbenzyloxy)-2-methylpropionyloxy]-2-methyl-1-naphthyl}ethyl)tetrahydro-4-t-butyldimethylsilyloxy-2H-pyran-2-one (Compound No. 1-371)

A procedure similar to that described in Example 1, above, was followed, but using 786 mg of 2-(4-trifluoromethylbenzyloxy)-2-methylpropionic acid and 1.10 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.28 g of the title compound as a colorless foam.

Nuclear Magnetic Resonance Spectrum (270 MHz, CDCl$_3$) δ ppm: 1.53 (3H, singlet); 1.51 (3H, singlet); 4.25–4.27 (1H, multiplet); 4.33–4.38 (1H, multiplet); 4.54 (2H, broad singlet); 4.58–4.63 (1H, multiplet); 5.42 (2H, broad singlet); 5.85 (1H, doublet of doublets, J=6.4 & 9.8 Hz); 5.99 (1H, doublet, J=9.8 Hz); 7.50 (2H, doublet, J=8.3 Hz); 7.56 (2H, doublet, J=8.3 Hz).

EXAMPLE 146

(4R,6R)-6-([1S,2S,6S,8S,8aR]-2-{1,2,6,7,8,8a-Hexahydro-6-hydroxy-8-[2-(4-trifluoromethylbenzyloxy)-2-methylpropionyloxy]-2-methyl-1-naphthyl}ethyl)tetrahydro-4-hydroxy-2H-pyran-2-one (Compound No. 1-371)

A procedure similar to that described in Example 2, above, was followed, but using 1.16 g of (4R,6R)-6-([1S,2S,6S,8S,8aR]-2-{1,2,6,7,8,8a-hexahydro-6-t-butyldimethylsilyloxy-8-[2-(4-trifluoromethylbenzyloxy)-2-methylpropionyloxy]-2-methyl-1-naphthyl}ethyl)tetrahydro-4-t-butyldimethylsilyloxy-2H-pyran-2-one [prepared as described in Example 145, above] and 20.4 ml of a 1.0 molar solution of tetrabutylammonium fluoride in tetrahydrofuran, to give 0.75 g of the title compound as a colorless foam.

Nuclear Magnetic Resonance Spectrum (270 MHz, hexadeuterated dimethyl sulfoxide) δ ppm: 0.84 (3H, doublet, J=6.8 Hz); 1.41 (3H, singlet); 1.42 (3H, singlet); 4.08–4.15 (2H, multiplet); 4.47–4.51 (1H, multiplet); 4.52 (2H, singlet); 4.79 (1H, doublet, J=6.4 Hz); 5.17 (1H, doublet, J=3.4 Hz); 5.29 (1H, broad singlet); 5.48 (1H, broad singlet); 5.82 (1H, doublet of doublets, J=5.9 & 9.5 Hz); 5.97 (1H, doublet, J=9.5 Hz); 7.55 (2H, doublet, J=8.3 Hz); 7.66 (2H, doublet, J=8.3 Hz).

EXAMPLE 147

Sodium salt of (3R,5R)-3,5-dihydroxy-7-{(1S,2S,6S,8S,8aR)-1,2,6,7,8.8a-hexahydro-6-hydroxy-8-[2-(4-trifluoromethylbenzyloxy)-2-methylpropionyloxy]-2-methyl-1-naphthyl}heptanoic acid (Compound No. 1-371)

A procedure similar to that described in Example 3, above, was followed, but using 24.0 mg of (4R,6R)-6-([1S,2S,6S,8S,8aR]-2-{1,2,6,7,8,8a-hexahydro-6-hydroxy-8-[2-(4-trifluoromethylbenzyloxy)-2-methylpropionyloxy]-2-methyl-1-naphthyl}ethyl)tetrahydro-4-hydroxy-2H-pyran-2-one [prepared as de scribed in Example 146, above], to give 26.0 mg of the title compound, as a colorless hygroscopic powder.

EXAMPLE 148

(4R,6R)-6-([1S,2S,6S,8S,8aR]-2-{1,2,6,7,8,8a-Hexahydro-6-t-butyldimethylsilyloxy-8-[2-methoxy-2-methylpropionyloxy]-2-methyl-1-naphthyl}ethyl)tetrahydro-4-t-butyldimethylsilyloxy-2H-pyran-2-one (Compound No. 1-270)

A procedure similar to that described in Example 10, above, was followed, but using 860 mg of 2-methoxy-2-methylpropionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 836 mg of the title compound as a colorless foam.

Nuclear Magnetic Resonance Spectrum (400 MHz, CDCl$_3$) δ ppm: 3.28 (3H, singlet); 4.26–4.30 (1H, multiplet); 4.41–4.47 (1H, multiplet); 4.58–4.63 (1H, multiplet); 5.40 (1H, broad singlet); 5.48 (1H, broad singlet); 5.84 (1H, doublet of doublets, J=5.9 & 9.8 Hz); 5.98 (1H, doublet, J=9.8 Hz).

EXAMPLE 149

(4R,6R)-6-([1S,2S,6S,8S,8aR]-2-{1,2,6,7,8,8a-Hexahydro-6-hydroxy-8-(2-methoxy-2-methylpropionyloxy]-2-methyl-1-naphthyl}ethyl)tetrahydro-4-hydroxy-2 H -pyran -2-one (Compound No. 1-270)

A procedure similar to that described in Example 2, above, was followed, but using 814 mg of (4R,6R)-6-([1S,2S,6S,8S,8aR]-2-{1,2,6,7,8,8a-hexahydro-6-t-butyldimethylsilyloxy-8-(2-methoxy-2-methylpropionyloxy]-2-methyl-1-naphthyl}ethyl)tetrahydro-4-t-butyldimethylsilyloxy-2H-pyran-2-one [prepared as described in Example 148, above] and 17.5 ml of a 1.0 molar solution of tetrabutylammonium fluoride in tetrahydrofuran, to give 518 mg of the title compound as colorless needle-like crystals, melting at between 150° and 152° C.

Nuclear Magnetic Resonance Spectrum (400 MHz, hexadeuterated dimethyl sulfoxide) δ ppm: 0.85 (3H, doublet, J=7.3 Hz); 3.13 (3H, singlet); 4.07–4.16 (2H, multiplet); 4.45–4.52 (1H, multiplet); 4.80 (1H, doublet, J=5.9 Hz); 5.15 (1H, doublet, J=2.9 Hz); 5.26 (1H, broad singlet); 5.51 (1H, broad singlet); 5.85 (1H, doublet of doublets, J=5.9 & 9.8 Hz); 5.98 (1H, doublet, J=9.8 Hz).

EXAMPLE 150

Sodium salt of (3R,5R)-3,5-dihydroxy-7-{(1S,2S,6S,8S,8aR)-1,2,6,7,8.8a-hexahydro-6-hydroxy-8-[2-methoxy-2-methylpropionyloxy]-2-methyl-1-naphthyl}heptanoic acid (Compound No. 1-270)

A procedure similar to that described in Example 3, above, was followed, but using 21.9 mg of (4R,6R)-6-([1S,2S,6S,8S,8aR]-2-{1,2,6,7,8,8a-hexahydro-6-hydroxy-8-(2-methoxy-2-methylpropionyloxy]-2-methyl-1-naphthyl}ethyl)tetrahydro-4-hydroxy-2H-pyran-2-one [prepared as described in Example 149, above], to give 25.0 mg of the title compound, as a colorless hygroscopic powder.

EXAMPLE 151

(4R,6R)-6-{(1S,2S,6S,8S,8aR)-2-[1,2,6,7,8,8a-Hexahydro-6-t-butyldimethylsilyloxy-8-(2-ethoxy-2-methylpropionyloxy)-2-methyl-1-naphthyl]ethyl}tetrahydro-4-t-butyldimethylsilyloxy-2H-pyran-2-one (Compound No. 1-271)

A procedure similar to that described in Example 10, above, was followed, but using 1.15 g of 2-ethoxy-2-methylpropionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 414 mg of a fraction containing the title compound. This fraction was used in the next step without further purification.

EXAMPLE 152

(4R,6R)-6-{(1S,2S,6S,8S,8aR)-2-[1,2,6,7,8,8a-Hexahydro-6-hydroxy-8-(2-ethoxy-2-methylpropionyloxy)-2-methyl-1-naphthyl]ethyl}tetrahydro-4-hydroxy-2H-pyran-2-one (Compound No. 1-271)

A procedure similar to that described in Example 2, above, was followed, but using the whole of the fraction (414 mg) containing (4R,6R)-6-{(1S,2S,6S,8S, 8aR)-2-[1, 2,6,7,8,8a-hexahydro-6-t-butyldimethylsilyloxy-8-(2-ethoxy-2-methylpropionyloxy)-2-methyl-1-naphthyl]ethyl}tetrahydro-4-t-butyldimethylsilyloxy-2H-pyran-2-one [prepared as described in Example 151, above] and 6.2 ml of a 1.0 molar solution of tetrabutylammonium fluoride in tetrahydrofuran, to give 25 mg of the title compound as colorless needle-like crystals, melting at 132° C.

Nuclear Magnetic Resonance Spectrum 400 MHz, CDCl$_3$) δ ppm: 0.91 (3H, doublet, J=6.8 Hz); 1.18 (3H, triplet, J=6.8 Hz); 3.38–3.48 (2H, multiplet); 4.33–4.42 (2H, multiplet); 4.57–4.64 (1H, multiplet); 5.44 (1H, broad singlet); 5.57 (1H, broad singlet); 5.89 (1H, doublet of doublets, J=5.9 & 9.8 Hz); 6.00 (1H, doublet, J=9.8 Hz).

EXAMPLE 153

Sodium salt of (3R,5R)-3,5-dihydroxy-7-{(1S,2S,6S,8S,8aR)-1,2,6,7,8,8a-hexahydro-6-hydroxy-8-[2-ethoxy-2-methylpropionyloxy]-2-methyl-1-naphthyl}heptanoic acid (Compound No. 1-271)

A procedure similar co that described in Example 3, above, was followed, but using 10.0 mg of (4R,6R)-6-{(1S,2S,6S,8S,8aR)-2-[1,2,6,7,8,8a-hexahydro-6-hydroxy-8-(2-ethoxy-2-methylpropionyloxy)-2-methyl-1-naphthyl]ethyl}tetrahydro-4-hydroxy-2H-pyran-2-one [prepared as described in Example 152, above], to give 11.0 mg of the title compound, as a colorless hygroscopic powder.

EXAMPLE 154

(4R,6R)-6-{(1S,2S,6S,8S,8aR)-2-[1,2,6,7,8,8a-Hexahydro-6-t-butyldimethylsilyloxy-8-(2-ethyl-2-methoxybutyryloxy)-2-methyl-1-naphthyl]ethyl}tetrahydro-4-t-butyldimethylsilyloxy-2H-pyran-2-one (Compound No. 1-366)

A procedure similar to that described in Example 10, above, was followed, but using 1.28 g of 2-ethyl-2-methoxybutyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 558 mg of the title compound as a colorless foam.

Nuclear Magnetic Resonance Spectrum (400 MHz, CDCl$_3$) δ ppm: 3.22 (3H, singlet); 4.24–4.29 (1H, multiplet); 4.40–4.46 (1H, multiplet); 5.46 (2H, broad singlet); 5.85 (1H, doublet of doublets, J=5.9 & 9.8 Hz); 5.98 (1H, doublet, J=9.8 Hz).

EXAMPLE 155

(4R,6R)-6-{(1S,2S,6S,8S,8aR)-2-[1,2,6,7,8,8a-Hexahydro-6-hydroxy-8-(2-ethyl-2-methoxybutyryloxy)-2-methyl-1-naphthyl]ethyl}tetrahydro-4-hydroxy-2H-pyran-2-one (Compound No. 1-366)

A procedure similar to that described in Example 2, above, was followed, but using 548 mg of (4R,6R)-6-{(1S,2S,6S,8S,8aR)-2-[1,2,6,7,8,8a-hexahydro-6-t-butyldimethylsilyloxy-8-(2-ethyl-2-methoxybutyryloxy)-2-methyl-1-naphthyl]ethyl}tetrahydro-4-t-butyldimethylsiloxy-2H-pyran-2-one [prepared as described in Example 154, above] and 11.3 ml of a 1.0 molar solution of tetrabutylammonium fluoride in tetrahydrofuran, to give 288 mg of the title compound as a colorless foam.

Nuclear Magnetic Resonance Spectrum (400 MHz, CDCl$_3$) δ ppm: 3.22 (3H, singlet); 4.33–4.47 (2H, multiplet); 4.55–4.65 (1H, multiplet); 5.52 (1H, broad singlet); 5.57 (1H, broad singlet); 5.88 (1H, doublet of doublets, J=5.9 & 9.8 Hz); 5.99 (1H, doublet, J=9.8 Hz).

EXAMPLE 156

Sodium salt of (3R,5R)-3,5-dihydroxy-7-{(1S,2S,6S,8S,8aR)-1,2,6,7,8,8a-hexahydro-6-hydroxy-8-[2-ethyl-2-methoxybutyryloxy]-2-methyl-1-naphthyl}heptanoic acid (Compound No. 1-366)

A procedure similar to that described in Example 3, above, was followed, but using 21.9 mg of (4R,6R)-6-{(1S,2S,6S,8S,8aR)-2-[1,2,6,7,8,8a-hexahydro-6-hydroxy-8-(2-ethyl-2-methoxybutyryloxy)-2-methyl-1-naphthyl]ethyl}tetrahydro-4-hydroxy-2H-pyran-2-one [prepared as described in Example 155, above], to give 24.0 mg of the title compound, as a colorless hygroscopic powder.

EXAMPLE 157

(4R,6R)-6-{(1S,2S,6S,8S,8aR)-2-[1,2,6,7,8,8a-Hexahydro-6-t-butyldimethylsilyloxy-8-(2-ethoxy-2-ethylbutyryloxy)-2-methyl-1-naphthyl]ethyl}tetrahydro-4-t-butyldimethylsilyloxy-2H-pyran-2-one (Compound No. 1-367)

A procedure similar to that described in Example 10, above, was followed, but using 875 mg of 2-ethoxy-2-ethylbutyric acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 271 mg of the title compound as a colorless foam.

Nuclear Magnetic Resonance Spectrum (400 MHz, CDCl$_3$) δ ppm: 3.36 (2H, quartet, J=6.8 Hz); 4.25–4.30 (1H, multiplet); 4.39–4.45 (1H, multiplet); 4.54–4.59 (1H, multiplet); 5.43 (1H, broad singlet); 5.45 (1H, broad singlet); 5.84 (1H, doublet of doublets, J=5.9 & 9.8 Hz); 5.98 (1H, doublet, J=9.8 Hz).

EXAMPLE 158

(4R,6R)-6-{(1S,2S,6S,8S,8aR)-2-[1,2,6,7,8,8a-Hexahydro-6-hydroxy-8-(2-ethoxy-2-ethylbutyryloxy)-2-methyl-1-naphthyl]ethyl}tetrahydro-4-hydroxy-2H-pyran-2-one (Compound No. 1-367)

A procedure similar to that described in Example 2, above, was followed, but using 263 mg of (4R,6R)-6-{(1S,2S,6S,8S,8aR)-2-[1,2,6,7,8,8a-hexahydro-6-t-butyldimethylsilyloxy-8-(2-ethoxy-2-ethylbutyryloxy)-2-methyl-1-naphthyl]ethyl}tetrahydro-4-t-butyldimethylsilyloxy-2H-pyran-2-one [prepared as described in Example 157, above] and 5.3 ml of a 1.0 molar solution of tetrabutylammonium fluoride in tetrahydrofuran, to give 149 mg of the title compound as a colorless foam.

Nuclear Magnetic Resonance Spectrum (400 MHz, CDCl$_3$) δ ppm: 3.36 (2H, quartet, J=6.8 Hz); 4.34–4.43 (2H, multiplet); 4.55–4.64 (1H, multiplet); 5.49 (1H, multiplet); 5.57 (1H, multiplet); 5.89 (1H, doublet of doublets, J:5.9 & 9.8 Hz); 6.00 (1H, doublet, J=9.8 Hz).

EXAMPLE 159

Sodium salt of
(3R,5R)-3,5-dihydroxy-7-{(1S,2S,6S,8S,8aR)-
1,2,6,7,8a-hexahydro-6-hydroxy-8-[2-ethoxy-2-
ethylbutyryloxy]-2-methyl-1-naphthyl}heptanoic
acid (Compound No. 1-367)

A procedure similar to that described in Example 3, above, was followed, but using 21.9 mg of (4R,6R)-6-{(1S,2S,6S,8S,8aR)-2-[1,2,6,7,8,8a-hexahydro-6-hydroxy-8-(2-ethoxy-2-ethylbutyryloxy)-2-methyl-1-naphthyl]ethyl}tetrahydro-4-hydroxy-2H-pyran-2-one [prepared as described in Example 158, above], to give 25.0 mg of the title compound, as a colorless hygroscopic powder.

EXAMPLE 160

(4R,6R)-6-{(1S,2S,6S,8S,8aR)-2-[1,2,6,7,8,8a-
Hexahydro-6-t-butyldimethylsilyloxy-8-(2,2-
bis[methoxymethyl]propionyloxy)-2-methyl-1-
naphthyl]ethyl}tetrahydro-
4-t-butyldimethylsilyloxy-2H-pyran-2-one
(Compound No. 1-368)

A procedure similar to that described in Example 10, above, was followed, but using 786 mg of 2,2-bis-methoxymethyl)propionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 201 mg of the title compound as a colorless foam.

Nuclear Magnetic Resonance Spectrum (270 MHz, CDCl$_3$) δ ppm: 3.30 (6H, singlet); 4.27–4.30 (1H, multiplet); 4.40–4.50 (1H, multiplet); 4.52–4.63 (1H, multiplet); 5.38 (1H, broad singlet); 5.47 (1H, broad singlet); 5.84 (1H, doublet of doublets, J=5.9 & 9.9 Hz); 5.98 (1H, doublet, J=9.9 Hz).

EXAMPLE 161

(4R,6R)-6-{(1S,2S,6S,8S,8aR)-2-[1,2,6,7,8,8a-
Hexahydro-6-hydroxy-8-(2,2-
bis[methoxymethyl]propionyloxy)-
2-methyl-1-naphthyl]ethyl}tetrahydro-4-hydroxy-2H-
pyran-2-one (Compound No. 1-368)

A procedure similar to that described in Example 2, above, was followed, but using 200 mg of (4R,6R)-6-{(1S,2S,6S,8S,8aR)-2-[1,2,6,7,8,8a-hexahydro-6-t-butyldimethylsilyloxy-8-(2,2-bis[methoxymethyl]propionyloxy)-2-methyl-1-naphthyl]ethyl}tetrahydro-4-t-butyldimethylsilyloxy-2H-pyran-2-one [prepared as described in Example 160, above] and 4.0 ml of a 1.0 molar solution of tetrabutylammonium fluoride in tetrahydrofuran, to give 105 mg of the title compound as colorless needle-like crystals, melting at between 122° and 123° C.

Nuclear Magnetic Resonance Spectrum (400 MHz, CDCl$_3$) δ ppm: 0.93 (3H, doublet, J=6.8 Hz); 1.23 (3H, singlet); 3.29 (3H, singlet); 3.30 (3H, singlet); 4.31–4.45 (2H, multiplet); 4.58–4.63 (1H, multiplet); 5.43 (1H, broad singlet); 5.58 (1H, broad singlet); 5.89 (1H, doublet of doublets, J=5.9 & 9.8 Hz); 6.00 (1H, doublet, J=9.8 Hz).

EXAMPLE 162

Sodium salt of
(3R,5R)-3,5-dihydroxy-7-{(1S,2S,6S,8S,8aR)-
1,2,6,7,8,8a-hexahydro-6-hydroxy-8-[2,2-
bis[methoxymethyl]propionyloxy]-2-methyl-1-
naphthyl}heptanoic acid (Compound No. 1-368)

A procedure similar to that described in Example 3, above, was followed, but using 17.8 mg of (4R,6R)-6-{(1S,2S,6S,8S,8aR)-2-[1,2,6,7,8,8a-hexahydro-6-hydroxy-8-(2,2-bis[methoxymethyl]propionyloxy)-2-methyl-1-naphthyl]ethyl}tetrahydro-4-hydroxy-2H-pyran-2-one [prepared as described in Example 161, above], to give 21.0 mg of the title compound, as a colorless hygroscopic powder.

EXAMPLE 163

(4R,6R)-6-{(1S,2S,6S,8S,8aR)-2-[1,2,6,7,8,8a-
Hexahydro-6-t-butyldimethylsilyloxy-8-(2-
methoxymethyl-2-methylpropionyloxy)-2-methyl-1-
naphthyl]ethyl}tetrahydro-4-t-butyldimethylsilyloxy-
2H-pyran-2-one (Compound No. 1-372)

A procedure similar to that described in Example 10, above, was followed, but using 960 mg of 2-methoxymethyl-2-methylpropionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 423 mg of the title compound as a colorless foam.

Nuclear Magnetic Resonance Spectrum (270 MHz, CDCl$_3$) δ ppm: 3.28 (3H, singlet); 3.32 (2H, doublet, J=2.4 Hz); 4.27–4.31 (1H, multiplet); 4.41–4.47 (1H, multiplet); 4.58–4.60 (1H, multiplet); 5.34 (1H, broad singlet); 5.47 (1H, broad singlet); 5.84 (1H, doublet of doublets, J=5.9 & 9.8 Hz); 5.96 (1H, doublet, J=9.8 Hz).

EXAMPLE 164

(4R,6R)-6-{(1S,2S,6S,8S,8aR)-2-[1,2,6,7,8,8a-
Hexahydro-6-hydroxy-8-(2-methoxymethyl-2-
methylpropionyloxy)-2-methyl-1-
naphthyl]ethyl}tetrahydro-4-hydroxy-2H-pyran-2-one
(Compound No. 1-372)

A procedure similar to that described in Example 2, above, was followed, but using 360 mg of (4R,6R)-6-{(1S,2S,6S,8S,8aR)-2-[1,2,6,7,8,8a-hexahydro-6-t-butyldimethylsilyloxy-8-2-methoxymethyl-2-methylpropionyloxy)-2-methyl-1-naphthyl]ethyl}tetrahydro-4-t-butyldimethylsilyloxy-2H-pyran-2-one [prepared as described in Example 163, above] and 7.6 ml of a 1.0 molar solution of tetrabutylammonium fluoride in tetrahydrofuran, to give 177 mg of the title compound as white crystals, melting at between 140° and 142° C.

Nuclear Magnetic Resonance Spectrum (270 MHz, CDCl$_3$) δ ppm: 0.89 (3H, doublet, J=6.8 Hz); 3.28 (3H, singlet); 3.32 (2H, singlet); 4.34–4.40 (2H, multiplet); 4.58–4.65 (1H, multiplet); 5.39 (1H, broad singlet); 5.57 (1H, broad singlet); 5.89 (1H, doublet of doublets, J=5.9 & 9.3 Hz); 5.98 (1H, doublet, J=9.3 Hz).

EXAMPLE 165

Sodium salt of
(3R,5R)-3,5-dihydroxy-7-{(1S,2S,6S,8S,8aR)-
1,2,6,7,8,8a-hexahydro-6-hydroxy-8-[2-methoxymethyl
-2-methylpropionyloxy]-2-methyl-1-naphthyl}heptanoic
acid (Compound No. 1-372)

A procedure similar to that described in Example 3, above, was followed, but using 20.0 mg of (4R,6R)-6-{(1S, 2S,6S,8S,8aR)-2-[1,2,6,7,8,8a-hexahydro-6-hydroxy-8-(2-methoxymethyl-2-methylpropionyloxy)-2-methyl-1-naphthyl]ethyl}tetrahydro-4-hydroxy-2H-pyran-2-one [prepared as described in Example 164, above], to give 23.5 mg of the title compound, as a colorless hygroscopic powder.

EXAMPLE 166

(4R,6R)-6-([1S,2S,6S,8S,8aR]-2-{1,2,6,7,8,8a-
Hexahydro-6-t-butyldimethylsilyloxy-8-[2-(4-
fluorobenzyloxy)-2-methylpropionyloxy]-2-methyl-1-
naphthyl}ethyl)tetrahydro-4-t-butyldimethylsilyloxy-
2H-pyran-2-one (Compound No. 1-272)

A procedure similar to that described in Example 10, above, was followed, but using 770 mg of 2-(4-fluorobenzyloxy)-2-methylpropionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.17 g of the title compound as a colorless foam.

Nuclear Magnetic Resonance Spectrum (270 MHz, $CDCl_3$) δ ppm: 1.47 (6H, doublet, J=3.9 Hz); 4.21–4.24 (1H, multiplet); 4.33–4.37 (1H, multiplet); 4.41 (2H, doublet, J=3.4 Hz); 4.54–4.58 (1H, multiplet); 5.42 (2H, broad singlet); 5.83 (1H, doublet of doublets, J=5.9 & 9.8 Hz); 5.96 (1H, doublet, J=9.8 Hz); 6.93–6.99 (2H, multiplet); 7.31–7.35 (2H, multiplet).

EXAMPLE 167

(4R,6R)-6-([1S,2S,6S,8S,8aR]-2-{1,2,6,7,8,8a-
Hexahydro-6-hydroxy-8-[2-(4-fluorobenzyloxy)-2-
methylpropionyloxy]-2-methyl-1-
naphthyl}ethyl)tetrahydro-4-hydroxy-2H-pyran-2-one
(Compound No. 1-272)

A procedure similar to that described in Example 2, above, was followed, but using 1.03 g of (4R,6R)-6-([1S, 2S,6S,8S,8aR]-2-{1,2,6,7,8,8a-hexahydro-6-t-butyldimethylsilyloxy- 8-[2-(4-fluorobenzyloxy)-2-methylpropionyloxy]-2-methyl-1-naphthyl}ethyl)tetrahydro-4-t-butyldimethylsilyloxy-2H-pyran-2-one [prepared as described in Example 166, above] and 19.4 ml of a 1.0 molar solution of tetrabutylammonium fluoride in tetrahydrofuran, to give 666 mg of the title compound as a colorless foam.

Nuclear Magnetic Resonance Spectrum (270 MHz, $CDCl_3$) δ ppm: 0.88 (3H, doublet, J=7.3 Hz); 1.48(6H, singlet); 4.26–4.29 (1H, multiplet); 4.34–4.38 (1H, multiplet); 4.43 (2H, doublet, J=3.4 Hz); 4.53–4.62 (1H, multiplet); 5.46 (1H, broad singlet); 5.54 (1H, broad singlet); 5.89 (1H, doublet of doublets, J=5.9 & 9.8 Hz); 6.02 (1H, doublet, J=9.8 Hz); 6.95–7.03 (2H, multiplet); 7.31–7.37 (2H, multiplet).

EXAMPLE 168

Sodium salt of
(3R,5R)-3.5-dihydroxy-7-{(1S,2S,6S,8S,8aR)-
1,2,6,7,8,8a-hexahydro-6-hydroxy-8-[2-(4-
fluorobenzyloxy)-2-methyl-propionyloxy]-2-methyl-
1-naphthyl}heptanoic acid (Compound No. 1-272)

A procedure similar to that described in Example 3, above, was followed, but using 20.0 mg of (4R,6R)-6-([1S, 2S,6S,8S,8aR]-2-{1,2,6,7,8,8a-hexahydro-6-hydroxy-8-[2-(4-fluorobenzyloxy)-2-methylpropionyloxy]-2-methyl-1-naphthyl}ethyl)tetrahydro-4-hydroxy-2H-pyran-2-one [prepared as described in Example 167, above], to give 21.6 mg of the title compound, as a colorless hygroscopic powder.

EXAMPLE 169

(4R,6R)-6-{(1S,2S,6S,8S,8aR)-2-[1,2,6,7,8,8a-
Hexahydro-6-t-butyldimethylsilyloxy-8-(2-benzyloxy-
2-methylpropionyloxy)-2-methyl-1-
naphthyl]ethyl}tetrahydro-4-t-butyldimethylsilyloxy-
2H-pyran-2-one (Compound No. 1-210)

A procedure similar to that described in Example 10, above, was followed, but using 705 mg of 2-benzyloxy-2-methylpropionic acid and 1.0 g of (4R,6R)-6-{(1S,2S,6S, 8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.04 g of the title compound as white crystals, melting at between 135° and 136° C.

Nuclear Magnetic Resonance Spectrum (270 MHz, $CDCl_3$) δ ppm: 1.50 (6H, doublet, J=2.9 Hz); 4.22–4.27 (1H, multiplet); 4.38–4.44 (1H, multiplet); 4.47 (2H, doublet, J=3.4 Hz); 4.52–4.61 (1H, multiplet); 5.46 (2H, broad singlet); 5.86 (1H, doublet of doublets, J=5.9 & 9.8 Hz); 6.00 (1H, doublet, J=9.8 Hz); 7.23–7.40 (5H, multiplet).

EXAMPLE 170

(4R,6R)-6-{(1S,2S,6S,8S,8aR)-2-[1,2,6,7,8,8a-
Hexahydro-6-hydroxy-8-(2-benzyloxy-2-
methylpropionyloxy)-2-methyl-1-
naphthyl]ethyl}tetrahydro-4-hydroxy-2H-pyran-2-one
(Compound No. 1-210)

A procedure similar to that described in Example 2, above, was followed, but using 419 mg of (4R,6R)-6-{(1S, 2S,6S,8S,8aR)-2-[1,2,6,7,8,8a-hexahydro-6-t-butyldimethylsilyloxy-8-(2-benzyloxy-2-methylpropionyloxy)-2-methyl-1-naphthyl]ethyl}tetrahydro-4-t-butyldimethylsilyloxy-2H-pyran-2-one [prepared as described in Example 169, above] and 8.1 ml of a 1.0 molar solution of tetrabutylammonium fluoride in tetrahydrofuran, to give 263 mg of the title compound as a colorless foam.

Nuclear Magnetic Resonance Spectrum (270 MHz, $CDCl_3$) δ ppm: 0.91 (3H, doublet, J=6.8 Hz); 1.49 (6H, singlet); 4.21–4.29 (1H, multiplet); 4.35–4.42 (1H, multiplet); 4.48 (2H, doublet, J=5.4 Hz); 4.51–4.59 (1H, multiplet); 5.46 (1H, broad singlet); 5.50 (1H, broad singlet); 5.89 (1H, doublet of doublets, J=5.9 & 9.8 Hz); 6.00 (1H, doublet, J=9.8 Hz); 7.22–7.38 (5H, multiplet).

EXAMPLE 171

Sodium salt of
(3R,5R)-3,5-dihydroxy-7-{(1S,2S,6S,8S,8aR)-1,2,6,7,8,8a-hexahydro-6-hydroxy-8-[2-benzyloxy-2-methylpropionyloxy]-2-methyl-1-naphthyl}heptanoic acid (Compound No. 1-210)

A procedure similar to that described in Example 3, above, was followed, but using 20.0 mg of (4R,6R)-6-{(1S,2S,6S,8S,8aR)-2-[1,2,6,7,8,8a-hexahydro-6-hydroxy-8-(2-benzyloxy-2-methylpropionyloxy)-2-methyl-1-naphthyl]ethyl}tetrahydro-4-hydroxy-2H-pyran-2-one [prepared as described in Example 170, above], to give 21.0 mg of the title compound, as a colorless hygroscopic powder.

EXAMPLE 172

(4R,6R)-6-{(1S,2S,6S,8S,8aR)-2-[1,2,6,7,8,8a-Hexahydro-6-t-butyldimethylsilyloxy-8-(2-methyl-2-phenoxypropionyloxy)-2-methyl-1-naphthyl]ethyl}tetrahydro-4-t-butyldimethylsilyloxy-2H-pyran-2-one (Compound No. 1-209)

A procedure similar to that described in Example 10, above, was followed, but using 654 mg of 2-methyl-2-phenoxypropionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.13 g of the title compound as a colorless foam.

Nuclear Magnetic Resonance Spectrum (270 MHz, $CDCl_3$) δ ppm: 4.22–4.29 (2H, multiplet); 4.51–4.58 (1H, multiplet); 5.47 (1H, broad singlet); 5.48 (1H, broad singlet); 5.73–5.85 (1H, multiplet); 5.94 (1H, doublet, J=9.8 Hz); 6.83–6.88 (2H, multiplet); 6.93–6.98 (1H, multiplet); 7.05–7.33 (2H, multiplet).

EXAMPLE 173

(4R,6R)-6-{(1S,2S,6S,8S,8aR)-2-[1,2,6,7,8,8a-Hexahydro-6-hydroxy-8-(2-methyl-2-phenoxypropionyloxy)-2-methyl-1-naphthyl]ethyl}tetrahydro-4-hydroxy-2H-pyran-2-one (Compound No. 1-209)

A procedure similar to that described in Example 2, above, was followed, but using 1.0 g of (4R,6R)-6-{(1S,2S,6S,8S,8aR)-2-[1,2,6,7,8,8a-hexahydro-6-t-butyldimethylsilyloxy-8-(2-methyl-2-phenoxypropionyloxy)-2-methyl-1-naphthyl]ethyl}tetrahydro-4-t-butyldimethylsilyloxy-2H-pyran-2-one [prepared as described in Example 172, above] and 19.6 ml of a 1.0 molar solution of tetrabutylammonium fluoride in tetrahydrofuran, to give 520 mg of the title compound as colorless crystals, melting at between 155° and 158° C.

Nuclear Magnetic Resonance Spectrum (270 MHz, $CDCl_3$) δ ppm: 0.89 (3H, doublet, J=6.6 Hz); 3.85–3.89 (1H, multiplet); 4.31–4.36 (1H, multiplet); 4.55–4.60 (1H, multiplet); 5.45 (1H, broad singlet); 5.49 (1H, broad singlet); 5.83–5.87 (1H, multiplet); 5.94 (1H, doublet, J=9.5 Hz); 6.78–6.88 (2H, multiplet); 6.94–6.99 (1H, multiplet); 7.04–7.29 (2H, multiplet).

EXAMPLE 174

Sodium salt of
(3R,5R)-3,5-dihydroxy-7-{(1S,2S,6S,8S,8aR)-1,2,6,7,8,8a-hexahydro-6-hydroxy-8-[2-methyl-2-phenoxypropionyloxy]-2-methyl-1-naphthyl}heptanoic acid (Compound No. 1-209)

A procedure similar to that described in Example 3, above, was followed, but using 20.0 mg of (4R,6R)-6-{(1S,2S,6S,8S,8aR)-2-[1,2,6,7,8,8a-hexahydro-6-hydroxy-8-(2-methyl-2-phenoxypropionyloxy)-2-methyl-1-naphthyl]ethyl}tetrahydro-4-hydroxy-2H-pyran-2-one [prepared as described in Example 173, above], to give 22.7 mg of the title compound, as a colorless hygroscopic powder.

EXAMPLE 175

(4R,6R)-6-([1S,2S,6S,8S,8aR]-2-{1,2,6,7,8,8a-Hexahydro-6-t-butyldimethylsilyloxy-8-[2-(4-fluorophenoxy)-2-methylpropionyloxy]-2-methyl-1-naphthyl}ethyl)tetrahydro-4-t-butyldimethylsilyloxy-2H-pyran-2-one (Compound No. 1-243)

A procedure similar to that described in Example 1, above, was followed, but using 719 mg of 2-(4-fluorophenoxy)-2-methylpropionic acid and 1.0 g of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 1.26 g of the title compound as a colorless foam.

Nuclear Magnetic Resonance Spectrum (270 MHz, $CDCl_3$) δ ppm: 1.49 (6H, singlet); 4.21–4.30 (2H, multiplet); 4.51–4.61 (1H, multiplet); 5.41–5.45 (2H, multiplet); 5.84 (1H, doublet of doublets, J=5.9 & 9.8 Hz); 5.94 (1H, doublet, J=9.8 Hz); 6.83–6.93 (4H, multiplet).

EXAMPLE 176

(4R,6R)-6-([1S,2S,6S,8S,8aR]-2-{1,2,6,7,8,8a-Hexahydro-6-hydroxy-8-[2-(4-fluorophenoxy)-2-methylpropionyloxy]-2-methyl-1-naphthyl}ethyl)tetrahydro-4-hydroxy-2H-pyran-2-one (Compound No. 1-243)

A procedure similar to that described in Example 2, above, was followed, but using 1.08 g of (4R,6R)-6-([1S,2S,6S,8S,8aR]-2-{1,2,6,7,8,8a-hexahydro-6-t-butyldimethylsilyloxy-8-[2-(4-fluorophenoxy)-2-methylpropionyloxy]-2-methyl-1-naphthyl}ethyl)tetrahydro-4-t-butyldimethylsilyloxy-2H-pyran-2-one [prepared as described in Example 175, above] and 20.8 ml of a 1.0 molar solution of tetrabutylammonium fluoride in tetrahydrofuran, to give 565 mg of the title compound as white crystals, melting at between 142° and 145° C.

Nuclear Magnetic Resonance Spectrum (270 MHz, $CDCl_3$) δ ppm: 0.88 (3H, doublet, J=6.8 Hz); 1.52 (6H, doublet, j=4.4 Hz); 4.10–4.15 (1H, multiplet); 4.33–4.39 (1H, multiplet); 4.52–4.61 (1H, multiplet); 5.46 (1H, broad singlet); 5.51 (1H, broad singlet); 5.89 (1H, doublet of doublets, J=5.9 & 9.3 Hz); 5.98 (1H, doublet, J=9.3 Hz); 6.83–6.9.7 (4H, multiplet).

EXAMPLE 177

Sodium salt of
(3R,5R)-3,5-dihydroxy-7-{(1S,2S,6S,8S,8aR)-
1,2,6,7,8,8a-hexahydro-6-hydroxy-8-[2-(4-
fluorophenoxy)-2-methylpropionyloxy]-2-methyl-1-
naphthyl}heptanoic acid (Compound No. 1-243)

A procedure similar to that described in Example 3, above, was followed, but using 20.0 mg of (4R,6R)-6-([1S, 2S,6S,8S,8aR]-2-{1,2,6,7,8,8a-hexahydro-6-hydroxy-8-[2-(4-fluorophenoxy)-2-methylpropionyloxy]-2-methyl-1-naphthyl}ethyl)tetrahydro-4-hydroxy-2H-pyran-2-one [prepared as described in Example 176, above], to give 22.0 mg of the title compound, as a colorless hygroscopic powder.

EXAMPLE 178

(4R,6R)-6-([1S,2S,6S,8S,8aR]-2-{1,2,6,7,8,8a-
Hexahydro-6-t-butyldimethylsilyloxy-8-[2-(3,5-
dimethylphenoxy)-2-methylpropionyloxy]-2-methyl-1-
naphthyl}ethyl)tetrahydro-4-t-butyldimethylsilyloxy-
2H-pyran-2-one (Compound No. 1-224)

A procedure similar to that described in Example 1, above, was followed, but using 755 mg of 2-(3,5-dimethylphenoxy)-2-methylpropionic acid and 1.0 g of (4R,6R)-6-{(1S,2S,6S,8S,8aR]-2-[1,2,6,7,8,8a-hexahydro-6-t-butyldimethylsilyloxy-8-hydroxy-2-methyl-1-naphthyl] ethyl}tetrahydro-4-t-butyldimethylsilyloxy-2H-pyran-2-one [prepared as described in Example B, above], to give 1.10 g of the title compound as a colorless foam.

Nuclear Magnetic Resonance Spectrum (270 MHz, CDCl$_3$) δ ppm: 1.52 (6H, doublet, J=3.4 Hz); 2.23 (6H, singlet); 4.22–4.29 (2H, multiplet); 4.54–4.59 (1H, multiplet); 5.42 (1H, multiplet); 5.50 (1H, multiplet); 5.83 (1H, doublet of doublets, J=5.9 & 9.8 Hz); 5.96 (1H, doublet, J=9.8 Hz); 6.51 (2H, singlet); 6.62 (1H, singlet).

EXAMPLE 179

(4R,6R)-6-([1S,2S,6S,8S,8aR]-2-{1,2,6,7,8,8a-
Hexahydro-6-hydroxy-8-[2-(3,5-dimethylphenoxy)-2-
methylpropionyloxy]-2-methyl-1-
naphthyl}ethyl)tetrahydro-4-hydroxy-2H
-pyran-2-one (Compound No. 1-224)

A procedure similar to that described in Example 2, above, was followed, but using 978 mg of (4R,6R)-6 -([1S, 2S,6S,8S,8aR]-2-{1,2,6,7,8,8a-hexahydro-6-t-butyldimethylsilyloxy-8-[2-(3,5-dimethylphenoxy)-2-methylpropionyloxy]-2-methyl-1-naphthyl}ethyl)tetrahydro-4-t-butyldimethylsilyloxy-2H-pyran-2-one [prepared as described in Example 178, above] and 18.5 ml of a 1.0 molar solution of tetrabutylammonium fluoride in tetrahydrofuran, to give 464 mg of the title compound as white crystals, melting at between 129° and 131° C.

Nuclear Magnetic Resonance Spectrum (270 MHz, CDCl$_3$) δ ppm: 0.88 (3H, doublet, J=6.8 Hz); 1.52 (3H, singlet); 1.58 (3H, singlet); 2.25 (6H, singlet); 3.84–3.91 (1H, multiplet); 4.31–4.37 (1H, multiplet); 4.51–4.61 (1H, multiplet); 5.45 (1H, broad singlet); 5.49 (1H, broad singlet); 5.86 (1H, doublet of doublets, J=5.9 & 9.8 Hz); 5.96 (1H, doublet, J=9.8 Hz); 6.49 (2H, singlet); 6.66 (1H, singlet).

EXAMPLE 180

Sodium salt of
(3R,5R)-3,5-dihydroxy-7-{(1S,2S,6S,8S,8aR)-
1,2,6,7,8,8a-hexahydro-6-hydroxy-8-[2-(3,5-
dimethylphenoxy)-2-methylpropionyloxy]-2-methyl-1-
naphthyl}heptanoic acid (Compound No. 1-224)

A procedure similar to that described in Example 3, above, was followed, but using 20.0 mg of (4R,6R)-6-([1S, 2S,6S,8S,8aR]-2-{1,2,6,7,8,8a-hexahydro-6-hydroxy-8-[2-(3,5-dimethylphenoxy)-2-methylpropionyloxy]-2-methyl-1-naphthyl}ethyl)tetrahydro-4-hydroxy-2H-pyran-2-one [prepared as described in Example 179, above], to give 21.9 mg of the title compound, as a colorless hygroscopic powder.

EXAMPLE 181

(4R,6R)-6-([1S,2S,6S,8S,8aR]-2-{1,2,6,7,8,8a-
Hexahydro-6-t-butyldimethylsilyloxy-8-[2-(4-t-
butylphenoxy)-2-methylpropionyloxy]-2-methyl-1-
naphthyl}ethyl)tetrahydro-4-t-butyldimethylsilyloxy-
2H-pyran-2-one (Compound No. 1-231)

A procedure similar to that described in Example 1, above, was followed, but using 858 mg of 2-(4-t-butylphenoxy)-2-methylpropionic acid and 1.0 g of (4R,6R)-6-{(1S, 2S,6S,8S,8aR]-2-[1,2,6,7,8,8a-hexahydro-6-t-butyldimethylsilyloxy-8-hydroxy-2-methyl-1-naphthyl] ethyl}tetrahydro-4-t-butyldimethyl silyloxy-2H-pyran-2-one [prepared as described in Example B, above], to give 1.12 g of the title compound as a colorless foam.

Nuclear Magnetic Resonance Spectrum (270 MHz, CDCl$_3$) δ ppm: 1.27 (9H, singlet); 1.51 (6H, doublet, J=5.3 Hz); 4.27–4.29 (1H, multiplet); 4.36–4.39 (1H, multiplet); 4.58–4.64 (1H, multiplet); 5.44 (1H, singlet); 5.51 (1H, singlet); 5.84 (1H, doublet of doublets, J=5.9 & 9.8 Hz); 5.96 (1H, doublet, J=9.8 Hz); 6.78 (2H, doublet, J=8.7 Hz); 7.22 (2H, doublet, J=8.7 Hz).

EXAMPLE 182

(4R,6R)-6-([1S,2S,6S,8S,8aR]-2-{1,2,6,7,8,8a-
Hexahydro-6-hydroxy-8-[2-(4-t-butylphenoxy)-2-
methylpropionyloxy]-2-methyl-1-
naphthyl}ethyl)tetrahdyro-4-hydroxy-2H-pyran-2-one
(Compound No. 1-231)

A procedure similar to that described in Example 2, above, was followed, but using 1.01 g of (4R,6R)-6-([1S, 2S,6S,8S,8aR]-2-{1,2,6,7,8,8a-hexahydro-6-t-butyldimethylsilyloxy-8-[2-(4-t-butylphenoxy)-2-methylpropionyloxy]-2-methyl-1-naphthyl}ethyl)tetrahydro-4-t-butyldimethylsilyloxy-2H-pyran-2-one [prepared as described in Example 181, above] and 18.6 ml of a 1.0 molar solution of tetrabutylammonium fluoride in tetrahydrofuran, to give 547 mg of the title compound as white crystals, melting at between 160° and 163° C.

Nuclear Magnetic Resonance Spectrum (270 MHz, CDCl$_3$) δ ppm: 0.89 (3H, doublet, J=6.9 Hz); 1.28 (9H, singlet); 1.53 (3H, singlet); 1.58 (3H, singlet); 3.89 (1H, broad singlet); 4.34–4.36 (1H, multiplet); 4.59–4.64 (1H, multiplet); 5.45 (1H, singlet); 5.52 (1H, singlet); 5.86 (1H, doublet of doublets, J=5.9 & 9.7 Hz); 5.96 (1H, doublet, J=9.7 Hz); 6.78 (2H, doublet, J=8.8 Hz); 7.23 (2H, doublet, J=8.8 Hz).

EXAMPLE 183

Sodium salt Of
(3R,5R)-3,5-dihydroxy-7-{(1S,2S,6S,8S,8aR)-1,2,6,7,8,8a-hexahydro-6-hydroxy-8-[2-(4-t-butylphenoxy)-2-methylpropionyloxy]-2-methyl-1-naphthyl}heptanoic acid (Compound No. 1-231)

A procedure similar to that described in Example 3, above, was followed, but using 20.0 mg of (4R,6R)-6-([1S,2S,6S,8S,8aR]-2-{1,2,6,7,8,8a-hexahydro-6-hydroxy-8-[2-(4-t-butylphenoxy)-2-methylpropionyloxy]-2-methyl-1-naphthyl}ethyl)tetrahydro-4-hydroxy-2H-pyran-2-one [prepared a s described in Example 182, above], to give 23.0 mg of the title compound, as a colorless hygroscopic powder.

EXAMPLE 184

(4R,6R)-6-([1S,2S,6S,8S,8aR]-2-{1,2,6,7,8,8a-Hexahydro-6-t-butyldimethylsilyloxy-8-[2-(4-nitrophenoxy)-2-methylpropionyloxy]-2-methyl-1-naphthyl}ethyl)tetrahydro-4-t-butyldimethylsilyloxy-2H-pyran-2-one (Compound No. 1-373)

A procedure similar to that described in Example 1, above, was followed, but using 597 mg of 2-(4-nitrophenoxy)-2-methylpropionic acid and 731 mg of (4R,6R)-6-{(1S,2S,6S,8S,8aR)-2-[1,2,6,7,8,8a-hexahydro-6-t-butyldimethylsilyloxy-8-hydroxy-2-methyl-1-naphthyl]ethyl}tetrahydro-4-t-butyldimethylsilyloxy-2H-pyran-2-one [prepared as described in Example B, above], to give 880 mg of the title compound as a colorless foam.

Nuclear Magnetic Resonance Spectrum (270 MHz, $CDCl_3$) $\delta$ ppm: 1.65 (6H, singlet); 4.16–4.20 (1H, multiplet); 4.30–4.32 (1H, multiplet); 4.62–4.68 (1H, multiplet); 5.38 (1H, singlet); 5.51 (1H, singlet); 5.83 (1H, doublet of doublets, J=5.9 & 9.6 Hz); 5.94 (1H, doublet, J=9.6 Hz); 6.90 (2H, doublet, J=9 Hz); 8.14 (2H, doublet, J=9 Hz).

EXAMPLE 185

(4R,6R)-6-([1S,2S,6S,8S,8aR]-2-{1,2,6,7,8,8a-Hexahydro-6-hydroxy-8-[2-(4-nitrophenoxy)-2-methylpropionyloxy]-2-methyl-1-naphthyl}ethyl)tetrahydro-4-hydroxy-2 H -pyran-2-one (Compound No. 1-373)

A procedure similar to that described in Example 2, above, was followed, but using 801 mg of (4R,6R)-6-([1S,2S,6S,8S,8aR]-2-{1,2,6,7,8,8a-hexahydro-6-t-butyldimethylsilyloxy-8-[2-(4-nitrophenoxy)-2-methylpropionyloxy]-2-methyl-1-naphthyl}ethyl)tetrahydro-4-t-butyldimethylsilyloxy-2H-pyran-2-one [prepared as described in Example 184, above] and 14.8 ml of a 1.0 molar solution of tetrabutylammonium fluoride in tetrahydrofuran, to give 548 mg of the title compound as a colorless foam.

Nuclear Magnetic Resonance Spectrum (270 MHz, $CDCl_3$) $\delta$ ppm: 0.87 (3H, doublet, J=7.0 Hz); 1.65 (6H, singlet); 4.04–4.09 (1H, multiplet); 4.38–4.40 (1H, multiplet); 4.57–4.62 (1H, multiplet); 5.48 (2H, singlet); 5.87 (1H, doublet of doublets, J=5.9 & 9.7 Hz); 5.96 (1H, doublet, J=9.7 Hz); 6.90 (2H, doublet, J=9.4 Hz); 8.15 (2H, doublet, J=9.0 Hz).

EXAMPLE 186

Sodium salt of
(3R,5R)-3,5-dihydroxy-7-{(1S,2S,6S,8S,8aR)-1,2,6,7,8,8a-hexahydro-6-hydroxy-8-[2-(4-nitrophenoxy)-2-ethylpropionyloxy]-2-methyl-1-naphthyl}heptanoic acid (Compound No. 1-373)

A procedure similar to that described in Example 3, above, was followed, but using 20.0 mg of (4R,6R)-6-([1S,2S,6S,8S,8aR]-2-{1,2,6,7,8,8a-hexahydro-6-hydroxy-8-[2-(4-nitrophenoxy)-2-methylpropionyloxy]-2-methyl-1-naphthyl}ethyl)tetrahydro-4-hydroxy-2H-pyran-2-one [prepared as described in Example 185, above], to give 22.4 mg of the title compound, as a colorless hygroscopic powder.

EXAMPLE 187

(4R,6R)-6-([1S,2S,8S,8aR]-2-{1,2,6,7,8,8a-Hexahydro-8-[(2R)-2-(4-methylphenoxy)butyryloxy]-2-methyl-1-naphthyl}ethyl)tetrahydro-4-hydroxy-2H-pyran-2-one (Compound No. 1-71)

187-(1): (4R,6R)-6-([1S,2S,8S,8aR]-2-{1,2,6,7,8,8a-Hexahydro-8-[(2R)-(4-methylphenoxy)butyryloxy]-2-methyl-1-naphthyl}ethyl)tetrahydro-4-t-butyldimethylsilyloxy-2H-pyran-2-one 1.97 g (4.68 mmol) of (4R,6R)-6-{2-[(1S,2S,8S,8aR)-1,2,6,7,8,8a-hexahydro-8-hydroxy-2-methyl-1-naphthyl]ethyl}tetrahydro-4-t-butyldimethylsilyloxy-2H-pyran-2-one [prepared as described in Japanese Unexamined Patent Publication (Kokai) No. Sho 59-175450], 2.15 ml (15.4 mmol) of triethylamine and a catalytic amount of 4-(1-pyrrolidinyl)pyridine were dissolved in 50 ml of anhydrous benzene. A solution of 1.0 g (5.15 mmol) of (2R)-2-(4-methylphenoxy)butyric acid and 1.76 ml (20.6 mmol) of oxalyl chloride in 10 ml of anhydrous methylene chloride was then added dropwise to the mixture, whilst stirring and ice-cooling. The resulting mixture was stirred at room temperature for 1 hour, after which 100 ml of ethyl acetate were added to the reaction mixture. The mixture was then washed with an aqueous solution of citric acid, with a solution of aqueous sodium hydrogencarbonate and with a solution of aqueous sodium chloride, in that order, and then dried over anhydrous magnesium sulfate. The solvent was then removed by evaporation under reduced pressure. The resulting residue was separated and purified by silica gel column chromatography, using a 5:1 by volume mixture of hexane and ethyl acetate as the eluent, to give 2.57 g of the title compound as a colorless oil.

Nuclear Magnetic Resonance Spectrum (270 MHz, $CDCl_3$) $\delta$ ppm: 1.06 (3H, triplet, J=7.3 Hz); 2.25 (3H, singlet); 4.16–4.18 (1H, multiplet); 4.42–4.62 (2H, multiplet); 5.40–4.58 (2H, multiplet); 5.75 (1H, doublet of doublets, J=6 & 10 Hz); 5.97 (1H, doublet, J=10 Hz); 6.76 (2H, doublet, J=8.6 Hz); 7.02 (2H, doublet, J=8.6 Hz).

187-(2): (4R,6R)-6-([1S,2S,8S,8aR]-2-{1,2,6,7,8,8a-Hexahydro-8-[(2R)-2-(4-methylphenoxy)butyryloxy]-2-methyl-1-naphthyl}ethyl)tetrahydro-4-hydroxy-2H-pyran-2-one 2.57 g of (4R,6R)-6-([1S,2S,8S,8aR]-2-{1,2,6,7,8,8a-hexahydro-8-[(2R)-(4-methylphenoxy)butyryloxy]-2-methyl-1-naphthyl}ethyl)tetrahydro-4-t-butyldimethylsilyloxy-2H-pyran-2-one [prepared as described in Step (1), above] were dissolved in 30 ml of a 5:95 by volume mixture of 48% v/v aqueous hydrogen fluoride and acetonitrile, and the solution was stirred at room temperature for 2 hours. At the end of this time, the reaction mixture was neutralized by the addition of aqueous sodium bicarbonate, and the acetonitrile was removed by distillation under reduced pressure. The resulting residue was then extracted by the addition of 100 ml of ethyl acetate to the residue, after which the extract was separated and washed with a saturated aqueous sodium hydrogencarbonate solution and with an aqueous sodium chloride solution. The mixture was then dried over anhydrous magnesium sulfate and the solvent was removed by evaporation under reduced pressure. The oil thus obtained was purified by silica gel column chromatography, using a 1:1 by volume mixture of hexane and ethyl acetate as the eluent, to give 1.22 g of the title compound as a colorless foam.

Nuclear Magnetic Resonance Spectrum (270 MHz, $CDCl_3$) δ ppm: 1.07 (3H, triplet, J=7.3 Hz); 2.25 (3H, singlet); 4.17 (1H, broad singlet); 4.40–4.60 (1H, multiplet); 4.57 (1H, triplet, J=6.0 Hz); 5.52 (2H, broad singlet); 5.77 (1H, doublet of doublets, J=6.6 & 9.9 Hz); 6.00 (1H, doublet, J=9.2 Hz); 6.77 (2H, doublet, J=8.6 Hz); 7.03 (2H, doublet, J=8.6 Hz).

EXAMPLE 188

Sodium salt of (3R,5R)-3,5-dihydroxy-7-{(1S,2S,8S,8aR)-1,2,6,7,8,8a-hexahydro-8-[(2R)-2-(4-methylphenoxy)butyryloxy]-2-methyl-1-naphthyl}heptanoic acid (Compound No. 2-71)

A procedure similar to that described in Example 3, above, was followed, but using 500 mg of (4R,6R)-6-([1S,2S,8S,8aR]-2-{1,2,6,7,8,8a-hexahydro-8-[(2R)-2-(4-methylphenoxy)butyryloxy]-2-methyl-1-naphthyl}ethyl)tetrahydro-4-hydroxy-2H-pyran-2-one [prepared as described in Example 187, above] and 10.36 ml of a 0.1N aqueous solution of sodium hydroxide, to give 537 mg of the title compound, as a colorless hygroscopic powder.

EXAMPLE 189

Sodium salt of (3R,5R)-3,5-dihydroxy-7-{(1S,2S,6S,8S,8aR)-1,2,6,7,8,8a-hexahydro-6-hydroxy-8-[(2R)-2-(4-methylphenoxy)butyryloxy]-2-methyl-1-naphthyl}heptanoic acid (Compound No. 1-71)

*Streptomyces carbophilus* strain SANK 62585 was used to inoculate a 100 ml Erlenmeyer flask containing 20 ml of SC medium, having the composition shown below, and the flask was cultured on a rotary shaker at 28° C. and at a speed of 200 revolutions per minute. At the end of three days cultivation, 0.5 ml of the culture was used to inoculate a 100 ml Erlenmeyer flask containing 10 ml of fresh SC medium. This flask was then cultured at 28° C. on a rotary shaker at a speed of 200 revolutions per minute. After 18 hours of cultivation under these conditions, 100 μl of an aqueous solution (1 mg/ml) of the sodium salt of (3R,5R)-3,5-dihydroxy-7-{(1S,2S,8S,8aR)-1,2,6,7,8,8 a-hexahydro-8-[(2R)-2-(4-methylphenoxy)butyryloxy]-2-methyl-1-naphthyl}heptanoic [prepared as described in Example 188, above] and 50 μl of a 25% w/v aqueous solution of glucose were added to the culture and the mixture was further cultivated using a rotary shaker at 28° C. and 200 revolutions per minute for 24 hours. At the end of this time the culture liquid was centrifuged at 10,000 revolutions per minute for 10 minutes, after which the supernatant was poured into a Novapack Cartridge C18™ column (18 mm diameter×100 mm, Millipore). The liquid was analyzed using a mixture of acetonitrile and 0.1% w/v phosphate buffer containing 0.1% w/v triethylamine (pH 3.2) as a mobile layer, at a flow rate of 1.5 ml/min. Detection was carried out by monitoring the ultraviolet absorption at 237 nm. The title compound was eluted at 7.70 min. High performance liquid chromatography (HPLC) of the culture liquid indicated that the *Streptomyces carbophilus* strain SANK 62585 was responsible for the production of 23.5 μg of the title compound in the culture liquid.

| SC medium | |
|---|---|
| Yeast extract (Difco) | 0.1% (w/v) |
| Polypeptone | 1.0% (w/v) |
| (Nihon Pharmaceutical Co., Ltd.) | |
| Glucose | 2.0% (w/v) |
| Tap water | to 100% |
| pH before sterilization: | pH 7.0. |

PREPARATION 1

Preparation of ML-236B

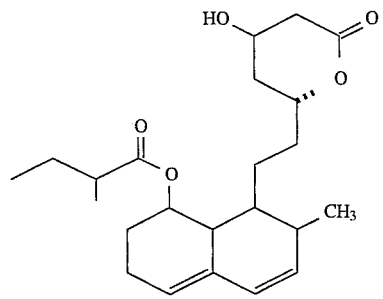

(1) Culture
Seed culture medium:

| | |
|---|---|
| Glycerin | 30 g |
| Glucose | 20 g |
| Soybean meal | 20 g |
| Mikuni-peptone | 8 g |
| (Mikuni Chemical Industries Co., Ltd.) | |
| Sodium nitrate | 2 g |
| Magnesium sulfate | 1 g |
| Tap water | to 1000 ml |
| (pH: 6.0–6.5). | |

50 ml of the seed culture medium having the composition described above was charged into a 500 ml Erlenmeyer flask and autoclaved at 120° C. for 30 minutes. One platinum loop from a slant of *Penicillium citrinum* Thom SANK 13380 (FERM BP-4129) was aseptically transferred into the flask containing this medium. The inoculated flask was incubated at 24° C. for 3 days on a rotary shaker at a speed of 210 revolutions per minute.

A 2000 ml Erlenmeyer flask containing 700 ml of the seed culture medium was then autoclaved at 120° C. for 30 minutes, after which it was inoculated with the whole (about 50 ml) of the fermentation broth obtained as described above. This flask was incubated for 2 days at 24° C. on a rotary shaker at a speed of 210 revolutions per minute, to prepare a second generation culture.

The following media were used in the subsequent production of the title compound.

| Production culture medium: | |
|---|---|
| Glycerol | 150 g |
| (sterilized separately before addition) | |
| Liquid Sanmalt (Sanwa Denpun) | 600 g |
| (sterilized separately before addition) | |
| Soybean flour | 300 g |
| Mikuni peptone | 150 g |
| (Mikuni Chemical Industries Co., Ltd.) | |
| Honen CSL | 300 g |
| (Honen Corp.) | |
| Gluten meal | 150 g |
| (Nihon Food Processing Co.) | |
| Magnesium sulfate | 15 g |

Made up to 15 liters by the addition of tap water (pH 6.0 to 6.5).

Feed liquor A

Tap water was added to a mixture of 1600 g of glycerin and 6400 g of Sanmalt S (Sanwa Cornstarch Industry, Ltd.), and then the mixture was heated to above 90° C. After the Sanmalt S had completely dissolved, tap water was added to the solution to make a total volume of 10 liters. The solution was then autoclaved 120° C. for 30 minutes.

Feed liquor B 600 ml of Sannicks PP 2000 (Sanyo Chemical Industries Ltd.) medium were autoclaved at 120° C. for 30 minutes.

15 liters of the production culture medium having the composition shown above were charged into a stainless-steel 30 liter fermentation tank, and the tank was then autoclaved at 120° C. for 30 minutes.

The whole contents of an Erlenmeyer flask (about 700 ml) containing the second generation culture prepared as described above was then used to inoculate the autoclaved production culture medium in the jar fermentor. The fermentor was incubated at 24° C. with stirring at an automatically controlled range of 260 to 500 revolutions per minute, whilst aerating at an air flow of 7.5 liters per minute and at a pressure of 0.5 kg/cm$^2$ such as to maintain a dissolved oxygen concentration of from 3 to 5 ppm.

During the period from the third to the sixth day after commencement of the incubation, 150 ml of Feed liquor B were added to the culture medium once per day (a total of 4 times). After the concentration of reducing sugar was estimated to be no more than 1%, Feed liquor A was continuously added in order to ensure that the pH of the broth was kept at a value of about pH 4.

After 14 days, the resulting broth was harvested.

(2) Isolation

The pH of the culture broth (40 liters) was adjusted to a value of 12 by the addition of 800 ml of a 6N aqueous solution of sodium hydroxide, and the resulting mixture was stirred for 60 minutes at room temperature. At the end of this time, the broth was mixed with 1.5 kg of a Celite filter aid (Celite #545, a trade mark for a product of Johns-Manville Products Corp.), and the mixture was stirred. The resulting mixture was filtered through a filter press to produce a filtrate.

850 ml of 6N aqueous hydrochloric acid were carefully added to the filtrate, and the pH of the mixture was adjusted to a value of 5.0. 80 liters of ethyl acetate were added to the resulting solution, and the mixture was stirred to extract the desired product. The organic layer was separated and the aqueous layer was treated with 40 liters of ethyl acetate and stirred to extract the desired product. The combined ethyl acetate extracts were then extracted with 10 liters of a 3% w/v aqueous solution of sodium hydrogencarbonate. The aqueous layer was separated and the organic layer was again extracted with a 3% w/v aqueous solution of sodium hydrogencarbonate.

1600 ml of 6N aqueous hydrochloric acid were carefully added to the combined aqueous extracts, and the pH of the mixture was adjusted to a value of 5.0. 20 liters of ethyl acetate were added to the resulting mixture, and the mixture was stirred to extract the desired product. The organic layer was separated and the aqueous layer was treated with 10 liters of ethyl acetate and stirred to extract the desired product. The combined ethyl acetate extracts were washed with 15 liters of a 10% w/v aqueous solution of sodium chloride. The extract was then dried over 3000 g of anhydrous sodium sulfate, and the solvent was removed by evaporation to dryness under reduced pressure, using a rotary evaporator to afford an oily residue.

This oily residue was dissolved in 1000 ml of ethyl acetate. 0.5 ml of trifluoroacetic acid was added to the solution, and the mixture was heated under reflux for 30 minutes in a vessel fitted with a reflux condenser. The contents were cooled to 10° C., and then washed twice, each time with 500 ml of a 3% w/v aqueous solution of sodium hydrogencarbonate, and then twice more, each time with 500 ml of a 10% w/v aqueous solution of sodium chloride, in that order. The organic layer was dried over 100 g of anhydrous sodium sulfate and filtered. The filtrate was freed from the solvent by evaporation to dryness under reduced pressure, using a rotary evaporator, to afford 50 g of an oily residue.

The whole of this oily residue was dissolved in 500 ml of acetonitrile, and the resulting solution was divided into five parts. Each part was purified by chromatography through an ODS reverse phase column [ODS-1050-20SR, 10 cm (internal diameter)×50 cm, 15–30 µm (particle size); Kurita Water Industries Ltd.]. The column was eluted with 70% v/v aqueous acetonitrile, used as the mobile phase, at a flow rate of 200 ml/minute. The fractions recovered from the column were monitored by ultraviolet absorption and, on the basis of the peaks thus detected, those fractions having retention times between 30 and 36 minutes were collected.

The purity of these fractions was assessed by high performance liquid chromatography through a column (ODS-262, Senshu Scientific Co., Ltd.) using 70% v/v aqueous methanol as the mobile phase at flow rate of 1.0 ml/minute, whilst monitoring the fractions by ultraviolet absorption at 236 nm. A fraction having a retention time of 11 minutes showed a single peak of characteristic ultraviolet absorption.

Those fractions having a retention time between 30 and 36 minutes from the reverse phase column chromatography were concentrated by distillation under reduced pressure, using a rotary evaporator to distill off the acetonitrile. The concentrate was twice extracted with one half its volume of ethyl acetate. The ethyl acetate extracts were combined and concentrated by evaporation to dryness under reduced pressure, to afford 30 g of oily residue.

The oil was triturated with a mixture of ethanol and water to induce crystallization. 17 g of the title compound were obtained as colorless needle-like crystals.

The physico-chemical properties of this compound are known and are identical with those described in Japanese Patent Publication No. Sho 56-12114 (=GB Patent No. 1453425) and other literature.

PREPARATION 2

Preparation of the sodium salt of Pravastatin

A 500 ml Erlenmeyer flask containing 100 ml of yeast MY culture medium having the composition shown below, was inoculated with a platinum loop from a slant of *Amycolata autotrophica* SANK 62981 (FERM BP-4105). The flask was incubated at 28° C. on a rotary shaker at a speed of 200 revolutions per minute to form a seed culture.

After 3 days, twenty 500 ml Erlenmeyer flasks each containing 100 ml of the yeast MY culture medium, having the composition shown below, were each inoculated with 0.5% of the flask contents of the seed culture. The cultures were then incubated at 28° C. on a rotary shaker at a speed of 200 revolutions per minute. After 2 days, an aqueous solution of the sodium salt of ML-236B was added to a final concentration of 0.1% of the sodium salt, and the mixture was incubated at 28° C. on a rotary shaker at a speed of 200 revolutions per minute for 5 days.

| Yeast MY Medium: | |
|---|---|
| Yeast extract (Difco) | 0.3% (w/v) |
| Malt extract (Difco) | 0.3% (w/v) |
| Polypeptone | 0.5% (w/v) |
| (Daigo Nutrition Chemical Co.) | |
| Glucose | 1.0% (w/v) |
| Tap water | to 100% |

The pH was not adjusted.

At the end of this time, the fermentation broth was filtered, and the filtrate was absorbed on 200 ml of a non-ionic resin, Diaion HP-20 (trade mark). The resin was washed with 300 ml of distilled water and the fractions containing the title compound were eluted with 800 ml of 50% v/v aqueous acetone.

The eluate was concentrated by evaporation to dryness under reduced pressure, and the concentrate was purified by chromatography through a preparative ODS column (ODS-H-5251) using a 480:520:1 by volume mixture of acetonitrile, water and acetic acid as the eluent, whilst monitoring the fractions by ultraviolet absorption at 237 nm. The desired fractions were collected, and their pH was adjusted to a value of 8.0 by the addition of an aqueous solution of sodium hydroxide. The mixture was then concentrated by evaporation under reduced pressure. The concentrate was dissolved in 50 ml of water, and the resulting aqueous solution was treated with 50 ml of Diaion HP-20. The resin was washed with 100 ml of distilled water and then eluted with 200 ml of 50% v/v aqueous acetone, to afford 618 mg of the title compound.

The physico-chemical properties are known and are identical with those described in Japanese Patent Publication No. Sho 61-13699 (=GB Patent No. 2077264) and other literature.

FORMULATION 1

Hard Capsules

The following ingredients were filled into standard 2-piece hard gelatin capsules to prepare a unit capsule, which was then washed and dried.

| | |
|---|---|
| Compound of Example 3 | 5 mg |
| Hydroxypropyl cellulose (low substitution) | 10 mg |
| Hydroxypropyl cellulose | 3 mg |
| Magnesium stearate | 1 mg |
| Lactose | 81 mg |
| Total | 100 mg |

FORMULATION 2

Powder Formulation

A powdered formulation containing the ingredients listed below was prepared using conventional techniques.

| | |
|---|---|
| Compound of Example 6 | 5 mg |
| Hydroxypropyl cellulose (low substitution) | 20 mg |
| Hydroxypropyl cellulose | 40 mg |
| Magnesium stearate | 5 mg |
| Lactose | 930 mg |
| Total | 1000 mg |

FORMULATION 3

Tablet Formulation

Tablets containing the ingredients listed below were prepared using conventional techniques.

| | |
|---|---|
| Compound of Example 3 | 5 mg |
| Hydroxypropyl cellulose (low substitution) | 10 mg |
| Hydroxypropyl cellulose | 3 mg |
| Magnesium stearate | 1 mg |
| Lactose | 81 mg |
| Total | 100 mg |

The tablets may, if desired, be coated. Coating procedures and the components of the coatings are well known in the art.

We claim:

1. A compound of formula (I):

$$R^5-O-W-C(=O)-O-[\text{bicyclic structure with } R^1, R^2, CH_3]$$ (I)

wherein $R^1$ represents a group of formula (II):

$$R^{3b}O-CH_2-CH(OR^{3a})-CH_2-COOR^4$$ (II)

$R^2$ represents a hydrogen atom or a group of formula $-OR^3$;

$R^3$, $R^{3a}$ and $R^{3b}$ are independently selected from the group consisting of hydrogen atoms, hydroxy-protecting groups, alkyl groups having from 1 to 6 carbon atoms, alkanesulfonyl groups having from 1 to 6 carbon atoms, halogenated alkanesulfonyl groups having from 1 to 6 carbon atoms and arylsulfonyl groups, in which the aryl part is an aromatic hydrocarbon ring which has from 6 to 14 ring carbon atoms and is unsubstituted or is substituted by at least one substituent selected from the group consisting of substituents α, defined below;

$R^4$ represents a hydrogen atom or a carboxy-protecting group;

$R^5$ represents an aryl group having from 6 to 14 ring carbon atoms; an aryl group having from 6 to 14 ring carbon atoms and substituted by at least one substituent selected from the group consisting of substituents α, defined below; an aralkyl group in which the or each aryl portion has from 6 to 14 ring carbon atoms, and the alkyl portion has from 1 to 6 carbon atoms; or an aralkyl group, in which the or each aryl portion has from 6 to 14 ring carbon atoms, and the alkyl portion has from 1 to 6 carbon atoms, substituted on the ring by at least one substituent selected from the group consisting of substituents α, defined below; and W represents an alkylene group having from 1 to 6 carbon atoms, or an alkylene group having from 1 to 6 carbon atoms and substituted by at least one substituent selected from the group consisting of substituents β, defined below;

said substituents α are selected from the group consisting of alkyl groups having from 1 to 6 carbon atoms;

said substituents β are selected from the group consisting of alkyl groups having from 1 to 6 carbon atoms;

wherein said hydroxy protecting group is selected from the group consisting of: methoxymethyl, ethoxymethyl, propoxymethyl, isopropoxymethyl, butoxymethyl, t-butoxymethyl, 2-methoxyethoxymethyl, 2,2,2-trichloroethoxymethyl, bis(2-chloroethoxy)methyl, 1-ethoxyethyl, 1-methyl-1-methoxyethyl, 1-isopropoxyethyl, 2,2,2-trichloroethyl, 2-(phenylselenyl)ethyl, acetoxymethyl, dimethylaminoacetoxy methyl, propionyloxymethyl, butyryloxymethyl, isobutyryloxymethyl, pivaloyloxymethyl, 1-pivaloyloxyethyl, 1-acetoxyethyl, 1-isobutyryloxyethyl, 1-pivaloyloxypropyl, 2-methyl-1-pivaloyloxypropyl, 2-pivaloyloxypropyl, 1-isobutyryloxyethyl, 1-isobutyryloxypropyl, 1-acetoxypropyl, 1-acetoxy-2-methylpropyl, 1-propionyloxyethyl, 1-propionyloxypropyl, 2-acetoxypropyl, 1-butyryloxyethyl, 1-(alkoxycarbonyloxy)ethyl, methoxycarbonyloxymethyl, ethoxycarbonyloxymethyl, propoxycarbonyloxymethyl, isopropoxycarbonyloxymethyl, butoxycarbonyloxymethyl, isobutoxycarbonyloxy methyl, 1-methoxycarbonyloxyethyl, 1-ethoxy carbonyloxyethyl, 1-propoxycarbonyloxyethyl, 1-isopropoxycarbonyloxyethyl, 1-butoxycarbonyloxyethyl, 1-isobutoxycarbonyloxyethyl, 1-sec-butoxycarbonyloxyethyl, 1-t-butoxycarbonyloxyethyl, 1-(1-ethylpropoxycarbonyloxy)ethyl, 1-(1,1-dipropylbutoxycarbonyloxy)ethyl, 2-methyl-1-(isopropoxycarbonyloxy)propyl, 2-(isopropoxycarbonyloxy)propyl, isopropoxycarbonyloxymethyl, t-butoxycarbonyloxymethyl, methoxycarbonyloxymethyl, ethoxycarbonyloxymethyl, cyclohexyloxycarbonyloxymethyl, 1-methylcyclohexylcarbonyloxymethyl, 1-methylcyclohexyloxycarbonyloxymethyl, cyclopentyloxycarbonyloxymethyl, cyclopentylcarbonyloxymethyl, 1-cyclohexyloxycarbonyloxyethyl, 1-cyclohexylcarbonyloxyethyl, 1-cyclopentyloxycarbonyloxyethyl, 1-cyclopentylcarbonyloxyethyl, 1-cycloheptyloxycarbonyloxyethyl, 1-cycloheptylcarbonyloxyethyl, 1-methylcyclopentylcarbonyloxymethyl, 1-methylcyclopentyloxycarbonyloxymethyl, 2-methyl-1-(1-methylcyclohexylcarbonyloxy)propyl, 1-(1-methylcyclohexylcarbonyony)propyl, 2-(1-methylcyclohexylcarbonyloxy)propyl, 1-(cyclohexylcarbonyloxy)propyl, 2-(cyclohexylcarbonyloxy)propyl, 2-methyl-1-(1-methylcyclopentylcarbonyloxy)propyl, 1-(1-methylcyclopentylcarbonyloxy)propyl, 2-(1-methylcyclopentylcarbonyloxy)propyl, 1-(cyclopentylcarbonyloxy)propyl, 2-(cyclopentylcarbonyloxy)propyl, 1-(1-methylcyclopentylcarbonyloxy)ethyl, 1-(1-methylcyclopentylcarbonyloxy)propyl, adamantyloxycarbonyloxymethyl, adamantylcarbonyloxymethyl, 1-adamantyloxycarbonyloxyethyl, 1-adamantylcarbonyloxyethyl, cyclohexyloxycarbonyloxy-(cyclohexyl)methyl, (cyclohexyl-acetoxy)methyl, 1-(cyclohexylacetoxy)ethyl, 1-(cyclohexylacetoxy)propyl, 2-methyl-1-(cyclohexylacetoxy)propyl, (cyclopentylacetoxy)methyl, 1-(cyclopentylacetoxy)ethyl, 1-(cyclopentylacetoxy)propyl, 2-methyl-1-(cyclopentylacetoxy)propyl, cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl, 1-(cyclohexylmethoxycarbonyloxy)ethyl, 1-(menthyloxycarbonyloxy)ethyl, 1-(menthylcarbonyloxy)ethyl, menthyloxycarbonyloxymethyl, menthylcarbonyloxymethyl, 1-(3-pinanyloxycarbonyloxy)ethyl, 1-(3-pinanylcarbonyloxy)ethyl, 3-pinanyloxycarbonyloxymethyl, 3-pinanylcarbonyloxymethyl, (5-methyl-2-oxo-1,3-dioxolen-4-yl)methyl, (5-phenyl-2-oxo-1,3-dioxolen-4-yl)methyl, (5-isopropyl-2-oxo-1,3-dioxolen-4-yl)methyl, (5-t-butyl-2-oxo-1,3-dioxolen-4-yl)methyl, 1-(5-methyl-2-oxo-1,3-dioxolen-4-yl)ethyl, phthalidyl, dimethylphthalidyl, dimethoxyphthalidyl, carboxymethyl and phenylalanine;

said carboxy-protecting groups are groups which can be cleaved by chemical means or in vivo by biological means and wherein said carboxy-protecting groups which can be cleaved by chemical means are selected from the group consisting of alkyl groups having from 1 to 20 carbon atoms;

halogenated alkyl groups having from 1 to 6 carbon atoms, and wherein the halogen atom is chlorine, fluorine, bromine or iodine;

cycloalkyl groups having from 3 to 7 carbon atoms, aralkyl groups, in which the alkyl part has from 1 to 3 carbon atoms and the or each aryl part is a carbocyclic aromatic group having from 6 to 14 carbon atoms, which may be substituted or unsubstituted and, if substituted, has at least one of substituents α, defined above;

aryl groups having 6 to 14 carbon atoms and being optionally substituted by one or more substituents α, defined above, phenacyl groups optionally substituted by one or more substituents α, defined above;

terpenyl groups, selected from the group consisting of geranyl, neryl, linalyl, phytyl, menthyl, thujyl, caryl, pinanyl, bornyl, norcaryl, norpinanyl, norbornyl, menthenyl, camphenyl and norbornenyl groups; and said carboxy-protecting group which can be cleaved in vivo by biological means is selected from the group consisting of alkoxyalkyl groups, in which the alkoxy and alkyl parts each have from 1 to 5 carbon atoms;

halogenated ethyl groups; and arylselenyl-substituted ethyl groups, in which the aryl part is as defined above, aliphatic acyloxyalkyl groups, in which the acyl group is an alkanoyl group having from 2 to 6 carbon atoms, and the alkyl part has from 1 to 6 carbon atoms;

alkoxycarbonyloxyalkyl groups wherein the alkoxy part has from 1 to 10 carbon atoms, and the alkyl part has from 1 to 6 carbon atoms;

cycloalkylcarbonyloxyalkyl and cycloalkyloxycarboxyloxyalkyl groups, in which the cycloalkyl group has from 3 to 10, carbon atoms, is mono- or poly-cyclic and is optionally substituted by alkyl having from 1 to 4 carbon atoms and the alkyl part has from 1 to 6 carbon atoms;

cycloalkyl-substituted aliphatic acyloxyalkyl groups, in which the acyl group is an alkanoyl group having from 2 to 6 carbon atoms, the cycloalkyl substituent has from 3 to 7 carbon atoms, and the alkyl part has from 1 to 6 carbon atoms;

cycloalkylalkoxycarbonyloxyalkyl groups selected from the group consisting of cyclopropylmethoxycarbonyloxymethyl, cyclobutylmethoxycarbonyloxymethyl, cyclopentylmethoxycarbonyloxymethyl, cyclohexylmethoxycarbonyloxymethyl, 1-(cyclopropylmethoxycarbonyloxy)ethyl, 1-(cyclobutylmethoxycarbonyloxy)ethyl, 1-(cyclopentylmethoxycarbonyloxy)ethyl and 1-(cyclohexylmethoxycarbonyloxy)ethyl groups;

terpenylcarbonyloxy(2-oxo-1,3-dioxolen-4-yl)alkyl groups in which each alkyl group, which may be the same or different has from 1 to 6 carbon atoms, and the phthalidyl group, which may be unsubstituted or may be substituted by at least one substituent selected from the group consisting of substituents α defined above; or a pharmaceutically acceptable salt or ester thereof.

2. The compound of claim 1, having the formula (Ia):

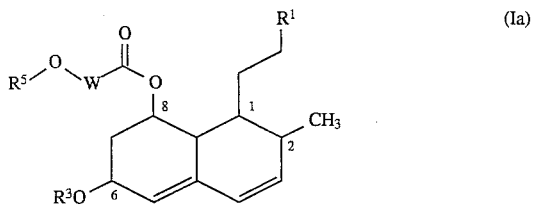

3. The compound of claim 1, having the formula (Ib):

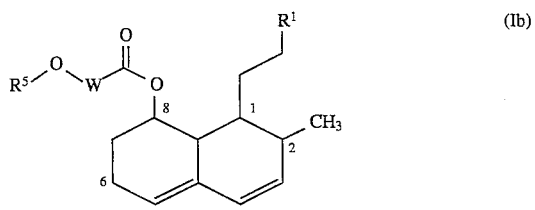

4. The compound of claim 1, in which $R^4$ represents a hydrogen atom.

5. The compound of claim 1, in which $R^4$ represents a hydrogen atom, in the form of a pharmaceutically acceptable salt.

6. The compound of claim 1, in which $R^3$, $R^{3a}$ and $R^{3b}$ may be the same or different and each represents a hydrogen atom or said hydroxy protecting group.

7. The compound of claim 1, in which $R^3$, $R^{3a}$ and $R^{3b}$ may be the same or different and each represents a hydrogen atom or said protecting group capable of being cleaved in vivo by biological methods.

8. The compound of claim 1, in which $R^3$, $R^{3a}$ and $R^{3b}$ each represent a hydrogen atom.

9. The compound of claim 1, in which $R^4$ represents a hydrogen atom or said protecting group capable of being cleaved in vivo by biological methods.

10. The compound of claim 1, in which $R^4$ represents a hydrogen atom.

11. The compound of claim 1, in which $R^5$ represents an alkyl group having from 1 to 6 carbon atoms, an alkenyl group having from 2 to 6 carbon atoms, an alkynyl group having from 2 to 6 carbon atoms, an aryl group having from 6 to 14 ring carbon atoms, or an aryl group having from 6 to 14 ring carbon atoms and substituted by a substituent selected from the group consisting of substituents α, defined in claim 1.

12. The compound of claim 1, in which $R^5$ represents an aryl group or an aryl group substituted by a substituent selected from the group consisting of substituents α, defined in claim 1.

13. The compound of claim 1, in which $R^5$ represents an aryl group substituted by a substituent selected from the group consisting of substituents α, defined in claim 1.

14. The compound of claim 1, in which $R^5$ represents a phenyl group substituted by a substituent selected from the group consisting of substituents α, defined in claim 1.

15. The compound of claim 1, in which $R^5$ represents an aryl group substituted by a substituent selected from the group consisting of substituents α.

16. The compound of claim 1, in which $R^5$ represents a phenyl group substituted by a substituent selected from the group consisting of substituents α.

17. The compound of claim 1, in which W represents a linear alkylene group having from 1 to 4 carbon atoms or a linear alkylene group having from 1 to 4 carbon atoms substituted by a substituent selected from the group consisting of substituents β, defined in claim 1.

18. The compound of claim 1, in which W represents a linear alkylene group having 1 or 2 carbon atoms or a linear alkylene group having 1 or 2 carbon atoms substituted by a substituent selected from the group consisting of substituents β, defined in claim 1.

19. The compound of claim 1, in which W represents a methylene group or a methylene group substituted by a substituent selected from the group consisting of substituents β, defined in claim 1.

20. The compound of claim 1, in which W represents a methylene group substituted by an alkyl group having from 1 to 6 carbon atoms.

21. The compound of claim 1, designated 3,5-dihydroxy-7-[1,2,6,7,8,8a-hexahydro-6-hydroxy-8-(2-phenoxybutyryloxy)-2-methyl-1-naphthyl]heptanoic acid and pharmaceutically acceptable salts and esters thereof.

22. The compound of claim 1, designated 3,5,-dihydroxy-7-{1,2,6,7,8,8a-hexahydro-6-hydroxy-8-[2-(1-naphthyloxy)butyryloxy]-2-methyl-1-naphthyl}heptanoic acid and pharmaceutically acceptable salts and esters thereof.

23. The compound of claim 1, designated 3,5,-dihydroxy-7-{1,2,6,7,8,8a-hexahydro-6-hydroxy-8-[2-(2-methylphenoxy)butyryloxy]-2-methyl-1-naphthyl}heptanoic acid and pharmaceutically acceptable salts and esters thereof.

24. The compound of claim 1, designated 3,5,-dihydroxy-7-{1,2,6,7,8,8a-hexahydro-6-hydroxy-8-[2-(3-methylphenoxy)butyryloxy]-2-methyl-1-naphthyl}heptanoic acid and pharmaceutically acceptable salts and esters thereof.

25. The compound of claim 1, designated 3,5,-dihydroxy-7-{1,2,6,7,8,8a-hexahydro-6-hydroxy-8-[2-(4-methylphenoxy)butyryloxy]-2-methyl-1-naphthyl}heptanoic acid and pharmaceutically acceptable salts and esters thereof.

26. The compound of claim 1, designated 3,5-dihydroxy-7-{1,2,6,7,8,8a-hexahydro-6-hydroxy-8-[2-(4-ethylphenoxy)butyryloxy]-2-methyl-1-naphthyl}heptanoic acid and pharmaceutically acceptable salts and esters thereof.

27. The compound of claim 1, designated 3,5-dihydroxy-7-{1,2,6,7,8,8a-hexahydro-6-hydroxy-8-[2-(2,3-dimethylphenoxy)butyryloxy]-2-methyl-1-naphthyl}heptanoic acid and pharmaceutically acceptable salts and esters thereof.

28. The compound of claim 1, designated 3,5-dihydroxy-7-{1,2,6,7,8,8a-hexahydro-6-hydroxy-8-[2-(2,5-dimethylphenoxy)butyryloxy]-2-methyl-1-naphthyl}heptanoic acid and pharmaceutically acceptable salts and esters thereof.

29. The compound of claim 1, designated 3,5-dihydroxy-7-{1,2,6,7,8,8a-hexahydro-6-hydroxy-8-[2-(2,6-dimethylphenoxy)butyryloxy]-2-methyl-1-naphthyl}heptanoic acid and pharmaceutically acceptable salts and esters thereof.

30. The compound of claim 1, designated 3,5-dihydroxy-7-{1,2,6,7,8,8a-hexahydro-6-hydroxy-8-[2-(3,4-dimethylphenoxy)butyryloxy]-2-methyl-1-naphthyl}heptanoic acid and pharmaceutically acceptable salts and esters thereof.

31. The compound of claim 1, designated 3,5-dihydroxy-7-{1,2,6,7,8,8a-hexahydro-6-hydroxy-8-[2-(2,4,6-trimethylphenoxy)butyryloxy]-2-methyl-1-naphthyl}heptanoic acid and pharmaceutically acceptable salts and esters thereof.

32. The compound of claim 1, designated 3,5-dihydroxy-7-{1,2,6,7,8,8a-hexahydro-6-hydroxy-8-[2-(2-isopropylphenoxy)butyryloxy]-2-methyl-1-naphthyl}heptanoic acid and the ring-closed lactone corresponding thereto and pharmaceutically acceptable salts and esters thereof.

33. The compound of claim 1, designated 3,5-dihydroxy-7-{1,2,6,7,8,8a-hexahydro-6-hydroxy-8-[2-(2-allylphenoxy)butyryloxy]-2-methyl-1-naphthyl}heptanoic acid and pharmaceutically acceptable salts and esters thereof.

34. The compound of claim 1, designated of 3,5-dihydroxy-7-{1,2,6,7,8,8a-hexahydro-6-hydroxy-8-[2-(4-chlorophenoxy)butyryloxy]-2-methyl-1-naphthyl}heptanoic acid and pharmaceutically acceptable salts and esters thereof.

35. The compound of claim 1, designated 3,5-dihydroxy-7-{1,2,6,7,8,8a-hexahydro-6-hydroxy-8-[2-(2-fluorophenoxy)butyryloxy]-2-methyl-1-naphthyl}heptanoic acid and pharmaceutically acceptable salts and esters thereof.

36. The compound of claim 1, designated 3,5-dihydroxy-7-{1,2,6,7,8,8a-hexahydro-6-hydroxy-8-[2-(4-fluorophenoxy)butyryloxy]-2-methyl-1-naphthyl}heptanoic acid and pharmaceutically acceptable salts and esters thereof.

37. The compound of claim 1, designated 3,5-dihydroxy-7-{1,2,6,7,8,8a-hexahydro-6-hydroxy-8-[2-(2-bromophenoxy)butyryloxy]-2-methyl-1-naphthyl}heptanoic acid and pharmaceutically acceptable salts and esters thereof.

38. The compound of claim 1, designated 3,5-dihydroxy-7-{1,2,6,7,8,8a-hexahydro-6-hydroxy-8-[2-(2,6-dichlorophenoxy)butyryloxy]-2-methyl-1-naphthyl}heptanoic acid and pharmaceutically acceptable salts and esters thereof.

39. The compound of claim 1, designated 3,5-dihydroxy-7-{1,2,6,7,8,8a-hexahydro-6-hydroxy-8-[2-(2,4-difluorophenoxy)butyryloxy]-2-methyl-1-naphthyl}heptanoic acid and pharmaceutically acceptable salts and esters thereof.

40. The compound of claim 1, designated 3,5-dihydroxy-7-{1,2,6,7,8,8a-hexahydro-6-hydroxy-8-[2-(2,6-dibromophenoxy)butyryloxy]-2-methyl-1-naphthyl}heptanoic acid and pharmaceutically acceptable salts and esters thereof.

41. The compound of claim 1, designated 3,5-dihydroxy-7-[1,2,6,7,8,8a-hexahydro-6-hydroxy-8-(2-phenoxyvaleryloxy)-2-methyl-1-naphthyl]heptanoic acid and pharmaceutically acceptable salts and esters thereof.

42. The compound of claim 1, designated 3,5-dihydroxy-7-[1,2,6,7,8,8a-hexahydro-6-hydroxy-8-(2-phenoxy-2-methylpropionyloxy)-2-methyl-1-naphthyl]heptanoic acid and pharmaceutically acceptable salts and esters thereof.

43. The compound of claim 1, designated 3,5-dihydroxy-7-{1,2,6,7,8,8a-hexahydro-6-hydroxy-8-[2-(4-fluorophenoxy)-2-methylpropionyloxy]-2-methyl-1-naphthyl}heptanoic acid and pharmaceutically acceptable salts and esters thereof.

44. The compound of claim 1, designated 3,5-dihydroxy-7-{1,2,6,7,8,8a-hexahydro-6-hydroxy-8-[2-(4-methylphenoxy)-2-methylbutyryloxy]-2-methyl-1-naphthyl}heptanoic acid and pharmaceutically acceptable salts and esters thereof.

45. The compound of claim 1, designated 3,5-dihydroxy-7-{1,2,6,7,8,8a-hexahydro-6-hydroxy-8-[2-(2-methyl-1-naphthyloxy)butyryloxy]-2-methyl-1-naphthyl}heptanoic acid and pharmaceutically acceptable salts and esters thereof.

46. The compound of claim 1, designated 3,5-dihydroxy-7-[1,2,6,7,8,8a-hexahydro-8-(2-phenoxybutyryloxy)-2-methyl-1-naphthyl]heptanoic acid and pharmaceutically acceptable salts and esters thereof.

47. The compound of claim 1, designated 3,5,-dihydroxy-7-{1,2,6,7,8,8a-hexahydro-8-[2-(1-naphthyloxy)butyryloxy]-2-methyl-1-naphthyl}heptanoic acid and pharmaceutically acceptable salts and esters thereof.

48. The compound of claim 1, designated 3,5,-dihydroxy-7-{1,2,6,7,8,8a-hexahydro-8-[2-(2-methylphenoxy)butyryloxy]-2-methyl-1-naphthyl}heptanoic acid and pharmaceutically acceptable salts and esters thereof.

49. The compound of claim 1, designated 3,5,-dihydroxy-7-{1,2,6,7,8,8a-hexahydro-8-[2-(3-methylphenoxy)butyryloxy]-2-methyl-1-naphthyl}heptanoic acid and pharmaceutically acceptable salts and esters thereof.

50. The compound of claim 1, designated 3,5,-dihydroxy-7-{1,2,6,7,8,8a-hexahydro-8-[2-(4-methylphenoxy)butyryloxy]-2-methyl-1-naphthyl}heptanoic acid and pharmaceutically acceptable salts and esters thereof.

51. The compound of claim 1, designated 3,5-dihydroxy-7-{1,2,6,7,8,8a-hexahydro-8-[2-(4-ethylphenoxy)butyryloxy]-2-methyl-1-naphthyl}heptanoic acid and pharmaceutically acceptable salts and esters thereof.

52. The compound of claim 1, designated 3,5-dihydroxy-7-{1,2,6,7,8,8a-hexahydro-8-[2-(2,3-dimethylphenoxy)butyryloxy]-2-methyl-1-naphthyl}heptanoic acid and pharmaceutically acceptable salts and esters thereof.

53. The compound of claim 1, designated 3,5-dihydroxy-7-{1,2,6,7,8,8a-hexahydro-8-[2-(2,5-dimethylphenoxy)butyryloxy]-2-methyl-1-naphthyl}heptanoic acid and pharmaceutically acceptable salts and esters thereof.

54. The compound of claim 1, designated 3,5-dihydroxy-7-{1,2,6,7,8,8a-hexahydro-8-[2-(2,6-dimethylphenoxy)butyryloxy]-2-methyl-1-naphthyl}heptanoic acid and pharmaceutically acceptable salts and esters thereof.

55. The compound of claim 1, designated 3,5-dihydroxy-7-{1,2,6,7,8,8a-hexahydro-8-[2-(3,4-dimethylphenoxy)butyryloxy]-2-methyl-1-naphthyl}heptanoic acid and pharmaceutically acceptable salts and esters thereof.

56. The compound of claim 1, designated 3,5-dihydroxy-7-{1,2,6,7,8,8a-hexahydro-8-[2-(2,4,6-trimethylphenoxy-)butyryloxy]-2-methyl-1-naphthyl}heptanoic acid and pharmaceutically acceptable salts and esters thereof.

57. The compound of claim 1, designated 3,5-dihydroxy-7-{1,2,6,7,8,8a-hexahydro-8-[2-(2-isopropylphenoxy)butyryloxy]-2-methyl-1-naphthyl}heptanoic acid and pharmaceutically acceptable salts and esters thereof.

58. The compound of claim 1, designated 3,5-dihydroxy-7-{1,2,6,7,8,8a-hexahydro-8-[2-(2-allylphenoxy)butyryloxy]-2-methyl-1-naphthyl}heptanoic acid and pharmaceutically acceptable salts and esters thereof.

59. The compound of claim 1, designated 3,5-dihydroxy-7-{1,2,6,7,8,8a-hexahydro-8-[2-(4-chlorophenoxy)butyryloxy]-2-methyl-1-naphthyl}heptanoic acid and pharmaceutically acceptable salts and esters thereof.

60. The compound of claim 1, designated 3,5-dihydroxy-7-{1,2,6,7,8,8a-hexahydro-8-[2-(2-fluorophenoxy)butyryloxy]-2-methyl-1-naphthyl}heptanoic acid and pharmaceutically acceptable salts and esters thereof.

61. The compound of claim 1, designated 3,5-dihydroxy-7-{1,2,6,7,8,8a-hexahydro-8-[2-(4-fluorophenoxy)butyryloxy]-2-methyl-1-naphthyl}heptanoic acid and pharmaceutically acceptable salts and esters thereof.

62. The compound of claim 1, designated 3,5-dihydroxy-7-{1,2,6,7,8,8a-hexahydro-8-[2-(2-bromophenoxy)butyryloxy]-2-methyl-1-naphthyl}heptanoic acid and pharmaceutically acceptable salts and esters thereof.

63. The compound of claim 1, designated 3,5-dihydroxy-7-{1,2,6,7,8,8a-hexahydro-8-[2-(2,6-dichlorophenoxy)butyryloxy]-2-methyl-1-naphthyl}heptanoic acid and pharmaceutically acceptable salts and esters thereof.

64. The compound of claim 1, designated 3,5-dihydroxy-7-{1,2,6,7,8,8a-hexahydro-8-[2-(2,4-difluorophenoxy)butyryloxy]-2-methyl-1-naphthyl}heptanoic acid and pharmaceutically acceptable salts and esters thereof.

65. The compound of claim 1, designated 3,5-dihydroxy-7-{1,2,6,7,8,8a-hexahydro-8-[2-(2,6-dibromophenoxy)butyryloxy]-2-methyl-1-naphthyl}heptanoic acid and pharmaceutically acceptable salts and esters thereof.

66. The compound of claim 1, designated 3,5-dihydroxy-7-[1,2,6,7,8,8a-hexahydro-8 -(2-phenoxyvaleryloxy)-2-methyl-1-naphthyl]heptanoic acid and pharmaceutically acceptable salts and esters thereof.

67. The compound of claim 1, designated 3,5-dihydroxy-7-[1,2,6,7,8,8a-hexahydro-8 -(2-phenoxy-2-methylpropionyloxy)-2-methyl-1-naphthyl]heptanoic acid and pharmaceutically acceptable salts and esters thereof.

68. The compound of claim 1, designated 3,5-dihydroxy-7-{1,2,6,7,8,8a-hexahydro-8-[2-(4-fluorophenoxy)-2-methylpropionyloxy]-2-methyl-1-naphthyl}heptanoic acid and pharmaceutically acceptable salts and esters thereof.

69. The compound of claim 1, selected from the group consisting of 3,5-dihydroxy-7-{1,2,6,7,8,8a-hexahydro-8-[2-(4-methylphenoxy)-2-methylbutyryloxy]-2-methyl-1-naphthyl}-heptanoic acid and the ring-closed lactone corresponding thereto and pharmaceutically acceptable salts and esters thereof.

70. The compound of claim 1, selected from the group consisting of 3,5-dihydroxy-7-{1,2,6,7,8,8a-hexahydro-8-[2-(2-methyl-1-naphthyloxy)butyryloxy]-2-methyl-1-naphthyl}heptanoic acid and the ring-closed lactone corresponding thereto and pharmaceutically acceptable salts and esters thereof.

71. A pharmaceutical composition comprising an agent for inhibiting cholesterol biosynthesis in admixture with a pharmaceutically acceptable carrier or diluent, wherein said agent is selected from the group consisting of compounds of formula (I) and pharmaceutically acceptable salts and esters thereof, as claimed in claim 1.

72. The composition of claim 71, wherein said agent has the formula (Ia):

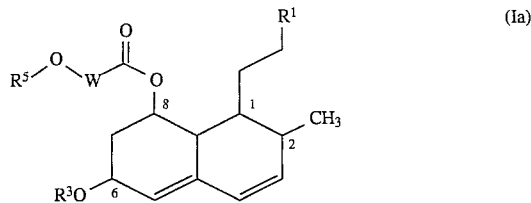

73. The composition of claim 71, wherein said agent has the formula (Ib):

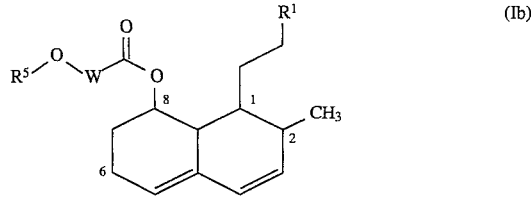

74. The composition of claim 71, in which $R^3$, $R^{3a}$ and $R^{3b}$ may be the same or different and each represents a hydrogen atom or said hydroxy protecting group.

75. The composition of claim 71, in which $R^4$ represents said hydrogen atom or a protecting group capable of being cleaved in vivo by biological methods.

76. The composition of claim 71, in which $R^5$ represents a alkyl group having from 1 to 6 carbon atoms, an alkenyl group having from 2 to 6 carbon atoms, an alkynyl group having from 2 to 6 carbon atoms, an aryl group having from 6 to 14 ring carbon atoms, or an aryl group having from 6 to 14 ring carbon atoms and substituted by a substituent selected from the group consisting of substituents α, defined in claim 1.

77. The composition of claim 71, in which W represents a linear alkylene group having from 1 to 4 carbon atoms or a linear alkylene group having from 1 to 4 carbon atoms substituted by a substituent selected from the group consisting of substituents β, defined in claim 1.

78. The composition of claim 71, wherein said agent is selected from the group consisting of:
3,5-dihydroxy-7-[1,2,6,7,8,8a-hexahydro-6-hydroxy-8-(2-phenoxybutyryloxy)-2-methyl-1-naphthyl]heptanoic acid;
3,5,-dihydroxy-7-{1,2,6,7,8,8a-hexahydro-6-hydroxy- 8-[2-(1-naphthyloxy)butyryloxy]-2-methyl-1-naphthyl}heptanoic acid;
3,5,-dihydroxy-7-{1,2,6,7,8,8a-hexahydro-6-hydroxy-8 -[2-(2-methylphenoxy)butyryloxy]-2-methyl-1-naphthyl}heptanoic acid;
3,5,-dihydroxy-7-{1,2,6,7,8,8a-hexahydro-6-hydroxy-8 -[2-(3-methylphenoxy)butyryloxy]-2-methyl-1-naphthyl}heptanoic acid;
3,5,-dihydroxy-7-{1,2,6,7,8,8a-hexahydro-6-hydroxy-8 -[2-(4-methylphenoxy)butyryloxy]-2-methyl-1-naphthyl}heptanoic acid;
3,5-dihydroxy-7-{1,2,6,7,8,8a-hexahydro-6-hydroxy-8-[2 -(4-ethylphenoxy)butyryloxy]-2-methyl-1-naphthyl}heptanoic acid;

3,5-dihydroxy-7-{1,2,6,7,8,8a-hexahydro-6-hydroxy-8-[2-(2,3-dimethylphenoxy)butyryloxy]-2-methyl-1-naphthyl}heptanoic acid;
3,5-dihydroxy-7-{1,2,6,7,8,8a-hexahydro-6-hydroxy-8-[2-(2,5-dimethylphenoxy)butyryloxy]-2-methyl-1-naphthyl}heptanoic acid;
3,5-dihydroxy-7-{1,2,6,7,8,8a-hexahydro-6-hydroxy-8-[2-(2,6-dimethylphenoxy)butyryloxy]-2-methyl-1-naphthyl}heptanoic acid;
3,5-dihydroxy-7-{1,2,6,7,8,8a-hexahydro-6-hydroxy-8-[2-(3,4-dimethylphenoxy)butyryloxy]-2-methyl-1-naphthyl}heptanoic acid;
3,5-dihydroxy-7-{1,2,6,7,8,8a-hexahydro-6-hydroxy-8-[2-(2,4,6-trimethylphenyloxy)butyryloxy]-2-methyl-1-naphthyl}heptanoic acid;
3,5-dihydroxy-7-{1,2,6,7,8,8a-hexahydro-6-hydroxy-8-[2-(2-isopropylphenoxy)butyryloxy]-2-methyl-1-naphthyl}heptanoic acid;
3,5-dihydroxy-7-{1,2,6,7,8,8a-hexahydro-6-hydroxy-8-[2-(2-allylphenoxy)butyryloxy]-2-methyl-1-naphthyl}heptanoic acid;
3,5-dihydroxy-7-{1,2,6,7,8,8a-hexahydro-6-hydroxy-8-[2-(4-chlorophenoxy)butyryloxy]-2-methyl-1-naphthyl}heptanoic acid;
3,5-dihydroxy-7-{1,2,6,7,8,8a-hexahydro-6-hydroxy-8-[2-(2-fluorophenoxy)butyryloxy]-2-methyl-1-naphthyl}heptanoic acid;
3,5-dihydroxy-7-{1,2,6,7,8,8a-hexahydro-6-hydroxy-8-[2-(4-fluorophenoxy)butyryloxy]-2-methyl-1-naphthyl}heptanoic acid;
3,5-dihydroxy-7-{1,2,6,7,8,8a-hexahydro-6-hydroxy-8-[2-(2-bromophenoxy)butyryloxy]-2-methyl-1-naphthyl}heptanoic acid;
3,5-dihydroxy-7-{1,2,6,7,8,8a-hexahydro-6-hydroxy-8-[2-(2,6-dichlorophenoxy)butyryloxy]-2-methyl-1-naphthyl}heptanoic acid;
3,5-dihydroxy-7-{1,2,6,7,8,8a-hexahydro-6-hydroxy-8-[2-(2,4-difluorophenoxy)butyryloxy]-2-methyl-1-naphthyl}heptanoic acid;
3,5-dihydroxy-7-{1,2,6,7,8,8a-hexahydro-6-hydroxy-8-[2-(2,6-dibromophenoxy)butyryloxy]-2-methyl-1-naphthyl}heptanoic acid;
3,5-dihydroxy-7-[1,2,6,7,8,8a-hexahydro-6-hydroxy-8-(2-phenoxyvaleryloxy)-2-methyl-1-naphthyl]heptanoic acid;
3,5-dihydroxy-7-[1,2,6,7,8,8a-hexahydro-6-hydroxy-8-(2-phenoxy-2-methylpropionyloxy)-2-methyl-1-naphthyl]heptanoic acid;
3,5-dihydroxy-7-{1,2,6,7,8,8a-hexahydro-6-hydroxy-8-[2-(4-fluorophenoxy)-2-methylpropionyloxy]-2-methyl-1-naphthyl}heptanoic acid;
3,5-dihydroxy-7-{1,2,6,7,8,8a-hexahydro-6-hydroxy-8-{2(4-methylphenoxy)-2-methylbutyryloxy]-2-methyl-1-naphthyl}heptanoic acid;
3,5-dihydroxy-7-{1,2,6,7,8,8a-hexahydro-6-hydroxy-8-[2-(2-methyl-1-naphthyloxy)butyryloxy]-2-methyl-1-naphthyl}heptanoic acid;
3,5-dihydroxy-7-[1,2,6,7,8,8a-hexahydro-8-(2-phenoxybutyryloxy)- 2-methyl-1-naphthyl]heptanoic acid;
3,5,-dihydroxy-7-{1,2,6,7,8,8a-hexahydro-8-[2-(1-naphthyloxy)butyryloxy]-2-methyl-1-naphthyl}heptanoic acid;
3,5,-dihydroxy-7-{1,2,6,7,8,8a-hexahydro-8-[2-(2-methylphenoxy)butyryloxy]-2-methyl-1-naphthyl}heptanoicacid;
3,5,-dihydroxy-7-{1,2,6,7,8,8a-hexahydro-8-[2-(3-methylphenoxy)butyryloxy]-2-methyl-1-naphthyl}heptanoic acid;
3,5,-dihydroxy-7-{1,2,6,7,8,8a-hexahydro-8-[2-(4-methylphenoxy)butyryloxy]-2-methyl-1-naphthyl}heptanoic acid;
3,5-dihydroxy-7-{1,2,6,7,8,8a-hexahydro-8-[2-(4-ethylphenoxy)butyryloxy]-2-methyl-1-naphthyl}heptanoic acid;
3,5-dihydroxy-7-{1,2,6,7,8,8a-hexahydro-8-[2-(2,3-dimethylphenoxy)butyryloxy]-2-methyl-1-naphthyl}heptanoic acid;
3,5-dihydroxy-7-{1,2,6,7,8,8a-hexahydro-8-[2-(2,5-dimethylphenoxy)butyryloxy]-2-methyl-1-naphthyl}heptanoic acid;
3,5-dihydroxy-7-{1,2,6,7,8,8a-hexahydro-8-[2-(2,6-dimethylphenoxy)butyryloxy]-2-methyl-1-naphthyl}heptanoic acid;
3,5-dihydroxy-7-{1,2,6,7,8,8a-hexahydro-8-[2-(3,4-dimethylphenoxy)butyryloxy]-2-methyl-1-naphthyl}heptanoic acid;
3,5-dihydroxy-7-{1,2,6,7,8,8a-hexahydro-8-[2-(2,4,6-trimethylphenoxy)butyryloxy]-2-methyl-1-naphthyl}heptanoic acid;
3,5-dihydroxy-7-{1,2,6,7,8,8a-hexahydro-8-[2-(2-isopropylphenoxy)butyryloxy]-2-methyl-1-naphthyl}heptanoic acid;
3,5-dihydroxy-7-{1,2,6,7,8,8a-hexahydro-8-[2-(2-allylphenoxy)butyryloxy]-2-methyl-1-naphthyl}heptanoic acid;
3,5-dihydroxy-7-{1,2,6,7,8,8a-hexahydro-8-[2-(4-chlorophenoxy)butyryloxy] -2-methyl-1-naphthyl}heptanoic acid;
3,5-dihydroxy-7-{1,2,6,7,8,8a-hexahydro-8-[2-(2-fluorophenoxy)butyryloxy] -2-methyl-1-naphthyl}heptanoic acid;
3,5-dihydroxy-7-{1,2,6,7,8,8a-hexahydro-8-[2-(4-fluorophenoxy)butyryloxy] -2-methyl-1-naphthyl}heptanoic acid;
3,5-dihydroxy-7-{1,2,6,7,8,8a-hexahydro-8-[2-(2-bromophenoxy)butyryloxy] -2-methyl-1-naphthyl}heptanoic acid;
3,5-dihydroxy-7-{1,2,6,7,8,8a-hexahydro-8-[2-(2,6-dichlorophenoxy)butyryloxy] -2-methyl-1-naphthyl}heptanoic acid;
3,5-dihydroxy-7-{1,2,6,7,8,8a-hexahydro-8-[2-(2,4-difluorophenoxy)butyryloxy] -2-methyl-1-naphthyl}heptanoic acid;
3,5-dihydroxy-7-{1,2,6,7,8,8a-hexahydro-8-[2-(2,6-dibromophenoxy)butyryloxy] -2-methyl-1-naphthyl}heptanoic acid;
3,5-dihydroxy-7-[1,2,6,7,8,8a-hexahydro-8-(2-phenoxyvaleryloxy)- 2-methyl-1-naphthyl]heptanoic acid;
3,5-dihydroxy-7-[1,2,6,7,8,8a-hexahydro-8-(2-phenoxy-2-methylpropionyloxy)-2-methyl-1-naphthyl]heptanoic acid;
3,5-dihydroxy-7-{1,2,6,7,8,8a-hexahydro-8-[2-(4-fluorophenoxy)- 2-methylpropionyloxy]-2-methyl-1-naphthyl}heptanoic acid;
3,5-dihydroxy-7-{1,2,6,7,8,8a-hexahydro-8-[2-(4-methylphenoxy)- 2-methylbutyryloxy]-2-methyl-1-naphthyl}heptanoic acid;
3,5-dihydroxy-7-{1,2,6,7,8,8a-hexahydro-8-[2-(2-methyl-1-naphthyloxy)butyryloxy]-2-methyl-1-naphthyl}heptanoic acid;
and pharmaceutically acceptable salts and esters thereof.

79. A method of treating a mammal suffering from a disorder arising from a blood cholesterol imbalance, which comprises administering to said mammal an effective amount of an agent inhibiting cholesterol biosynthesis, wherein said agent is selected from the group consisting of compounds of formula (I), and pharmaceutically acceptable salts and esters thereof, as claimed in claim 1.

80. The method of claim 79, wherein said agent has the formula (Ia):

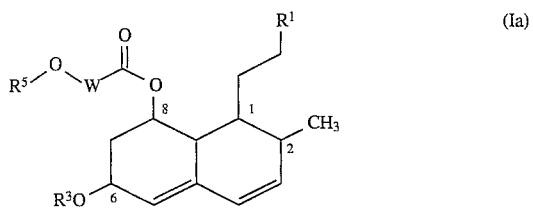

81. The method of claim 79, wherein said agent has the formula (Ib):

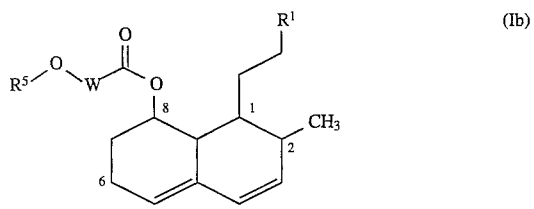

82. The method of claim 79, in which $R^1$ represents a group of the formula (II).

83. The method of claim 79, in which $R^3$, $R^{3a}$ and $R^{3b}$ may be the same or different and each represents a hydrogen atom or said hydroxy protecting group.

84. The method of claim 79, in which $R^4$ represents a hydrogen atom or said protecting group capable of being cleaved in vivo by biological methods.

85. The method of claim 79, in which $R^5$ represents a alkyl group having from 1 to 6 carbon atoms, an alkenyl group having from 2 to 6 carbon atoms, an alkynyl group having from 2 to 6 carbon atoms, an aryl group having from 6 to 14 ring carbon atoms, or an aryl group having from 6 to 14 ring carbon atoms and substituted by a substituent selected from the group consisting of substituents α, defined in claim 1.

86. The method of claim 79, in which W represents a linear alkylene group having from 1 to 4 carbon atoms or a linear alkylene group having from 1 to 4 carbon atoms substituted by a substituent selected from the group consisting of substituents β, defined in claim 1.

87. The method of claim 79, wherein said agent is selected from the group consisting of:

3,5-dihydroxy-7-[1,2,6,7,8,8a-hexahydro-6-hydroxy-8-(2-phenoxybutyryloxy)-2-methyl-1-naphthyl]heptanoic acid;

3,5,-dihydroxy-7-{1,2,6,7,8,8a-hexahydro-6-hydroxy-8 -[2-(1-naphthyloxy)butyryloxy]-2-methyl-1-naphthyl}heptanoic acid;

3,5,-dihydroxy-7-{1,2,6,7,8,8a-hexahydro-6-hydroxy-8 -[2-(2-methylphenoxy)butyryloxy]-2-methyl-1-naphthyl}heptanoic acid;

3,5,-dihydroxy-7-{1,2,6,7,8,8a-hexahydro-6-hydroxy-8 -[2-(3-methylphenoxy)butyryloxy]-2-methyl-1-naphthyl}heptanoic acid;

3,5,-dihydroxy-7-{1,2,6,7,8,8a-hexahydro-6-hydroxy-8 -[2-(4-methylphenoxy)butyryloxy]-2-methyl-1-naphthyl}heptanoic acid;

3,5-dihydroxy-7-{1,2,6,7,8,8a-hexahydro-6-hydroxy-8-[2-(4-ethylphenoxy)butyryloxy]-2-methyl-1-naphthyl}heptanoic acid;

3,5-dihydroxy-7-{1,2,6,7,8,8a-hexahydro-6-hydroxy-8-[2-(2,3-dimethylphenoxy)butyryloxy]-2-methyl-1-naphthyl}heptanoic acid;

3,5-dihydroxy-7-{1,2,6,7,8,8a-hexahydro-6-hydroxy-8-[2-(2,5-dimethylphenoxy)butyryloxy]-2-methyl-1-naphthyl}heptanoic acid;

3,5-dihydroxy-7-{1,2,6,7,8,8a-hexahydro-6-hydroxy-8-[2-(2,6-dimethylphenoxy)butyryloxy]-2-methyl-1-naphthyl}heptanoic acid;

3,5-dihydroxy-7-{1,2,6,7,8,8a-hexahydro-6-hydroxy-8-[2-(3,4-dimethylphenoxy)butyryloxy]-2-methyl-1-naphthyl}heptanoic acid;

3,5-dihydroxy-7-{1,2,6,7,8,8a-hexahydro-6-hydroxy-8-[2-(2,4,6-trimethylphenoxy)butyryloxy]-2-methyl-1-naphthyl}heptanoic acid;

3,5-dihydroxy-7-{1,2,6,7,8,8a-hexahydro-6-hydroxy-8-[2-(2-isopropylphenoxy)butyryloxy]-2-methyl-1-naphthyl}heptanoic acid;

3,5-dihydroxy-7-{1,2,6,7,8,8a-hexahydro-6-hydroxy-8-[2-(2-allylphenoxy)butyryloxy]-2-methyl-1-naphthyl}heptanoic acid;

3,5-dihydroxy-7-{1,2,6,7,8,8a-hexahydro-6-hydroxy-8-[2-(4-chlorophenoxy)butyryloxy]-2-methyl-1-naphthyl}heptanoic acid;

3,5-dihydroxy-7-{1,2,6,7,8,8a-hexahydro-6-hydroxy-8-[2-(2-fluorophenoxy)butyryloxy]-2-methyl-1-naphthyl}heptanoic acid;

3,5-dihydroxy-7-{1,2,6,7,8,8a-hexahydro-6-hydroxy-8-[2-(4-fluorophenoxy)butyryloxy]-2-methyl-1-naphthyl}heptanoic acid;

3,5-dihydroxy-7-{1,2,6,7,8,8a-hexahydro-6-hydroxy-8-[2-(2-bromophenoxy)butyryloxy]-2-methyl-1-naphthyl}heptanoic acid;

3,5-dihydroxy-7-{1,2,6,7,8,8a-hexahydro-6-hydroxy-8-[2-(2,6-dichlorophenoxy)butyryloxy]-2-methyl-1-naphthyl}heptanoic acid;

3,5-dihydroxy-7-{1,2,6,7,8,8a-hexahydro-6-hydroxy-8-[2-(2,4-difluorophenoxy)butyryloxy]-2-methyl-1-naphthyl}heptanoic acid;

3,5-dihydroxy-7-{1,2,6,7,8,8a-hexahydro-6-hydroxy-8-[2-(2,6-dibromophenoxy)butyryloxy]-2-methyl-1-naphthyl}heptanoic acid;

3,5-dihydroxy-7-[1,2,6,7,8,8a-hexahydro-6-hydroxy-8-(2-phenoxyvaleryloxy)-2-methyl-1-naphthyl]heptanoic acid;

3,5-dihydroxy-7-[1,2,6,7,8,8a-hexahydro-6-hydroxy-8-(2-phenoxy-2-methylpropionyloxy)-2-methyl-1-naphthyl]heptanoic acid;

3,5-dihydroxy-7-{1,2,6,7,8,8a-hexahydro-6-hydroxy-8-[2-(4-fluorophenoxy)-2-methylpropionyloxy]-2-methyl-1-naphthyl}heptanoic acid;

3,5-dihydroxy-7-{1,2,6,7,8,8a-hexahydro-6-hydroxy-8-[2-(4-methylphenoxy)-2-methylbutyryloxy]-2-methyl-1-naphthyl}heptanoic acid;

3,5-dihydroxy-7-{1,2,6,7,8,8a-hexahydro-6-hydroxy-8-[2-(2-methyl-1-naphthyloxy)butyryloxy]-2-methyl-1-naphthyl}heptanoic acid;

3,5-dihydroxy-7-[1,2,6,7,8,8a-hexahydro-8-(2-phenoxybutyryloxy)- 2-methyl-1-naphthyl]heptanoic acid;

3,5,-dihydroxy-7-{1,2,6,7,8,8a-hexahydro-8-[2-(1-naphthyloxy)butyryloxy]-2-methyl-1-naphthyl}heptanoic acid;

3,5,-dihydroxy-7-{1,2,6,7,8,8a-hexahydro-8-[2 -(2-methylphenoxy)butyryloxy]-2-methyl-1-naphthyl}heptanoicacid;

3,5,-dihydroxy-7-{1,2,6,7,8,8a-hexahydro-8-[2 -(3-methylphenoxy)butyryloxy]-2-methyl-1-naphthyl}heptanoic acid;

3,5,-dihydroxy-7-{1,2,6,7,8,8a-hexahydro-8-[2 -(4-methylphenoxy)butyryloxy]-2-methyl-1-naphthyl}heptanoic acid;

3,5-dihydroxy-7-{1,2,6,7,8,8a-hexahydro-8-[2-(4-ethylphenoxy)butyryloxy]-2-methyl-1-naphthyl}heptanoic acid;

3,5-dihydroxy-7-{1,2,6,7,8,8a-hexahydro-8-[2-(2,3-dimethylphenoxy)butyryloxy]-2-methyl-1-naphthyl}heptanoic acid;

3,5-dihydroxy-7-{1,2,6,7,8,8a-hexahydro-8-[2-(2,5-dimethylphenoxy)butyryloxy]-2-methyl-1-naphthyl}heptanoic acid;

3,5-dihydroxy-7-{1,2,6,7,8,8a-hexahydro-8-[2-(2,6-dimethylphenoxy)butyryloxy]-2-methyl-1-naphthyl}heptanoic acid;

3,5-dihydroxy-7-{1,2,6,7,8,8a-hexahydro-8-[2-(3,4-dimethylphenoxy)butyryloxy]-2-methyl-1-naphthyl}heptanoic acid;

3,5-dihydroxy-7-{1,2,6,7,8,8a-hexahydro-8-[2-(2,4,6-trimethylphenoxy)butyryloxy]-2-methyl-1-naphthyl}heptanoic acid;

3,5-dihydroxy-7-{1,2,6,7,8,8a-hexahydro-8-[2-(2-isopropylphenoxy)butyryloxy]-2-methyl-1-naphthyl}heptanoic acid;

3,5-dihydroxy-7-{1,2,6,7,8,8a-hexahydro-8-[2-(2-allylphenoxy)butyryloxy]-2-methyl-1-naphthyl}heptanoic acid;

3,5-dihydroxy-7-{1,2,6,7,8,8a-hexahydro-8-[2-(4-chlorophenoxy)butyryloxy]-2-methyl-1-naphthyl}heptanoic acid;

3,5-dihydroxy-7-{1,2,6,7,8,8a-hexahydro-8-[2-(2-fluorophenoxy)butyryloxy]-2-methyl-1-naphthyl}heptanoic acid;

3,5-dihydroxy-7-{1,2,6,7,8,8a-hexahydro-8-[2-(4-fluorophenoxy)butyryloxy]-2-methyl-1-naphthyl}heptanoic acid;

3,5-dihydroxy-7-{1,2,6,7,8,8a-hexahydro-8-[2-(2-bromophenoxy)butyryloxy]-2-methyl-1-naphthyl{heptanoic acid;

3,5-dihydroxy-7-{1,2,6,7,8,8a-hexahydro-8-[2-(2,6-dichlorophenoxy)butyryloxy]-2-methyl-1-naphthyl}heptanoic acid;

3,5-dihydroxy-7-{1,2,6,7,8,8a-hexahydro-8-[2-(2,4-difluorophenoxy)butyryloxy]-2-methyl-1-naphthyl}heptanoic acid;

3,5-dihydroxy-7-{1,2,6,7,8,8a-hexahydro-8-[2-(2,6-dibromophenoxy)butyryloxy]-2-methyl-1-naphthyl}heptanoic acid;

3,5-dihydroxy-7-[1,2,6,7,8,8a-hexahydro-8-(2-phenoxyvaleryloxy)-2-methyl-1-naphthyl]heptanoic acid;

3,5-dihydroxy-7-[1,2,6,7,8,8a-hexahydro-8-(2-phenoxy-2-methylpropionyloxy)-2-methyl-1-naphthyl]heptanoic acid;

3,5-dihydroxy-7-{1,2,6,7,8,8a-hexahydro-8-[2-(4-fluorophenoxy)-2-methylpropionyloxy]-2-methyl-1-naphthyl}heptanoic acid;

3,5-dihydroxy-7-{1,2,6,7,8,8a-hexahydro-8-[2-(4-methylphenoxy)-2-methylbutyryloxy]-2-methyl-1-naphthyl}heptanoic acid;

3,5-dihydroxy-7-{1,2,6,7,8,8a-hexahydro-8-[2-(2-methyl-1-naphthyloxy)butyryloxy]-2-methyl-1-naphthyl}heptanoic acid;

and pharmaceutically acceptable salts and esters thereof.

* * * * *

UNITED STATES PATENT AND TRADEMARK OFFICE
CERTIFICATE OF CORRECTION

PATENT NO. : 5,491,167
DATED : February 13, 1996
INVENTOR(S) : ISHIHARA et al

It is certified that error appears in the above-identified patent and that said Letters Patent is hereby corrected as shown below:

Item [57] ABSTRACT: after the structural formula (I), insert the following:

--[wherein $R^1$ represents a group of formula (II) or (III):

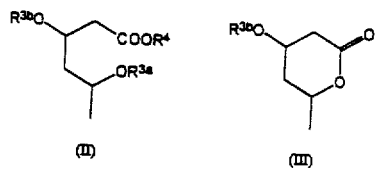

$R^2$ is hydrogen or a group of formula $-OR^3$; $R^3$, $R^{3a}$ and $R^{3b}$ are each hydrogen, a hydroxy-protecting group, alkyl, alkanesulfonyl, halogenated alkanesulfonyl or arylsulfonyl; $R^4$ is hydrogen or a carboxy-protecting group; $R^5$ is alkyl, alkenyl, alkynyl, aryl, aralkyl or a fused polycycle; and W is alkylene]--.

Column 159, line 40 (Claim 32): delete "and the ring-closed lactone corresponding thereto".

Signed and Sealed this

Second Day of December, 1997

Attest:

BRUCE LEHMAN

*Attesting Officer*

*Commissioner of Patents and Trademarks*